US012617825B2

(12) United States Patent
Emtage et al.

(10) Patent No.: US 12,617,825 B2
(45) Date of Patent: May 5, 2026

(54) METHODS AND COMPOSITIONS FOR REDUCING THE IMMUNOGENICITY OF CHIMERIC NOTCH RECEPTORS

(71) Applicant: Cell Design Labs, Inc., Emeryville, CA (US)

(72) Inventors: Peter Emtage, Lafayette, CA (US); Amy E. Gilbert, San Francisco, CA (US); Anselm Levskaya, Oakland, CA (US); Spencer Scott, San Francisco, CA (US); Vladimir Slepushkin, Vallejo, CA (US)

(73) Assignee: Cell Design Labs, Inc., Emeryville, CA (US)

( * ) Notice: Subject to any disclaimer, the term of this patent is extended or adjusted under 35 U.S.C. 154(b) by 0 days.

(21) Appl. No.: 17/716,636

(22) Filed: Apr. 8, 2022

(65) Prior Publication Data

US 2022/0363728 A1 Nov. 17, 2022

Related U.S. Application Data

(62) Division of application No. 16/010,805, filed on Jun. 18, 2018, now Pat. No. 11,325,957.

(Continued)

(51) Int. Cl.

| | |
|---|---|
| *A61K 40/11* | (2025.01) |
| *A61K 40/31* | (2025.01) |
| *A61K 40/35* | (2025.01) |
| *A61K 40/42* | (2025.01) |
| *A61K 48/00* | (2006.01) |
| *C07K 14/47* | (2006.01) |
| *C07K 14/705* | (2006.01) |
| *C07K 14/71* | (2006.01) |
| *C07K 16/28* | (2006.01) |
| *C07K 16/30* | (2006.01) |
| *C07K 19/00* | (2006.01) |
| *C12N 5/0783* | (2010.01) |
| *C12N 5/0786* | (2010.01) |
| *C12N 5/10* | (2006.01) |
| *C12N 15/63* | (2006.01) |
| *C12N 15/85* | (2006.01) |

(Continued)

(52) U.S. Cl.
CPC .......... *C07K 14/4702* (2013.01); *A61K 40/11* (2025.01); *A61K 40/31* (2025.01); *A61K 40/35* (2025.01); *A61K 40/4202* (2025.01); *A61K 40/4211* (2025.01); *A61K 48/00* (2013.01); *C07K 14/4705* (2013.01); *C07K 14/705* (2013.01); *C07K 14/70517* (2013.01); *C07K 14/71* (2013.01); *C07K 16/28* (2013.01); *C07K 16/2803* (2013.01); *C07K 16/30* (2013.01); *C07K 19/00* (2013.01); *C12N 5/0636* (2013.01); *C12N 5/0645* (2013.01); *C12N 5/10* (2013.01); *C12N 15/63* (2013.01); *C12N 15/85* (2013.01); *A61K 2039/5156* (2013.01); *A61P 35/04* (2018.01); *C07K 16/462* (2013.01); *C07K 2317/569* (2013.01); *C07K 2317/622* (2013.01); *C07K 2317/626* (2013.01); *C07K 2317/70* (2013.01); *C07K 2319/00* (2013.01); *C07K 2319/02* (2013.01); *C07K 2319/03* (2013.01); *C07K 2319/09* (2013.01); *C07K 2319/33* (2013.01); *C07K 2319/41* (2013.01); *C07K 2319/50* (2013.01); *C07K 2319/70* (2013.01); *C07K 2319/71* (2013.01); *C07K 2319/80* (2013.01); *C07K 2319/95* (2013.01); *C12N 2740/16043* (2013.01); *C12N 2830/15* (2013.01); *C12N 2830/85* (2013.01)

(58) Field of Classification Search
CPC .......... A61K 2039/505; A61K 39/3955; A61K 48/00; A61K 2039/5156; A61K 38/177; A61K 40/11; A61K 40/31; A61K 40/4211; A61K 40/4202; A61K 40/35; C07K 16/28; C07K 16/2803; C07K 16/2851; C07K 16/2896; C07K 16/30; C07K 16/2866; C07K 16/2863; C07K 19/00; C07K 2319/00; C07K 2319/02; C07K 2319/03; C07K 2319/09; C07K 2319/33; C07K 2319/50; C07K 2319/71; C07K 2319/70; C07K 2319/80; C07K 2319/91; C07K 14/705
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |

(Continued)

FOREIGN PATENT DOCUMENTS

| | | |
|---|---|---|
| CN | 101883786 A | 11/2010 |
| EP | 0404097 B1 | 9/1996 |

(Continued)

OTHER PUBLICATIONS

Zhou et al. Notch signaling pathway: architecture, disease, and therapeutics. Signal Transduct Targeted Ther 7: 95, 2022 (33 total pages).*

(Continued)

*Primary Examiner* — Bridget E Bunner
(74) *Attorney, Agent, or Firm* — Fish & Richardson P.C.

(57) ABSTRACT

The present invention relates to methods and compositions for reducing the immunogenicity of chimeric Notch receptors, and specifically to transcription factors useful for controlling gene expression delivered to tissues by such chimeric Notch receptors.

22 Claims, 7 Drawing Sheets

Specification includes a Sequence Listing.

Related U.S. Application Data

(60) Provisional application No. 62/603,993, filed on Jun. 19, 2017, provisional application No. 62/556,765, filed on Sep. 11, 2017.

(51) Int. Cl.
| | |
|---|---|
| *A61K 39/00* | (2006.01) |
| *A61P 35/04* | (2006.01) |
| *C07K 16/46* | (2006.01) |

(56) References Cited

U.S. PATENT DOCUMENTS

| | | | |
|---|---|---|---|
| 4,946,778 A | 8/1990 | Ladner et al. | |
| 5,225,539 A | 7/1993 | Winter | |
| 5,476,786 A | 12/1995 | Huston et al. | |
| 7,612,181 B2 | 11/2009 | Wu et al. | |
| 8,258,268 B2 | 9/2012 | Wu et al. | |
| 8,586,714 B2 | 11/2013 | Ghayur et al. | |
| 8,716,450 B2 | 5/2014 | Ghayur et al. | |
| 8,722,855 B2 | 5/2014 | Ghayur et al. | |
| 8,735,546 B2 | 5/2014 | Ghayur et al. | |
| 8,822,645 B2 | 9/2014 | Ghayur et al. | |
| 9,670,281 B2 | 6/2017 | Lim et al. | |
| 9,834,608 B2 | 12/2017 | Lim et al. | |
| 11,325,957 B2 | 5/2022 | Gilbert et al. | |
| 12,297,243 B2 | 5/2025 | Gilbert et al. | |
| 2003/0109678 A1 | 6/2003 | Cortese et al. | |
| 2016/0115217 A1 | 4/2016 | Kitajewski et al. | |
| 2016/0264665 A1 | 9/2016 | Lim et al. | |
| 2018/0362603 A1 | 12/2018 | Gilbert et al. | |
| 2019/0202918 A1 | 7/2019 | Lim et al. | |
| 2022/0372090 A1 | 11/2022 | Gilbert et al. | |

FOREIGN PATENT DOCUMENTS

| | | |
|---|---|---|
| WO | 1986001533 A1 | 3/1986 |
| WO | 1993011161 A1 | 6/1993 |
| WO | 2009025867 A2 | 2/2009 |
| WO | 2014127261 A1 | 8/2014 |
| WO | 2016138034 A1 | 9/2016 |
| WO | 2017123559 A2 | 7/2017 |
| WO | 2018039247 A1 | 3/2018 |
| WO | 2019164979 A1 | 8/2019 |

OTHER PUBLICATIONS

Sadelain Michel. "Chimeric antigen receptors: driving immunology towards synthetic biology." Current opinion in Immunology 41 (2016): 68-76.
Najafabadi et al., "C2H2 zinc finger proteins greatly expand the human regulatory lexicon," Nature Biotechnol. 33 (5):555-562, May 2015.
Ngo et al., "Computational Copmlexity, Protein Structure Prediction, and the Levinthal Paradox," The Protein Folding Problems and Tertiary Structure Prediction, (1994), pp. 492-495.
Omori et al., "CREB-H: a novel mammalian transcription factor belonging to the CREB/ATF family and functioning via the box-B element with a liver-specific expression," Nucleic Acids Res., 29(10):2154-2162, May 2001.
Pancewicz and Nicot, "Current views on the role of Notch signaling and the pathogenesis of human leukemia," BMC Cancer 11(1):502, Dec. 2011.
PCT International Search Report and Written Opinion in International Appln. No. PCT/US2018/038218, dated Sep. 14, 2018, 16 pages.
Pegram et al., "CD28z CARs and Armored CARs," CancerJ 20(2):127-133, Mar. 2014.
Pluckthun, "Antibodies from *Escherichia coli*," Pharmacol. Monoclonal Antibodies 113:269-315, 1994.
Priyanka et al., "Linkers in the structural biology of protein-protein interactions," Protein Sci. 22(2):153-167, Feb. 2013.
Riddell et al, "Adoptive Therapy with Chimeric Antigen Receptor Modified T Cells of Defined Subset Composition," Cancer J 20(2):141-144, Mar. 2014.
Roybal et al., "Precision Tumor Recognition by T Cells With Combinatorial Antigen-Sensing Circuits," Cell 164 (4):770-779, Feb. 2016.
Roybal et al., "Engineering T Cells with Customized Therapeutic Response Programs Using Synthetic Notch Receptors," Cell, vol. 167, No. 2, (2016), pp. 419-432.e1-e6.
Sadelain et al., "The basic principles of chimeric antigen receptor (CAR) design," Cancer Discov. 3(4):388-398, Apr. 2013.
Skolnick et al., "From Genes to Protein Structure and Function: Novel Applications of Computational Approaches in the Genomic Era," Trends in Biotech, vol. 18, No. 1, (2000), pp. 34-39.
Smith et al., The Challenges of Genome Sequence Annotation or "The Devil is in the Details," Nature Biotech, vol. 15, (1997), pp. 1222-1223.
Thiel et al., "Regulation of life and death by the zinc finger transcription factor Egr-1," J Cell. Physiol. 193(3):287-282, Dec. 2002.
Tokuriki et al., "Stability Effects of Mutations and Protein Evolvability," Curr Opin Structural Biol., vol. 19, (2009), pp. 596-604.
Urlaub and Chasin, "Isolation of Chinese hamster cell mutants deficient in dihydrofolate reductase activity," Proc. Natl. Acad. Sci. U.S.A. 77:4216-4220, Jul. 1980.
Wang et al., "The nuclear facto-kB RelA transcription factor is constitutively activated in human pancreatic adenocarcinoma cells," Clin. Cancer Res. 5(1):119-127, 1999.
Weintraub and Davis, "The myoD gene family: nodal point during specification of the muscle cell lineage," Science 251 (4995):761, Feb. 1991.
Wells, "Additivity of Mutational Effects in Proteins," Biochemistry, vol. 29, No. 37, (1990), pp. 8509-8517.
Yong et al., "Car T-Cell Therapy of Solid Tumors," Immunology and Cell Biology, vol. 95, (2017), pp. 356-363.
Zapata et al., "Engineering linear F(ab ')2 fragments for efficient production in *Escherichia coli* and enhanced antiproliferative activity," Protein Enz. 8(10):1057-1062, Oct. 1995.
Barrett et al., "Chimeric antigen receptor therapy for cancer," Ann. Rev. Med. 65:333-347, Jan. 2014.
Beatty et al., "Chimeric Antigen Receptor-Modified T Cells for the Treatment of Solid Tumors: Defining the Challenges and Next Steps," Pharmacology & Therapeutics, vol. 166, (2015), pp. 30-39.
Bird et al., "Single-chain antigen-binding proteins," Science 242:423-426, Oct. 1988.
Bork, "Go Hunting in Sequence Databases but watch out for Traps," TIG, vol. 12, No. 10, (1996), pp. 425-427.
Bork, "Powers and Pitfalls in Sequence Analysis: The 70% Hurdle," Genome Res., vol. 10, (2000), pp. 398-400.
Brenner, "Errors in Genome Annotation," TIG, vol. 15, No. 4, (1999), pp. 132-133.
Cartellieri et al., "Chimeric antigen receptor-engineered T cells for immunotherapy of cancer," J Biomed. Biotechnol. vol. 2010, Article ID 956304, May 2010.
Cheadle et al., "CART cells: driving the road from the laboratory to the clinic," Immunol. Rev.257(1):91-106, Jan. 2014.
Chen et al., "Fusion protein linkers: property, design and functionality," Adv. Drug Deliv. Rev.65:1357-1369, Oct. 2013.
Doerks, "Protein Annotation: Detective Work for Function Prediction," TIG, vol. 14, No. 6, (1998), pp. 248-250.
Fedorov et al., "PD-1- and CTLA-4-based inhibitory chimeric antigen receptors (iCARs) divert off-target immunotherapy responses," Sci. Transl. Med. 5(215):215ral72, Dec. 2013.
Frain, "The liver-specific transcription factor LF-B1 contains a highly diverged homeobox DNA binding domain," Cell 59:145-157, Oct. 1990.
Furukawa et al., "Crx, a novel otx-like homeobox gene, shows photoreceptor-specific expression and regulates photoreceptor differentiation," Cell 91(4):531-541, Nov. 1997.
Galfre and Milstein, "Preparation of Monoclonal Antibodies: Strategies and Procedures," Methods Enzymol. 73 (B):3-46, 1981.
Glienke et al., "Advantages and applications of CAR-expressing natural killer cells," Front. Pharmacol. 6:21, Feb. 2015.

(56) References Cited

OTHER PUBLICATIONS

Gordon et al. The molecular logic of Notch signaling—a structural and biochemical perspective. J Cell Sci 121: 3109-3119, 2008.

Graham et al., "Characteristics of a human cell line transformed by DNA from human adenovirus type 5," J Gen. Virol. 36:59-74, Jul. 1977.

Holliger et al., "Diabodies: small bivalent and bispecific antibody fragments," Proc. Natl. Acad. Sci. U.S.A. 90: 6444-6448, Jul. 1993.

Holt et al., "Domain antibodies: proteins for therapy," Trends Biotechnol. 21:484-490, Nov. 2003.

Hong et al., "TAZ, a transcriptional modulator of mesenchymal stem cell differentiation," Science 309 (5737):1074-1078, Aug. 2005.

Hrecka et al., "Vpx relieves the inhibition of HIV-1 infection of macrophages mediated by the SAMHDI protein," Nature 474(7353):658-661, Jun. 2011.

International Preliminary Report on Patentability, issued in PCT/US2019/0018813, dated Aug. 27, 2020.

International Search Report, issued in PCT/US2019/018813, dated Jun. 11, 2019.

Jacobson et al., "Structure of Pit-1 POU domain bound to DNA as a dimer: unexpected arrangement and flexibility," Genes Develop. 11(2):198-212, Jan. 1997.

Kakarla and Gottschalk, "CART cells for solid tumors: armed and ready to go?" Cancer J 20(2):151-155, Mar.-Apr. 2014.

Kipniss et al., "Engineering Cell Sensing and Responses using a GPCR-Coupled CRISPR-Cas System," Nature Communications, vol. 8, No. 1, (2017), pp. 1-10.

Klebanoff et al., "Customizing Functionality and Payload Delivery for Receptor-Engineered T Cells," Cell 167 (2):304-306, Oct. 2016.

Klein et al., "Design and characterization of structured protein linkers with differing flexibilities," Protein Eng Design Select. 27(10): 325-330, Oct. 2014.

Kojika et al., "Notch Receptors and Hematopoiesis," Experimental Hematology, vol. 29, (2001), pp. 1041-1052.

Lian et al., "The role of YAP transcription coactivator in regulating stem cell self-renewal and differentiation," Genes Develop. 24(11):1106-1118, Jun. 2010.

Liu et al., "Comparative Analysis of Notch1 and Notch2 Binding Sites in the Genome of BxPC3 Pancreatic Cancer Cells," Journal of Cancer, vol. 8, (2017), pp. 65-73.

Long et al., "Harnessing the antitumor potential of macrophages for cancer immunotherapy," Oncoimmunology 2: e26860, Dec. 2013.

Mizutani et al. Conservation of the biochemical mechanisms of signal transduction among mammalian Notch family members. Proc Natl Acad Sci USA 98(16): 9026-9031, 2001.

Morsut et al., "Engineering Customized Cell Sensing and Response Behaviors Using Synthetic Notch Receptors," Cell 164(4):780-791, Feb. 2016.

Moyes et al., "Genetically Engineered Macrophages: A Potential Platform for Cancer Immunotherapy," Human Gene Therapy 28(2):200-215, Feb. 2017.

Cromie et al., "Nanobodies and Their Use in GPCR Drug Discovery," Curr. Top. Med. Chem., vol. 15, (2016), pp. 2543-2557.

De Genst et al., "Antibody Repertoire Development in Camelids," Dev. and Comp. Immunol., vol. 30, (2006), pp. 187-198.

De Meyer et al., "Nanobody-Based Products as Research and Diagnostic Tools," Trends Biotechnol., vol. 32, (2014), pp. 263-270.

DiGiammarino et al., "Design and Generation of DVD-Ig™ Molecules for Dual-Specific Targeting," Methods Mol. Biol., vol. 899, (2012), pp. 145-156.

Kovaleva et al., "Shark Variable New Antigen Receptor Biologics—A Novel Technology Platform for Therapeutic Drug Development," Expert. Opin. Biol. Ther., vol. 14, (2014), pp. 1527-1539.

Garber, "Bispecific Antibodies Rise Again," Nature Reviews Drug Discovery, vol. 13, (2014), pp. 799-801.

Jakob et al., "Structure Reveals Function of the Dual Variable Domain Immunoglobulin (DVD-Ig™) Molecule," MABs, vol. 5, (2013), pp. 358-363.

Kijanka et al., "Nanobody-Based Cancer Therapy of Solid Tumors," Nanomedicine, vol. 10, (2015), pp. 161-174.

Krah et al., "Single Domain Antibodies for Biomedical Applications," Immunopharmacol. Immunotoxicol., vol. 38, (2016), pp. 1-22.

Mujic-Delic et al., "GPCR-Targeting Nanobodies: Attractive Research Tools, Diagnostics, and Therapeutics," Trends Pharmacol. Sci., vol. 35, (2014), pp. 247-255.

Muyldermans et al., "Recognition of Antigens by Single-Domain Antibody Fragments: The Superfluous Luxury of Paired Domains," Trends Biochem. Sci., vol. 26, (2001), pp. 230-235.

Muyldermans, "Nanobodies: Natural Single-Domain Antibodies," Ann. Rev. Biochem., vol. 82, (2013), pp. 775-797.

Muyldermans., "Single Domain Camel Antibodies: Current Status," Reviews in Molecular Biotechnology, vol. 74, (2001), pp. 277-302.

Navarro et al., "A Novel Destabilizing Domain based on a Small-Molecule Dependent Fluorophore," ACS Chem Biol., (2016), 11 (8): 2101-21054.

Rahbarizadeh et a., "Nanobody: An Old Concept and New Vehicle for Immunotargeting," Immunol. Invest., vol. 40, (2011), pp. 299-338.

Rakhit et al., "Chemical Biology Strategies for Posttranslational Control of Protein Function," Chem Biol, 2014, 21 (9) : 1238-1252.

Sakemura et al., "A Tet-On Inducible System for Controlling CD19-Chiimeric Antigen Receptor Expression upon Drug Administration," Cancer Immunol Res., (2016), 4 (8) : 658-668.

Van Audenhove et al., "Nanobodies as Versatile Tools to Understand, Diagnose, Visualize and Treat Cancer," EBioMedicine, vol. 8, (2015), pp. 40-48.

Van Bockstaele et al., "The Development of Nanobodies for Therapeutic Applications," Curr. Opin. Investig. Drugs, vol. 10, (2009), pp. 1212-1224.

Vincke et al., "Introduction to Heavy Chain Antibodies and derived Nanobodies," Methods Mol. Biol., vol. 911, (2012), pp. 15-26.

Wesolowski et al., "Single Domain Antibodies: Promising Experimental and Therapeutic Tools in Infection and Immunity," Med., Microbiol. Immunol., vol. 198, (2009), pp. 157-174.

Wu et al., "Remote Control of Therapeutic T Cells Through a Small Molecule-Gated Chimeric Receptor," Science, (2015), 350 (6258: aab4077.

Borggrefe, Tilman, and Franz Oswald. "The Notch signaling pathway: transcriptional regulation at Notch target genes." Cellular and Molecular Life Sciences 66 (2009): 1631-1646.

Groot, Arjan J., "Regulated proteolysis of NOTCH2 and NOTCH3 receptors by ADAM10 and presenilins." Molecular and cellular biology 34.15 (2014): 2822-2832.

Habets, Roger AJ, et al. "Human NOTCH2 is resistant to ligand-independent activation by metalloprotease Adam17." Journal of biological chemistry 290.23 (2015): 14705-14716.

Lobry, Camille, et al. "Notch signaling: switching an oncogene to a tumor suppressor." Blood, The Journal of the American Society of Hematology 123.16 (2014): 2451-2459.

Communication issued in EP Application No. 18745721.3, dated Aug. 5, 2021.

Examination Report from corresponding AU Application No. 2021232761 dated Feb. 7, 2024.

Examination Report issued in related Australian Application No. 2018289383, dated Oct. 22, 2020.

Examination Report issued in related Canadian Application No. 3065549, dated Oct. 23, 2020.

Final Rejection issued in KR Application No. 10-2020-7001681, dated Aug. 10, 2021.

International Preliminary Report on Patentability in International Appln. No. PCT/US2018/038218, Jan. 2, 2020, 8 pages.

Notice of Preliminary Rejection issued in related Korean Application No. 10-2020-7001681, dated Dec. 2, 2020.

Office Action from corresponding Argentine Application No. 20180101716 dated Jan. 30, 2024.

Office Action in AE Appln No. P6001818/2019, dated Jul. 21, 2025, 5 pages.

Office Action in AE Appln No. P6001818/2019, dated Oct. 16, 2023, 9 pages.

(56)           References Cited

OTHER PUBLICATIONS

Office Action in AU Appln. No. 2021232761, dated Aug. 23, 2024, 2 pages.

Office Action in BR Appln No. 112019026309-8, dated Feb. 28, 2025, 4 pages (English translation).

Office Action in CA Appln. No. 3065549, dated Jul. 5, 2022, 4 pages.

Office Action in CN Appln. No. 201880039563.8, May 31, 2023, 15 pages (with English translation).

Office Action in CN Appln. No. 201880039563.8, Oct. 10, 2022, 23 pages (with English translation).

Office Action in EG Appln. No. PCT1898/2019, Apr. 8, 2022, 7 pages (with English translation).

Office Action in EG Appln. No. PCT1898/2019, Aug. 4, 2022, 7 pages (with English translation).

Office Action in EG Appln. No. PCT1898/2019, Jan. 22, 2024, 11 pages (with English translation).

Office Action in EG Appln. No. PCT1898/2019, May 6, 2025, 10 pages (with English translation).

Office Action in Israeli Appln. No. 271144, dated Aug. 9, 2023, 4 pages.

Office Action in Israeli Appln. No. 271144, dated Feb. 27, 2025, 3 pages.

Office Action in Israeli Appln. No. 271144, dated Jan. 25, 2024, 5 pages.

Office Action in Israeli Appln. No. 271144, dated Oct. 15, 2024, 4 pages.

Office Action in Japanese Appln. No. 2019-569872, mailed on Jan. 4, 2022, 10 pages (with English translation).

Office Action in Japanese Appln. No. 2022-075722, mailed on Jan. 9, 2024, 12 pages (with English translation).

Office Action in Japanese Appln. No. 2022-075722, mailed on May 23, 2023, 13 pages (with English translation).

Office Action in Japanese Appln. No. 2024-076576, mailed on Jun. 3, 2025, 6 pages (with English translation).

Office Action in Korean Appln. No. 10-2021-7043321, dated Mar. 4, 2022, 10 pages (with English translation).

Office Action in Korean Appln. No. 10-2023-7001521, dated Apr. 20, 2023, 13 pages (with English translation).

Office Action in Korean Appln. No. 10-2023-7001521, dated Oct. 6, 2023, 8 pages (with English translation).

Office Action in Korean Appln. No. 10-2024-7015253, dated Jul. 18, 2024, 9 pages (with English translation).

Office Action in Mexican Appln. No. MX/a/2019/015513, dated Jan. 11, 2024, 11 pages (with English translation).

Office Action in Mexican Appln. No. MX/a/2019/015513, dated Jun. 27, 2024, 7 pages (with English translation).

Office Action in New Zealand Appln. No. 759712, dated Feb. 18, 2022, 5 pages.

Office Action in Saudi Arabian Appln. No. 519410835, dated Feb. 2, 2022, 8 pages (with English translation).

Office Action in Saudi Arabian Appln. No. 522432612, dated Feb. 6, 2023, 5 pages (with English summary).

Office Action in Saudi Arabian Appln. No. 522432612, dated Sep. 10, 2023, 7 pages (with English translation).

Office Action in Saudi Arabian Appln. No. 522432612, dated Sep. 12, 2022, 6 pages (with English summary).

Office Action in Singapore Appln. No. 11201911639T, dated Sep. 11, 2024, 6 pages.

Office Action in Taiwanese Appln. No. 112144909, dated Dec. 17, 2024, 18 pages (with English translation).

Office Action in Taiwanese Appln. No. 112144909, dated May 21, 2025, 8 pages (with English translation).

Office Action issued in CA Application No. 3065549, dated Sep. 8, 2021.

Office Action, issued in related Japanese Application No. 2019-569872, dated Mar. 9, 2021.

Substantive Examination Report issued in SA Application No. 519410835, dated Aug. 31, 2021.

Communication pursuant to Article 94(3) EPC issued in EP Appln. No. 18745721.3, mailed on Dec. 15, 2025, 3 pages.

* cited by examiner

Domain Architecture of Natural Human Notch Proteins and Engineered Synthetic Notch Proteins (SynNotch)

METHODS AND COMPOSITIONS FOR REDUCING THE IMMUNOGENICITY OF CHIMERIC NOTCH RECEPTORS

CROSS-REFERENCE TO RELATED APPLICATIONS

This application claims priority to U.S. Provisional Patent Application Ser. No. 62/603,993, filed Jun. 19, 2017, and U.S. Provisional Patent Application Ser. No. 62/556,765, filed Sep. 11, 2017, both of which are hereby incorporated by reference in their entirety.

STATEMENT REGARDING SEQUENCE LISTING

The Sequence Listing associated with this application is provided in text format in lieu of paper copy, and is hereby incorporated by reference into the specification. The name of the text file containing the Sequence Listing is "356829_ST25.txt." The text file is 218,000 bytes, was created on Jul. 25, 2022, and is being submitted electronically via EFS-Web.

TECHNICAL FIELD

The present invention relates to molecular biology, and particularly to methods and compositions for reducing the immunogenicity of certain receptors useful for controlling selective gene expression in cells of the monocyte/macrophage lineage, and applications thereof.

BACKGROUND

An important problem which limits the development of gene therapy in humans is the regulation of therapeutic gene expression, such that gene expression or the vehicle used to realize expression, does not give rise to enhanced immunogenicity resulting in host rejection. One way to realize gene expression is described in U.S. Pat. No. 9,670,281, and Roybal et al., *Cell*, Feb. 11, 2016. There is described activation of gene expression using chimeric Notch receptors.

Notch receptors are single pass transmembrane proteins that mediate cell-cell contact signaling and play a central role in development and other aspects of cell-to-cell communication between two contacting cells, in which one contacting cell has the Notch receptor, and the other contacting cell is a cell that exhibits a ligand on its surface which binds to the corresponding Notch receptor. The engagement of native Notch and Delta, it's native ligand, leads to two-step proteolysis of the Notch receptor that ultimately causes the release of the intracellular portion of the receptor from the membrane into the cytoplasm, where it moves to the nucleus. There the released domain alters cell behavior by functioning as a transcriptional regulator. Notch receptors are involved in and are required for a variety of cellular functions during development and are critical for the function of numerous cell-types across species.

Described in U.S. Pat. No. 9,670,281 are chimeric Notch receptors which show that the Notch expressing cell can have one or more different binding moieties on the cell surface, for example, scFVs, nanobodies, single chain T-cell receptors, to name a few, that recognize a ligand associated with a cell ultimately causing the release of the intracellular, transcriptional regulatory portion of the receptor from the membrane into the cytoplasm resulting in transcriptional regulation. Engineered cells bearing chimeric Notch receptors that encounter their specific target antigen will then be cleaved such that their cytosolic fragment is free to translocate into the cell nucleus to regulate the transcription of any open reading frame (ORF) under the control of a synthetic promoter. The ORF expressed could be a cytokine to locally induce and recruit immune activity to the location of target antigen detection. Further, the ORF expressed could be a chimeric antigen T-cell receptor (CAR-T) that targets a separate, distinct target antigen for target cell killing, only after the priming target antigen detected by the chimeric Notch receptor has been detected. This enables highly-specific combinatorial antigen pattern recognition to allow greater discrimination between diseased or cancerous cells and healthy cells. This could greatly enable the application of engineered CAR-T cells to safely target a wider range of tumors with less side-effects on healthy tissue.

To date, the transcriptional machinery used in chimeric Notch constructs has been GAL4-VP16. Since the DNA-binding fragment, GAL4, is of yeast origin, and VP16, a highly acidic portion of the herpes simplex virus protein, GAL4-VP16 is highly immunogenic, and thus limits the use of chimeric Notch receptors for treating human disease.

Another major obstacle in the efficacy of many immuno-therapy-based approaches for solid tumors, including cell therapy, is delivery of drugs or activation of immune cells in the solid tumor. Cells of the monocyte/macrophage lineage make up a major component of immune cells that infiltrate into solid tumors (Long et al., *Oncoimmunology* 2:e26860, 2013 doi:10.4161/onci26860). Because these cell types are actively recruited and retained in the solid tumor they could be an important cell type for the delivery of gene therapy.

The genetic engineering of macrophages with clinically approved vectors such has HIV-1-based lentivirus has been difficult due to the inhibition of HIV-1 infection in macrophages. Hrecka et al. ("Vpx relieves the inhibition of HIV-1 infection of macrophages mediated by the SAMHD1 protein," *Nature* 474(7353):658-661, 2011) demonstrated that the addition of the viron associated Vpx accessory proteins found in HIV-2 and simian immunodeficiency viruses relieves the inhibition of HIV-1 infection of macrophages through the degradation of a macrophage restriction factor SAMHD1. Subsequently, it has been demonstrated by the monocyte-derived macrophages can be efficiently transduced with Vpx+ lentivirus encoding for the production cytokines from macrophages aimed at modulating the tumor microenvironment (Moyes et al., *Human Gene Therapy* 28(2):200-215, 2017).

SUMMARY OF THE INVENTION

The present invention relates to methods and compositions for reducing the immunogenicity of chimeric Notch receptors. The Notch receptors described herein can be genetically engineered in cells of the monocyte/macrophage lineage.

Another embodiment of the invention relates to methods and compositions for reducing the immunogenicity of chimeric Notch receptors by humanizing transcription factors useful for controlling gene expression delivered to tissues by chimeric Notch receptors.

In yet another embodiment of the invention are methods and compositions for reducing the immunogenicity of chimeric Notch receptors by humanizing transcription factors used to express genes in cells that contain the chimeric Notch receptors wherein such transcription factors comprise a transcription factor from the family of Hepatocyte Nuclear Factor transcription factors.

The invention also relates to the use of the DNA binding domains (DBD) of HNF1 transcription factors, such as HNF1 alpha and vHNF1 beta, for generating chimeric transcription factors with reduced immunogenicity, useful for delivery of transgenes with chimeric Notch receptors to tissues preferably not expressing endogenous HNF1 or vHNF1. US Patent Application No. 200301096678.

A further embodiment of the invention is a human HNF1 DNA binding domain that is used in conjunction with a human transcriptional activator (TAD) or repressor domain, and optionally a human regulatory domain.

A further embodiment of the invention is a human HNF1 DNA binding domain that is used in conjunction with a human transcriptional activator domain (TAD) derived from the WWTR1 (TAZ) protein.

A further embodiment of the invention is a human HNF1 DNA binding domain that is used in conjunction with a human transcriptional activator domain (TAD) derived from the CREB3 (LZIP) protein.

A further embodiment of the invention is a human HNF1 DNA binding domain that is used in conjunction with a human transcriptional activator domain (TAD) derived from the NF-κB system factor, p65 (RelA).

The present invention also relates to nucleic acid molecules and proteins useful for regulating the expression of genes in eukaryotic cells and organisms using chimeric Notch receptors having low immunogenicity.

The present invention further provides low immunogenicity chimeric Notch receptor polypeptides, nucleic acids comprising nucleotide sequences encoding the chimeric Notch receptor polypeptides, and host cells genetically modified with the nucleic acids wherein the low immunogenicity is realized by using transcription factor comprising a human HNF1 DNA binding domain in conjunction with a human transcriptional activator domain (TAD) derived from the NF-κB system factor, p65 (RelA).

In one specific embodiment of the invention, the humanized chimeric notch receptor is comprised of the following sequences, 5' to 3':

Human CD8a signal peptide 1-22 (NP_001139345 amino acids 1-22, (MALPVTALLLPLALLLHAARPS) (SEQ ID NO: 1))—directs protein expression to the cell surface.

Myc-tag (EQKLISEEDL) (SEQ ID NO: 2)—peptide tag for antibody labelling of surface-expressed synthetic receptor. A Myc antibody: Cell Signaling Technology, Myc-Tag (9B11) Mouse mAb (Alexa Fluor®647 Conjugate; Catalogue No. 2233.

Anti-Human B cell (CD19) Antibody, clone FMC63.

Human Notch3 core (gi|134244285|NP_000426.2 amino acids 1374-1738) comprising the three NLR domains, the transmembrane domain, and a short cytosolic fragment including the native Nuclear Localization Sequence (NLS) of human Notch3.

GS flexible Linker (GSAAAGGSGGSGGS) (SEQ ID NO: 3).

Human HNF1alpha (gi|807201167|NP_001293108.1 amino acids 1-283) comprising the dimerization and DNA-Binding Domain (DBD) of *Homo sapiens* hepatocyte nuclear factor 1-alpha isoform 1.

GS flexible Linker (GGGSGGGS) (SEQ ID NO: 4).

Human Rel-A (p65) (gi|223468676|NP_068810.3 amino acids 1-551) comprising the transactivation domain of transcription factor p65 isoform 1 [*Homo sapiens*].

Also provided herein is a method of treating disease, including cancer, in a subject (e.g., a human) that includes administering to the subject a mammalian cell comprising a humanized chimeric Notch receptor. In some embodiments, the mammalian cell can be a monocyte/macrophage cell.

Other features and advantages of the invention will be apparent from the following Detailed Description of the Invention, and from the claims. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1:
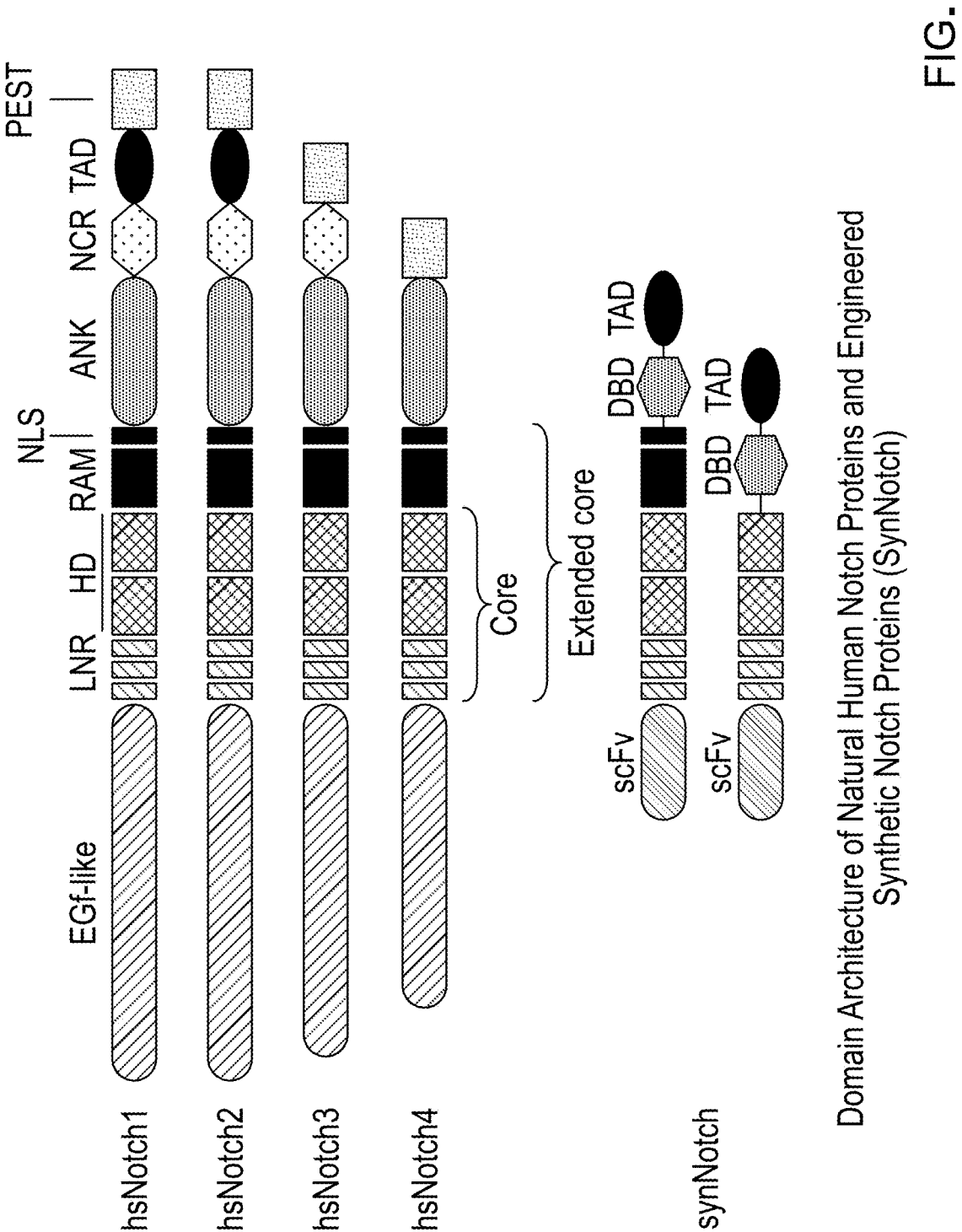
FIG. 1. Schematic of synthetic Notch receptor and the constituent domains comprising it.

Incorporation by reference: All publications mentioned herein, including patents, patent application publications, and scientific papers, are incorporated by reference in their entirety.

DETAILED DESCRIPTION OF THE INVENTION

Definitions

"Chimeric Notch polypeptide" also referred to as "Chimeric Notch receptor polypeptide," or "chimeric Notch" or "synNotch" is described in U.S. Pat. No. 9,670,281, and comprises, from N-terminal to C-terminal and in covalent linkage: a) an extracellular domain comprising a first member of a specific binding pair; b) wherein the Notch receptor polypeptide has a length of from 50 amino acids to 1000 amino acids, and comprises one or more ligand-inducible proteolytic cleavage sites; and c) an intracellular domain, wherein the first member of the specific binding pair is heterologous to the Notch receptor polypeptide, and wherein binding of the first member of the specific binding pair to a second member of the specific binding pair induces cleavage of the Notch receptor polypeptide at the one or more ligand-inducible proteolytic cleavage sites, thereby releasing the intracellular domain. In some cases, the Notch receptor polypeptide has a length of from 300 amino acids to 400 amino acids.

Further, the "chimeric Notch receptor polypeptide" comprises a linker interposed between the extracellular domain and the Notch receptor polypeptide. In some cases, the intracellular domain is a transcriptional activator. In some cases, the intracellular domain is a transcriptional repressor. In some cases, the first member of the specific binding pair comprises an antibody-based recognition scaffold. In some cases, the first member of the specific binding pair comprises an antibody. In some cases, where the first member of the specific binding pair is an antibody, the antibody specifically binds a tumor-specific antigen, a disease-associated antigen, or an extracellular matrix component. In some cases, where the first member of the specific binding pair is an antibody, the antibody specifically binds a cell surface antigen, a soluble antigen, or an antigen immobilized on an insoluble substrate. In some cases, where the first member of the specific binding pair is an antibody, the antibody is a single-chain Fv. In some cases, the first member of the specific binding pair is a nanobody, a single-domain antibody, a diabody, a triabody, or a minibody. In some cases, the first member of the specific binding pair is a non-antibody-based recognition scaffold. In some cases, where the first member of the specific binding pair is a non-antibody-based recognition scaffold, the non-antibody-based recognition scaffold is an avimer, a DARPin, an adnectin, an avimer, an affibody, an anticalin, or an affilin. In some cases, the first member of the specific binding pair is an antigen. In some cases, where the first member of the specific binding pair is an antigen, the antigen is an endogenous antigen. In some cases, where the first member of the specific binding pair is an antigen, the antigen is an exogenous antigen. In some cases, the first member of the specific binding pair is a ligand for a receptor. In some cases, the first member of the specific binding pair is a receptor. In some cases, the first member of the specific binding pair is a cellular adhesion molecule (e.g., all or a portion of an extracellular region of a cellular adhesion molecule).

The term "transmembrane domain" means a domain of a polypeptide that includes at least one contiguous amino acid sequence that traverses a lipid bilayer when present in the corresponding endogenous polypeptide when expressed in a mammalian cell. For example, a transmembrane domain can include one, two, three, four, five, six, seven, eight, nine, or ten contiguous amino acid sequences that each traverse a lipid bilayer when present in the corresponding endogenous polypeptide when expressed in a mammalian cell. As is known in the art, a transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Non-limiting examples of transmembrane domains are described herein. Additional examples of transmembrane domains are known in the art.

The phrase "extracellular side of the plasma membrane" when used to describe the location of a polypeptide means that the polypeptide includes at least one transmembrane domain that traverses the plasma membrane and at least one domain (e.g., at least one antigen-binding domain) that is located in the extracellular space.

"GFP" or green fluorescent protein (GFP), is a commonly used reporter of gene expression. Arun et al., *J. Pharmacol. Toxicol. Methods* 51(1):1-23, 2005.

By "HNF1 binding site" is intended any specific binding site for any of the known forms of HNF. HNF1 (also called LF-B1 or HNF1alpha) is a 628 aa long protein DNA binding protein that has been implicated as a major determinant of hepatocyte-specific transcription of several genes (Frain, *Cell* 59, 145-157, 1990).

In some embodiments, the DNA binding domain of human origin is a DNA-binding domain of a HNF1 transcription factor (e.g., any of the HNF1 transcription factors described herein or known in the art) and the transactivation domain is a human RelA protein or a portion thereof.

In some embodiments, the amino acid sequence of HNF1alpha is NCBI Nos. NP_001293108.1, NP_000536.5, or XP_005253988.1. In some embodiments, the amino acid sequence of the transcriptional regulator of the humanized chimeric Notch receptor comprises hepatocyte nuclear factor 1-alpha isoform 1 (NP_001293108.1), hepatocyte nuclear factor 1-alpha isoform 1 (NP_000536.5), or hepatocyte nuclear factor 1-alpha isoform X1 (XP_005253988.1), or a portion thereof. In some embodiments, the amino acid sequence of the transcriptional regulator of the humanized Notch receptor comprises all or a portion of SEQ ID NO: 5, SEQ ID NO: 6, or SEQ ID NO: 7.

As used herein, a "portion" of a polypeptide or protein refers at least 10 amino acids of the reference sequence, e.g., 10 to 200, 25 to 300, 50 to 400, 100 to 500, 200 to 600, 300 to 700, 400 to 800, 500 to 900, or 600 to 1000 or more amino acids of the reference sequence. In some embodiments, the portion of a polypeptide or protein is functional. In some embodiments, the transcriptional regulator is or comprises the dimerization and DNA-Binding Domain (DBD) of hepatocyte nuclear factor 1-alpha isoform 1 (NP_001293108.1), hepatocyte nuclear factor 1-alpha isoform 1 (NP_000536.5), or hepatocyte nuclear factor 1-alpha isoform X1 (XP_005253988.1). In some embodiments, the amino acid sequence of the transcriptional regulator of the humanized Notch receptor is amino acids is or comprises the dimerization and DNA-Binding Domain (DBD) of SEQ ID NO: 5, SEQ ID NO: 6, or SEQ ID NO:7. In some embodiments, the amino acid sequence of the transcriptional regulator of the humanized Notch receptor is or comprises amino acids 1-283 of SEQ ID NO: 5.

```
Human hepatocyte nuclear factor 1-alpha isoform 1
NP_001293108.1
                                        (SEQ ID NO: 5)
MVSKLSQLQTELLAALLESGLSKEALIQALGEPGPYLLAGEGPLDKGESCG

GGRGELAELPNGLGETRGSEDETDDDGEDFTPPILKELENLSPEEAAHQKA
```

-continued

VVETLLQEDPWRVAKMVKSYLQQHNIPQREVVDTTGLNQSHLSQHLNKGTP

MKTQKRAALYTWYVRKQREVAQQFTHAGQGGLIEEPTGDELPTKKGRRNRF

KWGPASQQILFQAYERQKNPSKEERETLVEECNRAECIQRGVSPSQAQGLG

SNLVTEVRVYNWFANRRKEEAFRHKLAMDTYSGPPPGPGPGPALPAHSSPG

LPPPALSPSKVHGVRYGQPATSETAEVPSSSGGPLVTVSTPLHQVSPTGLE

PSHSLLSTEAKLVSAAGGPLPPVSTLTALHSLEQTSPGLNQQPQNLIMASL

PGVMTIGPGEPASLGPTFTNTGASTLVIGLASTQAQSVPVINSMGSSLTTL

QPVQFSQPLHPSYQQPLMPPVQSHVTQSPFMATMAQLQSPHALYSHKPEVA

QYTHTGLLPQTMLITDTTNLSALASLTPTKQEAALLPQVFTSDTEASSESG

LHTPASQATTLHVPSQDPAGIQHLQPAHRLSASPTVSSSSLVLYQSSDSSN

GQSHLLPSNHSVIETFISTQMASSSQ

Human hepatocyte nuclear factor 1-alpha isoform 2
NP_000536.5

(SEQ ID NO: 6)
MVSKLSQLQTELLAALLESGLSKEALIQALGEPGPYLLAGEGPLDKGESCG

GGRGELAELPNGLGETRGSEDETDDDGEDFTPPILKELENLSPEEAAHQKA

VVETLLQEDPWRVAKMVKSYLQQHNIPQREVVDTTGLNQSHLSQHLNKGTP

MKTQKRAALYTWYVRKQREVAQQFTHAGQGGLIEEPTGDELPTKKGRRNRF

KWGPASQQILFQAYERQKNPSKEERETLVEECNRAECIQRGVSPSQAQGLG

SNLVTEVRVYNWFANRRKEEAFRHKLAMDTYSGPPPGPGPGPALPAHSSPG

LPPPALSPSKVHGVRYGQPATSETAEVPSSSGGPLVTVSTPLHQVSPTGLE

PSHSLLSTEAKLVSAAGGPLPPVSTLTALHSLEQTSPGLNQQPQNLIMASL

PGVMTIGPGEPASLGPTFTNTGASTLVIGLASTQAQSVPVINSMGSSLTTL

QPVQFSQPLHPSYQQPLMPPVQSHVTQSPFMATMAQLQSPHALYSHKPEVA

QYTHTGLLPQTMLITDTTNLSALASLTPTKQVFTSDTEASSESGLHTPASQ

ATTLHVPSQDPAGIQHLQPAHRLSASPTVSSSSLVLYQSSDSSNGQSHLLP

SNHSVIETFISTQMASSSQ

-continued

Human hepatocyte nuclear factor 1-alpha isoform X1
(predicted) XP_005253988.1

(SEQ ID NO: 7)
MVSKLSQLQTELLAALLESGLSKEALIQALGEPGPYLLAGEGPLDKGESCG

GGRGELAELPNGLGETRGSEDETDDDGEDFTPPILKELENLSPEEAAHQKA

VVETLLQEDPWRVAKMVKSYLQQHNIPQREVVDTTGLNQSHLSQHLNKGTP

MKTQKRAALYTWYVRKQREVAQQFTHAGQGGLIEEPTGDELPTKKGRRNRF

KWGPASQQILFQAYERQKNPSKEERETLVEECNRAECIQRGVSPSQAQGLG

SNLVTEVRVYNWFANRRKEEAFRHKLAMDTYSGPPPGPGPGPALPAHSSPG

LPPPALSPSKVHGVRYGQPATSETAEVPSSSGGPLVTVSTPLHQVSPTGLE

PSHSLLSTEAKLVSAAGGPLPPVSTLTALHSLEQTSPGLNQQPQNLIMASL

PGVMTIGPGEPASLGPTFTNTGASTLVIGLASTQAQSVPVINSMGSSLTTL

QPVQFSQPLHPSYQQPLMPPVQSHVTQSPFMATMAQLQSPHALYSHKPEVA

QYTHTGLLPQTMLITDTTNLSALASLTPTKQVRSRPAGPPLACDRAPHPHI

PRAQEAALLPQVFTSDTEASSESGLHTPASQATTLHVPSQDPASIQHLQPA

HRLSASPTVSSSSLVLYQSSDSSNGQSHLLPSNHSVIETFISTQMASSSQ

In some embodiments, the amino acid sequence of HNF1alpha or the portion thereof, as described herein, is at least 80% identical to a corresponding amino acid sequence in SEQ ID NO: 5, SEQ ID NO: 6, or SEQ ID NO: 7. In some embodiments, the amino acid sequence of HNF1alpha or portion thereof is 80%, 81%, 82%, 83%, 84%, 85%, 86%, 87%, 88%, 89%, 90%, 91%, 92%, 93%, 94%, 95%, 96%, 97%, 98%, or 99% identical to a corresponding amino acid sequence in SEQ ID NO: 5, SEQ ID NO: 6, or SEQ ID NO: 7. In some embodiments, the amino acid sequence of HNF1alpha or the portion thereof, as described herein, can vary from the corresponding amino acid sequence in SEQ ID NO: 5, SEQ ID NO: 6, or SEQ ID NO: 7 by 1 amino acid, 2 amino acids, 3 amino acids, 4 amino acids, 5 amino acids, 6 amino acids, 7 amino acids, 8 amino acids, 9 amino acids, or 10 or more amino acids.

In some embodiments, the mRNA sequence of HFN1alpha is NCBI No. NM_001306179.1, NM_00545.6, or XM_005253931.3. In some embodiments, the mRNA sequence of HFN1alpha is SEQ ID NO: 8, SEQ ID NO: 9, or SEQ ID NO: 10.

Human HNF1 homeobox A (HNF1A), transcript variant 1, mRNA
NM_001306179.1

(SEQ ID NO: 8)
GGGGCCCTGATTCACGGGCCGCTGGGGCCAGGGGTTGGGGGTTGGGGGTGCCCAC

AGGGCTTGGCTAGTGGGGTTTTGGGGGGGCAGTGGGTGCAAGGAGTTTGGTTTG

TGTCTGCCGGCCGGCAGGCAAACGCAACCCACGCGGTGGGGGAGGCGGCTAGCG

TGGTGGACCCGGGCCGCGTGGCCCTGTGGCAGCCGAGCCATGGTTTCTAAACTG

AGCCAGCTGCAGACGGAGCTCCTGGCGGCCCTGCTCGAGTCAGGGCTGAGCAAA

GAGGCACTGATCCAGGCACTGGGTGAGCCGGGGCCCTACCTCCTGGCTGGAGAA

GGCCCCCTGGACAAGGGGGAGTCCTGCGGCGGCGGTCGAGGGGAGCTGGCTGAG

CTGCCCAATGGGCTGGGGGAGACTCGGGGCTCCGAGGACGAGACGGACGACGAT

GGGGAAGACTTCACGCCACCCATCCTCAAAGAGCTGGAGAACCTCAGCCCTGAG

GAGGCGGCCCACCAGAAAGCCGTGGTGGAGACCCTTCTGCAGGAGGACCCGTGG

CGTGTGGCGAAGATGGTCAAGTCCTACCTGCAGCAGCACAACATCCCACAGCGG

GAGGTGGTCGATACCACTGGCCTCAACCAGTCCCACCTGTCCCAACACCTCAAC

AAGGGCACTCCCATGAAGACGCAGAAGCGGGCCGCCCTGTACACCTGGTACGTC

CGCAAGCAGCGAGAGGTGGCGCAGCAGTTCACCCATGCAGGGCAGGGAGGGCTG

ATTGAAGAGCCCACAGGTGATGAGCTACCAACCAAGAAGGGGCGGAGGAACCGT

TTCAAGTGGGGCCCAGCATCCCAGCAGATCCTGTTCCAGGCCTATGAGAGGCAG

AAGAACCCTAGCAAGGAGGAGCGAGAGACGCTAGTGGAGGAGTGCAATAGGGCG

GAATGCATCCAGAGAGGGGTGTCCCCATCACAGGCACAGGGGCTGGGCTCCAAC

CTCGTCACGGAGGTGCGTGTCTACAACTGGTTTGCCAACCGGCGCAAAGAAGAA

GCCTTCCGGCACAAGCTGGCCATGGACACGTACAGCGGGCCCCCCCCCAGGGCCA

GGCCCGGGACCTGCGCTGCCCGCTCACAGCTCCCCTGGCCTGCCTCCACCTGCC

CTCTCCCCCAGTAAGGTCCACGGTGTGCGCTATGGACAGCCTGCGACCAGTGAG

ACTGCAGAAGTACCCTCAAGCAGCGGCGGTCCCTTAGTGACAGTGTCTACACCC

CTCCACCAAGTGTCCCCCACGGGCCTGGAGCCCAGCCACAGCCTGCTGAGTACA

GAAGCCAAGCTGGTCTCAGCAGCTGGGGGCCCCCTCCCCCCTGTCAGCACCCTG

ACAGCACTGCACAGCTTGGAGCAGACATCCCCAGGCCTCAACCAGCAGCCCCAG

AACCTCATCATGGCCTCACTTCCTGGGGTCATGACCATCGGGCCTGGTGAGCCT

GCCTCCCTGGGTCCTACGTTCACCAACACAGGTGCCTCCACCCTGGTCATCGGC

CTGGCCTCCACGCAGGCACAGAGTGTGCCGGTCATCAACAGCATGGGCAGCAGC

CTGACCACCCTGCAGCCCGTCCAGTTCTCCCAGCCGCTGCACCCCTCCTACCAG

CAGCCGCTCATGCCACCTGTGCAGAGCCATGTGACCCAGAGCCCCTTCATGGCC

ACCATGGCTCAGCTGCAGAGCCCCCACGCCCTCTACAGCCACAAGCCCGAGGTG

GCCCAGTACACCCACACGGGCCTGCTCCCGCAGACTATGCTCATCACCGACACC

ACCAACCTGAGCGCCCTGGCCAGCCTCACGCCCACCAAGCAGGAGGCTGCTCTG

CTCCCCCAGGTCTTCACCTCAGACACTGAGGCCTCCAGTGAGTCCGGGCTTCAC

ACGCCGGCATCTCAGGCCACCACCCTCCACGTCCCCAGCCAGGACCCTGCCGGC

ATCCAGCACCTGCAGCCGGCCCACCGGCTCAGCGCCCAGCCCCACAGTGTCCTCC

AGCAGCCTGGTGCTGTACCAGAGCTCAGACTCCAGCAATGGCCAGAGCCACCTG

CTGCCATCCAACCACAGCGTCATCGAGACCTTCATCTCCACCCAGATGGCCTCT

TCCTCCCAGTAACCACGGCACCTGGGCCCTGGGGCCTGTACTGCCTGCTTGGGG

GGTGATGAGGGCAGCAGCCAGCCCTGCCTGGAGGACCTGAGCCTGCCGAGCAAC

CGTGGCCCTTCCTGGACAGCTGTGCCTCGCTCCCCACTCTGCTCTGATGCATCA

GAAAGGGAGGGCTCTGAGGCGCCCCAACCCGTGGAGGCTGCTCGGGGTGCACAG

GAGGGGGTCGTGGAGAGCTAGGAGCAAAGCCTGTTCATGGCAGATGTAGGAGGG

ACTGTCGCTGCTTCGTGGGATACAGTCTTCTTACTTGGAACTGAAGGGGGCGGC

CTATGACTTGGGCACCCCCAGCCTGGGCCTATGGAGAGCCCTGGGACCGCTACA

CCACTCTGGCAGCCACACTTCTCAGGACACAGGCCTGTGTAGCTGTGACCTGCT

GAGCTCTGAGAGGCCCTGGATCAGCGTGGCCTTGTTCTGTCACCAATGTACCCA

CCGGGCCACTCCTTCCTGCCCCAACTCCTTCCAGCTAGTGACCCACATGCCATT

TGTACTGACCCCATCACCTACTCACACAGGCATTTCCTGGGTGGCTACTCTGTG

CCAGAGCCTGGGGCTCTAACGCCTGAGCCCAGGGAGGCCGAAGCTAACAGGGAA

-continued

GGCAGGCAGGGCTCTCCTGGCTTCCCATCCCCAGCGATTCCCTCTCCCAGGCCC

CATGACCTCCAGCTTTCCTGTATTTGTTCCCAAGAGCATCATGCCTCTGAGGCC

AGCCTGGCCTCCTGCCTCTACTGGGAAGGCTACTTCGGGGCTGGGAAGTCGTCC

TTACTCCTGTGGGAGCCTCGCAACCCGTGCCAAGTCCAGGTCCTGGTGGGGCAG

CTCCTCTGTCTCGAGCGCCCTGCAGACCCTGCCCTTGTTTGGGGCAGGAGTAGC

TGAGCTCACAAGGCAGCAAGGCCCGAGCAGCTGAGCAGGGCCGGGGAACTGGCC

AAGCTGAGGTGCCCAGGAGAAGAAAGAGGTGACCCCAGGGCACAGGAGCTACCT

GTGTGGACAGGACTAACACTCAGAAGCCTGGGGGCCTGGCTGGCTGAGGGCAGT

TCGCAGCCACCCTGAGGAGTCTGAGGTCCTGAGCACTGCCAGGAGGGACAAAGG

AGCCTGTGAACCCAGGACAAGCATGGTCCCACATCCCTGGGCCTGCTGCTGAGA

ACCTGGCCTTCAGTGTACCGCGTCTACCCTGGGATTCAGGAAAAGGCCTGGGGT

GACCCGGCACCCCCTGCAGCTTGTAGCCAGCCGGGGCGAGTGGCACGTTTATTT

AACTTTTAGTAAAGTCAAGGAGAAATGCGGTGGAAA

Human HNF1 homeobox A (HNF1A), transcript variant 2, mRNA
NM_000545.6

(SEQ ID NO: 9)

GGGGCCCTGATTCACGGGCCGCTGGGGCCAGGGTTGGGGGTTGGGGGTGCCCAC

AGGGCTTGGCTAGTGGGGTTTTGGGGGGGCAGTGGGTGCAAGGAGTTTGGTTTG

TGTCTGCCGGCCGGCAGGCAAACGCAACCCACGCGGTGGGGGAGGCGGCTAGCG

TGGTGGACCCGGGCCGCGTGGCCCTGTGGCAGCCGAGCCATGGTTTCTAAACTG

AGCCAGCTGCAGACGGAGCTCCTGGCGGCCCTGCTCGAGTCAGGGCTGAGCAAA

GAGGCACTGATCCAGGCACTGGGTGAGCCGGGGCCCTACCTCCTGGCTGGAGAA

GGCCCCCTGGACAAGGGGGAGTCCTGCGGCGGCGGTCGAGGGGAGCTGGCTGAG

CTGCCCAATGGGCTGGGGGAGACTCGGGGCTCCGAGGACGAGACGGACGACGAT

GGGGAAGACTTCACGCCACCCATCCTCAAAGAGCTGGAGAACCTCAGCCCTGAG

GAGGCGGCCCACCAGAAAGCCGTGGTGGAGACCCTTCTGCAGGAGGACCCGTGG

CGTGTGGCGAAGATGGTCAAGTCCTACCTGCAGCAGCACAACATCCCACAGCGG

GAGGTGGTCGATACCACTGGCCTCAACCAGTCCCACCTGTCCCAACACCTCAAC

AAGGGCACTCCCATGAAGACGCAGAAGCGGGCCGCCCTGTACACCTGGTACGTC

CGCAAGCAGCGAGAGGTGGCGCAGCAGTTCACCCATGCAGGGCAGGGAGGGCTG

ATTGAAGAGCCCACAGGTGATGAGCTACCAACCAAGAAGGGGCGGAGGAACCGT

TTCAAGTGGGGGCCCAGCATCCCAGCAGATCCTGTTCCAGGCCTATGAGAGGCAG

AAGAACCCTAGCAAGGAGGAGCGAGAGACGCTAGTGGAGGAGTGCAATAGGGCG

GAATGCATCCAGAGAGGGGTGTCCCCATCACAGGCACAGGGGCTGGGCTCCAAC

CTCGTCACGGAGGTGCGTGTCTACAACTGGTTTGCCAACCGGCGCAAAGAAGAA

GCCTTCCGGCACAAGCTGGCCATGGACACGTACAGCGGGCCCCCCCCAGGGCCA

GGCCCGGGACCTGCGCTGCCCGCTCACAGCTCCCCTGGCCTGCCTCCACCTGCC

CTCTCCCCCAGTAAGGTCCACGGTGTGCGCTATGGACAGCCTGCGACCAGTGAG

ACTGCAGAAGTACCCTCAAGCAGCGGCGGTCCCTTAGTGACAGTGTCTACACCC

CTCCACCAAGTGTCCCCCACGGGCCTGGAGCCCAGCCACAGCCTGCTGAGTACA

GAAGCCAAGCTGGTCTCAGCAGCTGGGGGCCCCCTCCCCCCTGTCAGCACCCTG

ACAGCACTGCACAGCTTGGAGCAGACATCCCCAGGCCTCAACCAGCAGCCCCAG

-continued

```
AACCTCATCATGGCCTCACTTCCTGGGGTCATGACCATCGGGCCTGGTGAGCCT

GCCTCCCTGGGTCCTACGTTCACCAACACAGGTGCCTCCACCCTGGTCATCGGC

CTGGCCTCCACGCAGGCACAGAGTGTGCCGGTCATCAACAGCATGGGCAGCAGC

CTGACCACCCTGCAGCCCGTCCAGTTCTCCCAGCCGCTGCACCCCTCCTACCAG

CAGCCGCTCATGCCACCTGTGCAGAGCCATGTGACCCAGAGCCCCTTCATGGCC

ACCATGGCTCAGCTGCAGAGCCCCCACGCCCTCTACAGCCACAAGCCCGAGGTG

GCCCAGTACACCCACACGGGCCTGCTCCCGCAGACTATGCTCATCACCGACACC

ACCAACCTGAGCGCCCTGGCCAGCCTCACGCCCACCAAGCAGGTCTTCACCTCA

GACACTGAGGCCTCCAGTGAGTCCGGGCTTCACACGCCGGCATCTCAGGCCACC

ACCCTCCACGTCCCCAGCCAGGACCCTGCCGGCATCCAGCACCTGCAGCCGGCC

CACCGGCTCAGCGCCAGCCCCACAGTGTCCTCCAGCAGCCTGGTGCTGTACCAG

AGCTCAGACTCCAGCAATGGCCAGAGCCACCTGCTGCCATCCAACCACAGCGTC

ATCGAGACCTTCATCTCCACCCAGATGGCCTCTTCCTCCCAGTAACCACGGCAC

CTGGGCCCTGGGGCCTGTACTGCCTGCTTGGGGGGTGATGAGGGCAGCAGCCAG

CCCTGCCTGGAGGACCTGAGCCTGCCGAGCAACCGTGGCCCTTCCTGGACAGCT

GTGCCTCGCTCCCCACTCTGCTCTGATGCATCAGAAAGGGAGGGCTCTGAGGCG

CCCCAACCCGTGGAGGCTGCTCGGGGTGCACAGGAGGGGGTCGTGGAGAGCTAG

GAGCAAAGCCTGTTCATGGCAGATGTAGGAGGGACTGTCGCTGCTTCGTGGGAT

ACAGTCTTCTTACTTGGAACTGAAGGGGGCGGCCTATGACTTGGGCACCCCCAG

CCTGGGCCTATGGAGAGCCCTGGGACCGCTACACCACTCTGGCAGCCACACTTC

TCAGGACACAGGCCTGTGTAGCTGTGACCTGCTGAGCTCTGAGAGGCCCTGGAT

CAGCGTGGCCTTGTTCTGTCACCAATGTACCCACCGGGCCACTCCTTCCTGCCC

CAACTCCTTCCAGCTAGTGACCCACATGCCATTTGTACTGACCCCATCACCTAC

TCACACAGGCATTTCCTGGGTGGCTACTCTGTGCCAGAGCCTGGGGCTCTAACG

CCTGAGCCCAGGGAGGCCGAAGCTAACAGGGAAGGCAGGCAGGGCTCTCCTGGC

TTCCCATCCCCAGCGATTCCCTCTCCCAGGCCCCATGACCTCCAGCTTTCCTGT

ATTTGTTCCCAAGAGCATCATGCCTCTGAGGCCAGCCTGGCCTCCTGCCTCTAC

TGGGAAGGCTACTTCGGGGCTGGGAAGTCGTCCTTACTCCTGTGGGAGCCTCGC

AACCCGTGCCAAGTCCAGGTCCTGGTGGGGCAGCTCCTCTGTCTCGAGCGCCCT

GCAGACCCTGCCCTTGTTTGGGGCAGGAGTAGCTGAGCTCACAAGGCAGCAAGG

CCCGAGCAGCTGAGCAGGGCCGGGGAACTGGCCAAGCTGAGGTGCCCAGGAGAA

GAAAGAGGTGACCCCAGGGCACAGGAGCTACCTGTGTGGACAGGACTAACACTC

AGAAGCCTGGGGGCCTGGCTGGCTGAGGGCAGTTCGCAGCCACCCTGAGGAGTC

TGAGGTCCTGAGCACTGCCAGGAGGGACAAAGGAGCCTGTGAACCCAGGACAAG

CATGGTCCCACATCCCTGGGCCTGCTGCTGAGAACCTGGCCTTCAGTGTACCGC

GTCTACCCTGGGATTCAGGAAAAGGCCTGGGGTGACCCGGCACCCCCTGCAGCT

TGTAGCCAGCCGGGGCGAGTGGCACGTTTATTTAACTTTTAGTAAAGTCAAGGA

GAAATGCGGTGGAAA
```

-continued

Human HNF1 homeobox A (HNF1A), transcript variant X1, mRNA
XM_005253931.3

(SEQ ID NO: 10)

```
ATAAATATGAACCTTGGAGAATTTCCCGAGCTCCAATGTAAACAGAACAGGGAG

GGGCCCTGATTCACGGGCCGCTGGGGCCAGGGTTGGGGGTTGGGGGTGCCCACA

GGGCTTGGCTAGTGGGGTTTTGGGGGGGCAGTGGGTGCAAGGAGTTTGGTTTGT

GTCTGCCGGCCGGCAGGCAAACGCAACCCACGCGGTGGGGGAGGCGGCTAGCGT

GGTGGACCCGGGCCGCGTGGCCCTGTGGCAGCCGAGCCATGGTTTCTAAACTGA

GCCAGCTGCAGACGGAGCTCCTGGCGGCCCTGCTCGAGTCAGGGCTGAGCAAAG

AGGCACTGATCCAGGCACTGGGTGAGCCGGGGCCCTACCTCCTGGCTGGAGAAG

GCCCCCTGGACAAGGGGGAGTCCTGCGGCGGCGGTCGAGGGGAGCTGGCTGAGC

TGCCCAATGGGCTGGGGGAGACTCGGGGCTCCGAGGACGAGACGGACGACGATG

GGGAAGACTTCACGCCACCCATCCTCAAAGAGCTGGAGAACCTCAGCCCTGAGG

AGGCGGCCCACCAGAAAGCCGTGGTGGAGACCCTTCTGCAGGAGGACCCGTGGC

GTGTGGCGAAGATGGTCAAGTCCTACCTGCAGCAGCACAACATCCCACAGCGGG

AGGTGGTCGATACCACTGGCCTCAACCAGTCCCACCTGTCCCAACACCTCAACA

AGGGCACTCCCATGAAGACGCAGAAGCGGGCCGCCCTGTACACCTGGTACGTCC

GCAAGCAGCGAGAGGTGGCGCAGCAGTTCACCCATGCAGGGCAGGGAGGGCTGA

TTGAAGAGCCCACAGGTGATGAGCTACCAACCAAGAAGGGGCGGAGGAACCGTT

TCAAGTGGGGCCCAGCATCCCAGCAGATCCTGTTCCAGGCCTATGAGAGGCAGA

AGAACCCTAGCAAGGAGGAGCGAGAGACGCTAGTGGAGGAGTGCAATAGGGCGG

AATGCATCCAGAGAGGGGTGTCCCCATCACAGGCACAGGGGCTGGGCTCCAACC

TCGTCACGGAGGTGCGTGTCTACAACTGGTTTGCCAACCGGCGCAAAGAAGAAG

CCTTCCGGCACAAGCTGGCCATGGACACGTACAGCGGGCCCCCCCCCAGGGCCAG

GCCCGGGACCTGCGCTGCCCGCTCACAGCTCCCCTGGCCTGCCTCCACCTGCCC

TCTCCCCCAGTAAGGTCCACGGTGTGCGCTATGGACAGCCTGCGACCAGTGAGA

CTGCAGAAGTACCCTCAAGCAGCGGCGGTCCCTTAGTGACAGTGTCTACACCCC

TCCACCAAGTGTCCCCCACGGGCCTGGAGCCCAGCCACAGCCTGCTGAGTACAG

AAGCCAAGCTGGTCTCAGCAGCTGGGGGCCCCCTCCCCCCTGTCAGCACCCTGA

CAGCACTGCACAGCTTGGAGCAGACATCCCCAGGCCTCAACCAGCAGCCCCAGA

ACCTCATCATGGCCTCACTTCCTGGGGTCATGACCATCGGGCCTGGTGAGCCTG

CCTCCCTGGGTCCTACGTTCACCAACACAGGTGCCTCCACCCTGGTCATCGGCC

TGGCCTCCACGCAGGCACAGAGTGTGCCGGTCATCAACAGCATGGGCAGCAGCC

TGACCACCCTGCAGCCCGTCCAGTTCTCCCAGCCGCTGCACCCCTCCTACCAGC

AGCCGCTCATGCCACCTGTGCAGAGCCATGTGACCCAGAGCCCCTTCATGGCCA

CCATGGCTCAGCTGCAGAGCCCCCACGCCCTCTACAGCCACAAGCCCGAGGTGG

CCCAGTACACCCACACGGGCCTGCTCCCGCAGACTATGCTCATCACCGACACCA

CCAACCTGAGCGCCCTGGCCAGCCTCACGCCCACCAAGCAGGTAAGGTCCAGGC

CTGCTGGCCCTCCCTTGGCCTGTGACAGAGCCCCTCACCCCCACATCCCCCGGG

CTCAGGAGGCTGCTCTGCTCCCCCAGGTCTTCACCTCAGACACTGAGGCCTCCA

GTGAGTCCGGGCTTCACACGCCGGCATCTCAGGCCACCACCCTCCACGTCCCCA

GCCAGGACCCTGCCAGCATCCAGCACCTGCAGCCGGCCCACCGGCTCAGCGCCA
```

-continued

```
GCCCCACAGTGTCCTCCAGCAGCCTGGTGCTGTACCAGAGCTCAGACTCCAGCA

ATGGCCAGAGCCACCTGCTGCCATCCAACCACAGCGTCATCGAGACCTTCATCT

CCACCCAGATGGCCTCTTCCTCCCAGTAACCACGGCACCTGGGCCCTGGGGCCT

GTACTGCCTGCTTGGGGGGTGATGAGGGCAGCAGCCAGCCCTGCCTGGAGGACC

TGAGCCTGCCGAGCAACCGTGGCCCTTCCTGGACAGCTGTGCCTCGCTCCCCAC

TCTGCTCTGATGCATCAGAAAGGGAGGGCTCTGAGGCGCCCCAACCCGTGGAGG

CTGCTCGGGGTGCACAGGAGGGGGTCGTGGAGAGCTAGGAGCAAAGCCTGTTCA

TGGCAGATGTAGGAGGGACTGTCGCTGCTTCGTGGGATACAGTCTTCTTACTTG

GAACTGAAGGGGGCGGCCTATGACTTGGGCACCCCCAGCCTGGGCCTATGGAGA

GCCCTGGGACCGCTACACCACTCTGGCAGCCACACTTCTCAGGACACAGGCCTG

TGTAGCTGTGACCTGCTGAGCTCTGAGAGGCCCTGGATCAGCGTGGCCTTGTTC

TGTCACCAATGTACCCACCGGGCCACTCCTTCCTGCCCCAACTCCTTCCAGCTA

GTGAGCCACATGCCATTTGTACTGAGCCCATCACCTACTCACACAGGCATTTCC

TGGGTGGCTACTCTGTGCCAGAGCCTGGGGCTCTAACGCCTGAGCCCAGGGAGG

CCGAAGCTAACAGGGAAGGCAGGCAGGGCTCTCCTGGCTTCCCATCCCCAGCGA

TTCCCTCTCCCAGGCCCCATGACCTCCAGCTTTCCTGTATTTGTTCCCAAGAGC

ATCATGCCTCTGAGGCCAGCCTGGCCTCCTGCCTCTACTGGGAAGGCTACTTCG

GGGCTGGGAAGTCGTCCTTACTCCTGTGGGAGCCTCGCAACCCGTGCCAAGTCC

AGGTCCTGGTGGGGCAGCTCCTCTGTCTCGAGCGCCCTGCAGACCCTGCCCTTG

TTTGGGGCAGGAGTAGCTGAGCTCACAAGGCAGCAAGGCCCGAGCAGCTGAGCA

GGGCCGGGGAACTGGCCAAGCTGAGGTGCCCAGGAGAAGAAAGAGGTGACCCCA

GGGCACAGGAGCTACCTGTGTGGACAGGACTAACACTCAGAAGCCTGGGGGCCT

GGCTGGCTGAGGGCAGTTCGCAGCCACCCTGAGGAGTCTGAGGTCCTGAGCACT

GCCAGGAGGGACAAAGGAGCCTGTGAACCCAGGACAAGCATGGTCCCACATCCC

TGGGCCTGCTGCTGAGAACCTGGCCTTCAGTGTACCGCGTCTACCCTGGGATTC

AGGAAAAGGCCTGGGGTGACCCGGCACCCCCTGCAGCTTGTAGCCAGCCGGGGC

GAGTGGCACGTTTATTTAACTTTTAGTAAAGTCAAGGAGAAATGCGGTGGAAA
```

In some embodiments, the HNF1alpha binds to the inverted palindrome 5-GTTAATNATTAAC-3 (SEQ ID NO: 11).

In some embodiments, the nucleic acid sequence encoding HNF1alpha, as described herein, is at least 80% identical to the sequence of SEQ ID NO: 8, SEQ ID NO: 9, or SEQ ID NO: 10. In some embodiments, the nucleic acid sequence encoding HNF1alpha is 80%, 81%, 82%, 83%, 84%, 85%, 86%, 87%, 88%, 89%, 90%, 91%, 92%, 93%, 94%, 95%, 96%, 97%, 98%, or 99% identical to the sequence of SEQ ID NO: 8, SEQ ID NO: 9, or SEQ ID NO: 10. In some embodiments, the nucleic acid nucleotide sequence encoding HNF1alpha, as described herein, can vary from the sequence of SEQ ID NO: 8, SEQ ID NO: 9, or SEQ ID NO: 10 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more nucleotides.

In some embodiments, the amino acid sequence of Rel-A (p65) is NCBI No. NP_068810.3, NP_001138610.1, NP_001230913.1, NP_001230914.1, XP_011543508.1, or XP_011543509.1. In some embodiments, the amino acid sequence of Rel-A (p65) is or comprises all or a portion of SEQ ID NO: 12, SEQ ID NO:13, SEQ ID NO: 14, SEQ ID NO: 15, SEQ ID NO: 16, or SEQ ID NO: 17. In some embodiments, the amino acid sequence of the transactivation domain of the humanized chimeric Notch receptor comprises all or a portion of transcription factor p65 isoform 1 (NP_068810.3), transcription factor p65 isoform 2 (NP_001138610.1), transcription factor p65 isoform 3 (NP_001230913.1), transcription factor p65 isoform 4 (NP_001230914.1), transcription factor p65 isoform X1 (XP_011543508.1), or transcription factor p65 isoform X2 (XP_011543509.1). In some embodiments, the amino acid sequence of the transactivation domain of the humanized Notch receptor comprises all or a portion of SEQ ID NO: 12, SEQ ID NO:13, SEQ ID NO: 14, SEQ ID NO: 15, SEQ ID NO: 16, or SEQ ID NO: 17. In some embodiments, the amino acid sequence of the transactivation domain of the humanized Notch receptor is or comprises amino acids 1-551 of SEQ ID NO: 12.

Human transcription factor p65 isoform 1
NP_068810.3
                                        (SEQ ID NO: 12)
MDELFPLIFPAEPAQASGPYVEIIEQPKQRGMRFRYKCEGRSAGSIPGERS

TDTTKTHPTIKINGYTGPGTVRISLVTKDPPHRPHPHELVGKDCRDGFYEA

ELCPDRCIHSFQNLGIQCVKKRDLEQAISQRIQTNNNPFQVPIEEQRGDYD

LNAVRLCFQVTVRDPSGRPLRLPPVLSHPIFDNRAPNTAELKICRVNRNSG

SCLGGDEIFLLCDKVQKEDIEVYFTGPGWEARGSFSQADVHRQVAIVFRTP

PYADPSLQAPVRVSMQLRRPSDRELSEPMEFQYLPDTDDRHRIEEKRKRTY

ETFKSIMKKSPESGPTDPRPPPRRIAVPSRSSASVPKPAPQPYPFTSSLST

INYDEFPTMVFPSGQISQASALAPAPPQVLPQAPAPAPAPAMVSALAQAPA

PVPVLAPGPPQAVAPPAPKPTQAGEGTLSEALLQLQFDDEDLGALLGNSTD

PAVFTDLASVDNSEFQQLLNQGIPVAPHTTEPMLMEYPEAITRLVTGAQRP

PDPAPAPLGAPGLPNGLLSGDEDFSSIADMDFSALLSQISS

Human transcription factor p65 isoform 2
NP_001138610.1
                                        (SEQ ID NO: 13)
MDELFPLIFPAEPAQASGPYVEIIEQPKQRGMRFRYKCEGRSAGSIPGERS

TDTTKTHPTIKINGYTGPGTVRISLVTKDPPHRPHPHELVGKDCRDGFYEA

ELCPDRCIHSFQNLGIQCVKKRDLEQAISQRIQTNNNPFQEEQRGDYDLNA

VRLCFQVTVRDPSGRPLRLPPVLSHPIFDNRAPNTAELKICRVNRNSGSCL

GGDEIFLLCDKVQKEDIEVYFTGPGWEARGSFSQADVHRQVAIVFRTPPYA

DPSLQAPVRVSMQLRRPSDRELSEPMEFQYLPDTDDRHRIEEKRKRTYETF

KSIMKKSPFSGPTDPRPPPRRIAVPSRSSASVPKPAPQPYPFTSSLSTINY

DEFPTMVFPSGQISQASALAPAPPQVLPQAPAPAPAPAMVSALAQAPAPVP

VLAPGPPQAVAPPAPKPTQAGEGTLSEALLQLQFDDEDLGALLGNSTDPAV

FTDLASVDNSEFQQLLNQGIPVAPHTTEPMLMEYPEAITRLVTGAQRPPDP

APAPLGAPGLPNGLLSGDEDFSSIADMDFSALLSQISS

Human transcription factor p65 isoform 3
NP_001230913.1
                                        (SEQ ID NO: 14)
MDELFPLIFPAEPAQASGPYVEIIEQPKQRGMRFRYKCEGRSAGSIPGERS

TDTTKTHPTIKINGYTGPGTVRISLVTKDPPHRPHPHELVGKDCRDGFYEA

ELCPDRCIHSFQNLGIQCVKKRDLEQAISQRIQTNNNPFQVPIEEQRGDYD

LNAVRLCFQVTVRDPSGRPLRLPPVLSHPIFDNRAPNTAELKICRVNRNSG

SCLGGDEIFLLCDKVQKEDIEVYFTGPGWEARGSFSQADVHRQVAIVFRTP

PYADPSLQAPVRVSMQLRRPSDRELSEPMEFQYLPDTDDRHRIEEKRKRTY

ETFKSIMKKSPESGPTDPRPPPRRIAVPSRSSASVPKPAPGPPQAVAPPAP

KPTQAGEGTLSEALLQLQFDDEDLGALLGNSTDPAVFTDLASVDNSEFQQL

LNQGIPVAPHTTEPMLMEYPEAITRLVTGAQRPPDPAPAPLGAPGLPNGLL

SGDEDFSSIADMDFSALLSQISS

Human transcription factor p65 isoform 4
NP_001230914.1
                                        (SEQ ID NO: 15)
MDELFPLIFPAEPAQASGPYVEIIEQPKQRGMRFRYKCEGRSAGSIPGERS

TDTTKTHPTIKINGYTGPGTVRISLVTKDPPHRPHPHELVGKDCRDGFYEA

ELCPDRCIHSFQNLGIQCVKKRDLEQAISQRIQTNNNPFQVPIEEQRGDYD

LNAVRLCFQVTVRDPSGRPLRLPPVLSHPIFDNRAPNTAELKICRVNRNSG

SCLGGDEIFLLCDKVQKEDIEVYFTGPGWEARGSFSQADVHRQVAIVFRTP

PYADPSLQAPVRVSMQLRRPSDRELSEPMEFQYLPDTDDRHRIEEKRKRTY

ETFKSIMKKSPESGPTDPRPPPRRIAVPSRSSASVPKPAPQPYPFTSSLST

INYDEFPTMVFPSGQISQASALAPAPPQVLPQAPAPAPAPAMVSALAQRPP

DPAPAPLGAPGLPNGLLSGDEDFSSIADMDFSALLSQISS

Human transcription factor p65 isoform X1
XP_011543508.1
                                        (SEQ ID NO: 16)
MDELFPLIFPAEPAQASGPYVEIIEQPKQRGMRFRYKCEGRSAGSIPGERS

TDTTKTHPTIKINGYTGPGTVRISLVTKDPPHRPHPHELVGKDCRDGFYEA

ELCPDRCIHSFQNLGIQCVKKRDLEQAISQRIQTNNNPFQVPIEEQRGDYD

LNAVRLCFQVTVRDPSGRPLRLPPVLSHPIFDNRAPNTAELKICRVNRNSG

SCLGGDEIFLLCDKVQKDDRHRIEEKRKRTYETFKSIMKKSPFSGPTDPRP

PPRRIAVPSRSSASVPKPAPQPYPFTSSLSTINYDEFPTMVFPSGQISQAS

ALAPAPPQVLPQAPAPAPAPAMVSALAQAPAPVPVLAPGPPQAVAPPAPKP

TQAGEGTLSEALLQLQFDDEDLGALLGNSTDPAVFTDLASVDNSEFQQLLN

QGIPVAPHTTEPMLMEYPEAITRLVTGAQRPPDPAPAPLGAPGLPNGLLSG

DEDFSSIADMDFSALLSQISS

Human transcription factor p65 isoform X2
XP_011543509.1
                                        (SEQ ID NO: 17)
MDELFPLIFPAEPAQASGPYVEIIEQPKQRGMRFRYKCEGRSAGSIPGERS

TDTTKTHPTIKINGYTGPGTVRISLVTKDPPHRPHPHELVGKDCRDGFYEA

ELCPDRCIHSFQNLGIQCVKKRDLEQAISQRIQTNNNPFQVPIEEQRGDYD

LNAVRLCFQVTVRDPSGRPLRLPPVLSHPIFDNHDRHRIEEKRKRTYETFK

SIMKKSPFSGPTDPRPPPRRIAVPSRSSASVPKPAPQPYPFTSSLSTINYD

EFPTMVFPSGQISQASALAPAPPQVLPQAPAPAPAPAMVSALAQAPAPVPV

LAPGPPQAVAPPAPKPTQAGEGTLSEALLQLQFDDEDLGALLGNSTDPAVF

TDLASVDNSEFQQLLNQGIPVAPHTTEPMLMEYPEAITRLVTGAQRPPDPA

PAPLGAPGLPNGLLSGDEDFSSIADMDFSALLSQISS

In some embodiments, the amino acid sequence of Rel-A (p65), as described herein, is at least 80% identical to the amino acid sequence of SEQ ID NO: 12, SEQ ID NO:13, SEQ ID NO: 14, SEQ ID NO: 15, SEQ ID NO: 16, or SEQ ID NO: 17. In some embodiments, the amino acid sequence of Rel-A (p65) is 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of SEQ ID NO: 12, SEQ ID NO:13, SEQ ID NO: 14, SEQ ID NO: 15, SEQ ID NO: 16, or SEQ ID NO: 17. In some embodiments, the amino acid sequence of Rel-A (p65), as described herein, can vary from the amino acid sequence of SEQ ID NO: 12, SEQ ID NO:13, SEQ ID NO: 14, SEQ ID NO: 15, SEQ ID NO: 16, or SEQ ID NO: 17 by 1 amino acid, 2 amino acids, 3 amino acids, 4 amino acids, 5 amino acids, 6 amino acids, 7 amino acids, 8 amino acids, 9 amino acids, or 10 or more amino acids.

In some embodiments, the nucleic acid sequence encoding Rel-A (p65) is provided by NCBI No. NM_021975.3, NM_001145138.1, NM_001243984.1, NM_001243985.1, XM_011545206.1, or XM_011545207.1. In some embodiments, the nucleic acid sequence encoding Rel-A (p65) is or comprises SEQ ID NO: 18, SEQ ID NO: 19, SEQ ID NO: 20, SEQ ID NO: 21, SEQ ID NO: 22, or SEQ ID NO: 23.

Human RELA proto-oncogene, NF-kB subunit (RELA), transcript variant 1, mRNA NM_021975.3

(SEQ ID NO: 18)

AGCGCGCAGGCGCGGCCGGATTCCGGGCAGTGACGCGACGGCGGGCCGCGCGGC

GCATTTCCGCCTCTGGCGAATGGCTCGTCTGTAGTGCACGCCGCGGGCCCAGCT

GCGACCCCGGCCCCGCCCCGGGACCCCGGCCATGGACGAACTGTTCCCCCTCA

TCTTCCCGGCAGAGCCAGCCCAGGCCTCTGGCCCCTATGTGGAGATCATTGAGC

AGCCCAAGCAGCGGGGCATGCGCTTCCGCTACAAGTGCGAGGGGCGCTCCGCGG

GCAGCATCCCAGGCGAGAGGAGCACAGATACCACCAAGACCCACCCCACCATCA

AGATCAATGGCTACACAGGACCAGGGACAGTGCGCATCTCCCTGGTCACCAAGG

ACCCTCCTCACCGGCCTCACCCCCACGAGCTTGTAGGAAAGGACTGCCGGGATG

GCTTCTATGAGGCTGAGCTCTGCCCGGACCGCTGCATCCACAGTTTCCAGAACC

TGGGAATCCAGTGTGTGAAGAAGCGGGACCTGGAGCAGGCTATCAGTCAGCGCA

TCCAGACCAACAACAACCCCTTCCAAGTTCCTATAGAAGAGCAGCGTGGGGACT

ACGACCTGAATGCTGTGCGGCTCTGCTTCCAGGTGACAGTGCGGGACCCATCAG

GCAGGCCCCTCCGCCTGCCGCCTGTCCTTTCTCATCCCATCTTTGACAATCGTG

CCCCCAACACTGCCGAGCTCAAGATCTGCCGAGTGAACCGAAACTCTGGCAGCT

GCCTCGGTGGGGATGAGATCTTCCTACTGTGTGACAAGGTGCAGAAAGAGGACA

TTGAGGTGTATTTCACGGGACCAGGCTGGGAGGCCCGAGGCTCCTTTTCGCAAG

CTGATGTGCACCGACAAGTGGCCATTGTGTTCCGGACCCCTCCCTACGCAGACC

CCAGCCTGCAGGCTCCTGTGCGTGTCTCCATGCAGCTGCGGCGGCCTTCCGACC

GGGAGCTCAGTGAGCCCATGGAATTCCAGTACCTGCCAGATACAGACGATCGTC

ACCGGATTGAGGAGAAACGTAAAAGGAGATATGAGACCTTCAAGAGCATCATGA

AGAAGAGTCCTTTCAGCGGACCCACCGACCCCCGGCCTCCACCTCGACGCATTG

CTGTGCCTTCCCGCAGCTCAGCTTCTGTCCCCAAGCCAGCACCCCAGCCCTATC

CCTTTACGTCATCCCTGAGCACCATCAACTATGATGAGTTTCCCACCATGGTGT

TTCCTTCTGGGCAGATCAGCCAGGCCTCGGCCTTGGCCCCGGCCCCTCCCCAAG

TCCTGCCCCAGGCTCCAGCCCCTGCCCCTGCTCCAGCCATGGTATCAGCTCTGG

CCCAGGCCCCAGCCCCTGTCCCAGTCCTAGCCCCAGGCCCTCCTCAGGCTGTGG

CCCCACCTGCCCCCAAGCCCACCCAGGCTGGGGAAGGAACGCTGTCAGAGGCCC

TGCTGCAGCTGCAGTTTGATGATGAAGACCTGGGGGCCTTGCTTGGCAACAGCA

CAGACCCAGCTGTGTTCACAGACCTGGCATCCGTCGACAACTCCGAGTTTCAGC

AGCTGCTGAACCAGGGCATACCTGTGGCCCCCCACACAACTGAGCCCATGCTGA

TGGAGTACCCTGAGGCTATAACTCGCCTAGTGACAGGGGCCCAGAGGCCCCCCG

ACCCAGCTCCTGCTCCACTGGGGGCCCCGGGGCTCCCCAATGGCCTCCTTTCAG

GAGATGAAGACTTCTCCTCCATTGCGGACATGGACTTCTCAGCCCTGCTGAGTC

AGATCAGCTCCTAAGGGGGTGACGCCTGCCCTCCCCAGAGCACTGGGTTGCAGG

GGATTGAAGCCCTCCAAAAGCACTTACGGATTCTGGTGGGGTGTGTTCCAACTG

CCCCCAACTTTGTGGATGTCTTCCTTGGAGGGGGGAGCCATATTTTATTCTTTT

ATTGTCAGTATCTGTATCTCTCTCTCTTTTTTGGAGGTGCTTAAGCAGAAGCATT

AACTTCTCTGGAAAGGGGGGAGCTGGGGAAACTCAAACTTTTCCCCTGTCCTGA

TGGTCAGCTCCCTTCTCTGTAGGGAACTCTGGGGTCCCCCATCCCCATCCTCCA

GCTTCTGGTACTCTCCTAGAGACAGAAGCAGGCTGGAGGTAAGGCCTTTGAGCC

CACAAAGCCTTATCAAGTGTCTTCCATCATGGATTCATTACAGCTTAATCAAAA

TAACGCCCCAGATACCAGCCCCTGTATGGCACTGGCATTGTCCCTGTGCCTAAC

ACCAGCGTTTGAGGGGCTGGCCTTCCTGCCCTACAGAGGTCTCTGCCGGCTCTT

TCCTTGCTCAACCATGGCTGAAGGAAACCAGTGCAACAGCACTGGCTCTCTCCA

GGATCCAGAAGGGGTTTGGTCTGGGACTTCCTTGCTCTCCCTCTTCTCAAGTGC

CTTAATAGTAGGGTAAGTTGTTAAGAGTGGGGGAGAGCAGGCTGGCAGCTCTCC

AGTCAGGAGGCATAGTTTTTACTGAACAATCAAAGCACTTGGACTCTTGCTCTT

TCTACTCTGAACTAATAAATCTGTTGCCAAGCTGGCTAGAAAAAAAAAAAAAAA

AAA

Human RELA proto-oncogene, NF-kB subunit (RELA), transcript
variant 2 mRNA NM_001145138.1

(SEQ ID NO: 19)

AGCGCGCAGGCGCGGCCGGATTCCGGGCAGTGACGCGACGGCGGGCCGCGCGGC

GCATTTCCGCCTCTGGCGAATGGCTCGTCTGTAGTGCACGCCGCGGGCCCAGCT

GCGACCCCGGCCCCGCCCCGGGACCCCGGCCATGGACGAACTGTTCCCCCTCA

TCTTCCCGGCAGAGCCAGCCCAGGCCTCTGGCCCCTATGTGGAGATCATTGAGC

AGCCCAAGCAGCGGGGCATGCGCTTCCGCTACAAGTGCGAGGGGCGCTCCGCGG

GCAGCATCCCAGGCGAGAGGAGCACAGATACCACCAAGACCCACCCCACCATCA

AGATCAATGGCTACACAGGACCAGGGACAGTGCGCATCTCCCTGGTCACCAAGG

ACCCTCCTCACCGGCCTCACCCCCACGAGCTTGTAGGAAAGGACTGCCGGGATG

GCTTCTATGAGGCTGAGCTCTGCCCGGACCGCTGCATCCACAGTTTCCAGAACC

TGGGAATCCAGTGTGTGAAGAAGCGGGACCTGGAGCAGGCTATCAGTCAGCGCA

TCCAGACCAACAACAACCCCTTCCAAGAAGAGCAGCGTGGGGACTACGACCTGA

ATGCTGTGCGGCTCTGCTTCCAGGTGACAGTGCGGGACCCATCAGGCAGGCCCC

TCCGCCTGCCGCCTGTCCTTTCTCATCCCATCTTTGACAATCGTGCCCCCAACA

CTGCCGAGCTCAAGATCTGCCGAGTGAACCGAAACTCTGGCAGCTGCCTCGGTG

GGGATGAGATCTTCCTACTGTGTGACAAGGTGCAGAAAGAGGACATTGAGGTGT

ATTTCACGGGACCAGGCTGGGAGGCCCGAGGCTCCTTTTCGCAAGCTGATGTGC

ACCGACAAGTGGCCATTGTGTTCCGGACCCCTCCCTACGCAGACCCCAGCCTGC

AGGCTCCTGTGCGTGTCTCCATGCAGCTGCGGCGGCCTTCCGACCGGGAGCTCA

GTGAGCCCATGGAATTCCAGTACCTGCCAGATACAGACGATCGTCACCGGATTG

AGGAGAAACGTAAAAGGACATATGAGACCTTCAAGAGCATCATGAAGAAGAGTC

CTTTCAGCGGACCCACCGACCCCCGGCCTCCACCTCGACGCATTGCTGTGCCTT

CCCGCAGCTCAGCTTCTGTCCCCAAGCCAGCACCCCAGCCCTATCCCTTTACGT

CATCCCTGAGCACCATCAACTATGATGAGTTTCCCACCATGGTGTTTCCTTCTG

GGCAGATCAGCCAGGCCTCGGCCTTGGCCCCGGCCCCTCCCCAAGTCCTGCCCC

AGGCTCCAGCCCCTGCCCCTGCTCCAGCCATGGTATCAGCTCTGGCCCAGGCCC

CAGCCCCTGTCCCAGTCCTAGCCCCAGGCCCTCCTCAGGCTGTGGCCCCACCTG

CCCCCAAGCCCACCCAGGCTGGGGAAGGAACGCTGTCAGAGGCCCTGCTGCAGC

TGCAGTTTGATGATGAAGACCTGGGGGCCTTGCTTGGCAACAGCACAGACCCAG

-continued

CTGTGTTCACAGACCTGGCATCCGTCGACAACTCCGAGTTTCAGCAGCTGCTGA

ACCAGGGCATACCTGTGGCCCCCCACACAACTGAGCCCATGCTGATGGAGTACC

CTGAGGCTATAACTCGCCTAGTGACAGGGGCCCAGAGGCCCCCCGACCCAGCTC

CTGCTCCACTGGGGGCCCCGGGGCTCCCCAATGGCCTCCTTTCAGGAGATGAAG

ACTTCTCCTCCATTGCGGACATGGACTTCTCAGCCCTGCTGAGTCAGATCAGCT

CCTAAGGGGGTGACGCCTGCCCTCCCCAGAGCACTGGGTTGCAGGGGATTGAAG

CCCTCCAAAAGCACTTACGGATTCTGGTGGGGTGTGTTCCAACTGCCCCCAACT

TTGTGGATGTCTTCCTTGGAGGGGGGAGCCATATTTTATTCTTTTATTGTCAGT

ATCTGTATCTCTCTCTCTTTTTGGAGGTGCTTAAGCAGAAGCATTAACTTCTCT

GGAAAGGGGGGAGCTGGGGAAACTCAAACTTTTCCCCTGTCCTGATGGTCAGCT

CCCTTCTCTGTAGGGAACTCTGGGGTCCCCCATCCCCATCCTCCAGCTTCTGGT

ACTCTCCTAGAGACAGAAGCAGGCTGGAGGTAAGGCCTTTGAGCCCACAAAGCC

TTATCAAGTGTCTTCCATCATGGATTCATTACAGCTTAATCAAAATAACGCCCC

AGATACCAGCCCCTGTATGGCACTGGCATTGTCCCTGTGCCTAACACCAGCGTT

TGAGGGGCTGGCCTTCCTGCCCTACAGAGGTCTCTGCCGGCTCTTTCCTTGCTC

AACCATGGCTGAAGGAAACCAGTGCAACAGCACTGGCTCTCTCCAGGATCCAGA

AGGGGTTTGGTCTGGGACTTCCTTGCTCTCCCTCTTCTCAAGTGCCTTAATAGT

AGGGTAAGTTGTTAAGAGTGGGGGAGAGCAGGCTGGCAGCTCTCCAGTCAGGAG

GCATAGTTTTTACTGAACAATCAAAGCACTTGGACTCTTGCTCTTTCTACTCTG

AACTAATAAATCTGTTGCCAAGCTGGCTAGAAAAAAAAAAAAAAAAAA

Human RELA proto-oncogene, NF-kB subunit (RELA), transcript
variant 3, mRNA NM_001243984.1
                                        (SEQ ID NO: 20)
AGCGCGCAGGCGCGGCCGGATTCCGGGCAGTGACGCGACGGCGGGCCGCGCGGC

GCATTTCCGCCTCTGGCGAATGGCTCGTCTGTAGTGCACGCCGCGGGCCCAGCT

GCGACCCCGGCCCCGCCCCCGGGACCCCGGCCATGGACGAACTGTTCCCCCTCA

TCTTCCCGGCAGAGCCAGCCCAGGCCTCTGGCCCCTATGTGGAGATCATTGAGC

AGCCCAAGCAGCGGGGCATGCGCTTCCGCTACAAGTGCGAGGGGCGCTCCGCGG

GCAGCATCCCAGGCGAGAGGAGCACAGATACCACCAAGACCCACCCCACCATCA

AGATCAATGGCTACACAGGACCAGGGACAGTGCGCATCTCCCTGGTCACCAAGG

ACCCTCCTCACCGGCCTCACCCCCACGAGCTTGTAGGAAAGGACTGCCGGGATG

GCTTCTATGAGGCTGAGCTCTGCCCGGACCGCTGCATCCACAGTTTCCAGAACC

TGGGAATCCAGTGTGTGAAGAAGCGGGACCTGGAGCAGGCTATCAGTCAGCGCA

TCCAGACCAACAACAACCCCTTCCAAGTTCCTATAGAAGAGCAGCGTGGGGACT

ACGACCTGAATGCTGTGCGGCTCTGCTTCCAGGTGACAGTGCGGGACCCATCAG

GCAGGCCCCTCCGCCTGCCGCCTGTCCTTTCTCATCCCATCTTTGACAATCGTG

CCCCCAACACTGCCGAGCTCAAGATCTGCCGAGTGAACCGAAACTCTGGCAGCT

GCCTCGGTGGGGATGAGATCTTCCTACTGTGTGACAAGGTGCAGAAAGAGGACA

TTGAGGTGTATTTCACGGGACCAGGCTGGGAGGCCCGAGGCTCCTTTTCGCAAG

CTGATGTGCACCGACAAGTGGCCATTGTGTTCCGGACCCCTCCCTACGCAGACC

CCAGCCTGCAGGCTCCTGTGCGTGTCTCCATGCAGCTGCGGCGGCCTTCCGACC

GGGAGCTCAGTGAGCCCATGGAATTCCAGTACCTGCCAGATACAGACGATCGTC

-continued

ACCGGATTGAGGAGAAACGTAAAAGGAGATATGAGACCTTCAAGAGCATCATGA

AGAAGAGTCCTTTCAGCGGACCCACCGACCCCCGGCCTCCACCTCGACGCATTG

CTGTGCCTTCCCGCAGCTCAGCTTCTGTCCCCAAGCCAGCCCCAGGCCCTCCTC

AGGCTGTGGCCCCACCTGCCCCCAAGCCCACCCAGGCTGGGGAAGGAACGCTGT

CAGAGGCCCTGCTGCAGCTGCAGTTTGATGATGAAGACCTGGGGGCCTTGCTTG

GCAACAGCACAGACCCAGCTGTGTTCACAGACCTGGCATCCGTCGACAACTCCG

AGTTTCAGCAGCTGCTGAACCAGGGCATACCTGTGGCCCCCCACACAACTGAGC

CCATGCTGATGGAGTACCCTGAGGCTATAACTCGCCTAGTGACAGGGGCCCAGA

GGCCCCCCGACCCAGCTCCTGCTCCACTGGGGGCCCCGGGGCTCCCCAATGGCC

TCCTTTCAGGAGATGAAGACTTCTCCTCCATTGCGGACATGGACTTCTCAGCCC

TGCTGAGTCAGATCAGCTCCTAAGGGGGTGACGCCTGCCCTCCCCAGAGCACTG

GGTTGCAGGGGATTGAAGCCCTCCAAAAGCACTTACGGATTCTGGTGGGGTGTG

TTCCAACTGCCCCCAACTTTGTGGATGTCTTCCTTGGAGGGGGGAGCCATATTT

TATTCTTTTATTGTCAGTATCTGTATCTCTCTCTTTTTGGAGGTGCTTAAGC

AGAAGCATTAACTTCTCTGGAAAGGGGGGAGCTGGGGAAACTCAAACTTTTCCC

CTGTCCTGATGGTCAGCTCCCTTCTCTGTAGGGAACTCTGGGGTCCCCCATCCC

CATCCTCCAGCTTCTGGTACTCTCCTAGAGACAGAAGCAGGCTGGAGGTAAGGC

CTTTGAGCCCACAAAGCCTTATCAAGTGTCTTCCATCATGGATTCATTACAGCT

TAATCAAAATAACGCCCCAGATACCAGCCCCTGTATGGCACTGGCATTGTCCCT

GTGCCTAACACCAGCGTTTGAGGGGCTGGCCTTCCTGCCCTACAGAGGTCTCTG

CCGGCTCTTTCCTTGCTCAACCATGGCTGAAGGAAACCAGTGCAACAGCACTGG

CTCTCTCCAGGATCCAGAAGGGGTTTGGTCTGGGACTTCCTTGCTCTCCCTCTT

CTCAAGTGCCTTAATAGTAGGGTAAGTTGTTAAGAGTGGGGGAGAGCAGGCTGG

CAGCTCTCCAGTCAGGAGGCATAGTTTTTACTGAACAATCAAAGCACTTGGACT

CTTGCTCTTTCTACTCTGAACTAATAAATCTGTTGCCAAGCTGGCTAGAAAAA

AAAAAAAAAAA

Human RELA proto-oncogene, NF-kB subunit (RELA), transcript
variant 4, mRNA NM_001243985.1
(SEQ ID NO: 21)
AGCGCGCAGGCGCGGCCGGATTCCGGGCAGTGACGCGACGGCGGGCCGCGCGGC

GCATTTCCGCCTCTGGCGAATGGCTCGTCTGTAGTGCACGCCGCGGGCCCAGCT

GCGACCCCGGCCCCGCCCCCGGGACCCCGGCCATGGACGAACTGTTCCCCCTCA

TCTTCCCGGCAGAGCCAGCCCAGGCCTCTGGCCCCTATGTGGAGATCATTGAGC

AGCCCAAGCAGCGGGGCATGCGCTTCCGCTACAAGTGCGAGGGGCGCTCCGCGG

GCAGCATCCCAGGCGAGAGGAGCACAGATACCACCAAGACCCACCCCACCATCA

AGATCAATGGCTACACAGGACCAGGGACAGTGCGCATCTCCCTGGTCACCAAGG

ACCCTCCTCACCGGCCTCACCCCCACGAGCTTGTAGGAAAGGACTGCCGGGATG

GCTTCTATGAGGCTGAGCTCTGCCCCGGACCGCTGCATCCACAGTTTCCAGAACC

TGGGAATCCAGTGTGTGAAGAAGCGGGACCTGGAGCAGGCTATCAGTCAGCGCA

TCCAGACCAACAACAACCCCTTCCAAGTTCCTATAGAAGAGCAGCGTGGGGACT

ACGACCTGAATGCTGTGCGGCTCTGCTTCCAGGTGACAGTGCGGGACCCATCAG

GCAGGCCCCTCCGCCTGCCGCCTGTCCTTTCTCATCCCATCTTTGACAATCGTG

-continued

```
CCCCCAACACTGCCGAGCTCAAGATCTGCCGAGTGAACCGAAACTCTGGCAGCT

GCCTCGGTGGGGATGAGATCTTCCTACTGTGTGACAAGGTGCAGAAAGAGGACA

TTGAGGTGTATTTCACGGGACCAGGCTGGGAGGCCCGAGGCTCCTTTTCGCAAG

CTGATGTGCACCGACAAGTGGCCATTGTGTTCCGGACCCCTCCCTACGCAGACC

CCAGCCTGCAGGCTCCTGTGCGTGTCTCCATGCAGCTGCGGCGGCCTTCCGACC

GGGAGCTCAGTGAGCCCATGGAATTCCAGTACCTGCCAGATACAGACGATCGTC

ACCGGATTGAGGAGAAACGTAAAAGGAGATATGAGACCTTCAAGAGCATCATGA

AGAAGAGTCCTTTCAGCGGACCCACCGACCCCCGGCCTCCACCTCGACGCATTG

CTGTGCCTTCCCGCAGCTCAGCTTCTGTCCCCAAGCCAGCACCCCAGCCCTATC

CCTTTACGTCATCCCTGAGCACCATCAACTATGATGAGTTTCCCACCATGGTGT

TTCCTTCTGGGCAGATCAGCCAGGCCTCGGCCTTGGCCCCGGCCCCTCCCCAAG

TCCTGCCCCAGGCTCCAGCCCCTGCCCCTGCTCCAGCCATGGTATCAGCTCTGG

CCCAGAGGCCCCCCGACCCAGCTCCTGCTCCACTGGGGGCCCCGGGGCTCCCCA

ATGGCCTCCTTTCAGGAGATGAAGACTTCTCCTCCATTGCGGACATGGACTTCT

CAGCCCTGCTGAGTCAGATCAGCTCCTAAGGGGGTGACGCCTGCCCTCCCCAGA

GCACTGGGTTGCAGGGGATTGAAGCCCTCCAAAAGCACTTACGGATTCTGGTGG

GGTGTGTTCCAACTGCCCCCAACTTTGTGGATGTCTTCCTTGGAGGGGGGAGCC

ATATTTTATTCTTTTATTGTCAGTATCTGTATCTCTCTCTTTTTGGAGGTGC

TTAAGCAGAAGCATTAACTTCTCTGGAAAGGGGGGAGCTGGGGAAACTCAAACT

TTTCCCCTGTCCTGATGGTCAGCTCCCTTCTCTGTAGGGAACTCTGGGGTCCCC

CATCCCCATCCTCCAGCTTCTGGTACTCTCCTAGAGACAGAAGCAGGCTGGAGG

TAAGGCCTTTGAGCCCACAAAGCCTTATCAAGTGTCTTCCATCATGGATTCATT

ACAGCTTAATCAAAATAACGCCCCAGATACCAGCCCCTGTATGGCACTGGCATT

GTCCCTGTGCCTAACACCAGCGTTTGAGGGGCTGGCCTTCCTGCCCTACAGAGG

TCTCTGCCGGCTCTTTCCTTGCTCAACCATGGCTGAAGGAAACCAGTGCAACAG

CACTGGCTCTCTCCAGGATCCAGAAGGGGTTTGGTCTGGGACTTCCTTGCTCTC

CCTCTTCTCAAGTGCCTTAATAGTAGGGTAAGTTGTTAAGAGTGGGGGAGAGCA

GGCTGGCAGCTCTCCAGTCAGGAGGCATAGTTTTTACTGAACAATCAAAGCACT

TGGACTCTTGCTCTTTCTACTCTGAACTAATAAATCTGTTGCCAAGCTGGCTAG

AAAAAAAAAAAAAAAAA
```

Human RELA proto-oncogene, NF-kB subunit (RELA), transcript
variant X1, mRNA XM_011545206.1

(SEQ ID NO: 22)

```
ATTCCGGGCAGTGACGCGACGGCGGGCCGCGCGGCGCATTTCCGCCTCTGGCGA

ATGGCTCGTCTGTAGTGCACGCCGCGGGCCCAGCTGCGACCCCGGCCCCGCCCC

CGGGACCCCGGCCATGGACGAACTGTTCCCCCTCATCTTCCCGGCAGAGCCAGC

CCAGGCCTCTGGCCCCTATGTGGAGATCATTGAGCAGCCCAAGCAGCGGGGCAT

GCGCTTCCGCTACAAGTGCGAGGGGCGCTCCGCGGGCAGCATCCCAGGCGAGAG

GAGCACAGATACCACCAAGACCCACCCCACCATCAAGATCAATGGCTACACAGG

ACCAGGGACAGTGCGCATCTCCCTGGTCACCAAGGACCCTCCTCACCGGCCTCA

CCCCCACGAGCTTGTAGGAAAGGACTGCCGGGATGGCTTCTATGAGGCTGAGCT

CTGCCCGGACCGCTGCATCCACAGTTTCCAGAACCTGGGAATCCAGTGTGTGAA
```

-continued

GAAGCGGGACCTGGAGCAGGCTATCAGTCAGCGCATCCAGACCAACAACAACCC

CTTCCAAGTTCCTATAGAAGAGCAGCGTGGGGACTACGACCTGAATGCTGTGCG

GCTCTGCTTCCAGGTGACAGTGCGGGACCCATCAGGCAGGCCCCTCCGCCTGCC

GCCTGTCCTTTCTCATCCCATCTTTGACAATCGTGCCCCCAACACTGCCGAGCT

CAAGATCTGCCGAGTGAACCGAAACTCTGGCAGCTGCCTCGGTGGGGATGAGAT

CTTCCTACTGTGTGAGAAGGTGCAGAAAGACGATCGTCACCGGATTGAGGAGAA

ACGTAAAAGGAGATATGAGACCTTCAAGAGCATCATGAAGAAGAGTCCTTTCAG

CGGACCCACCGACCCCCGGCCTCCACCTCGACGCATTGCTGTGCCTTCCCGCAG

CTCAGCTTCTGTCCCCAAGCCAGCACCCCAGCCCTATCCCTTTACGTCATCCCT

GAGCACCATCAACTATGATGAGTTTCCCACCATGGTGTTTCCTTCTGGGCAGAT

CAGCCAGGCCTCGGCCTTGGCCCCGGCCCCTCCCCAAGTCCTGCCCCAGGCTCC

AGCCCCTGCCCCTGCTCCAGCCATGGTATCAGCTCTGGCCCAGGCCCCAGCCCC

TGTCCCAGTCCTAGCCCCAGGCCCTCCTCAGGCTGTGGCCCCACCTGCCCCCAA

GCCCACCCAGGCTGGGGAAGGAACGCTGTCAGAGGCCCTGCTGCAGCTGCAGTT

TGATGATGAAGACCTGGGGGCCTTGCTTGGCAACAGCACAGACCCAGCTGTGTT

CACAGACCTGGCATCCGTCGACAACTCCGAGTTTCAGCAGCTGCTGAACCAGGG

CATACCTGTGGCCCCCCACACAACTGAGCCCATGCTGATGGAGTACCCTGAGGC

TATAACTCGCCTAGTGACAGGGGCCCAGAGGCCCCCCGACCCAGCTCCTGCTCC

ACTGGGGGCCCCGGGGCTCCCCAATGGCCTCCTTTCAGGAGATGAAGACTTCTC

CTCCATTGCGGACATGGACTTCTCAGCCCTGCTGAGTCAGATCAGCTCCTAAGG

GGGTGACGCCTGCCCTCCCCAGAGCACTGGGTTGCAGGGGATTGAAGCCCTCCA

AAAGCACTTACGGATTCTGGTGGGGTGTGTTCCAACTGCCCCCAACTTTGTGGA

TGTCTTCCTTGGAGGGGGGAGCCATATTTTATTCTTTTATTGTCAGTATCTGTA

TCTCTCTCTCTTTTTGGAGGTGCTTAAGCAGAAGCATTAACTTCTCTGGAAAGG

GGGGAGCTGGGGAAACTCAAACTTTTCCCCTGTCCTGATGGTCAGCTCCCTTCT

CTGTAGGGAACTCTGGGGTCCCCCATCCCCATCCTCCAGCTTCTGGTACTCTCC

TAGAGACAGAAGCAGGCTGGAGGTAAGGCCTTTGAGCCCACAAAGCCTTATCAA

GTGTCTTCCATCATGGATTCATTACAGCTTAATCAAAATAACGCCCCAGATACC

AGCCCCTGTATGGCACTGGCATTGTCCCTGTGCCTAACACCAGCGTTTGAGGGG

CTGGCCTTCCTGCCCTACAGAGGTCTCTGCCGGCTCTTTCCTTGCTCAACCATG

GCTGAAGGAAACCAGTGCAACAGCACTGGCTCTCTCCAGGATCCAGAAGGGGTT

TGGTCTGGGACTTCCTTGCTCTCCCTCTTCTCAAGTGCCTTAATAGTAGGGTAA

GTTGTTAAGAGTGGGGGAGAGCAGGCTGGCAGCTCTCCAGTCAGGAGGCATAGT

TTTTACTGAACAATCAAAGCACTTGGACTCTTGCTCTTTCTACTCTGAACTAAT

AAATCTGTTGCCAAGCTGG

Human RELA proto-oncogene, NF-kB subunit (RELA), transcript
variant X2, mRNA XM_011545207.1

(SEQ ID NO: 23)

ATTCCGGGCAGTGACGCGACGGCGGGCCGCGCGGCGCATTTCCGCCTCTGGCGA

ATGGCTCGTCTGTAGTGCACGCCGCGGGCCCAGCTGCGACCCCGGCCCCGCCCC

CGGGACCCCGGCCATGGACGAACTGTTCCCCCTCATCTTCCCGGCAGAGCCAGC

CCAGGCCTCTGGCCCCTATGTGGAGATCATTGAGCAGCCCAAGCAGCGGGGCAT

-continued

```
GCGCTTCCGCTACAAGTGCGAGGGGCGCTCCGCGGGCAGCATCCCAGGCGAGAG

GAGCACAGATACCACCAAGACCCACCCCACCATCAAGATCAATGGCTACACAGG

ACCAGGGACAGTGCGCATCTCCCTGGTCACCAAGGACCCTCCTCACCGGCCTCA

CCCCCACGAGCTTGTAGGAAAGGACTGCCGGGATGGCTTCTATGAGGCTGAGCT

CTGCCCGGACCGCTGCATCCACAGTTTCCAGAACCTGGGAATCCAGTGTGTGAA

GAAGCGGGACCTGGAGCAGGCTATCAGTCAGCGCATCCAGACCAACAACAACCC

CTTCCAAGTTCCTATAGAAGAGCAGCGTGGGGACTACGACCTGAATGCTGTGCG

GCTCTGCTTCCAGGTGACAGTGCGGGACCCATCAGGCAGGCCCCTCCGCCTGCC

GCCTGTCCTTTCTCATCCCATCTTTGACAATCACGATCGTCACCGGATTGAGGA

GAAACGTAAAAGGACATATGAGACCTTCAAGAGCATCATGAAGAAGAGTCCTTT

CAGCGGACCCACCGACCCCCGGCCTCCACCTCGACGCATTGCTGTGCCTTCCCG

CAGCTCAGCTTCTGTCCCCAAGCCAGCACCCCAGCCCTATCCCTTTACGTCATC

CCTGAGCACCATCAACTATGATGAGTTTCCCACCATGGTGTTTCCTTCTGGGCA

GATCAGCCAGGCCTCGGCCTTGGCCCCGGCCCCTCCCCAAGTCCTGCCCCAGGC

TCCAGCCCCTGCCCCTGCTCCAGCCATGGTATCAGCTCTGGCCCAGGCCCCAGC

CCCTGTCCCAGTCCTAGCCCCAGGCCCTCCTCAGGCTGTGGCCCCACCTGCCCC

CAAGCCCACCCAGGCTGGGGAAGGAACGCTGTCAGAGGCCCTGCTGCAGCTGCA

GTTTGATGATGAAGACCTGGGGGCCTTGCTTGGCAACAGCACAGACCCAGCTGT

GTTCACAGACCTGGCATCCGTCGACAACTCCGAGTTTCAGCAGCTGCTGAACCA

GGGCATACCTGTGGCCCCCCACACAACTGAGCCCATGCTGATGGAGTACCCTGA

GGCTATAACTCGCCTAGTGACAGGGGCCCAGAGGCCCCCCGACCCAGCTCCTGC

TCCACTGGGGGCCCCGGGGCTCCCCAATGGCCTCCTTTCAGGAGATGAAGACTT

CTCCTCCATTGCGGACATGGACTTCTCAGCCCTGCTGAGTCAGATCAGCTCCTA

AGGGGGTGACGCCTGCCCTCCCCAGAGCACTGGGTTGCAGGGGATTGAAGCCCT

CCAAAAGCACTTACGGATTCTGGTGGGGTGTGTTCCAACTGCCCCCAACTTTGT

GGATGTCTTCCTTGGAGGGGGGAGCCATATTTTATTCTTTTATTGTCAGTATCT

GTATCTCTCTCTCTTTTTGGAGGTGCTTAAGCAGAAGCATTAACTTCTCTGGAA

AGGGGGGAGCTGGGGAAACTCAAACTTTTCCCCTGTCCTGATGGTCAGCTCCCT

TCTCTGTAGGGAACTCTGGGGTCCCCCATCCCCATCCTCCAGCTTCTGGTACTC

TCCTAGAGACAGAAGCAGGCTGGAGGTAAGGCCTTTGAGCCCACAAAGCCTTAT

CAAGTGTCTTCCATCATGGATTCATTACAGCTTAATCAAAATAACGCCCCAGAT

ACCAGCCCCTGTATGGCACTGGCATTGTCCCTGTGCCTAACACCAGCGTTTGAG

GGGCTGGCCTTCCTGCCCTACAGAGGTCTCTGCCGGCTCTTTCCTTGCTCAACC

ATGGCTGAAGGAAACCAGTGCAACAGCACTGGCTCTCTCCAGGATCCAGAAGGG

GTTTGGTCTGGGACTTCCTTGCTCTCCCTCTTCTCAAGTGCCTTAATAGTAGGG

TAAGTTGTTAAGAGTGGGGGAGAGCAGGCTGGCAGCTCTCCAGTCAGGAGGCAT

AGTTTTTACTGAACAATCAAAGCACTTGGACTCTTGCTCTTTCTACTCTGAACT

AATAAATCTGTTGCCAAGCTGG
```

In some embodiments, the nucleic acid sequence encoding Rel-A (p65), as described herein, is at least 80% identical to the sequence of SEQ ID NO: 18, SEQ ID NO: 19, SEQ ID NO: 20. SEQ ID NO: 21, SEQ ID NO: 22, or SEQ ID NO: 23. In some embodiments, the nucleic acid sequence encoding Rel-A (p65) is 80%, 81%, 82%, 83%, 84%, 85%, 86%, 87%, 88%, 89%, 90%, 91%, 92%, 93%, 94%, 95%, 96%, 97%, 98%, or 99% identical to the sequence of SEQ ID NO: 18, SEQ ID NO: 19, SEQ ID NO: 20, SEQ ID NO: 21, SEQ ID NO: 22, or SEQ ID NO: 23. In some embodiments, the nucleic acid encoding Rel-A (p65), as described herein, can vary from the sequence of SEQ ID NO: 18, SEQ ID NO: 19, SEQ ID NO: 20, SEQ ID NO: 21, SEQ ID NO: 22, or SEQ ID NO: 23 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more nucleotides.

"Linkers" are short amino acid sequences created in nature to separate multiple domains in a single protein, and, generally, can be classified into three groups: flexible, rigid and cleavable. Chen, X., et al., 2013, Adv. Drug Deliv. Rev., 65, 1357-1369. Linkers can be natural or synthetic. A number of linkers are employed to realize the subject invention including "flexible linkers." The latter are rich in glycine. Klein et al., Protein Engineering, Design & Selection Vol. 27, No. 10, pp. 325-330, 2014; Priyanka et al., Protein Sci., 2013 February; 22(2): 153-167.

In some embodiments, the linker is a synthetic linker. A synthetic linker can have a length of from about 10 amino acids to about 200 amino acids, e.g., from 10 to 25 amino acids, from 25 to 50 amino acids, from 50 to 75 amino acids, from 75 to 100 amino acids, from 100 to 125 amino acids, from 125 to 150 amino acids, from 150 to 175 amino acids, or from 175 to 200 amino acids. A synthetic linker can have a length of from 10 to 30 amino acids, e.g., 10, 11, 12, 13, 14, 15, 16, 17, 18, 19, 20, 21, 22, 23, 24, 25, 26, 27, 28, 29, or 30 amino acids. A synthetic linker can have a length of from 30 to 50 amino acids, e.g., from 30 to 35 amino acids, from 35 to 40 amino acids, from 40 to 45 amino acids, or from 45 to 50 amino acids.

In some embodiments, the linker is a flexible linker. In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs. In some embodiments, the linker has one or more Gly-Gly-Gly-Ser (GGGS) sequences, e.g., 1, 2, 3, 4, 5, 6, 7, 8, 9, or 10 or more GGGS sequences. In some embodiments, the linker has one or more Gly-Gly-Gly-Gly-Ser (GGGGS) sequences, e.g., 1, 2, 3, 4, 5, 6, 7, 8, 9, or 10 or more GGGGS sequences. In some embodiments, the linker has one or more Gly-Gly-Ser-Gly (GGSG) sequences, e.g., 1, 2, 3, 4, 5, 6, 7, 8, 9, or 10 or more GGSG sequences. In some embodiments, the linker is GSAAAGGSGGSGGS (SEQ ID NO: 3). In some embodiments, the linker is GGGSGGGS (SEQ ID NO: 4). "Native or natural Notch" is meant to encompass all known forms of Notch receptors. In humans, 4 forms of Notch are known. Joanna Pancewicz: BMC Cancer 11(1):502•November 2011. The human Notch family includes four receptors and five ligands.

In some embodiments, the chimeric Notch receptor polypeptide contains all or a portion of human Notch1, Notch2, Notch3, or Notch4. In some embodiments, the chimeric Notch receptor polypeptide contains all or a portion of SEQ ID NO: 24, SEQ ID NO: 25, SEQ ID NO: 26, SEQ ID NO: 27, or SEQ ID NO: 28. In some embodiments, a "portion" of Notch comprises the three NLR domains, the transmembrane domain, and a short cytosolic fragment including the native Nuclear Localization Sequence (NLS) of Notch.

```
Human neurogenic locus notch homolog protein 1 preprotein
NP_0600687.3
                                              (SEQ ID NO: 24)
MPPLLAPLLCLALLPALAARGPRCSQPGETCLNGGKCEAANGTEACVCGGAFVG

PRCQDPNPCLSTPCKNAGTCHVVDRRGVADYACSCALGFSGPLCLTPLDNACLT

NPCRNGGTCDLLTLTEYKCRCPPGWSGKSCQQADPCASNPCANGGQCLPFEASY

ICHCPPSFHGPTCRQDVNECGQKPGLCRHGGTCHNEVGSYRCVCRATHTGPNCE

RPYVPCSPSPCQNGGTCRPTGDVTHECACLPGFTGQNCEENIDDCPGNNCKNGG

ACVDGVNTYNCRCPPEWTGQYCTEDVDECQLMPNACQNGGTCHNTHGGYNCVCV

NGWTGEDCSENIDDCASAACFHGATCHDRVASFYCECPHGRTGLLCHLNDACIS

NPCNEGSNCDTNPVNGKAICTCPSGYTGPACSQDVDECSLGANPCEHAGKCINT

LGSFECQCLQGYTGPRCEIDVNECVSNPCQNDATCLDQIGEFQCICMPGYEGVH

CEVNTDECASSPCLHNGRCLDKINEFQCECPTGFTGHLCQYDVDECASTPCKNG

AKCLDGPNTYTCVCTEGYTGTHCEVDIDECDPDPCHYGSCKDGVATFTCLCRPG

YTGHHCETNINECSSQPCRHGGTCQDRDNAYLCFCLKGTTGPNCEINLDDCASS

PCDSGTCLDKIDGYECACEPGYTGSMCNINIDECAGNPCHNGGTCEDGINGFTC

RCPEGYHDPTCLSEVNECNSNPCVHGACRDSLNGYKCDCDPGWSGTNCDINNNE

CESNPCVNGGTCKDMTSGYVCTCREGFSGPNCQTNINECASNPCLNQGTCIDDV

AGYKCNCLLPYTGATCEVVLAPCAPSPCRNGGECRQSEDYESFSCVCPTGWQGQ

TCEVDINECVLSPCRHGASCQNTHGGYRCHCQAGYSGRNCETDIDDCRPNPCHN

GGSCTDGINTAFCDCLPGFRGTFCEEDINECASDPCRNGANCTDCVDSYTCTCP

AGFSGIHCENNTPDCTESSCFNGGTCVDGINSFTCLCPPGFTGSYCQHDVNECD
```

-continued

SQPCLHGGTCQDGCGSYRCTCPQGYTGPNCQNLVHWCDSSPCKNGGKCWQTHTQ

YRCECPSGWTGLYCDVPSVSCEVAAQRQGVDVARLCQHGGLCVDAGNTHHCRCQ

AGYTGSYCEDLVDECSPSPCQNGATCTDYLGGYSCKCVAGYHGVNCSEEIDECL

SHPCQNGGTCLDLPNTYKCSCPRGTQGVHCEINVDDCNPPVDPVSRSPKCFNNG

TCVDQVGGYSCTCPPGFVGERCEGDVNECLSNPCDARGTQNCVQRVNDFHCECR

AGHTGRRCESVINGCKGKPCKNGGTCAVASNTARGFICKCPAGFEGATCENDAR

TCGSLRCLNGGTCISGPRSPTCLCLGPFTGPECQFPASSPCLGGNPCYNQGTCE

PTSESPFYRCLCPAKFNGLLCHILDYSFGGGAGRDIPPPLIEEACELPECQEDA

GNKVCSLQCNNHACGWDGGDCSLNFNDPWKNCTQSLQCWKYFSDGHCDSQCNSA

GCLFDGFDCQRAEGQCNPLYDQYCKDHFSDGHCDQGCNSAECEWDGLDCAEHVP

ERLAAGTLVVVVLMPPEQLRNSSFHFLRELSRVLHTNVVFKRDAHGQQMIFPYY

GREEELRKHPIKRAAEGWAAPDALLGQVKASLLPGGSEGGRRRRELDPMDVRGS

IVYLEIDNRQCVQASSQCFQSATDVAAFLGALASLGSLNIPYKIEAVQSETVEP

PPPAQLHFMYVAAAAFVLLFFVGCGVLLSRKRRRQHGQLWFPEGFKVSEASKKK

RREPLGEDSVGLKPLKNASDGALMDDNQNEWGDEDLETKKFRFEEPVVLPDLDD

QTDHRQWTQQHLDAADLRMSAMAPTPPQGEVDADCMDVNVRGPDGFTPLMIASC

SGGGLETGNSEEEEDAPAVISDFIYQGASLHNQTDRTGETALHLAARYSRSDAA

KRLLEASADANIQDNMGRTPLHAAVSADAQGVFQILIRNRATDLDARMHDGTTP

LILAARLAVEGMLEDLINSHADVNAVDDLGKSALHWAAAVNNVDAAVVLLKNGA

NKDMQNNREETPLFLAAREGSYETAKVLLDHFANRDITDHMDRLPRDIAQERMH

HDIVRLLDEYNLVRSPQLHGAPLGGTPTLSPPLCSPNGYLGSLKPGVQGKKVRK

PSSKGLACGSKEAKDLKARRKKSQDGKGCLLDSSGMLSPVDSLESPHGYLSDVA

SPPLLPSPFQQSPSVPLNHLPGMPDTHLGIGHLNVAAKPEMAALGGGGRLAFET

GPPRLSHLPVASGTSTVLGSSSGGALNFTVGGSTSLNGQCEWLSRLQSGMVPNQ

YNPLRGSVAPGPLSTQAPSLQHGMVGPLHSSLAASALSQMMSYQGLPSTRLATQ

PHLVQTQQVQPQNLQMQQQNLQPANIQQQQSLQPPPPPPQPHLGVSSAASGHLG

RSFLSGEPSQADVQPLGPSSLAVHTILPQESPALPTSLPSSLVPPVTAAQFLTP

PSQHSYSSPVDNTPSHQLQVPEHPFLTPSPESPDQWSSSSPHSNVSDWSEGVSS

PPTSMQSQIARIPEAFK

Human neurogenic locus notch homolog protein 2 isoform 1
preprotein NP_077719.2
                                        (SEQ ID NO: 25)
MPALRPALLWALLALWLCCAAPAHALQCRDGYEPCVNEGMCVTYHNGTGYCKCP

EGFLGEYCQHRDPCEKNRCQNGGTCVAQAMLGKATCRCASGFTGEDCQYSTSHP

CFVSRPCLNGGTCHMLSRDTYECTCQVGFTGKECQWTDACLSHPCANGSTCTTV

ANQFSCKCLTGFTGQKCETDVNECDIPGHCQHGGTCLNLPGSYQCQCPQGETGQ

YCDSLYVPCAPSPCVNGGTCRQTGDFTFECNCLPGFEGSTCERNIDDCPNHRCQ

NGGVCVDGVNTYNCRCPPQWTGQFCTEDVDECLLQPNACQNGGTCANRNGGYGC

VCVNGWSGDDCSENIDDCAFASCTPGSTCIDRVASFSCMCPEGKAGLLCHLDDA

CISNPCHKGALCDTNPLNGQYICTCPQGYKGADCTEDVDECAMANSNPCEHAGK

CVNTDGAFHCECLKGYAGPRCEMDINECHSDPCQNDATCLDKIGGFTCLCMPGF

KGVHCELEINECQSNPCVNNGQCVDKVNRFQCLCPPGFTGPVCQIDIDDCSSTP

CLNGAKCIDHPNGYECQCATGFTGVLCEENIDNCDPDPCHHGQCQDGIDSYTCI

CNPGYMGAICSDQIDECYSSPCLNDGRCIDLVNGYQCNCQPGTSGVNCEINFDD

CASNPCIHGICMDGINRYSCVCSPGFTGQRCNIDIDECASNPCRKGATCINGVN

GFRCICPEGPHHPSCYSQVNECLSNPCIHGNCTGGLSGYKCLCDAGWVGINCEV

DKNECLSNPCQNGGTCDNLVNGYRCTCKKGFKGYNCQVNIDECASNPCLNQGTC

FDDISGYTCHCVLPYTGKNCQTVLAPCSPNPCENAAVCKESPNFESYTCLCAPG

WQGQRCTIDIDECISKPCMNHGLCHNTQGSYMCECPPGFSGMDCEEDIDDCLAN

PCQNGGSCMDGVNTFSCLCLPGFTGDKCQTDMNECLSEPCKNGGTCSDYVNSYT

CKCQAGFDGVHCENNINECTESSCFNGGTCVDGINSFSCLCPVGFTGSFCLHEI

NECSSHPCLNEGTCVDGLGTYRCSCPLGYTGKNCQTLVNLCSRSPCKNKGTCVQ

KKAESQCLCPSGWAGAYCDVPNVSCDIAASRRGVLVEHLCQHSGVCINAGNTHY

CQCPLGYTGSYCEEQLDECASNPCQHGATCSDFIGGYRCECVPGYQGVNCEYEV

DECQNQPCQNGGTCIDLVNHFKCSCPPGTRGLLCEENIDDCARGPHCLNGGQCM

DRIGGYSCRCLPGFAGERCEGDINECLSNPCSSEGSLDCIQLTNDYLCVCRSAF

TGRHCETFVDVCPQMPCLNGGTCAVASNMPDGFICRCPPGFSGARCQSSCGQVK

CRKGEQCVHTASGPRCFCPSPRDCESGCASSPCQHGGSCHPQRQPPYYSCQCAP

PFSGSRCELYTAPPSTPPATCLSQYCADKARDGVCDEACNSHACQWDGGDCSLT

MENPWANCSSPLPCWDYINNQCDELCNTVECLFDNFECQGNSKTCKYDKYCADH

FKDNHCDQGCNSEECGWDGLDCAADQPENLAEGTLVIVVLMPPEQLLQDARSFL

RALGTLLHTNLRIKRDSQGELMVYPYYGEKSAAMKKQRMTRRSLPGEQEQEVAG

SKVFLEIDNRQCVQDSDHCFKNTDAAAALLASHAIQGTLSYPLVSVVSESLTPE

RTQLLYLLAVAVVIILFIILLGVIMAKRKRKHGSLWLPEGFTLRRDASNHKRRE

PVGQDAVGLKNLSVQVSEANLIGTGTSEHWVDDEGPQPKKVKAEDEALLSEEDD

PIDRRPWTQQHLEAADIRRTPSLALTPPQAEQEVDVLDVNVRGPDGCTPLMLAS

LRGGSSDLSDEDEDAEDSSANIITDLVYQGASLQAQTDRTGEMALHLAARYSRA

DAAKRLLDAGADANAQDNMGRCPLHAAVAADAQGVFQILIRNRVTDLDARMNDG

TTPLILAARLAVEGMVAELINCQADVNAVDDHGKSALHWAAAVNNVEATLLLLK

NGANRDMQDNKEETPLFLAAREGSYEAAKILLDHFANRDITDHMDRLPRDVARD

RMHHDIVRLLDEYNVTPSPPGTVLTSALSPVICGPNRSFLSLKHTPMGKKSRRP

SAKSTMPTSLPNLAKEAKDAKGSRRKKSLSEKVQLSESSVTLSPVDSLESPHTY

VSDTTSSPMITSPGILQASPNPMLATAAPPAPVHAQHALSFSNLHEMQPLAHGA

STVLPSVSQLLSHHHIVSPGSGSAGSLSRLHPVPVPADWMNRMEVNETQYNEMF

GMVLAPAEGTHPGIAPQSRPPEGKHITTPREPLPPIVTFQLIPKGSIAQPAGAP

QPQSTCPPAVAGPLPTMYQIPEMARLPSVAFPTAMMPQQDGQVAQTILPAYHPF

PASVGKYPTPPSQHSYASSNAAERTPSHSGHLQGEHPYLTPSPESPDQWSSSSP

HSASDWSDVTTSPTPGGAGGGQRGPGTHMSEPPHNNMQVYA

Human neurogenic locus notch homolog protein 2 isoform 2
precursor NP_001186930.1
                                              (SEQ ID NO: 26)
MPALRPALLWALLALWLCCAAPAHALQCRDGYEPCVNEGMCVTYHNGTGYCKCP

EGFLGEYCQHRDPCEKNRCQNGGTCVAQAMLGKATCRCASGFTGEDCQYSTSHP

CFVSRPCLNGGTCHMLSRDTYECTCQVGFTGKECQWTDACLSHPCANGSTCTTV

-continued

ANQFSCKCLTGFTGQKCETDVNECDIPGHCQHGGTCLNLPGSYQCQCPQGFTGQ

YCDSLYVPCAPSPCVNGGTCRQTGDFTFECNCLPGFEGSTCERNIDDCPNHRCQ

NGGVCVDGVNTYNCRCPPQWTGQFCTEDVDECLLQPNACQNGGTCANRNGGYGC

VCVNGWSGDDCSENIDDCAFASCTPGSTCIDRVASFSCMCPEGKAGLLCHLDDA

CISNPCHKGALCDTNPLNGQYICTCPQGYKGADCTEDVDECAMANSNPCEHAGK

CVNTDGAFHCECLKGYAGPRCEMDINECHSDPCQNDATCLDKIGGFTCLCMPGF

KGVHCELEINECQSNPCVNNGQCVDKVNRFQCLCPPGFTGPVCQIDIDDCSSTP

CLNGAKCIDHPNGYECQCATGFTGVLCEENIDNCDPDPCHHGQCQDGIDSYTCI

CNPGYMGAICSDQIDECYSSPCLNDGRCIDLVNGYQCNCQPGTSGVNCEINFDD

CASNPCIHGICMDGINRYSCVCSPGFTGQRCNIDIDECASNPCRKGATCINGVN

GFRCICPEGPHHPSCYSQVNECLSNPCIHGNCTGGLSGYKCLCDAGWVGINCEV

DKNECLSNPCQNGGTCDNLVNGYRCTCKKGFKGYNCQVNIDECASNPCLNQGTC

FDDISGYTCHCVLPYTGKNCQTVLAPCSPNPCENAAVCKESPNFESYTCLCAPG

WQGQRCTIDIDECISKPCMNHGLCHNTQGSYMCECPPGFSGMDCEEDIDDCLAN

PCQNGGSCMDGVNTFSCLCLPGFTGDKCQTDMNECLSEPCKNGGTCSDYVNSYT

CKCQAGFDGVHCENNINECTESSCFNGGTCVDGINSFSCLCPVGFTGSFCLHEI

NECSSHPCLNEGTCVDGLGTYRCSCPLGYTGKNCQTLVNLCSRSPCKNKGTCVQ

KKAESQCLCPSGWAGAYCDVPNVSCDIAASRRGVLVEHLCQHSGVCINAGNTHY

CQCPLGYTGSYCEEQLDECASNPCQHGATCSDFIGGYRCECVPGYQGVNCEYEV

DECQNQPCQNGGTCIDLVNHFKCSCPPGTRGMKSSLSIFHPGHCLKL

Human neurogenic locus notch homolog protein 3 precursor
NP_000426.2

(SEQ ID NO: 27)

MGPGARGRRRRRRPMSPPPPPPPVRALPLLLLLAGPGAAAPPCLDGSPCANGGR

CTQLPSREAACLCPPGWVGERCQLEDPCHSGPCAGRGVCQSSVVAGTARFSCRC

PRGFRGPDCSLPDPCLSSPCAHGARCSVGPDGRFLCSCPPGYQGRSCRSDVDEC

RVGEPCRHGGTCLNTPGSFRCQCPAGYTGPLCENPAVPCAPSPCRNGGTCRQSG

DLTYDCACLPGFEGQNCEVNVDDCPGHRCLNGGTCVDGVNTYNCQCPPEWTGQF

CTEDVDECQLQPNACHNGGTCFNTLGGHSCVCVNGWTGESCSQNIDDCATAVCF

HGATCHDRVASFYCACPMGKTGLLCHLDDACVSNPCHEDAICDTNPVNGRAICT

CPPGFTGGACDQDVDECSIGANPCEHLGRCVNTQGSFLCQCGRGYTGPRCETDV

NECLSGPCRNQATCLDRIGQFTCICMAGFTGTYCEVDIDECQSSPCVNGGVCKD

RVNGFSCTCPSGFSGSTCQLDVDECASTPCRNGAKCVDQPDGYECRCAEGFEGT

LCDRNVDDCSPDPCHHGRCVDGIASFSCACAPGYTGTRCESQVDECRSQPCRHG

GKCLDLVDKYLCRCPSGTTGVNCEVNIDDCASNPCTFGVCRDGINRYDCVCQPG

FTGPLCNVEINECASSPCGEGGSCVDGENGFRCLCPPGSLPPLCLPPSHPCAHE

PCSHGICYDAPGGFRCVCEPGWSGPRCSQSLARDACESQPCRAGGTCSSDGMGF

HCTCPPGVQGRQCELLSPCTPNPCEHGGRCESAPGQLPVCSCPQGWQGPRCQQD

VDECAGPAPCGPHGICTNLAGSFSCTCHGGYTGPSCDQDINDCDPNPCLNGGSC

QDGVGSFSCSCLPGFAGPRCARDVDECLSNPCGPGTCTDHVASFTCTCPPGYGG

FHCEQDLPDCSPSSCFNGGTCVDGVNSFSCLCRPGYTGAHCQHEADPCLSRPCL

HGGVCSAAHPGFRCTCLESFTGPQCQTLVDWCSRQPCQNGGRCVQTGAYCLCPP

-continued

GWSGRLCDIRSLPCREAAAQIGVRLEQLCQAGGQCVDEDSSHYCVCPEGRTGSH

CEQEVDPCLAQPCQHGGTCRGYMGGYMCECLPGYNGDNCEDDVDECASQPCQHG

GSCIDLVARYLCSCPPGTLGVLCEINEDDCGPGPPLDSGPRCLHNGTCVDLVGG

FRCTCPPGYTGLRCEADINECRSGACHAAHTRDCLQDPGGGFRCLCHAGFSGPR

CQTVLSPCESQPCQHGGQCRPSPGPGGGLTFTCHCAQPFWGPRCERVARSCREL

QCPVGVPCQQTPRGPRCACPPGLSGPSCRSFPGSPPGASNASCAAAPCLHGGSC

RPAPLAPFFRCACAQGWTGPRCEAPAAAPEVSEEPRCPRAACQAKRGDQRCDRE

CNSPGCGWDGGDCSLSVGDPWRQCEALQCWRLFNNSRCDPACSSPACLYDNFDC

HAGGRERTCNPVYEKYCADHFADGRCDQGCNTEECGWDGLDCASEVPALLARGV

LVLTVLLPPEELLRSSADFLQRLSAILRTSLRFRLDAHGQAMVFPYHRPSPGSE

PRARRELAPEVIGSVVMLEIDNRLCLQSPENDHCFPDAQSAADYLGALSAVERL

DFPYPLRDVRGEPLEPPEPSVPLLPLLVAGAVLLLVILVLGVMVARRKREHSTL

WFPEGFSLHKDVASGHKGRREPVGQDALGMKNMAKGESLMGEVATDWMDTECPE

AKRLKVEEPGMGAEEAVDCRQWTQHHLVAADIRVAPAMALTPPQGDADADGMDV

NVRGPDGFTPLMLASFCGGALEPMPTEEDEADDTSASIISDLICQGAQLGARTD

RTGETALHLAARYARADAAKRLLDAGADTNAQDHSGRTPLHTAVTADAQGVFQI

LIRNRSTDLDARMADGSTALILAARLAVEGMVEELIASHADVNAVDELGKSALH

WAAAVNNVEATLALLKNGANKDMQDSKEETPLFLAAREGSYEAAKLLLDHEANR

EITDHLDRLPRDVAQERLHQDIVRLLDQPSGPRSPPGPHGLGPLLCPPGAFLPG

LKAAQSGSKKSRRPPGKAGLGPQGPRGRGKKLTLACPGPLADSSVTLSPVDSLD

SPRPFGGPPASPGGFPLEGPYAAATATAVSLAQLGGPGRAGLGRQPPGGCVLSL

GLLNPVAVPLDWARLPPPAPPGPSFLLPLAPGPQLLNPGTPVSPQERPPPYLAV

PGHGEEYPAAGAHSSPPKARFLRVPSEHPYLTPSPESPEHWASPSPPSLSDWSE

STPSPATATGAMATTTGALPAQPLPLSVPSSLAQAQTQLGPQPEVTPKRQVLA

Human neurogenic locus notch homolog protein 4 preprotein
NP_004548.3
                                                (SEQ ID NO: 28)
MQPPSLLLLLLLLLLLCVSVVRPRGLLCGSFPEPCANGGTCLSLSLGQGTCQCA

PGFLGETCQFPDPCQNAQLCQNGGSCQALLPAPLGLPSSPSPLTPSFLCTCLPG

FTGERCQAKLEDPCPPSFCSKRGRCHIQASGRPQCSCMPGWTGEQCQLRDFCSA

NPCVNGGVCLATYPQIQCHCPPGFEGHACERDVNECFQDPGPCPKGTSCHNTLG

SFQCLCPVGQEGPRCELRAGPCPPRGCSNGGTCQLMPEKDSTFHLCLCPPGFIG

PDCEVNPDNCVSHQCQNGGTCQDGLDTYTCLCPETWTGWDCSEDVDECETQGPP

HCRNGGTCQNSAGSFHCVCVSGWGGTSCEENLDDCIAATCAPGSTCIDRVGSFS

CLCPPGRTGLLCHLEDMCLSQPCHGDAQCSTNPLTGSTLCLCQPGYSGPTCHQD

LDECLMAQQGPSPCEHGGSCLNTPGSFNCLCPPGYTGSRCEADHNECLSQPCHP

GSTCLDLLATFHCLCPPGLEGQLCEVETNECASAPCLNHADCHDLLNGFQCICL

PGFSGTRCEEDIDECRSSPCANGGQCQDQPGAFHCKCLPGFEGPRCQTEVDECL

SDPCPVGASCLDLPGAFFCLCPSGFTGQLCEVPLCAPNLCQPKQICKDQKDKAN

CLCPDGSPGCAPPEDNCTCHHGHCQRSSCVCDVGWTGPECEAELGGCISAPCAH

GGTCYPQPSGYNCTCPTGYTGPTCSEEMTACHSGPCLNGGSCNPSPGGYYCTCP

PSHTGPQCQTSTDYCVSAPCFNGGTCVNRPGTFSCLCAMGFQGPRCEGKLRPSC

-continued

```
ADSPCRNRATCQDSPQGPRCLCPTGYTGGSCQTLMDLCAQKPCPRNSHCLQTGP

SFHCLCLQGWTGPLCNLPLSSCQKAALSQGIDVSSLCHNGGLCVDSGPSYFCHC

PPGFQGSLCQDHVNPCESRPCQNGATCMAQPSGYLCQCAPGYDGQNCSKELDAC

QSQPCHNHGTCTPKPGGFHCACPPGFVGLRCEGDVDECLDQPCHPTGTAACHSL

ANAFYCQCLPGHTGQWCEVEIDPCHSQPCFHGGTCEATAGSPLGFICHCPKGFE

GPTCSHRAPSCGFHHCHHGGLCLPSPKPGFPPRCACLSGYGGPDCLTPPAPKGC

GPPSPCLYNGSCSETTGLGGPGFRCSCPHSSPGPRCQKPGAKGCEGRSGDGACD

AGCSGPGGNWDGGDCSLGVPDPWKGCPSHSRCWLLFRDGQCHPQCDSEECLFDG

YDCETPPACTPAYDQYCHDHFHNGHCEKGCNTAECGWDGGDCRPEDGDPEWGPS

LALLVVLSPPALDQQLFALARVLSLTLRVGLWVRKDRDGRDMVYPYPGARAEEK

LGGTRDPTYQERAAPQTQPLGKETDSLSAGFVVVMGVDLSRCGPDHPASRCPWD

PGLLLRFLAAMAAVGALEPLLPGPLLAVHPHAGTAPPANQLPWPVLCSPVAGVI

LLALGALLVLQLIRRRRREHGALWLPPGFTRRPRTQSAPHRRRPPLGEDSIGLK

ALKPKAEVDEDGVVMCSGPEEGEEVGQAEETGPPSTCQLWSLSGGCGALPQAAM

LTPPQESEMEAPDLDTRGPDGVTPLMSAVCCGEVQSGTFQGAWLGCPEPWEPLL

DGGACPQAHTVGTGETPLHLAARFSRPTAARRLLEAGANPNQPDRAGRTPLHAA

VAADAREVCQLLLRSRQTAVDARTEDGTTPLMLAARLAVEDLVEELIAAQADVG

ARDKWGKTALHWAAAVNNARAARSLLQAGADKDAQDNREQTPLFLAAREGAVEV

AQLLLGLGAARELRDQAGLAPADVAHQRNHWDLLTLLEGAGPPEARHKATPGRE

AGPFPRARTVSVSVPPHGGGALPRCRTLSAGAGPRGGGACLQARTWSVDLAARG

GGAYSHCRSLSGVGAGGGPTPRGRRFSAGMRGPRPNPAIMRGRYGVAAGRGGRV

STDDWPCDWVALGACGSASNIPIPPPCLTPSPERGSPQLDCGPPALQEMPINQG

GEGKK
```

In some embodiments, the Notch core of the chimeric Notch receptor polypeptide contains a portion of SEQ ID NO: 24, SEQ ID NO: 25, SEQ ID NO: 26, SEQ ID NO: 27, or SEQ ID NO: 28. In some embodiments, the chimeric Notch receptor polypeptide contains 50 to 1000 amino acids of SEQ ID NO: 24, SEQ ID NO: 25, SEQ ID NO: 26, SEQ ID NO: 27, or SEQ ID NO: 28. In some embodiments, the chimeric Notch receptor polypeptide contains 50 to 900 amino acids, 100 to 800 amino acids, 200 to 700 amino acids, 300 to 600 amino acids, 400 to 500 amino acids of SEQ ID NO: 24, SEQ ID NO: 25, SEQ ID NO: 26, SEQ ID NO: 27, or SEQ ID NO: 28. In some embodiments, the chimeric Notch receptor polypeptide contains amino acids 1374 to 1734 of SEQ ID NO: 27.

In some embodiments, the amino acid sequence of Notch, as described herein, is at least 80% identical to a corre-sponding amino acid sequence in SEQ ID NO: 24, SEQ ID NO: 25, SEQ ID NO: 26, SEQ ID NO: 27, or SEQ ID NO: 28. In some embodiments, the amino acid sequence of Notch is 80%, 81%, 82%, 83%, 84%, 85%, 86%, 87%, 88%, 89%, 90%, 91%, 92%, 93%, 94%, 95%, 96%, 97%, 98%, or 99% identical to a corresponding amino acid sequence in SEQ ID NO: 24, SEQ ID NO: 25, SEQ ID NO: 26, SEQ ID NO: 27, or SEQ ID NO: 28. In some embodiments, the amino acid sequence of Notch, as described herein, can vary from the amino acid sequence of SEQ ID NO: 24, SEQ ID NO: 25, SEQ ID NO: 26, SEQ ID NO: 27, or SEQ ID NO: 28 by 1 to 50 amino acids, e.g., 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 amino acids.

In some embodiments, the mRNA sequence of Notch, as described herein, is SEQ ID NO: 29, SEQ ID NO: 30, SEQ ID NO: 31, SEQ ID NO: 32, or SEQ ID NO: 33.

```
Human notch 1 (NOTCH1) mRNA NM_017617.4
                                            (SEQ ID NO: 29)
ATGCCGCCGCTCCTGGCGCCCCTGCTCTGCCTGGCGCTGCTGCCCGCGCTCGCC

GCACGAGGCCCGCGATGCTCCCAGCCCGGTGAGACCTGCCTGAATGGCGGGAAG

TGTGAAGCGGCCAATGGCACGGAGGCCTGCGTCTGTGGCGGGGCCTTCGTGGGC

CCGCGATGCCAGGACCCCAACCCGTGCCTCAGCACCCCCTGCAAGAACGCCGGG
```

-continued

```
ACATGCCACGTGGTGGACCGCAGAGGCGTGGCAGACTATGCCTGCAGCTGTGCC

CTGGGCTTCTCTGGGCCCCTCTGCCTGACACCCCTGGACAATGCCTGCCTCACC

AACCCCTGCCGCAACGGGGGCACCTGCGACCTGCTCACGCTGACGGAGTACAAG

TGCCGCTGCCCGCCCGGCTGGTCAGGGAAATCGTGCCAGCAGGCTGACCCGTGC

GCCTCCAACCCCTGCGCCAACGGTGGCCAGTGCCTGCCCTTCGAGGCCTCCTAC

ATCTGCCACTGCCCACCCAGCTTCCATGGCCCCACCTGCCGGCAGGATGTCAAC

GAGTGTGGCCAGAAGCCCGGGCTTTGCCGCCACGGAGGCACCTGCCACAACGAG

GTCGGCTCCTACCGCTGCGTCTGCCGCGCCACCCACACTGGCCCCAACTGCGAG

CGGCCCTACGTGCCCTGCAGCCCCTCGCCCTGCCAGAACGGGGGCACCTGCCGC

CCCACGGGCGACGTCACCCACGAGTGTGCCTGCCTGCCAGGCTTCACCGGCCAG

AACTGTGAGGAAAATATCGACGATTGTCCAGGAAACAACTGCAAGAACGGGGGT

GCCTGTGTGGACGGCGTGAACACCTACAACTGCCGCTGCCCGCCAGAGTGGACA

GGTCAGTACTGTACCGAGGATGTGGACGAGTGCCAGCTGATGCCAAATGCCTGC

CAGAACGGCGGGGACCTGCCACAACACCCACGGTGGCTACAACTGCGTGTGTGTC

AACGGCTGGACTGGTGAGGACTGCAGCGAGAACATTGATGACTGTGCCAGCGCC

GCCTGCTTCCACGGCGCCACCTGCCATGACCGTGTGGCCTCCTTCTACTGCGAG

TGTCCCCATGGCCGCACAGGTCTGCTGTGCCACCTCAACGACGCATGCATCAGC

AACCCCTGTAACGAGGGCTCCAACTGCGACACCAACCCTGTCAATGGCAAGGCC

ATCTGCACCTGCCCCTCGGGGTACACGGGCCCGGCCTGCAGCCAGGACGTGGAT

GAGTGCTCGCTGGGTGCCAACCCCTGCGAGCATGCGGGCAAGTGCATCAACACG

CTGGGCTCCTTCGAGTGCCAGTGTCTGCAGGGCTACACGGGCCCCCGATGCGAG

ATCGACGTCAACGAGTGCGTCTCGAACCCGTGCCAGAACGACGCCACCTGCCTG

GACCAGATTGGGGAGTTCCAGTGCATCTGCATGCCCGGCTACGAGGGTGTGCAC

TGCGAGGTCAACACAGACGAGTGTGCCAGCAGCCCCTGCCTGCACAATGGCCGC

TGCCTGGACAAGATCAATGAGTTCCAGTGCGAGTGCCCCACGGGCTTCACTGGG

CATCTGTGCCAGTACGATGTGGACGAGTGTGCCAGCACCCCCTGCAAGAATGGT

GCCAAGTGCCTGGACGGACCCAACACTTACACCTGTGTGTGCACGGAAGGGTAC

ACGGGGACGCACTGCGAGGTGGACATCGATGAGTGCGACCCCGACCCCTGCCAC

TACGGCTCCTGCAAGGACGGCGTCGCCACCTTCACCTGCCTCTGCCGCCCAGGC

TACACGGGCCACCACTGCGAGACCAACATCAACGAGTGCTCCAGCCAGCCCTGC

CGCCACGGGGGCACCTGCCAGGACCGCGACAACGCCTACCTCTGCTTCTGCCTG

AAGGGGACCACAGGACCCAACTGCGAGATCAACCTGGATGACTGTGCCAGCAGC

CCCTGCGACTCGGGCACCTGTCTGGACAAGATCGATGGCTACGAGTGTGCCTGT

GAGCCGGGCTACACAGGGAGCATGTGTAACATCAACATCGATGAGTGTGCGGGC

AACCCCTGCCACAACGGGGGCACCTGCGAGGACGGCATCAATGGCTTCACCTGC

CGCTGCCCCGAGGGCTACCACGACCCCACCTGCCTGTCTGAGGTCAATGAGTGC

AACAGCAACCCCTGCGTCCACGGGGCCTGCCGGGACAGCCTCAACGGGTACAAG

TGCGACTGTGACCCTGGGTGGAGTGGGACCAACTGTGACATCAACAACAATGAG

TGTGAATCCAACCCTTGTGTCAACGGCGGCACCTGCAAAGACATGACCAGTGGC

TACGTGTGCACCTGCCGGGAGGGCTTCAGCGGTCCCAACTGCCAGACCAACATC

AACGAGTGTGCGTCCAACCCCATGTCTGAACCAGGGCACGTGTATTGACGACGTT
```

-continued

```
GCCGGGTACAAGTGCAACTGCCTGCTGCCCTACACAGGTGCCACGTGTGAGGTG

GTGCTGGCCCCGTGTGCCCCCAGCCCCTGCAGAAACGGCGGGGAGTGCAGGCAA

TCCGAGGACTATGAGAGCTTCTCCTGTGTCTGCCCCACGGGCTGGCAAGGGCAG

ACCTGTGAGGTCGACATCAACGAGTGCGTTCTGAGCCCGTGCCGGCACGGCGCA

TCCTGCCAGAACACCCACGGCGGCTACCGCTGCCACTGCCAGGCCGGCTACAGT

GGGCGCAACTGCGAGACCGACATCGACGACTGCCGGCCCAACCCGTGTCACAAC

GGGGGCTCCTGCACAGACGGCATCAACACGGCCTTCTGCGACTGCCTGCCCGGC

TTCCGGGGCACTTTCTGTGAGGAGGACATCAACGAGTGTGCCAGTGACCCCTGC

CGCAACGGGGCCAACTGCACGGACTGCGTGGACAGCTACACGTGCACCTGCCCC

GCAGGCTTCAGCGGGATCCACTGTGAGAACAACACGCCTGACTGCACAGAGAGC

TCCTGCTTCAACGGTGGCACCTGCGTGGACGGCATCAACTCGTTCACCTGCCTG

TGTCCACCCGGCTTCACGGGCAGCTACTGCCAGCACGATGTCAATGAGTGCGAC

TCACAGCCCTGCCTGCATGGCGGCACCTGTCAGGACGGCTGCGGCTCCTACAGG

TGCACCTGCCCCCAGGGCTACACTGGCCCCAACTGCCAGAACCTTGTGCACTGG

TGTGACTCCTCGCCCTGCAAGAACGGCGGCAAATGCTGGCAGACCCACACCCAG

TACCGCTGCGAGTGCCCCAGCGGCTGGACCGGCCTTTACTGCGACGTGCCCAGC

GTGTCCTGTGAGGTGGCTGCGCAGCGACAAGGTGTTGACGTTGCCCGCCTGTGC

CAGCATGGAGGGCTCTGTGTGGACGCGGGCAACACGCACCACTGCCGCTGCCAG

GCGGGCTACACAGGCAGCTACTGTGAGGACCTGGTGGACGAGTGCTCACCCAGC

CCCTGCCAGAACGGGGCCACCTGCACGGACTACCTGGGCGGCTACTCCTGCAAG

TGCGTGGCCGGCTACCACGGGGTGAACTGCTCTGAGGAGATCGACGAGTGCCTC

TCCCACCCCTGCCAGAACGGGGGCACCTGCCTCGACCTCCCCAACACCTACAAG

TGCTCCTGCCCACGGGGCACTCAGGGTGTGCACTGTGAGATCAACGTGGACGAC

TGCAATCCCCCCGTTGACCCCGTGTCCCGGAGCCCCAAGTGCTTTAACAACGGC

ACCTGCGTGGACCAGGTGGGCGGCTACAGCTGCACCTGCCCCGCCGGGCTTCGTG

GGTGAGCGCTGTGAGGGGGATGTCAACGAGTGCCTGTCCAATCCCTGCGACGCC

CGTGGCACCCAGAACTGCGTGCAGCGCGTCAATGACTTCCACTGCGAGTGCCGT

GCTGGTCACACCGGGCGCCGCTGCGAGTCCGTCATCAATGGCTGCAAAGGCAAG

CCCTGCAAGAATGGGGGCACCTGCGCCGTGGCCTCCAACACCGCCCGCGGGTTC

ATCTGCAAGTGCCCTGCGGGCTTCGAGGGCGCCACGTGTGAGAATGACGCTCGT

ACCTGCGGCAGCCTGCGCTGCCTCAACGGCGGCACATGCATCTCCGGCCCGCGC

AGCCCCACCTGCCTGTGCCTGGGCCCCTTCACGGGCCCCGAATGCCAGTTCCCG

GCCAGCAGCCCCTGCCTGGGCGGCAACCCCTGCTACAACCAGGGGACCTGTGAG

CCCACATCCGAGAGCCCCTTCTACCGTTGCCTGTGCCCCGCCAAATTCAACGGG

CTCTTGTGCCACATCCTGGACTACAGCTTCGGGGGTGGGGCCGGGCGCGACATC

CCCCCGCCGCTGATCGAGGAGGCGTGCGAGCTGCCCGAGTGCCAGGAGGACGCG

GGCAACAAGGTCTGCAGCCTGCAGTGCAACAACCACGCGTGCGGCTGGGACGGC

GGTGACTGCTCCCTCAACTTCAATGACCCCTGGAAGAACTGCACGCGAGTCTCTG

CAGTGCTGGAAGTACTTCAGTGACGGCCACTGTGACAGCCAGTGCAACTCAGCC

GGCTGCCTCTTCGACGGCTTTGACTGCCAGCGTGCGGAAGGCCAGTGCAACCCC
```

-continued
CTGTACGACCAGTACTGCAAGGACCACTTCAGCGACGGGCACTGCGACCAGGGC

TGCAACAGCGCGGAGTGCGAGTGGGACGGGCTGGACTGTGCGGAGCATGTACCC

GAGAGGCTGGCGGCCGGCACGCTGGTGGTGGTGGTGCTGATGCCGCCGGAGCAG

CTGCGCAACAGCTCCTTCCACTTCCTGCGGGAGCTCAGCCGCGTGCTGCACACC

AACGTGGTCTTCAAGCGTGACGCACACGGCCAGCAGATGATCTTCCCCTACTAC

GGCCGCGAGGAGGAGCTGCGCAAGCACCCCATCAAGCGTGCCGCCGAGGGCTGG

GCCGCACCTGACGCCCTGCTGGGCCAGGTGAAGGCCTCGCTGCTCCCTGGTGGC

AGCGAGGGTGGGCGGCGGCGGAGGGAGCTGGACCCCATGGACGTCCGCGGCTCC

ATCGTCTACCTGGAGATTGACAACCGGCAGTGTGTGCAGGCCTCCTCGCAGTGC

TTCCAGAGTGCCACCGACGTGGCCGCATTCCTGGGAGCGCTCGCCTCGCTGGGC

AGCCTCAACATCCCCTACAAGATCGAGGCCGTGCAGAGTGAGACCGTGGAGCCG

CCCCCGCCGGCGCAGCTGCACTTCATGTACGTGGCGGCGGCCGCCTTTGTGCTT

CTGTTCTTCGTGGGCTGCGGGGTGCTGCTGTCCCGCAAGCGCCGGCGGCAGCAT

GGCCAGCTCTGGTTCCCTGAGGGCTTCAAAGTGTCTGAGGCCAGCAAGAAGAAG

CGGCGGGAGCCCCTCGGCGAGGACTCCGTGGGCCTCAAGCCCCTGAAGAACGCT

TCAGACGGTGCCCTCATGGACGACAACCAGAATGAGTGGGGGGACGAGGACCTG

GAGACCAAGAAGTTCCGGTTCGAGGAGCCCGTGGTTCTGCCTGACCTGGACGAC

CAGACAGACCACCGGCAGTGGACTCAGCAGCACCTGGATGCCGCTGACCTGCGC

ATGTCTGCCATGGCCCCCACACCGCCCCAGGGTGAGGTTGACGCCGACTGCATG

GACGTCAATGTCCGCGGGCCTGATGGCTTCACCCCGCTCATGATCGCCTCCTGC

AGCGGGGGCGGCCTGGAGACGGGCAACAGCGAGGAAGAGGAGGACGCGCCGGCC

GTCATCTCCGACTTCATCTACCAGGGCGCCAGCCTGCACAACCAGACAGACCGC

ACGGGCGAGACCGCCTTGCACCTGGCCGCCCGCTACTCACGCTCTGATGCCGCC

AAGCGCCTGCTGGAGGCCAGCGCAGATGCCAACATCCAGGACAACATGGGCCGC

ACCCCGCTGCATGCGGCTGTGTCTGCCGACGCACAAGGTGTCTTCCAGATCCTG

ATCCGGAACCGAGCCACAGACCTGGATGCCCGCATGCATGATGGCACGACGCCA

CTGATCCTGGCTGCCCGCCTGGCCGTGGAGGGCATGCTGGAGGACCTCATCAAC

TCACACGCCGACGTCAACGCCGTAGATGACCTGGGCAAGTCCGCCCTGCACTGG

GCCGCCGCCGTGAACAATGTGGATGCCGCAGTTGTGCTCCTGAAGAACGGGGCT

AACAAAGATATGCAGAACAACAGGGAGGAGACACCCCTGTTTCTGGCCGCCCGG

GAGGGCAGCTACGAGACCGCCAAGGTGCTGCTGGACCACTTTGCCAACCGGGAC

ATCACGGATCATATGGACCGCCTGCCGCGCGACATCGCACAGGAGCGCATGCAT

CACGACATCGTGAGGCTGCTGGACGAGTACAACCTGGTGCGCAGCCCGCAGCTG

CACGGAGCCCCGCTGGGGGGGCACGCCCACCCTGTCGCCCCCGCTCTGCTCGCCC

AACGGCTACCTGGGCAGCCTCAAGCCCGGCGTGCAGGGCAAGAAGGTCCGCAAG

CCCAGCAGCAAAGGCCTGGCCTGTGGAAGCAAGGAGGCCAAGGACCTCAAGGCA

CGGAGGAAGAAGTCCCAGGACGGCAAGGGCTGCCTGCTGGACAGCTCCGGCATG

CTCTCGCCCGTGGACTCCCTGGAGTCACCCCATGGCTACCTGTCAGACGTGGCC

TCGCCGCCACTGCTGCCCTCCCCGTTCCAGCAGTCTCCGTCCGTGCCCCTCAAC

CACCTGCCTGGGATGCCCGACACCCACCTGGGCATCGGGCACCTGAACGTGGCG

GCCAAGCCCGAGATGGCGGCGCTGGGTGGGGGCGGCCGGCTGGCCTTTGAGACT

-continued

GGCCCACCTCGTCTCTCCCACCTGCCTGTGGCCTCTGGCACCAGCACCGTCCTG

GGCTCCAGCAGCGGAGGGGCCCTGAATTTCACTGTGGGCGGGTCCACCAGTTTG

AATGGTCAATGCGAGTGGCTGTCCCGGCTGCAGAGCGGCATGGTGCCGAACCAA

TACAACCCTCTGCGGGGGAGTGTGGCACCAGGCCCCCTGAGCACACAGGCCCCC

TCCCTGCAGCATGGCATGGTAGGCCCGCTGCACAGTAGCCTTGCTGCCAGCGCC

CTGTCCCAGATGATGAGCTACCAGGGCCTGCCCAGCACCCGGCTGGCCACCCAG

CCTCACCTGGTGCAGACCCAGCAGGTGCAGCCACAAAACTTACAGATGCAGCAG

CAGAACCTGCAGCCAGCAAACATCCAGCAGCAGCAAAGCCTGCAGCCGCCACCA

CCACCACCACAGCCGCACCTTGGCGTGAGCTCAGCAGCCAGCGGCCACCTGGGC

CGGAGCTTCCTGAGTGGAGAGCCGAGCCAGGCAGACGTGCAGCCACTGGGCCCC

AGCAGCCTGGCGGTGCACACTATTCTGCCCCAGGAGAGCCCCGCCCTGCCCACG

TCGCTGCCATCCTCGCTGGTCCCACCCGTGACCGCAGCCCAGTTCCTGACGCCC

CCCTCGCAGCACAGCTACTCCTCGCCTGTGGACAACACCCCCAGCCACCAGCTA

CAGGTGCCTGAGCACCCCTTCCTCACCCCGTCCCCTGAGTCCCCTGACCAGTGG

TCCAGCTCGTCCCCGCATTCCAACGTCTCCGACTGGTCCGAGGGCGTCTCCAGC

CCTCCCACCAGCATGCAGTCCCAGATCGCCCGCATTCCGGAGGCCTTCAAGTAA

ACGGCGCGCCCCACGAGACCCCGGCTTCCTTTCCCAAGCCTTCGGGCGTCTGTG

TGCGCTCTGTGGATGCCAGGGCCGACCAGAGGAGCCTTTTTAAAACACATGTTT

TTATACAAAATAAGAACGAGGATTTTAATTTTTTTTAGTATTTATTTATGTACT

TTTATTTTACACAGAAACACTGCCTTTTTATTTATATGTACTGTTTTATCTGGC

CCGAGGTAGAAACTTTTATCTATTCTGAGAAAACAAGCAAGTTCTGAGAGCGAG

GGTTTTCCTAGGTAGGATGAAAAGATTCTTCTGTGTTTATAAAATATAAACAAA

GATTCATGATTTATAAATGCCATTTATTTATTGATTCCTTTTTTCAAAATCCAA

AAAGAAATGATGTTGGAGAAGGGAAGTTGAACGAGCATAGTCCAAAAAGCTCCT

GGGGCGTCCAGGCCGCGCCCTTTCCCCGACGCCCACCCAACCCCAAGCCAGCCC

GGCCGCTCCACCAGCATCACCTGCCTGTTAGGAGAAGCTGCATCCAGAGGCAAA

CGGAGGCAAAGCTGGCTCACCTTCCGCACGCGGATTAATTTGCATCTGAAATAG

GAAACAAGTGAAAGCATATGGGTTAGATGTTGCCATGTGTTTTAGATGGTTTCT

TGCAAGCATGCTTGTGAAAATGTGTTCTCGGAGTGTGTATGCCAAGAGTGCACC

CATGGTACCAATCATGAATCTTTGTTTCAGGTTCAGTATTATGTAGTTGTTCGT

TGGTTATACAAGTTCTTGGTCCCTCCAGAACCACCCCGGCCCCCTGCCCGTTCT

TGAAATGTAGGCATCATGCATGTCAAACATGAGATGTGTGGACTGTGGCACTTG

CCTGGGTCACACACGGAGGCATCCTACCCTTTTCTGGGGAAAGACACTGCCTGG

GCTGACCCCGGTGGCGGCCCCAGCACCTCAGCCTGCACAGTGTCCCCCAGGTTC

CGAAGAAGATGCTCCAGCAACACAGCCTGGGCCCCAGCTCGCGGGACCCGACCC

CCCGTGGGCTCCCGTGTTTTGTAGGAGACTTGCCAGAGCCGGGCACATTGAGCT

GTGCAACGCCGTGGGCTGCGTCCTTTGGTCCTGTCCCCGCAGCCCTGGCAGGGG

GCATGCGGTCGGGCAGGGGCTGGAGGGAGGCGGGGGCTGCCCTTGGGCCACCCC

TCCTAGTTTGGGAGGAGCAGATTTTTGCAATACCAAGTATAGCCTATGGCAGAA

AAAATGTCTGTAAATATGTTTTTAAAGGTGGATTTTGTTTAAAAAATCTTAATG

-continued

```
AATGAGTCTGTTGTGTGTCATGCCAGTGAGGGACGTCAGACTTGGCTCAGCTCG

GGGAGCCTTAGCCGCCCATGCACTGGGGACGCTCCGCTGCCGTGCCGCCTGCAC

TCCTCAGGGCAGCCTCCCCCGGCTCTACGGGGGCCGCGTGGTGCCATCCCCAGG

GGGCATGACCAGATGCGTCCCAAGATGTTGATTTTTACTGTGTTTTATAAAATA

GAGTGTAGTTTACAGAAAAAGACTTTAAAAGTGATCTAGATGAGGAACTGTAGA

TGATGTATTTTTTTCATCTTTTTTGTTAACTGATTTGCAATAAAAATGATACTG

ATGGTGATCTGGCTTCCAAAAAAAAAAAAAAAAAA
```

Human notch 2 (NOTCH2), transcript variant 1, mRNA NM_024408.3
(SEQ ID NO: 30)

```
GCTTGCGGTGGGAGGAGGCGGCTGAGGCGGAAGGACACACGAGGCTGCTTCGTT

GCACACCCGAGAAAGTTTCAGCCAAACTTCGGGCGGCGGCTGAGGCGGCGGCCG

AGGAGCGGCGGACTCGGGGCGCGGGGAGTCGAGGCATTTGCGCCTGGGCTTCGG

AGCGTAGCGCCAGGGCCTGAGCCTTTGAAGCAGGAGGAGGGGAGGAGAGAGTGG

GGCTCCTCTATCGGGACCCCCTCCCCATGTGGATCTGCCCAGGCGGCGGCGGCG

GCGGCGGAGGAGGAGGCGACCGAGAAGATGCCCGCCCTGCGCCCCGCTCTGCTG

TGGGCGCTGCTGGCGCTCTGGCTGTGCTGCGCGGCCCCCGCGCATGCATTGCAG

TGTCGAGATGGCTATGAACCCTGTGTAAATGAAGGAATGTGTGTTACCTACCAC

AATGGCACAGGATACTGCAAATGTCCAGAAGGCTTCTTGGGGGAATATTGTCAA

CATCGAGACCCCTGTGAGAAGAACCGCTGCCAGAATGGTGGGACTTGTGTGGCC

CAGGCCATGCTGGGGAAAGCCACGTGCCGATGTGCCTCAGGGTTTACAGGAGAG

GACTGCCAGTACTCAACATCTCATCCATGCTTTGTGTCTCGACCCTGCCTGAAT

GGCGGCACATGCCATATGCTCAGCCGGGATACCTATGAGTGCACCTGTCAAGTC

GGGTTTACAGGTAAGGAGTGCCAATGGACGGATGCCTGCCTGTCTCATCCCTGT

GCAAATGGAAGTACCTGTACCACTGTGGCCAACCAGTTCTCCTGCAAATGCCTC

ACAGGCTTCACAGGGCAGAAATGTGAGACTGATGTCAATGAGTGTGACATTCCA

GGACACTGCCAGCATGGTGGCACCTGCCTCAACCTGCCTGGTTCCTACCAGTGC

CAGTGCCCTCAGGGCTTCACAGGCCAGTACTGTGACAGCCTGTATGTGCCCTGT

GCACCCTCACCTTGTGTCAATGGAGGCACCTGTCGGCAGACTGGTGACTTCACT

TTTGAGTGCAACTGCCTTCCAGGTTTTGAAGGGAGCACCTGTGAGAGGAATATT

GATGACTGCCCTAACCACAGGTGTCAGAATGGAGGGGTTTGTGTGGATGGGGTC

AACACTTACAACTGCCGCTGTCCCCCACAATGGACAGGACAGTTCTGCACAGAG

GATGTGGATGAATGCCTGCTGCAGCCCAATGCCTGTCAAAATGGGGGCACCTGT

GCCAACCGCAATGGAGGCTATGGCTGTGTATGTGTCAACGGCTGGAGTGGAGAT

GACTGCAGTGAGAACATTGATGATTGTGCCTTCGCCTCCTGTACTCCAGGCTCC

ACCTGCATCGACCGTGTGGCCTCCTTCTCTTGCATGTGCCCAGAGGGGAAGGCA

GGTCTCCTGTGTCATCTGGATGATGCATGCATCAGCAATCCTTGCCACAAGGGG

GCACTGTGTGACACCAACCCCCTAAATGGGCAATATATTTGCACCTGCCCACAA

GGCTACAAAGGGGCTGACTGCACAGAAGATGTGGATGAATGTGCCATGGCCAAT

AGCAATCCTTGTGAGCATGCAGGAAAATGTGTGAACACGGATGGCGCCTTCCAC

TGTGAGTGTCTGAAGGGTTATGCAGGACCTCGTTGTGAGATGGACATCAATGAG

TGCCATTCAGACCCCTGCCAGAATGATGCTACCTGTCTGGATAAGATTGGAGGC

TTCACATGTCTGTGCATGCCAGGTTTCAAAGGTGTGCATTGTGAATTAGAAATA
```

-continued

```
AATGAATGTCAGAGCAACCCTTGTGTGAACAATGGGCAGTGTGTGGATAAAGTC

AATCGTTTCCAGTGCCTGTGTCCTCCTGGTTTCACTGGGCCAGTTTGCCAGATT

GATATTGATGACTGTTCCAGTACTCCGTGTCTGAATGGGGCAAAGTGTATCGAT

CACCCGAATGGCTATGAATGCCAGTGTGCCACAGGTTTCACTGGTGTGTTGTGT

GAGGAGAACATTGACAACTGTGACCCCGATCCTTGCCACCATGGTCAGTGTCAG

GATGGTATTGATTCCTACACCTGCATCTGCAATCCCGGGTACATGGGCGCCATC

TGCAGTGACCAGATTGATGAATGTTACAGCAGCCCTTGCCTGAACGATGGTCGC

TGCATTGACCTGGTCAATGGCTACCAGTGCAACTGCCAGCCAGGCACGTCAGGG

GTTAATTGTGAAATTAATTTTGATGACTGTGCAAGTAACCCTTGTATCCATGGA

ATCTGTATGGATGGCATTAATCGCTACAGTTGTGTCTGCTCACCAGGATTCACA

GGGCAGAGATGTAACATTGACATTGATGAGTGTGCCTCCAATCCCTGTCGCAAG

GGTGCAACATGTATCAACGGTGTGAATGGTTTCCGCTGTATATGCCCCGAGGGA

CCCCATCACCCCAGCTGCTACTCACAGGTGAACGAATGCCTGAGCAATCCCTGC

ATCCATGGAAACTGTACTGGAGGTCTCAGTGGATATAAGTGTCTCTGTGATGCA

GGCTGGGTTGGCATCAACTGTGAAGTGGACAAAAATGAATGCCTTTCGAATCCA

TGCCAGAATGGAGGAACTTGTGACAATCTGGTGAATGGATACAGGTGTACTTGC

AAGAAGGGCTTTAAAGGCTATAACTGCCAGGTGAATATTGATGAATGTGCCTCA

AATCCATGCCTGAACCAAGGAACCTGCTTTGATGACATAAGTGGCTACACTTGC

CACTGTGTGCTGCCATACACAGGCAAGAATTGTCAGACAGTATTGGCTCCCTGT

TCCCCAAACCCTTGTGAGAATGCTGCTGTTTGCAAAGAGTCACCAAATTTTGAG

AGTTATACTTGCTTGTGTGCTCCTGGCTGGCAAGGTCAGCGGTGTACCATTGAC

ATTGACGAGTGTATCTCCAAGCCCTGCATGAACCATGGTCTCTGCCATAACACC

CAGGGCAGCTACATGTGTGAATGTCCACCAGGCTTCAGTGGTATGGACTGTGAG

GAGGACATTGATGACTGCCTTGCCAATCCTTGCCAGAATGGAGGTTCCTGTATG

GATGGAGTGAATACTTTCTCCTGCCTCTGCCTTCCGGGTTTCACTGGGGATAAG

TGCCAGACAGACATGAATGAGTGTCTGAGTGAACCCTGTAAGAATGGAGGGAGC

TGCTCTGACTACGTCAACAGTTACACTTGCAAGTGCCAGGCAGGATTTGATGGA

GTCCATTGTGAGAACAACATCAATGAGTGCACTGAGAGCTCCTGTTTCAATGGT

GGCACATGTGTTGATGGGATTAACTCCTTCTCTTGCTTGTGCCCTGTGGGTTTC

ACTGGATCCTTCTGCCTCCATGAGATCAATGAATGCAGCTCTCATCCATGCCTG

AATGAGGGAACGTGTGTTGATGGCCTGGGTACCTACCGCTGCAGCTGCCCCCTG

GGCTACACTGGGAAAAACTGTCAGACCCTGGTGAATCTCTGCAGTCGGTCTCCA

TGTAAAAACAAAGGTACTTGCGTTCAGAAAAAAGCAGAGTCCCAGTGCCTATGT

CCATCTGGATGGGCTGGTGCCTATTGTGACGTGCCCAATGTCTCTTGTGACATA

GCAGCCTCCAGGAGAGGTGTGCTTGTTGAACACTTGTGCCAGCACTCAGGTGTC

TGCATCAATGCTGGCAACACGCATTACTGTCAGTGCCCCCTGGGCTATACTGGG

AGCTACTGTGAGGAGCAACTCGATGAGTGTGCGTCCAACCCCTGCCAGCACGGG

GCAACATGCAGTGACTTCATTGGTGGATACAGATGCGAGTGTGTCCCAGGCTAT

CAGGGTGTCAACTGTGAGTATGAAGTGGATGAGTGCCAGAATCAGCCCTGCCAG

AATGGAGGCACCTGTATTGACCTTGTGAACCATTTCAAGTGCTCTTGCCCACCA
```

-continued

```
GGCACTCGGGGCCTACTCTGTGAAGAGAACATTGATGACTGTGCCCGGGGTCCC

CATTGCCTTAATGGTGGTCAGTGCATGGATAGGATTGGAGGCTACAGTTGTCGC

TGCTTGCCTGGCTTTGCTGGGGAGCGTTGTGAGGGAGACATCAACGAGTGCCTC

TCCAACCCCTGCAGCTCTGAGGGCAGCCTGGACTGTATACAGCTCACCAATGAC

TACCTGTGTGTTTGCCGTAGTGCCTTTACTGGCCGGCACTGTGAAACCTTCGTC

GATGTGTGTCCCCAGATGCCCTGCCTGAATGGAGGGACTTGTGCTGTGGCCAGT

AACATGCCTGATGGTTTCATTTGCCGTTGTCCCCCGGGATTTTCCGGGGCAAGG

TGCCAGAGCAGCTGTGGACAAGTGAAATGTAGGAAGGGGGAGCAGTGTGTGCAC

ACCGCCTCTGGACCCCGCTGCTTCTGCCCCAGTCCCCGGGACTGCGAGTCAGGC

TGTGCCAGTAGCCCCTGCCAGCACGGGGGCAGCTGCCACCCTCAGCGCCAGCCT

CCTTATTACTCCTGCCAGTGTGCCCCACCATTCTCGGGTAGCCGCTGTGAACTC

TACACGGCACCCCCCAGCACCCCTCCTGCCACCTGTCTGAGCCAGTATTGTGCC

GACAAAGCTCGGGATGGCGTCTGTGATGAGGCCTGCAACAGCCATGCCTGCCAG

TGGGATGGGGGTGACTGTTCTCTCACCATGGAGAACCCCTGGGCCAACTGCTCC

TCCCCACTTCCCTGCTGGGATTATATCAACAACCAGTGTGATGAGCTGTGCAAC

ACGGTCGAGTGCCTGTTTGACAACTTTGAATGCCAGGGGAACAGCAAGACATGC

AAGTATGAGAAATACTGTGCAGACCACTTCAAAGACAACCACTGTGAGGAGGGG

TGCAACAGTGAGGAGTGTGGTTGGGATGGGCTGGACTGTGCTGCTGACCAACCT

GAGAACCTGGCAGAAGGTACCCTGGTTATTGTGGTATTGATGCCACCTGAACAA

CTGCTCCAGGATGCTCGCAGCTTCTTGCGGGCACTGGGTACCCTGCTCCACACC

AACCTGCGCATTAAGCGGGACTCCCAGGGGGGAACTCATGGTGTACCCCTATTAT

GGTGAGAAGTCAGCTGCTATGAAGAAACAGAGGATGACACGCAGATCCCTTCCT

GGTGAACAAGAACAGGAGGTGGCTGGCTCTAAAGTCTTTCTGGAAATTGACAAC

CGCCAGTGTGTTCAAGACTCAGACCACTGCTTCAAGAACACGGATGCAGCAGCA

GCTCTCCTGGCCTCTCACGCCATACAGGGGACCCTGTCATACCCTCTTGTGTCT

GTCGTCAGTGAATCCCTGACTCCAGAACGCACTCAGCTCCTCTATCTCCTTGCT

GTTGCTGTTGTCATCATTCTGTTTATTATTCTGCTGGGGGTAATCATGGCAAAA

CGAAAGCGTAAGCATGGCTCTCTCTGGCTGCCTGAAGGTTTCACTCTTCGCCGA

GATGCAAGCAATCACAAGCGTCGTGAGCCAGTGGGACAGGATGCTGTGGGGCTG

AAAAATCTCTCAGTGCAAGTCTCAGAAGCTAACCTAATTGGTACTGGAACAAGT

GAACACTGGGTCGATGATGAAGGGCCCCAGCCAAAGAAAGTAAAGGCTGAAGAT

GAGGCCTTACTCTCAGAAGAAGATGACCCCATTGATCGACGGCCATGGACACAG

CAGCACCTTGAAGCTGCAGACATCCGTAGGACACCATCGCTGGCTCTCACCCCT

CCTCAGGCAGAGCAGGAGGTGGATGTGTTAGATGTGAATGTCCGTGGCCCAGAT

GGCTGCACCCCATTGATGTTGGCTTCTCTCCGAGGAGGCAGCTCAGATTTGAGT

GATGAAGATGAAGATGCAGAGGACTCTTCTGCTAACATCATCACAGACTTGGTC

TACCAGGGTGCCAGCCTCCAGGCCCAGACAGACCGGACTGGTGAGATGGCCCTG

CACCTTGCAGCCCGCTACTCACGGGCTGATGCTGCCAAGCGTCTCCTGGATGCA

GGTGCAGATGCCAATGCCCAGGACAACATGGGCCGCTGTCCACTCCATGCTGCA

GTGGCAGCTGATGCCCAAGGTGTCTTCCAGATTCTGATTCGCAACCGAGTAACT

GATCTAGATGCCAGGATGAATGATGGTACTACACCCCTGATCCTGGCTGCCCGC
```

-continued

```
CTGGCTGTGGAGGGAATGGTGGCAGAACTGATCAACTGCCAAGCGGATGTGAAT

GCAGTGGATGACCATGGAAAATCTGCTCTTCACTGGGCAGCTGCTGTCAATAAT

GTGGAGGCAACTCTTTTGTTGTTGAAAAATGGGGCCAACCGAGACATGCAGGAC

AACAAGGAAGAGACACCTCTGTTTCTTGCTGCCCGGGAGGGGAGCTATGAAGCA

GCCAAGATCCTGTTAGACCATTTTGCCAATCGAGACATCACAGACCATATGGAT

CGTCTTCCCCGGGATGTGGCTCGGGATCGCATGCACCATGACATTGTGCGCCTT

CTGGATGAATACAATGTGACCCCAAGCCCTCCAGGCACCGTGTTGACTTCTGCT

CTCTCACCTGTCATCTGTGGGCCCAACAGATCTTTCCTCAGCCTGAAGCACACC

CCAATGGGCAAGAAGTCTAGACGGCCCAGTGCCAAGAGTACCATGCCTACTAGC

CTCCCTAACCTTGCCAAGGAGGCAAAGGATGCCAAGGGTAGTAGGAGGAAGAAG

TCTCTGAGTGAGAAGGTCCAACTGTCTGAGAGTTCAGTAACTTTATCCCCTGTT

GATTCCCTAGAATCTCCTCACACGTATGTTTCCGACACCACATCCTCTCCAATG

ATTACATCCCCTGGGATCTTACAGGCCTCACCCAACCCTATGTTGGCCACTGCC

GCCCCTCCTGCCCCAGTCCATGCCCAGCATGCACTATCTTTTTCTAACCTTCAT

GAAATGCAGCCTTTGGCACATGGGGCCAGCACTGTGCTTCCCTCAGTGAGCCAG

TTGCTATCCCACCACCACATTGTGTCTCCAGGCAGTGGCAGTGCTGGAAGCTTG

AGTAGGCTCCATCCAGTCCCAGTCCCAGCAGATTGGATGAACCGCATGGAGGTG

AATGAGACCCAGTACAATGAGATGTTTGGTATGGTCCTGGCTCCAGCTGAGGGC

ACCCATCCTGGCATAGCTCCCCAGAGCAGGCCACCTGAAGGGAAGCACATAACC

ACCCCTCGGGAGCCCTTGCCCCCCATTGTGACTTTCCAGCTCATCCCTAAAGGC

AGTATTGCCCAACCAGCGGGGGCTCCCCAGCCTCAGTCCACCTGCCCTCCAGCT

GTTGCGGGCCCCCTGCCCACCATGTACCAGATTCCAGAAATGGCCCGTTTGCCC

AGTGTGGCTTTCCCCACTGCCATGATGCCCCAGCAGGACGGGCAGGTAGCTCAG

ACCATTCTCCCAGCCTATCATCCTTTCCCAGCCTCTGTGGGCAAGTACCCCACA

CCCCCTTCACAGCACAGTTATGCTTCCTCAAATGCTGCTGAGCGAACACCCAGT

CACAGTGGTCACCTCCAGGGTGAGCATCCCTACCTGACACCATCCCCAGAGTCT

CCTGACCAGTGGTCAAGTTCATCACCCCACTCTGCTTCTGACTGGTCAGATGTG

ACCACCAGCCCTACCCCTGGGGGTGCTGGAGGAGGTCAGCGGGGACCTGGGACA

CACATGTCTGAGCCACCACACAACAACATGCAGGTTTATGCGTGAGAGAGTCCA

CCTCCAGTGTAGAGACATAACTGACTTTTGTAAATGCTGCTGAGGAACAAATGA

AGGTCATCCGGGAGAGAAATGAAGAAATCTCTGGAGCCAGCTTCTAGAGGTAGG

AAAGAGAAGATGTTCTTATTCAGATAATGCAAGAGAAGCAATTCGTCAGTTTCA

CTGGGTATCTGCAAGGCTTATTGATTATTCTAATCTAATAAGACAAGTTTGTGG

AAATGCAAGATGAATACAAGCCTTGGGTCCATGTTACTCTCTTCTATTTGGAG

AATAAGATGGATGCTTATTGAAGCCCAGACATTCTTGCAGCTTGGACTGCATTT

TAAGCCCTGCAGGCTTCTGCCATATCCATGAGAAGATTCTACACTAGCGTCCTG

TTGGGAATTATGCCCTGGAATTCTGCCTGAATTGACCTACGCATCTCCTCCTCC

TTGGACATTCTTTTGTCTTCATTTGGTGCTTTTGGTTTTGCACCTCTCCGTGAT

TGTAGCCCTACCAGCATGTTATAGGGCAAGACCTTTGTGCTTTTGATCATTCTG

GCCCATGAAAGCAACTTTGGTCTCCTTTCCCCTCCTGTCTTCCCGGTATCCCTT
```

-continued

```
GGAGTCTCACAAGGTTTACTTTGGTATGGTTCTCAGCACAAACCTTTCAAGTAT

GTTGTTTCTTTGGAAAATGGACATACTGTATTGTGTTCTCCTGCATATATCATT

CCTGGAGAGAGAAGGGGAGAAGAATACTTTTCTTCAACAAATTTTGGGGGCAGG

AGATCCCTTCAAGAGGCTGCACCTTAATTTTTCTTGTCTGTGTGCAGGTCTTCA

TATAAACTTTACCAGGAAGAAGGGTGTGAGTTTGTTGTTTTTCTGTGTATGGGC

CTGGTCAGTGTAAAGTTTTATCCTTGATAGTCTAGTTACTATGACCCTCCCCAC

TTTTTTAAAACCAGAAAAAGGTTTGGAATGTTGGAATGAGCAAGAGACAAGTTA

ACTCGTGCAAGAGCCAGTTACCCACCCACAGGTCCCCCTACTTCCTGCCAAGCA

TTCCATTGACTGCCTGTATGGAACACATTTGTCCCAGATCTGAGCATTCTAGGC

CTGTTTCACTCACTCACCCAGCATATGAAACTAGTCTTAACTGTTGAGCCTTTC

CTTTCATATCCACAGAAGACACTGTCTCAAATGTTGTACCCTTGCCATTTAGGA

CTGAACTTTCCTTAGCCCAAGGGACCCAGTGACAGTTGTCTTCCGTTTGTCAGA

TGATCAGTCTCTACTGATTATCTTGCTGCTTAAAGGCCTGCTCACCAATCTTTC

TTTCACACCGTGTGGTCCGTGTTACTGGTATACCCAGTATGTTCTCACTGAAGA

CATGGACTTTATATGTTCAAGTGCAGGAATTGGAAAGTTGGACTTGTTTTCTAT

GATCCAAAACAGCCCTATAAGAAGGTTGGAAAAGGAGGAACTATATAGCAGCCT

TTGCTATTTTCTGCTACCATTTCTTTTCCTCTGAAGCGGCCATGACATTCCCTT

TGGCAACTAACGTAGAAACTCAACAGAACATTTTCCTTTCCTAGAGTCACCTTT

TAGATGATAATGGAGAACTATAGACTTGCTCATTGTTCAGACTGATTGCCCCTC

ACCTGAATCCACTCTCTGTATTCATGCTCTTGGCAATTTCTTTGACTTTCTTTT

AAGGGCAGAAGCATTTTAGTTAATTGTAGATAAAGAATAGTTTTCTTCCTCTTC

TCCTTGGGCCAGTTAATAATTGGTCCATGGCTACACTGCAACTTCCGTCCAGTG

CTGTGATGCCCATGACACCTGCAAAATAAGTTCTGCCTGGGCATTTTGTAGATA

TTAACAGGTGAATTCCCGACTCTTTTGGTTTGAATGACAGTTCTCATTCCTTCT

ATGGCTGCAAGTATGCATCAGTGCTTCCCACTTACCTGATTTGTCTGTCGGTGG

CCCCATATGGAAACCCTGCGTGTCTGTTGGCATAATAGTTTACAAATGGTTTTT

TGAGTCCTATCCAAATTTATTGAACCAACAAAAATAATTACTTCTGCCCTGAGA

TAAGCAGATTAAGTTTGTTCATTCTCTGCTTTATTCTCTCCATGTGGCAACATT

CTGTCAGCCTCTTTCATAGTGTGCAAACATTTTATCATTCTAAATGGTGACTCT

CTGCCCTTGGACCCATTTATTATTCACAGATGGGGAGAACCTATCTGCATGGAC

CTCTGTGGACCACAGCGTACCTGCCCCTTTCTGCCCTCCTGCTCCAGCCCCACT

TCTGAAAGTATCAGCTACTGATCCAGCCACTGGATATTTTATATCCTCCCTTTT

CCTTAAGCACAATGTCAGACCAAATTGCTTGTTTCTTTTTCTTGGACTACTTTA

ATTTGGATCCTTTGGGTTTGGAGAAAGGGAATGTGAAAGCTGTCATTACAGACA

ACAGGTTTCAGTGATGAGGAGGACAACACTGCCTTTCAAACTTTTTAGTGATCT

CTTAGATTTTAAGAACTCTTGAATTGTGTGGTATCTAATAAAAGGGAAGGTAAG

ATGGATAATCACTTTCTCATTTGGGTTCTGAATTGGAGACTCAGTTTTTATGAG

ACACATCTTTTATGCCATGTATAGATCCTCCCCTGCTATTTTTGGTTTATTTTT

ATTGTTATAAATGCTTTCTTTCTTTGACTCCTCTTCTGCCTGCCTTTGGGGATA

GGTTTTTTTGTTTGTTTATTTGCTTCCTCTGTTTTGTTTTAAGCATCATTTTCT

TATGTGAGGTGGGGAAGGGAAAGGTATGAGGGAAAGAGAGTCTGAGAATTAAAA
```

-continued

TATTTTAGTATAAGCAATTGGCTGTGATGCTCAAATCCATTGCATCCTCTTATT

GAATTTGCCAATTTGTAATTTTTGCATAATAAAGAACCAAAGGTGTAATGTTTT

GTTGAGAGGTGGTTTAGGGATTTTGGCCCTAACCAATACATTGAATGTATGATG

ACTATTTGGGAGGACACATTTATGTACCCAGAGGCCCCCACTAATAAGTGGTAC

TATGGTTACTTCCTTGTGTACATTTCTCTTAAAAGTGATATTATATCTGTTTGT

ATGAGAAACCCAGTAACCAATAAAATGACCGCATATTCCTGACTAAACGTAGTA

AGGAAAATGCACACTTTGTTTTTACTTTTCCGTTTCATTCTAAAGGTAGTTAAG

ATGAAATTTATATGAAAGCATTTTTATCACAAAATAAAAAAGGTTTGCCAAGCT

CAGTGGTGTTGTATTTTTTATTTTCCAATACTGCATCCATGGCCTGGCAGTGTT

ACCTCATGATGTCATAATTTGCTGAGAGAGCAAATTTTCTTTTCTTTCTGAATC

CCACAAAGCCTAGCACCAAACTTCTTTTTTTCTTCCTTTAATTAGATCATAAAT

AAATGATCCTGGGGAAAAAGCATCTGTCAAATAGGAAACATCACAAAACTGAGC

ACTCTTCTGTGCACTAGCCATAGCTGGTGACAAACAGATGGTTGCTCAGGGACA

AGGTGCCTTCCAATGGAAATGCGAAGTAGTTGCTATAGCAAGAATTGGGAACTG

GGATATAAGTCATAATATTAATTATGCTGTTATGTAAATGATTGGTTTGTAACA

TTCCTTAAGTGAAATTTGTGTAGAACTTAATATACAGGATTATAAAATAATATT

TTGTGTATAAATTTGTTATAAGTTCACATTCATACATTTATTTATAAAGTCAGT

GAGATATTTGAACATGAAAAAAAAAA

Human notch 2 (NOTCH2), transcript variant 2, mRNA NM_001200001.1
                                                        (SEQ ID NO: 31)
GCTTGCGGTGGGAGGAGGCGGCTGAGGCGGAAGGACACACGAGGCTGCTTCGTT

GCACACCCGAGAAAGTTTCAGCCAAACTTCGGGCGGCGGCTGAGGCGGCGGCCG

AGGAGCGGCGGACTCGGGGCGCGGGGAGTCGAGGCATTTGCGCCTGGGCTTCGG

AGCGTAGCGCCAGGGCCTGAGCCTTTGAAGCAGGAGGAGGGGAGGAGAGAGTGG

GGCTCCTCTATCGGGACCCCCTCCCCATGTGGATCTGCCCAGGCGGCGGCGGCG

GCGGCGGAGGAGGAGGCGACCGAGAAGATGCCCGCCCTGCGCCCCGCTCTGCTG

TGGGCGCTGCTGGCGCTCTGGCTGTGCTGCGCGGCCCCCGCGCATGCATTGCAG

TGTCGAGATGGCTATGAACCCTGTGTAAATGAAGGAATGTGTGTTACCTACCAC

AATGGCACAGGATACTGCAAATGTCCAGAAGGCTTCTTGGGGGAATATTGTCAA

CATCGAGACCCCTGTGAGAAGAACCGCTGCCAGAATGGTGGGACTTGTGTGGCC

CAGGCCATGCTGGGGAAAGCCACGTGCCGATGTGCCTCAGGGTTTACAGGAGAG

GACTGCCAGTACTCAACATCTCATCCATGCTTTGTGTCTCGACCCTGCCTGAAT

GGCGGCACATGCCATATGCTCAGCCGGGATACCTATGAGTGCACCTGTCAAGTC

GGGTTTACAGGTAAGGAGTGCCAATGGACGGATGCCTGCCTGTCTCATCCCTGT

GCAAATGGAAGTACCTGTACCACTGTGGCCAACCAGTTCTCCTGCAAATGCCTC

ACAGGCTTCACAGGGCAGAAATGTGAGACTGATGTCAATGAGTGTGACATTCCA

GGACACTGCCAGCATGGTGGCACCTGCCTCAACCTGCCTGGTTCCTACCAGTGC

CAGTGCCCTCAGGGCTTCACAGGCCAGTACTGTGACAGCCTGTATGTGCCCTGT

GCACCCTCACCTTGTGTCAATGGAGGCACCTGTCGGCAGACTGGTGACTTCACT

TTTGAGTGCAACTGCCTTCCAGGTTTTGAAGGGAGCACCTGTGAGAGGAATATT

GATGACTGCCCTAACCACAGGTGTCAGAATGGAGGGGTTTGTGTGGATGGGGTC

-continued

```
AACACTTACAACTGCCGCTGTCCCCCACAATGGACAGGACAGTTCTGCACAGAG

GATGTGGATGAATGCCTGCTGCAGCCCAATGCCTGTCAAAATGGGGGCACCTGT

GCCAACCGCAATGGAGGCTATGGCTGTGTATGTGTCAACGGCTGGAGTGGAGAT

GACTGCAGTGAGAACATTGATGATTGTGCCTTCGCCTCCTGTACTCCAGGCTCC

ACCTGCATCGACCGTGTGGCCTCCTTCTCTTGCATGTGCCCAGAGGGGAAGGCA

GGTCTCCTGTGTCATCTGGATGATGCATGCATCAGCAATCCTTGCCACAAGGGG

GCACTGTGTGACACCAACCCCCTAAATGGGCAATATATTTGCACCTGCCCACAA

GGCTACAAAGGGGCTGACTGCACAGAAGATGTGGATGAATGTGCCATGGCCAAT

AGCAATCCTTGTGAGCATGCAGGAAAATGTGTGAACACGGATGGCGCCTTCCAC

TGTGAGTGTCTGAAGGGTTATGCAGGACCTCGTTGTGAGATGGACATCAATGAG

TGCCATTCAGACCCCTGCCAGAATGATGCTACCTGTCTGGATAAGATTGGAGGC

TTCACATGTCTGTGCATGCCAGGTTTCAAAGGTGTGCATTGTGAATTAGAAATA

AATGAATGTCAGAGCAACCCTTGTGTGAACAATGGGCAGTGTGTGGATAAAGTC

AATCGTTTCCAGTGCCTGTGTCCTCCTGGTTTCACTGGGCCAGTTTGCCAGATT

GATATTGATGACTGTTCCAGTACTCCGTGTCTGAATGGGGCAAAGTGTATCGAT

CACCCGAATGGCTATGAATGCCAGTGTGCCACAGGTTTCACTGGTGTGTTGTGT

GAGGAGAACATTGACAACTGTGACCCCGATCCTTGCCACCATGGTCAGTGTCAG

GATGGTATTGATTCCTACACCTGCATCTGCAATCCCGGGTACATGGGCGCCATC

TGCAGTGACCAGATTGATGAATGTTACAGCAGCCCTTGCCTGAACGATGGTCGC

TGCATTGACCTGGTCAATGGCTACCAGTGCAACTGCCAGCCAGGCACGTCAGGG

GTTAATTGTGAAATTAATTTTGATGACTGTGCAAGTAACCCTTGTATCCATGGA

ATCTGTATGGATGGCATTAATCGCTACAGTTGTGTCTGCTCACCAGGATTCACA

GGGCAGAGATGTAACATTGACATTGATGAGTGTGCCTCCAATCCCTGTCGCAAG

GGTGCAACATGTATCAACGGTGTGAATGGTTTCCGCTGTATATGCCCCGAGGGA

CCCCATCACCCCAGCTGCTACTCACAGGTGAACGAATGCCTGAGCAATCCCTGC

ATCCATGGAAACTGTACTGGAGGTCTCAGTGGATATAAGTGTCTCTGTGATGCA

GGCTGGGTTGGCATCAACTGTGAAGTGGACAAAAATGAATGCCTTTCGAATCCA

TGCCAGAATGGAGGAACTTGTGACAATCTGGTGAATGGATACAGGTGTACTTGC

AAGAAGGGCTTTAAAGGCTATAACTGCCAGGTGAATATTGATGAATGTGCCTCA

AATCCATGCCTGAACCAAGGAACCTGCTTTGATGACATAAGTGGCTACACTTGC

CACTGTGTGCTGCCATACACAGGCAAGAATTGTCAGACAGTATTGGCTCCCTGT

TCCCCAAACCCTTGTGAGAATGCTGCTGTTTGCAAAGAGTCACCAAATTTTGAG

AGTTATACTTGCTTGTGTGCTCCTGGCTGGCAAGGTCAGCGGTGTACCATTGAC

ATTGACGAGTGTATCTCCAAGCCCTGCATGAACCATGGTCTCTGCCATAACACC

CAGGGCAGCTACATGTGTGAATGTCCACCAGGCTTCAGTGGTATGGACTGTGAG

GAGGACATTGATGACTGCCTTGCCAATCCTTGCCAGAATGGAGGTTCCTGTATG

GATGGAGTGAATACTTTCTCCTGCCTCTGCCTTCCGGGTTTCACTGGGGATAAG

TGCCAGACAGACATGAATGAGTGTCTGAGTGAACCCTGTAAGAATGGAGGGAGC

TGCTCTGACTACGTCAACAGTTACACTTGCAAGTGCCAGGCAGGATTTGATGGA

GTCCATTGTGAGAACAACATCAATGAGTGCACTGAGAGCTCCTGTTTCAATGGT

GGCACATGTGTTGATGGGATTAACTCCTTCTCTTGCTTGTGCCCTGTGGGTTTC
```

-continued

ACTGGATCCTTCTGCCTCCATGAGATCAATGAATGCAGCTCTCATCCATGCCTG

AATGAGGGAACGTGTGTTGATGGCCTGGGTACCTACCGCTGCAGCTGCCCCCTG

GGCTACACTGGGAAAAACTGTCAGACCCTGGTGAATCTCTGCAGTCGGTCTCCA

TGTAAAAACAAAGGTACTTGCGTTCAGAAAAAAGCAGAGTCCCAGTGCCTATGT

CCATCTGGATGGGCTGGTGCCTATTGTGACGTGCCCAATGTCTCTTGTGACATA

GCAGCCTCCAGGAGAGGTGTGCTTGTTGAACACTTGTGCCAGCACTCAGGTGTC

TGCATCAATGCTGGCAACACGCATTACTGTCAGTGCCCCCTGGGCTATACTGGG

AGCTACTGTGAGGAGCAACTCGATGAGTGTGCGTCCAACCCCTGCCAGCACGGG

GCAACATGCAGTGACTTCATTGGTGGATACAGATGCGAGTGTGTCCCAGGCTAT

CAGGGTGTCAACTGTGAGTATGAAGTGGATGAGTGCCAGAATCAGCCCTGCCAG

AATGGAGGCACCTGTATTGACCTTGTGAACCATTTCAAGTGCTCTTGCCCACCA

GGCACTCGGGGTATGAAATCATCCTTATCCATTTTCCATCCAGGGCATTGTCTT

AAGTTATAAATCCATTCTTAGTGTTCAGGGGATTTTATAAAATTAAAGATAGGA

AGACTAGCTTCATTCCAAGCATTTAGTTCTACATCCTAGTAATTCAAGCCATTT

TATTCTCCCATCTCTTGCTAGCTCTGATGTTGTGGTTTATGTTGTCAGTTTTAT

CTGGTTGTTTGGCATCTTGATATTCCATGAAACACAGAATATGGAAGGGATACA

ACATTAGCATAACATTAAAAAATTAGCCTGGTCAGTAAGATTTCTTGTTGCTTC

ACAGAAAAGCAACTAATGGCCTCTAAAATAAACAATTTACATTTAAAAAAAAAA

AAAAAA

Human notch 3 (NOTCH3), mRNA NM_000435.2
                                          (SEQ ID NO: 32)
GCGGCGCGGAGGCTGGCCCGGGACGCGCCCGGAGCCCAGGGAAGGAGGGAGGAG

GGGAGGGTCGCGGCCGGCCGCCATGGGGCCGGGGGCCCGTGGCCGCCGCCGCCG

CCGTCGCCCGATGTCGCCGCCACCGCCACCGCCACCCGTGCGGGCGCTGCCCCT

GCTGCTGCTGCTAGCGGGGCCGGGGGCTGCAGCCCCCCCTTGCCTGGACGGAAG

CCCGTGTGCAAATGGAGGTCGTTGCACCCAGCTGCCCTCCCGGGAGGCTGCCTG

CCTGTGCCCGCCTGGCTGGGTGGGTGAGCGGTGTCAGCTGGAGGACCCCTGTCA

CTCAGGCCCCTGTGCTGGCCGTGGTGTCTGCCAGAGTTCAGTGGTGGCTGGCAC

CGCCCGATTCTCATGCCGGTGCCCCCGTGGCTTCCGAGGCCCTGACTGCTCCCT

GCCAGATCCCTGCCTCAGCAGCCCTTGTGCCCACGGTGCCCGCTGCTCAGTGGG

GCCCGATGGACGCTTCCTCTGCTCCTGCCCACCTGGCTACCAGGGCCGCAGCTG

CCGAAGCGACGTGGATGAGTGCCGGGTGGGTGAGCCCTGCCGCCATGGTGGCAC

CTGCCTCAACACACCTGGCTCCTTCCGCTGCCAGTGTCCAGCTGGCTACACAGG

GCCACTATGTGAGAACCCCGCGGTGCCCTGTGCACCCTCACCATGCCGTAACGG

GGGCACCTGCAGGCAGAGTGGCGACCTCACTTACGACTGTGCCTGTCTTCCTGG

GTTTGAGGGTCAGAATTGTGAAGTGAACGTGGACGACTGTCCAGGACACCGATG

TCTCAATGGGGGGACATGCGTGGATGGCGTCAACACCTATAACTGCCAGTGCCC

TCCTGAGTGGACAGGCCAGTTCTGCACGGAGGACGTGGATGAGTGTCAGCTGCA

GCCCAACGCCTGCCACAATGGGGGTACCTGCTTCAACACGCTGGGTGGCCACAG

CTGCGTGTGTGTCAATGGCTGGACAGGCGAGAGCTGCAGTCAGAATATCGATGA

CTGTGCCACAGCCGTGTGCTTCCATGGGGCCACCTGCCATGACCGCGTGGCTTC

-continued

```
TTTCTACTGTGCCTGCCCCATGGGCAAGACTGGCCTCCTGTGTCACCTGGATGA

CGCCTGTGTCAGCAACCCCTGCCACGAGGATGCTATCTGTGACACAAATCCGGT

GAACGGCCGGGCCATTTGCACCTGTCCTCCCGGCTTCACGGGTGGGGCATGTGA

CCAGGATGTGGACGAGTGCTCTATCGGCGCCAACCCCTGCGAGCACTTGGGCAG

GTGCGTGAACACGCAGGGCTCCTTCCTGTGCCAGTGCGGTCGTGGCTACACTGG

ACCTCGCTGTGAGACCGATGTCAACGAGTGTCTGTCGGGGCCCTGCCGAAACCA

GGCCACGTGCCTCGACCGCATAGGCCAGTTCACCTGTATCTGTATGGCAGGCTT

CACAGGAACCTATTGCGAGGTGGACATTGACGAGTGTCAGAGTAGCCCCTGTGT

CAACGGTGGGGTCTGCAAGGACCGAGTCAATGGCTTCAGCTGCACCTGCCCCTC

GGGCTTCAGCGGCTCCACGTGTCAGCTGGACGTGGACGAATGCGCCAGCACGCC

CTGCAGGAATGGCGCCAAATGCGTGGACCAGCCCGATGGCTACGAGTGCCGCTG

TGCCGAGGGCTTTGAGGGCACGCTGTGTGATCGCAACGTGGACGACTGCTCCCC

TGACCCATGCCACCATGGTCGCTGCGTGGATGGCATCGCCAGCTTCTCATGTGC

CTGTGCTCCTGGCTACACGGGCACACGCTGCGAGAGCCAGGTGGACGAATGCCG

CAGCCAGCCCTGCCGCCATGGCGGCAAATGCCTAGACCTGGTGGACAAGTACCT

CTGCCGCTGCCCTTCTGGGACCACAGGTGTGAACTGCGAAGTGAACATTGACGA

CTGTGCCAGCAACCCCTGCACCTTTGGAGTCTGCCGTGATGGCATCAACCGCTA

CGACTGTGTCTGCCAACCTGGCTTCACAGGGCCCCTTTGTAACGTGGAGATCAA

TGAGTGTGCTTCCAGCCCATGCGGCGAGGGAGGTTCCTGTGTGGATGGGGAAAA

TGGCTTCCGCTGCCTCTGCCCGCCTGGCTCCTTGCCCCCACTCTGCCTCCCCCC

GAGCCATCCCTGTGCCCATGAGCCCTGCAGTCACGGCATCTGCTATGATGCACC

TGGCGGGTTCCGCTGTGTGTGTGAGCCTGGCTGGAGTGGCCCCCGCTGCAGCCA

GAGCCTGGCCCGAGACGCCTGTGAGTCCCAGCCGTGCAGGGCCGGTGGGACATG

CAGCAGCGATGGAATGGGTTTCCACTGCACCTGCCCGCCTGGTGTCCAGGGACG

TCAGTGTGAACTCCTCTCCCCCTGCACCCCGAACCCCTGTGAGCATGGGGGCCG

CTGCGAGTCTGCCCCTGGCCAGCTGCCTGTCTGCTCCTGCCCCCAGGGCTGGCA

AGGCCCACGATGCCAGCAGGATGTGGACGAGTGTGCTGGCCCCGCACCCTGTGG

CCCTCATGGTATCTGCACCAACCTGGCAGGGAGTTTCAGCTGCACCTGCCATGG

AGGGTACACTGGCCCTTCCTGCGATCAGGACATCAATGACTGTGACCCCAACCC

ATGCCTGAACGGTGGCTCGTGCCAAGACGGCGTGGGCTCCTTTTCCTGCTCCTG

CCTCCCTGGTTTCGCCGGCCCACGATGCGCCCGCGATGTGGATGAGTGCCTGAG

CAACCCCTGCGGCCCGGGCACCTGTACCGACCACGTGGCCTCCTTCACCTGCAC

CTGCCCGCCAGGCTACGGAGGCTTCCACTGCGAACAGGACCTGCCCGACTGCAG

CCCCAGCTCCTGCTTCAATGGCGGGACCTGTGTGGACGGCGTGAACTCGTTCAG

CTGCCTGTGCCGTCCCGGCTACACAGGAGCCCACTGCCAACATGAGGCAGACCC

CTGCCTCTCGCGGCCCTGCCTACACGGGGCGTCTGCAGCGCCGCCCACCCTGG

CTTCCGCTGCACCTGCCTCGAGAGCTTCACGGGCCCGCAGTGCCAGACGCTGGT

GGATTGGTGCAGCCGCCAGCCTTGTCAAAACGGGGGTCGCTGCGTCCAGACTGG

GGCCTATTGCCTTTGTCCCCCTGGATGGAGCGGACGCCTCTGTGACATCCGAAG

CTTGCCCTGCAGGGAGGCCGCAGCCCAGATCGGGGTGCGGCTGGAGCAGCTGTG

TCAGGCGGGTGGGCAGTGTGTGGATGAAGACAGCTCCCACTACTGCGTGTGCCC
```

-continued

```
AGAGGGCCGTACTGGTAGCCACTGTGAGCAGGAGGTGGACCCCTGCTTGGCCCA

GCCCTGCCAGCATGGGGGGACCTGCCGTGGCTATATGGGGGGCTACATGTGTGA

GTGTCTTCCTGGCTACAATGGTGATAACTGTGAGGACGACGTGGACGAGTGTGC

CTCCCAGCCCTGCCAGCACGGGGGGTTCATGCATTGACCTCGTGGCCCGCTATCT

CTGCTCCTGTCCCCCAGGAACGCTGGGGGTGCTCTGCGAGATTAATGAGGATGA

CTGCGGCCCAGGCCCACCGCTGGACTCAGGGCCCCGGTGCCTACACAATGGCAC

CTGCGTGGACCTGGTGGGTGGTTTCCGCTGCACCTGTCCCCCAGGATACACTGG

TTTGCGCTGCGAGGCAGACATCAATGAGTGTCGCTCAGGTGCCTGCCACGCGGC

ACACACCCGGGACTGCCTGCAGGACCCAGGCGGAGGTTTCCGTTGCCTTTGTCA

TGCTGGCTTCTCAGGTCCTCGCTGTCAGACTGTCCTGTCTCCCTGCGAGTCCCA

GCCATGCCAGCATGGAGGCCAGTGCCGTCCTAGCCCGGGTCCTGGGGGTGGGCT

GACCTTCACCTGTCACTGTGCCCAGCCGTTCTGGGGTCCGCGTTGCGAGCGGGT

GGCGCGCTCCTGCCGGGAGCTGCAGTGCCCGGTGGGCGTCCCATGCCAGCAGAC

GCCCCGCGGGCCGCGCTGCGCCTGCCCCCCAGGGTTGTCGGGACCCTCCTGCCG

CAGCTTCCCGGGGTCGCCGCCGGGGGCCAGCAACGCCAGCTGCGCGGCCGCCCC

CTGTCTCCACGGGGGCTCCTGCCGCCCCGCGCCGCTCGCGCCCTTCTTCCGCTG

CGCTTGCGCGCAGGGCTGGACCGGGCCGCGCTGCGAGGCGCCCGCCGCGGCACC

CGAGGTCTCGGAGGAGCCGCGGTGCCCGCGCGCCGCCTGCCAGGCCAAGCGCGG

GGACCAGCGCTGCGACCGCGAGTGCAACAGCCCAGGCTGCGGCTGGGACGGCGG

CGACTGCTCGCTGAGCGTGGGCGACCCCTGGCGGCAATGCGAGGCGCTGCAGTG

CTGGCGCCTCTTCAACAACAGCCGCTGCGACCCCGCCTGCAGCTCGCCCGCCTG

CCTCTACGACAACTTCGACTGCCACGCCGGTGGCCGCGAGCGCACTTGCAACCC

GGTGTACGAGAAGTACTGCGCCGACCACTTTGCCGACGGCCGCTGCGACCAGGG

CTGCAACACGGAGGAGTGCGGCTGGGATGGGCTGGATTGTGCCAGCGAGGTGCC

GGCCCTGCTGGCCCGCGGCGTGCTGGTGCTCACAGTGCTGCTGCCGCCAGAGGA

GCTACTGCGTTCCAGCGCCGACTTTCTGCAGCGGCTCAGCGCCATCCTGCGCAC

CTCGCTGCGCTTCCGCCTGGACGCGCACGGCCAGGCCATGGTCTTCCCTTACCA

CCGGCCTAGTCCTGGCTCCGAACCCCGGGCCCGTCGGGAGCTGGCCCCCGAGGT

GATCGGCTCGGTAGTAATGCTGGAGATTGACAACCGGCTCTGCCTGCAGTCGCC

TGAGAATGATCACTGCTTCCCCGATGCCCAGAGCGCCGCTGACTACCTGGGAGC

GTTGTCAGCGGTGGAGCGCCTGGACTTCCCGTACCCACTGCGGGACGTGCGGGG

GGAGCCGCTGGAGCCTCCAGAACCCAGCGTCCCGCTGCTGCCACTGCTAGTGGC

GGGCGCTGTCTTGCTGCTGGTCATTCTCGTCCTGGGTGTCATGGTGGCCCGGCG

CAAGCGCGAGCACAGCACCCTCTGGTTCCCTGAGGGCTTCTCACTGCACAAGGA

CGTGGCCTCTGGTCACAAGGGCCGGCGGGAACCCGTGGGCCAGGACGCGCTGGG

CATGAAGAACATGGCCAAGGGTGAGAGCCTGATGGGGGAGGTGGCCACAGACTG

GATGGACACAGAGTGCCCAGAGGCCAAGCGGCTAAAGGTAGAGGAGCCAGGCAT

GGGGGCTGAGGAGGCTGTGGATTGCCGTCAGTGGACTCAACACCATCTGGTTGC

TGCTGACATCCGCGTGGCACCAGCCATGGCACTGACACCACCACAGGGCGACGC

AGATGCTGATGGCATGGATGTCAATGTGCGTGGCCCAGATGGCTTCACCCCGCT
```

-continued

```
AATGCTGGCTTCCTTCTGTGGGGGGGCTCTGGAGCCAATGCCAACTGAAGAGGA

TGAGGCAGATGACACATCAGCTAGCATCATCTCCGACCTGATCTGCCAGGGGGC

TCAGCTTGGGGCACGGACTGACCGTACTGGCGAGACTGCTTTGCACCTGGCTGC

CCGTTATGCCCGTGCTGATGCAGCCAAGCGGCTGCTGGATGCTGGGGCAGACAC

CAATGCCCAGGACCACTCAGGCCGCACTCCCCTGCACACAGCTGTCACAGCCGA

TGCCCAGGGTGTCTTCCAGATTCTCATCCGAAACCGCTCTACAGACTTGGATGC

CCGCATGGCAGATGGCTCAACGGCACTGATCCTGGCGGCCCGCCTGGCAGTAGA

GGGCATGGTGGAAGAGCTCATCGCCAGCCATGCTGATGTCAATGCTGTGGATGA

GCTTGGGAAATCAGCCTTACACTGGGCTGCGGCTGTGAACAACGTGGAAGCCAC

TTTGGCCCTGCTCAAAAATGGAGCCAATAAGGACATGCAGGATAGCAAGGAGGA

GACCCCCCTATTCCTGGCCGCCCGCGAGGGCAGCTATGAGGCTGCCAAGCTGCT

GTTGGACCACTTTGCCAACCGTGAGATCACCGACCACCTGGACAGGCTGCCGCG

GGACGTAGCCCAGGAGAGACTGCACCAGGACATCGTGCGCTTGCTGGATCAACC

CAGTGGGCCCCGCAGCCCCCCCGGTCCCCACGGCCTGGGGCCTCTGCTCTGTCC

TCCAGGGGCCTTCCTCCCTGGCCTCAAAGCGGCACAGTCGGGGTCCAAGAAGAG

CAGGAGGCCCCCCGGGAAGGCGGGGCTGGGGCCGCAGGGGCCCCGGGGGCGGGG

CAAGAAGCTGACGCTGGCCTGCCCGGGCCCCCTGGCTGACAGCTCGGTCACGCT

GTCGCCCGTGGACTCGCTGGACTCCCCGCGGCCTTTCGGTGGGCCCCCTGCTTC

CCCTGGTGGCTTCCCCCTTGAGGGGCCCTATGCAGCTGCCACTGCCACTGCAGT

GTCTCTGGCACAGCTTGGTGGCCCAGGCCGGGCGGGTCTAGGGCGCCAGCCCCC

TGGAGGATGTGTACTCAGCCTGGGCCTGCTGAACCCTGTGGCTGTGCCCCTCGA

TTGGGCCCGGCTGCCCCCACCTGCCCCTCCAGGCCCCTCGTTCCTGCTGCCACT

GGCGCCGGGACCCCAGCTGCTCAACCCAGGGACCCCCGTCTCCCCGCAGGAGCG

GCCCCCGCCTTACCTGGCAGTCCCAGGACATGGCGAGGAGTACCCGGCGGCTGG

GGCACACAGCAGCCCCCCAAAGGCCCGCTTCCTGCGGGTTCCCAGTGAGCACCC

TTACCTGACCCCATCCCCCGAATCCCCTGAGCACTGGGCCAGCCCCTCACCTCC

CTCCCTCTCAGACTGGTCCGAATCCACGCCTAGCCCAGCCACTGCCACTGGGGC

CATGGCCACCACCACTGGGGCACTGCCTGCCCAGCCACTTCCCTTGTCTGTTCC

CAGCTCCCTTGCTCAGGCCCAGACCCAGCTGGGGCCCCAGCCGGAAGTTACCCC

CAAGAGGCAAGTGTTGGCCTGAGACGCTCGTCAGTTCTTAGATCTTGGGGGCCT

AAAGAGACCCCCGTCCTGCCTCCTTTCTTTCTCTGTCTCTTCCTTCCTTTTAGT

CTTTTTCATCCTCTTCTCTTTCCACCAACCCTCCTGCATCCTTGCCTTGCAGCG

TGACCGAGATAGGTCATCAGCCCAGGGCTTCAGTCTTCCTTTATTTATAATGGG

TGGGGGCTACCACCCACCCTCTCAGTCTTGTGAAGAGTCTGGGACCTCCTTCTT

CCCCACTTCTCTCTTCCCTCATTCCTTTCTCTCTCCTTCTGGCCTCTCATTTCC

TTACACTCTGACATGAATGAATTATTATTATTTTTATTTTTCTTTTTTTTTTTA

CATTTTGTATAGAAACAAATTCATTTAAACAAACTTATTATTATTATTTTTTAC

AAAATATATATATGGAGATGCTCCCTCCCCCTGTGAACCCCCCAGTGCCCCCGT

GGGGCTGAGTCTGTGGGCCCATTCGGCCAAGCTGGATTCTGTGTACCTAGTACA

CAGGCATGACTGGGATCCCGTGTACCGAGTACACGACCCAGGTATGTACCAAGT

AGGCACCCTTGGGCGCACCCACTGGGGCCAGGGGTCGGGGGAGTGTTGGGAGCC
```

-continued

TCCTCCCCACCCCACCTCCCTCACTTCACTGCATTCCAGATGGGACATGTTCCA

TAGCCTTGCTGGGGAAGGGCCCACTGCCAACTCCCTCTGCCCCAGCCCCACCCT

TGGCCATCTCCCTTTGGGAACTAGGGGGCTGCTGGTGGGAAATGGGAGCCAGGG

CAGATGTATGCATTCCTTTGTGTCCCTGTAAATGTGGGACTACAAGAAGAGGAG

CTGCCTGAGTGGTACTTTCTCTTCCTGGTAATCCTCTGGCCCAGCCTCATGGCA

GAATAGAGGTATTTTTAGGCTATTTTTGTAATATGGCTTCTGGTCAAAATCCCT

GTGTAGCTGAATTCCCAAGCCCTGCATTGTACAGCCCCCCACTCCCCTCACCAC

CTAATAAAGGAATAGTTAACACTCAAAAAAAAAAAAAAAAAA

Human notch 4 (NOTCH4) mRNA NM_004557.3

(SEQ ID NO: 33)

AGACGTGAGGCTTGCAGCAGGCCGAGGAGGAAGAAGAGGGGCAGTGGGAGCAGA

GGAGGTGGCTCCTGCCCCAGTGAGAGCTCTGAGGGTCCCTGCCTGAAGAGGGAC

AGGGACCGGGGCTTGGAGAAGGGGCTGTGGAATGCAGCCCCCTTCACTGCTGCT

GCTGCTGCTGCTGCTGCTGCTATGTGTCTCAGTGGTCAGACCCAGAGGGCT

GCTGTGTGGGAGTTTCCCAGAACCCTGTGCCAATGGAGGCACCTGCCTGAGCCT

GTCTCTGGGACAAGGGACCTGCCAGTGTGCCCCTGGCTTCCTGGGTGAGACGTG

CCAGTTTCCTGACCCCTGCCAGAACGCCCAGCTCTGCCAAAATGGAGGCAGCTG

CCAAGCCCTGCTTCCCGCTCCCCTAGGGCTCCCCAGCTCTCCCTCTCCATTGAC

ACCCAGCTTCTTGTGCACTTGCCTCCCTGGCTTCACTGGTGAGAGATGCCAGGC

CAAGCTTGAAGACCCTTGTCCTCCCTCCTTCTGTTCCAAAAGGGGCCGCTGCCA

CATCCAGGCCTCGGGCCGCCCACAGTGCTCCTGCATGCCTGGATGGACAGGTGA

GCAGTGCCAGCTTCGGGACTTCTGTTCAGCCAACCCATGTGTTAATGGAGGGGT

GTGTCTGGCCACATACCCCCAGATCCAGTGCCACTGCCCACCGGGCTTCGAGGG

CCATGCCTGTGAACGTGATGTCAACGAGTGCTTCCAGGACCCAGGACCCTGCCC

CAAAGGCACCTCCTGCCATAACACCCTGGGCTCCTTCCAGTGCCTCTGCCCTGT

GGGGCAGGAGGGTCCACGTTGTGAGCTGCGGGCAGGACCCTGCCCTCCTAGGGG

CTGTTCGAATGGGGGCACCTGCCAGCTGATGCCAGAGAAAGACTCCACCTTTCA

CCTCTGCCTCTGTCCCCCAGGTTTCATAGGCCCAGACTGTGAGGTGAATCCAGA

CAACTGTGTCAGCCACCAGTGTCAGAATGGGGGCACTTGCCAGGATGGGCTGGA

CACCTACACCTGCCTCTGCCCAGAAACCTGGACAGGCTGGGACTGCTCCGAAGA

TGTGGATGAGTGTGAGACCCAGGGTCCCCCTCACTGCAGAAACGGGGGCACCTG

CCAGAACTCTGCTGGTAGCTTTCACTGCGTGTGTGTGAGTGGCTGGGGCGGCAC

AAGCTGTGAGGAGAACCTGGATGACTGTATTGCTGCCACCTGTGCCCCGGGATC

CACCTGCATTGACCGGGTGGGCTCTTTCTCCTGCCTCTGCCCACCTGGACGCAC

AGGACTCCTGTGCCACTTGGAAGACATGTGTCTGAGCCAGCCGTGCCATGGGGA

TGCCCAATGCAGCACCAACCCCCTCACAGGCTCCACACTCTGCCTGTGTCAGCC

TGGCTATTCGGGGCCCACCTGCCACCAGGACCTGGACGAGTGTCTGATGGCCCA

GCAAGGCCCAAGTCCCTGTGAACATGGCGGTTCCTGCCTCAACACTCCTGGCTC

CTTCAACTGCCTCTGTCCACCTGGCTACACAGGCTCCCGTTGTGAGGCTGATCA

CAATGAGTGCCTCTCCCAGCCCTGCCACCCAGGAAGCACCTGTCTGGACCTACT

TGCCACCTTCCACTGCCTCTGCCCGCCAGGCTTAGAAGGGCAGCTCTGTGAGGT

GGAGACCAACGAGTGTGCCTCAGCTCCCTGCCTGAACCACGCGGATTGCCATGA

CCTGCTCAACGGCTTCCAGTGCATCTGCCTGCCTGGATTCTCCGGCACCCGATG

TGAGGAGGATATCGATGAGTGCAGAAGCTCTCCCTGTGCCAATGGTGGGCAGTG

CCAGGACCAGCCTGGAGCCTTCCACTGCAAGTGTCTCCCAGGCTTTGAAGGGCC

ACGCTGTCAAACAGAGGTGGATGAGTGCCTGAGTGACCCATGTCCCGTTGGAGC

CAGCTGCCTTGATCTTCCAGGAGCCTTCTTTTGCCTCTGCCCCTCTGGTTTCAC

AGGCCAGCTCTGTGAGGTTCCCCTGTGTGCTCCCAACCTGTGCCAGCCCAAGCA

GATATGTAAGGACCAGAAAGACAAGGCCAACTGCCTCTGTCCTGATGGAAGCCC

TGGCTGTGCCCCACCTGAGGACAACTGCACCTGCCACCACGGGCACTGCCAGAG

ATCCTCATGTGTGTGTGACGTGGGTTGGACGGGGCCAGAGTGTGAGGCAGAGCT

AGGGGGCTGCATCTCTGCACCCTGTGCCCATGGGGGGACCTGCTACCCCCAGCC

CTCTGGCTACAACTGCACCTGCCCTACAGGCTACACAGGACCCACCTGTAGTGA

GGAGATGACAGCTTGTCACTCAGGGCCATGTCTCAATGGCGGCTCCTGCAACCC

TAGCCCTGGAGGCTACTACTGCACCTGCCCTCCAAGCCACACAGGGCCCCAGTG

CCAAACCAGCACTGACTACTGTGTGTCTGCCCCGTGCTTCAATGGGGGTACCTG

TGTGAACAGGCCTGGCACCTTCTCCTGCCTCTGTGCCATGGGCTTCCAGGGCCC

GCGCTGTGAGGGAAAGCTCCGCCCCAGCTGTGCAGACAGCCCCTGTAGGAATAG

GGCAACCTGCCAGGACAGCCCTCAGGGTCCCCGCTGCCTCTGCCCCACTGGCTA

CACCGGAGGCAGCTGCCAGACTCTGATGGACTTATGTGCCCAGAAGCCCTGCCC

ACGCAATTCCCACTGCCTCCAGACTGGGCCCTCCTTCCACTGCTTGTGCCTCCA

GGGATGGACCGGGCCTCTCTGCAACCTTCCACTGTCCTCCTGCCAGAAGGCTGC

ACTGAGCCAAGGCATAGACGTCTCTTCCCTTTGCCACAATGGAGGCCTCTGTGT

CGACAGCGGCCCCTCCTATTTCTGCCACTGCCCCCCCTGGATTCCAAGGCAGCCT

GTGCCAGGATCACGTGAACCCATGTGAGTCCAGGCCTTGCCAGAACGGGGCCAC

CTGCATGGCCCAGCCCAGTGGGTATCTCTGCCAGTGTGCCCCAGGCTACGATGG

ACAGAACTGCTCAAAGGAACTCGATGCTTGTCAGTCCCAACCCTGTCACAACCA

TGGAACCTGTACTCCCAAACCTGGAGGATTCCACTGTGCCTGCCCTCCAGGCTT

TGTGGGGCTACGCTGTGAGGGAGACGTGGACGAGTGTCTGGACCAGCCCTGCCA

CCCCACAGGCACTGCAGCCTGCCACTCTCTGGCCAATGCCTTCTACTGCCAGTG

TCTGCCTGGACACACAGGCCAGTGGTGTGAGGTGGAGATAGACCCCTGCCACAG

CCAACCCTGCTTTCATGGAGGGACCTGTGAGGCCACAGCAGGATCACCCCTGGG

TTTCATCTGCCACTGCCCCAAGGGTTTTGAAGGCCCCACCTGCAGCCACAGGGC

CCCTTCCTGCGGCTTCCATCACTGCCACCACGGAGGCCTGTGTCTGCCCTCCCC

TAAGCCAGGCTTCCCACCACGCTGTGCCTGCCTCAGTGGCTATGGGGGTCCTGA

CTGCCTGACCCCACCAGCTCCTAAAGGCTGTGGCCCTCCCTCCCCATGCCTATA

CAATGGCAGCTGCTCAGAGACCACGGGCTTGGGGGGCCCAGGCTTTCGATGCTC

CTGCCCTCACAGCTCTCCAGGGCCCCGGTGTCAGAAACCCGGAGCCAAGGGGTG

TGAGGGCAGAAGTGGAGATGGGGCCTGCGATGCTGGCTGCAGTGGCCCGGGAGG

AAACTGGGATGGAGGGGACTGCTCTCTGGGAGTCCCAGACCCCTGGAAGGGCTG

CCCCTCCCACTCTCGGTGCTGGCTTCTCTTCCGGGACGGGCAGTGCCACCCACA

GTGTGACTCTGAAGAGTGTCTGTTTGATGGCTACGACTGTGAGACCCCTCCAGC

-continued

```
CTGCACTCCAGCCTATGACCAGTACTGCCATGATCACTTCCACAACGGGCACTG

TGAGAAAGGCTGCAACACTGCAGAGTGTGGCTGGGATGGAGGTGACTGCAGGCC

TGAAGATGGGGACCCAGAGTGGGGGCCCTCCCTGGCCCTGCTGGTGGTACTGAG

CCCCCCAGCCCTAGACCAGCAGCTGTTTGCCCTGGCCCGGGTGCTGTCCCTGAC

TCTGAGGGTAGGACTCTGGGTAAGGAAGGATCGTGATGGCAGGGACATGGTGTA

CCCCTATCCTGGGGCCCGGGCTGAAGAAAAGCTAGGAGGAACTCGGGACCCCAC

CTATCAGGAGAGAGCAGCCCCTCAAACGCAGCCCCTGGGCAAGGAGACCGACTC

CCTCAGTGCTGGGTTTGTGGTGGTCATGGGTGTGGATTTGTCCCGCTGTGGCCC

TGACCACCCGGCATCCCGCTGTCCCTGGGACCCTGGGCTTCTACTCCGCTTCCT

TGCTGCGATGGCTGCAGTGGGAGCCCTGGAGCCCCTGCTGCCTGGACCACTGCT

GGCTGTCCACCCTCATGCAGGGACCGCACCCCCTGCCAACCAGCTTCCCTGGCC

TGTGCTGTGCTCCCCAGTGGCCGGGGTGATTCTCCTGGCCCTAGGGGCTCTTCT

CGTCCTCCAGCTCATCCGGCGTCGACGCCGAGAGCATGGAGCTCTCTGGCTGCC

CCCTGGTTTCACTCGACGGCCTCGGACTCAGTCAGCTCCCCACCGACGCCGGCC

CCCACTAGGCGAGGACAGCATTGGTCTCAAGGCACTGAAGCCAAAGGCAGAAGT

TGATGAGGATGGAGTTGTGATGTGCTCAGGCCCTGAGGAGGGGAGAGGAGGTGGG

CCAGGCTGAAGAAACAGGCCCCACCCTCCACGTGCCAGCTCTGGTCTCTGAGTGG

TGGCTGTGGGGCGCTCCCTCAGGCAGCCATGCTAACTCCTCCCCAGGAATCTGA

GATGGAAGCCCCTGACCTGGACACCCGTGGACCTGATGGGGTGACACCCCTGAT

GTCAGCAGTTTGCTGTGGGGAAGTACAGTCCGGGACCTTCCAAGGGGCATGGTT

GGGATGTCCTGAGCCCTGGGAACCTCTGCTGGATGGAGGGGCCTGTCCCCAGGC

TCACACCGTGGGCACTGGGGAGACCCCCCTGCACCTGGCTGCCCGATTCTCCCG

GCCAACCGCTGCCCGCCGCCTCCTTGAGGCTGGAGCCAACCCCAACCAGCCAGA

CCGGGCAGGGCGCACACCCCTTCATGCTGCTGTGGCTGCTGATGCTCGGGAGGT

CTGCCAGCTTCTGCTCCGTAGCAGACAAACTGCAGTGGACGCTCGCACAGAGGA

CGGGACCACACCCTTGATGCTGGCTGCCAGGCTGGCGGTGGAAGACCTGGTTGA

AGAACTGATTGCAGCCCAAGCAGACGTGGGGGCCAGAGATAAATGGGGGAAAAC

TGCGCTGCACTGGGCTGCTGCCGTGAACAACGCCCGAGCCGCCCGCTCGCTTCT

CCAGGCCGGAGCCGATAAAGATGCCCAGGACAACAGGGAGCAGACGCCGCTATT

CCTGGCGGCGCGGGAAGGAGCGGTGGAAGTAGCCCAGCTACTGCTGGGGCTGGG

GGCAGCCCGAGAGCTGCGGGACCAGGCTGGGCTAGCGCCGGCGGACGTCGCTCA

CCAACGTAACCACTGGGATCTGCTGACGCTGCTGGAAGGGGCTGGGCCACCAGA

GGCCCGTCACAAAGCCACGCCGGGCCGCGAGGCTGGGCCCTTCCCGCGCGCACG

GACGGTGTCAGTAAGCGTGCCCCCGCATGGGGGCGGGGCTCTGCCGCGCTGCCG

GACGCTGTCAGCCGGAGCAGGCCCTCGTGGGGCGGAGCTTGTCTGCAGGCTCG

GACTTGGTCCGTAGACTTGGCTGCGCGGGGGGGCGGGGCCTATTCTCATTGCCG

GAGCCTCTCGGGAGTAGGAGCAGGAGGAGGCCCGACCCCTCGCGGCCGTAGGTT

TTCTGCAGGCATGCGCGGGCCTCGGCCCAACCCTGCGATAATGCGAGGAAGATA

CGGAGTGGCTGCCGGGCGCGGAGGCAGGGTCTCAACGGATGACTGGCCCTGTGA

TTGGGTGGCCCTGGGAGCTTGCGGTTCTGCCTCCAACATTCCGATCCCGCCTCC
```

-continued
TTGCCTTACTCCGTCCCCGGAGCGGGGATCACCTCAACTTGACTGTGGTCCCCC

AGCCCTCCAAGAAATGCCCATAAACCAAGGAGGAGAGGGTAAAAAATAGAAGAA

TACATGGTAGGGAGGAATTCCAAAAATGATTACCCATTAAAAGGCAGGCTGGAA

GGCCTTCCTGGTTTTAAGATGGATCCCCCAAAATGAAGGGTTGTGAGTTTAGTT

TCTCTCCTAAAATGAATGTATGCCCACCAGAGCAGACATCTTCCACGTGGAGAA

GCTGCAGCTCTGGAAAGAGGGTTTAAGATGCTAGGATGAGGCAGGCCCAGTCCT

CCTCCAGAAAATAAGACAGGCCACAGGAGGGCAGAGTGGAGTGGAAATACCCCT

AAGTTGGAACCAAGAATTGCAGGCATATGGGATGTAAGATGTTCTTTCCTATAT

ATGGTTTCCAAAGGGTGCCCCTATGATCCATTGTCCCCACTGCCCACAAATGGC

TGACAAATATTTATTGGGCACCTACTATGTGCCAGGCACTGTGTAGGTGCTGAA

AAGTGGCCAAGGGCCACCCCCGCTGATGACTCCTTGCATTCCCTCCCCTCACAA

CAAAGAACTCCACTGTGGGGATGAAGCGCTTCTTCTAGCCACTGCTATCGCTAT

TTAAGAACCCTAAATCTGTCACCCATAATAAAGCTGATTTGAAGTGTTAAAAAA

AAAAAAAAAAA

In some embodiments, the nucleic acid sequence encoding Notch, as described herein, is at least 80% identical to the sequence of SEQ ID NO: 29, SEQ ID NO: 30, SEQ ID NO: 31. SEQ ID NO: 32, or SEQ ID NO: 33. In some embodiments, the nucleic acid sequence encoding Notch is 80%, 81%, 82%, 83%, 84%, 85%, 86%, 87%, 88%, 89%, 90%, 91%, 92%, 93%, 94%, 95%, 96%, 97%, 98%, or 99% identical to the sequence of SEQ ID NO: 29, SEQ ID NO: 30, SEQ ID NO: 31. SEQ ID NO: 32, or SEQ ID NO: 33. In some embodiments, the nucleic acid sequence of Notch, as described herein, can vary from the sequence of SEQ ID NO: 29, SEQ ID NO: 30, SEQ ID NO: 31. SEQ ID NO: 32, or SEQ ID NO: 33 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more nucleotides.

A "chimeric Notch receptor polypeptide" of the present disclosure comprises: a) an extracellular domain comprising a first member of a specific binding pair; b) a Notch receptor polypeptide, where the Notch receptor polypeptide has a length of from 50 amino acids to 1000 amino acids, and comprises one or more ligand-inducible proteolytic cleavage sites; and c) an intracellular domain Binding of the first member of the specific binding pair to a second member of the specific binding pair induces cleavage of the Notch receptor polypeptide at the one or more ligand-inducible proteolytic cleavage sites, thereby releasing the intracellular domain. Release of the intracellular domain modulates an activity of a cell that produces the chimeric Notch receptor polypeptide. The extracellular domain comprises a first member of a specific binding pair; the first member of a specific binding pair comprises an amino acid sequence that is heterologous to the Notch receptor polypeptide. The intracellular domain comprises an amino acid sequence that is heterologous to the Notch receptor polypeptide.

The term "antigen-binding domain" means a domain that binds specifically to a target antigen. In some examples, an antigen-binding domain can be formed from the amino acids present within a single-chain polypeptide. In other examples, an antigen-binding domain can be formed from amino acids present within a first single-chain polypeptide and the amino acids present in one or more additional single-chain polypeptides (e.g., a second single-chain polypeptide). Non-limiting examples of antigen-binding domains are described herein, including, without limitation, scFvs, or LBDs (Ligand Binding Domains) of growth factors. Additional examples of antigen-binding domains are known in the art.

As used herein, the term "antigen" refers generally to a binding partner specifically recognized by an antigen-binding domain described herein. Exemplary antigens include different classes of molecules, such as, but not limited to, polypeptides and peptide fragments thereof, small molecules, lipids, carbohydrates, and nucleic acids. Non-limiting examples of antigen or antigens that can be specifically bound by any of the antigen-binding domains are described herein. Additional examples of antigen or antigens that can be specifically bound by any of the antigen-binding domains are known in the art.

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, nanobodies, bi-specific antibodies, multi-specific antibodies, and fusion proteins comprising an antigen-binding (also referred to herein as antigen binding) portion of an antibody and a non-antibody protein. Also encompassed by the term are Fab', Fv, F(ab').sub.2, and or other antibody fragments that retain specific binding to antigen, and monoclonal antibodies. A monoclonal antibody can be produced using hybridoma production technology, other production methods known to those skilled in the art can also be used (e.g., antibodies derived from antibody phage display libraries). An antibody can be monovalent or bivalent.

The term "humanized immunoglobulin" as used herein refers to an immunoglobulin comprising portions of immunoglobulins of different origin, wherein at least one portion comprises amino acid sequences of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a complementarity-determining region (CDR) derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Boss et al., U.S. Pat. No. 4,816,397; Neuberger, M. S. et al., WO 86/01533; Winter, U.S. Pat. No. 5,225,539; See also, Ladner et al., U.S. Pat. No. 4,946,778; Huston, U.S. Pat. No. 5,476,786; and Bird, R. E. et al., Science, 242: 423-426 (1988)), regarding single chain antibodies.

The term "nanobody" (Nb) refers to the smallest antigen binding fragment or single variable domain (V.sub.HH) derived from naturally occurring heavy chain antibody. They are derived from heavy chain only antibodies, seen in camelids. In the family of "camelids" immunoglobulins devoid of light polypeptide chains are found. "Camelids" comprise old world camelids (*Camelus bactrianus* and *Camelus dromedarius*) and new world camelids (for example, *Llama paccos, Llama* glama, *Llama guanicoe* and *Llama vicugna*). A single variable domain heavy chain antibody is referred to herein as a nanobody or a $V_{HH}$ antibody.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); domain antibodies (dAb; Holt et al., *Trends Biotechnol.* 21:484, 2003); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CHI) of the heavy chain. Fab fragments differ from Fab' fragments by the addition of a few residues at the carboxyl terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in The Pharmacology of Monoclonal Antibodies, Vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). Diabodies are described in EP 404,097; WO 93/11161; and Hollinger et al., *Proc. Natl. Acad. Sci. U.S.A.* 90:6444-6448, 1993.

The terms "polypeptide," "peptide," and "protein," used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In some embodiments, the polypeptide will be purified to greater than 90%, greater than 95%, or greater than 98%, The terms "chimeric antigen receptor" and "CAR", used interchangeably herein, refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. The term CAR is not limited specifically to CAR molecules but also includes CAR variants, i.e., CAR variants are described, e.g., in PCT Application No. US2014/016527; Fedorov et al., *Sci Transl. Med.* 5(215):215ra172, 2013; Glienke et al., *Front. Pharmacol.* 6:21, 2015; Kakarla & Gottschalk, *Cancer J.* 20(2):151-155, 2014; Riddell et al., *Cancer J.* 20(2):141-144, 2014; Pegram et al., *Cancer J.* 20(2):127-33, 2014; Cheadle et al., *Immunol Rev.* 257(1):91-106, 2014; Barrett et al., *Ann. Rev. Med.* 65:333-347, 2014; Sadelain et al., *Cancer Discov.* 3(4):388-98, 2013; and Cartellieri et al., *J. Biomed. Biotechnol.*

956304, 2010; the disclosures of which are incorporated herein by reference in their entirety.

In the instant invention, transcription of a nucleotide sequence is activated by a transcriptional activator fusion protein composed of HNF1 DNA binding domain (e.g., a human HNF1 DNA-binding domain), which binds with high selectivity to selected DNA sequences, fused to different polypeptides responsible for the ligand-dependent activity of the transactivator and its transcriptional activity (e.g., a human RelA protein). The fusion proteins of the invention are useful for modulating the level of transcription of any target gene linked to the selected HNF1 DNA binding sites. The fusion proteins can be used to specifically activate transcription from genes controlled by HNF1 responsive promoters in tissues lacking endogenous HNF1 and vHNF1 proteins. The fusion proteins of the invention are composed primarily of human elements. Fully human proteins mitigate the risk of immune recognition of the transactivator. Repressors are also provided in similar fashion.

U.S. Pat. No. 9,670,281 describes various chimeric Notch receptors, how to construct them, and methods of using them. The examples described below which detail how to humanize chimeric Notch receptors to have low immunogenicity can employ the chimeric Notch receptors shown in U.S. Pat. No. 9,670,281, e.g., in cells of the monocyte/macrophage lineage.

Certain abbreviations are used throughout to describe the domains of the four human Notch proteins. These are: NEC: extracellular subunit; NTM: transmembrane subunit; EGF: epidermal growth factor; HD: heterodimerization domain; ICN: intracellular domain; LNR: cysteine-rich LNR repeats; TM: transmembrane domain; RAM: RAM domain; NLS: nuclear localizing signals; ANK: ankyrin repeat domain; NCR: cysteine response region; TAD: transactivation domain; PEST: region rich in proline (P), glutamine (E), serine (S) and threonine (T) residues.

Methods

Besides the use for gene therapy, ligand-dependent transcription factors incorporating a humanized DBD of the invention can be used to modulate expression of genes that are contained in recombinant viral vectors and that might interfere with the growth of the viruses in the packaging cell lines during the production processes. These recombinant viruses might be derivatives of Adenoviruses, Retroviruses, Lentiviruses, Herpesviruses, Adeno-associated viruses and other viruses which are familiar to those skilled in the art. Another use would be to provide large scale production of a toxic protein of interest using cultured cells in vitro that do not contain endogenous HNF1/vHNF1 and which have been modified to contain a nucleic acid encoding the transactivator carrying the DBD of the invention in a form suitable for expression of the transactivator in the cells and a gene encoding the protein of interest operatively linked to, for example, an HNF1-dependent promoter.

To induce or repress transcription in vivo the ligand may be administered to the body, or a tissue of interest (e.g. by injection). The body to be treated may be that of an animal, particularly a mammal, which may be human or non-human, such as rabbit, guinea pig, rat, mouse or other rodent, cat, dog, pig, sheep, goat, cattle or horse, or which is a bird, such as a chicken. Suitable routes of administration include oral, intraperitoneal, intramuscular, or i.v.

One convenient way of producing a polypeptide or fusion protein according to the present invention is to express nucleic acid encoding it, by use of nucleic acid in an expression system. Accordingly the present invention also provides in various aspects nucleic acid encoding the transcriptional activator or repressor of the invention, which may be used for production of the encoded protein.

Generally, whether encoding for a protein or component in accordance with the present invention, nucleic acid is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as encompassing reference to the RNA equivalent, with U substituted for T.

Nucleic acid sequences encoding a polypeptide or fusion protein in accordance with the present invention can be readily prepared by the skilled person using the information and references contained herein and techniques known in the art. Sambrook, et al., A Molecular Cloning, A Laboratory Manual, Cold Spring Harbor Laboratory Press (1989-2016), and Ausubel et al., Current Protocols in Molecular Biology, John Wiley and Sons, (1994-2016)). These techniques include (i) the use of the polymerase chain reaction (PCR) to amplify samples of such nucleic acid, e.g. from genomic sources, (ii) chemical synthesis, or (iii) preparing cDNA sequences. DNA encoding portions of full-length coding sequences (e.g. a DNA binding domain, or regulatory domain as the case may be) may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the relevant sequence may be made, e.g. using site directed mutagenesis, to lead to the expression of modified peptide or to take account of codon preference in the host cells used to express the nucleic acid.

In order to obtain expression of the nucleic acid sequences, the sequences may be incorporated in a vector having one or more control sequences operably linked to the nucleic acid to control its expression. The vectors may include other sequences such as promoters or enhancers to drive the expression of the inserted nucleic acid, nucleic acid sequences so that the polypeptide or peptide is produced as a fusion and/or nucleic acid encoding secretion signals so that the polypeptide produced in the host cell is secreted from the cell. Polypeptide can then be obtained by transforming the vectors into host cells in which the vector is functional, culturing the host cells so that the polypeptide is produced and recovering the polypeptide from the host cells or the surrounding medium. Prokaryotic and eukaryotic cells are used for this purpose in the art, including strains of E. coli, yeast, and eukaryotic cells such as COS or CHO cells.

Thus, the present invention also encompasses a method of making a polypeptide or fusion protein as disclosed, the method including expression from nucleic acid encoding the product (generally nucleic acid according to the invention). This may conveniently be achieved by growing a host cell in culture, containing such a vector, under appropriate conditions which cause or allow expression of the polypeptide. Polypeptides may also be expressed in in vitro systems.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is E. coli.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, Molecular cloning: a Laboratory Manual: 4th edition, Green and Sambrook et al., 2012, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al., Eds., John Wiley & Sons, 2016.

For use in mammalian cells, a recombinant expression vector's control functions may be provided by viral genetic material. Exemplary promoters include those derived from polyoma, Adenovirus 2, cytomegalovirus and SV40.

A regulatory sequences of a recombinant expression vector used in the present invention may direct expression of a polypeptide or fusion protein preferentially in a particular cell type, i.e., tissue-specific regulatory elements can be used. In one embodiment, the recombinant expression vector of the invention is a plasmid. Alternatively, a recombinant expression vector of the invention can be a virus, or portion thereof, which allows for expression of a nucleic acid introduced into the viral nucleic acid. For example, replication defective retroviruses, adenoviruses and adeno-associated viruses can be used. Protocols for producing recombinant retroviruses and for infecting cells in vitro or in vivo with such viruses can be found in Ausubel, et al. (supra). The genome of a virus such as adenovirus can be manipulated such that it encodes and expresses a transactivator or repressor protein but is inactivated in terms of its ability to replicate in a normal lytic viral life cycle.

Thus, a further aspect of the present invention provides a host cell containing heterologous nucleic acid as disclosed herein.

Still further, a recombinant expression vector can be designed to allow homologous recombination between the nucleic acid encoding the transactivator or repressor and a target gene in a host cell. Such homologous recombination vectors can be used to create homologous recombinant animals that express a fusion protein of the invention.

Examples of mammalian cell lines which may be used include CHO dhfr-cells (Urlaub and Chasin, Proc. Natl. Acad. Sci. U.S.A. 77:4216-4220, 1980), 293 cells (Graham et al., J. Gen. Virol. 36:59, 1977) and myeloma cells like SP2 or NS0 (Meth. Enzymol. 73(B):3-46, 2016). In addition to cell lines, the invention is applicable to normal cells, such as cells to be modified for gene therapy purposes or embryonic cells modified to create a transgenic or homologous recombinant animal. Examples of cell types of particular interest for gene therapy purposes include hematopoietic stem cells, myoblasts, hepatocytes, lymphocytes, muscle cells, neuronal cells and skin epithelium and airway epithelium. Additionally, for transgenic or homologous recombinant animals, embryonic stem cells and fertilized oocytes can be modified to contain nucleic acid encoding a transactivator or repressor fusion protein.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All four human Notch proteins (Notch 1-4) were tested for their ability of their core LNR, HD and transmembrane domains to selectively release a GAL4-VP16 transcription factor fused C-terminal to their intracellular portion in response to an N-terminal extracellular CD19 ScFv fusion binding to its cognate antigen. Human Notch2 and Notch3 released functional quantities of the transcription factor upon antigen binding. Human Notch1 released small amounts of transcription factor in response to antigen-binding, while human Notch 4 released no detectable amount of transcription factor. Human Notch3 showed the best functional release of transcription factor in response to antigen-binding, and was used for a number of designs.

We further improved the minimal LIN12-HD-transmembrane "core" Notch2 and Notch3 domains to include an extra, short (~60 aa) intracellular domain that includes the natural Notch Nuclear Localization Sequence (NLS) to improve nuclear import upon self-cleavage and release of the transcription factor domain.

In order to minimize immunogenicity of the chimeric Notch receptor, a series of synthetic humanized transcription factors were designed and built from (1) a minimized human DNA-Binding Domain (DBD) and (2) a minimized, strong Transactivation Domain (TAD). The reason for creating an unnatural but humanized chimera is to eliminate unwanted endogenous cofactor interactions between the chimeric Notch receptor-released humanized transcription factor and the natural binding partners that a full-length human transcription factor would interact with. This is to improve the robustness and predictability of the chimeric antigen receptor induced transcriptional response in cellular applications utilizing a humanized antigen receptor.

A comprehensive screen of human transcription factors was undertaken in order to find natural DNA-Binding Domains to satisfy several criteria: (1) that the DNA Binding Domain belonged to a transcription factor that is generally not naturally expressed in the target host-cell-type. In the present embodiment we sought DNA-binding domains absent from any hematopoietic lineage, including especially lymphoid and T-cell lineages; and (2) that the DNA Binding Domain bound to its target DNA sequence with high affinities, with a dissociation constant at or lower than 10 nM.

The DNA-Binding Domains were first tested for their ability to bind to multisite synthetic promoters by expressing the DNA-binding domain fused to a natural transactivation domain to verify that it could upregulate GFP driven by the synthetic multisite promoter. This verifies that the designed cognate promoter—DNA-Binding Domain pair were correct.

The verified DNA-Binding Domains were then tested as fusions to synNotch along with a strong transactivation domain and assayed for their ability to upregulate the cognate-multisite-promoter driving GFP upon stimulation by external antigen and release to the nucleus.

Examples of human DNA-binding domains tested with this strategy were those taken from human CRX (Furukawa, Takahisa, Eric M. Morrow, and Constance L. Cepko. "Crx, a novel otx-like homeobox gene, shows photoreceptor-specific expression and regulates photoreceptor differentiation." Cell 91.4 (1997):531-541, //doi.org/10.1016/S0092-8674(00)80439-0), POU1F1 (Jacobson, Eric M., et al. "Structure of Pit-1 POU domain bound to DNA as a dimer: unexpected arrangement and flexibility." Genes & Development 11.2 (1997): 198-212, doi:10.1101/gad.11.2.198), HNF1A, EGR1 (Thiel, Gerald, and Giuseppe Cibelli. "Regulation of life and death by the zinc finger transcription factor Egr-1." Journal of cellular physiology 193.3 (2002): 287-292, DOI: 10.1002/jcp.10178) ZBTB18 (Najafabadi, Hamed S., et al. "C2H2 zinc finger proteins greatly expand the human regulatory lexicon." (Nature biotechnology 33.5 (2015): 555-562. doi:10.1038/nbt.3128), and ZNF528 (Najafabadi, Hamed S., et al. "C2H2 zinc finger proteins greatly expand the human regulatory lexicon." Nature biotechnology 33.5 (2015): 555-562, doi:10.1038/nbt.3128). All DNA-binding domains were able to induce strong GFP expression under control of their cognate promoters when expressed as soluble transcription factors. However, only the DNA-binding domains of HNF1A and EGR1 were able to induce detectable expression of GFP under their cognate promoter when expressed and released from a chimeric Notch fusion construct. Only a small fraction of the expressed chimeric Notch protein will self-cleave on response to stimulation by antigen-binding, so the effective concentration of the liberated, nuclear-imported transcription factor will be much lower than compared to a directly expressed transcription factor. Thus, a chimeric Notch-released transcription factor must exhibit extremely strong binding to its cognate promoter in order to be functional.

Human Transactivation Domains were screened for activity in the context of chimeric Notch designs by expressing them as fusions to a Gal4 DNA Binding Domain and measuring relative levels of GFP expression under control of a cognate Gal4 multisite promoter. These were also compared against the GFP expression levels induced by the non-human VP64 transactivation domain.

Examples of human transactivation domains screened in this manner include RelA (p65) (Wang, Weixin, et al. "The nuclear factor-кB RelA transcription factor is constitutively activated in human pancreatic adenocarcinoma cells." Clinical Cancer Research 5.1 (1999): 119-127), YAP (Lian, Ian, et al. "The role of YAP transcription coactivator in regulating stem cell self-renewal and differentiation." Genes & development 24.11 (2010): 1106-1118, doi:10.1101/gad.1903310), WWTR1 (TAZ) (Hong, Jeong-Ho, et al. "TAZ, a transcriptional modulator of mesenchymal stem cell differentiation." Science 309.5737 (2005): 1074-1078, doi: 10.1126/science.1110955), CREB3 (LZIP) (Omori, Yoshihiro, et al. "CREB-H: a novel mammalian transcription factor belonging to the CREB/ATF family and functioning via the box-B element with a liver-specific expression." Nucleic acids research 29.10 (2001): 2154-2162, doi: //doi.org/10.1093/nar/29.10.2154), and MyoD (Weintraub, Harold, and Robert Davis. "The myoD gene family: nodal point during specification of the muscle cell lineage." Science 251.4995 (1991): 761, doi: 10.1126/science.1846704). Of these, the transactivation domains of RelA (p65), WWTR1 (TAZ), and CREB3 (LZIP) showed activity in chimeric Notch. The activity of the transactivation domain of RelA (p65) was measured to be the strongest in inducing GFP expression.

Combining the best performing human Notch domain, the best performing DNA-binding domain, and the best-performing Transactivation domain results in the Notch3-HNF1a-p65 design for a chimeric, humanized Notch receptor.

Applications of humanized chimeric Notch receptor are numerous. Such can, for example, deliver CARs or t-cell receptors to treat disease. U.S. Pat. No. 9,670,281.

Reference to nucleotide or protein sequences below, generally refer to sequences in the National Center for Biotechnology Information (NCBI) (ncbi.nlm.niv.gov). Nucleotide sequences are all 5' to 3.'

Example 1. Construction of Chimeric Notch with Notch3, DNA Binding Domain of HNF1Alpha and p65 Transactivation Domain The following sequences were ordered as double-stranded synthetic DNA fragments (IDT gBlocks) or single-stranded long-oligonucleotides (IDT ultramers) which were made double-stranded by annealing with a short 3' reverse-complement oligo and second-strand synthesis by Phusion polymerase (Thermo Scientific™ Phusion™ High-Fidelity DNA Polymerase; Catalogue No. F534S).

Four synthetic dsDNA pieces were ordered from Integrated DNA Technologies (IDT) containing:

1. Human CD8a signal peptide 1-22 (NP_001139345 amino acids 1-22, (MALPVTALLLPLALLL-HAARPS) (SEQ ID NO: 1)), Myc-tag (EQKLI-SEEDL) (SEQ ID NO: 2), Anti-Human B cell (CD19) Antibody, clone FMC63.

2. Human Notch3 core (gi|134244285|NP_000426.2 amino acids 1374-1734).

3. GS flexible Linker (GSAAAGGSGGSGGS) (SEQ ID NO: 3), Human HNF1alpha (gi|807201167|NP_001293108.1 amino acids 1-283), GS flexible Linker (GGGSGGGS) (SEQ ID NO: 4).

4. Human Rel-A (p65) (gi|223468676|NP_068810.3 amino acids 1-551) plus stop codon.

These were designed to incorporate 20 nt of homology with 5' and 3' neighboring fragments for in-vitro recombination by the In-fusion cloning system (Clontech). All fragments were assembled by the In-fusion into the MluI/NotI cut vector backbone of self-inactivating lentivirus vector pHR-SIN:SFFV (Addgene; Catalogue No. 79121.

A second reporter construct was constructed by assembling three synthetic dsDNA fragments:

1. a 4× repeated palindromic DNA binding sequence for the HNF1a DNA-binding domain dimer, immediately followed by a minimal CMV promoter

```
                                          (SEQ ID NO: 34)
atcgatGTTAATaATTAACatatatGTTAATcATTAACtatataGTTAAT tATTAACcgctatGTTAATgATTAACactagttaggcgtgtacggtggga ggcctatataagcagagctcgtttagtgaaccgtcagatcgcctggagac gccatccacgctgttttgacctccatagaagacaccgggaccgatccagc
```

2. A Kozak sequence (GCCGCCACC) (SEQ ID NO: 35) and coding sequence for EGFP.

3. An EF1α promoter sequence

4. A Kozak sequence (GCCGCCACC) (SEQ ID NO: 35) and coding sequence for mCherry.

These fragments were designed to incorporate an additional 20-25 nt of homology with 5' and 3' neighboring fragments for in-vitro recombination by the In-fusion cloning system (Clontech). All fragments were assembled by the In-fusion reaction into the MluI/NotI cut vector backbone of self-inactivating lentivirus vector pHR-SIN:SFFV.

The lentiviral construct was then co-transfected into 293T cells together with the viral packaging plasmids pCMVdR8.91 and pMD2.G using the transfection reagent FuGENE HD (Roche). Amphotropic VSV-G pseudotyped lentiviral particles in the supernatant were collected 48 hours later.

Viral particles from both synnotch and reporter constructs were used to transduce simultaneously either Jurkat cells or primary CD4+/CD8+ pan-T cells from human donors. An extended description of lentiviral protocols can be found in Morsut et al. *Cell.* 2016 Feb. 11; 164(4):780-91.

Transduced Jurkat cells were tested for expression 2 days post-transduction, transduced human primary pan-T cells were tested for expression 7 days post-transduction. Expression of the synnotch construct was tested by labelling the expressed cell-surface Myc-tag marker with alexa-647-conjugated anti-myc antibody (Cell Signaling Technology, Myc-Tag (9B11) Mouse mAb (Alexa Fluor®647 Conjugate; Catalogue No. 2233).

Expression of the cognate reporter construct for the synnotch was tested by observing the constitutive mCherry expression produced from the reporter vector. Double-positive cells were sorted for further assays.

Cells expressing both synnotch constructs and its reporter were assayed for synnotch activity by stimulating the cells for 24 hours with magnetic beads coated with anti-Myc-tag antibodies (obtained from Thermofisher Scientific, Catalog number: 88842) or magnetic beads coated with anti-HA-tag antibodies as a negative control (obtained from Pierce™ Anti-HA Magnetic Beads, catalog number 88836). The mean fluorescence intensity of the reporter's EGFP expression in response to the antibody-binding stimulation was measured for the stimulated cells vs that of the negative-control stimulated cells.

Cells expressing both synnotch constructs and its reporter were additionally assayed for synnotch activity by stimulating the cells for 24 hours by coincubating with a Raji cell line expressing high-levels of CD19 antigen (American Type Culture Collection (ATCC) CCL-86™ (Raji)) as well as coincubating with cell lines negative for cell-surface CD19. The mean fluorescence intensity of the cotransduced reporter's9 EGFP expression in response to the cell-bound-antigen stimulation was measured for the stimulated cells vs that of the negative-control stimulated cells.

Example 2. Construction of Chimeric Notch with Notch3, DNA Binding Domain of EGR1 and p65 Transactivation Domain Vector construction was similar to that of Example 1 with the exception that the synthetic DNA fragment containing the DNA-binding domain of human HNF1a was substituted for the following containing the human EGR1 DNA-binding domain:

GS flexible Linker (GSAAAGGSGGSGGS) (SEQ ID NO: 3), Human EGR1 (genbank NP_001955 amino acids 333-423), GS flexible Linker (GGGSGGGS) (SEQ ID NO: 4)

The reporter construct contained a cognate 4× binding site a 5× repeated DNA binding sequence for the EGR1 DNA-binding domain dimer, immediately followed by a minimal CMV promoter:

```
                                    (SEQ ID NO: 34)
acccggggggacagcagagatccagtttatcgatGCGTGGGCGataGCGG GGGCGtatGCGTGGGCGattGCGGGGGCGttaGCGTGGGCGactagttag gcgtgtacggtgggaggcctatataagcagagctcgtttagtgaaccgtc agatcgcctggagacgccatccacgctgttttgacctccatagaagacac cgggaccgatccagc
```

Example 3. Construction of Above Examples with WWTR1 (TAZ) Transactivation Domain Vector construction was identical to that of Example 1&2 with the exception that the synthetic DNA fragment containing the transactivation domain of human RelA (p65) was replaced by the following containing the transactivation domain of human WWTR1:

Human WWTR1 (TAZ) (Genpept NP_056287.1 amino acids 165-395) plus stop codon.

Example 4. Construction of Above Examples with CREB3 (LZIP) Transactivation Domain Vector construction was identical to that of Example 1 & 2 with the exception that the synthetic DNA fragment containing the transactivation domain of human RelA (p65) was replaced by the following containing the transactivation domain of human CREB3 (LZIP):

Human CREB3 (LZIP) (Genpept NP_006359.3 amino acids 1-95) plus stop codon.

Example 5. Construction of the Above Examples Using the Human Notch 2 Domain Vector construction was identical to that of Examples above with the exception that the synthetic DNA fragment containing the minimized human notch3 lin12-HD-NLS domains were replaced by the following fragment containing the minimized LIN12-HD-NLS domains of human notch2:Human Notch2 core (gi|24041035|NP_077719.2) amino acids 1413-1780.

Example 6. Transduction of Monocyte-Derived Macrophages with a Chimeric Notch Made from Notch3, the DNA Binding Domain of HNF1Alpha, and the p65 Transactivation Domain Mouse Notch 1 and human Notch 3 proteins were both tested for the ability of their core LNR, HD and transmembrane domains to selectively release a transcription factor, Gal4-VP64 for the mouse Notch protein or HNF1a-p65 for the human Notch protein, which was fused C-terminal to the intracellular portion of the protein, in response to the binding of the N-terminal extracellular CD19 scFv fusion portion of each protein to its cognate antigen in human monocyte-derived macrophages. The human Notch chimeric protein was constructed as described herein. The mouse Notch chimeric protein was constructed as described in U.S. Pat. No. 9,670,281.

Lentiviral constructs were co-transfected into 293T cells together with the viral packaging plasmids pCMV-dR8.91 and pMD2.G as well as the pVpx plasmid using the transfection reagent FuGENE HD (Roche). Amphotropic VSV-G pseudotyped lentiviral particles in the supernatant were collected 48 hours later. Jurkat cells were infected with different dilutions of viral supernatant and 7 days post infection and VCNs were determined by using the dd PCR.

Human macrophages were derived from monocytes isolated from freshly isolated (within 8 hours) healthy adult human blood (AllCells Inc.). CD14+ monocyte cells were enriched from blood utilizing RosetteSep negative selection (STEMCELL Technologies, RosetteSep™ Human Monocyte Enrichment Cocktail, Catalogue No. 15028). CD14+ cells were differentiated into macrophages as previously described (Hrecka et al., *Nature* 2011). Briefly, CD14% cells were placed in 24 well plates at a density of $3\times10^5$ cells/mL in 1 mL of media. Media was comprised of Dulbecco's Modified Eagle Media supplemented with 10% heat inactived foetal bovine serum, 2 mM L-glutamine, 100 u/ml Penicillin-G, 100 ug/mL streptomycin, 10 ng/mL macrophage-colony stimulating factor (M-CSF, Miltenyi Biotec) from day 0 to 2 than at 20 ng/mL from day 2 onwards.

Viral particles from both synNotch and reporter constructs were used to simultaneously to transduce monocyte-derived macrophage cells from human donors 4 days following isolation. Cells were transduced across a range of multiplicity of infections (0.1 to 1) with either the human Notch3, DNA binding domain of HNF1a and p65 transactivation domain (hNotch3/HNF1a/p65) or the mouse Notch 1, DNA binding domain of Gal4 and VP64 transactivation domain (mNotch1/Gal4/VP64). An extended description of lentiviral protocols can be found in Morsut L, et al. *Cell.* 2016 Feb. 11; 164(4):780-91.

Transduced human primary myeloid cells were tested for expression 7 days post-transduction by flow cytometry. Expression of the synNotch construct in myeloid cells was tested by labelling the myeloid cells with an PE-Cy7 anti-CD14+ antibody (BD Biosciences, PE-Cy™7 Mouse Anti-Human CD14 Antibody (Clone M5E2 (RUO)), Catalogue No. 557907) as well as the cell-surface expressed Myc-tag marker with an alexa-647-conjugated anti-my antibody (Cell Signaling Technology, Myc-Tag (9B11) Mouse mAb (Alexa Fluor® 647 Conjugate; Catalogue No. 2233).

Expression of the cognate reporter construct for the synNotch was tested by measuring the constitutive mCherry expression produced from the reporter vector by flow cytometry.

Cells were assayed for synNotch activity by stimulating the cells for 24 hours by co-culturing with a Daudi cell line expressing high-levels of CD19 antigen (American Type Culture Collection (ATCC) CCL-213™ cells (Daudi cells)) as well as cell lines negative for cell-surface CD19.

The fluorescence intensity of the cotransduced reporter's EGFP expression in response to the cell-bound-antigen stimulation was measured for these CD14+ monocyte-derived macrophages when stimulated with antigen positive CD19+ cells versus that of the negative-control stimulated cells.

Figure 2:
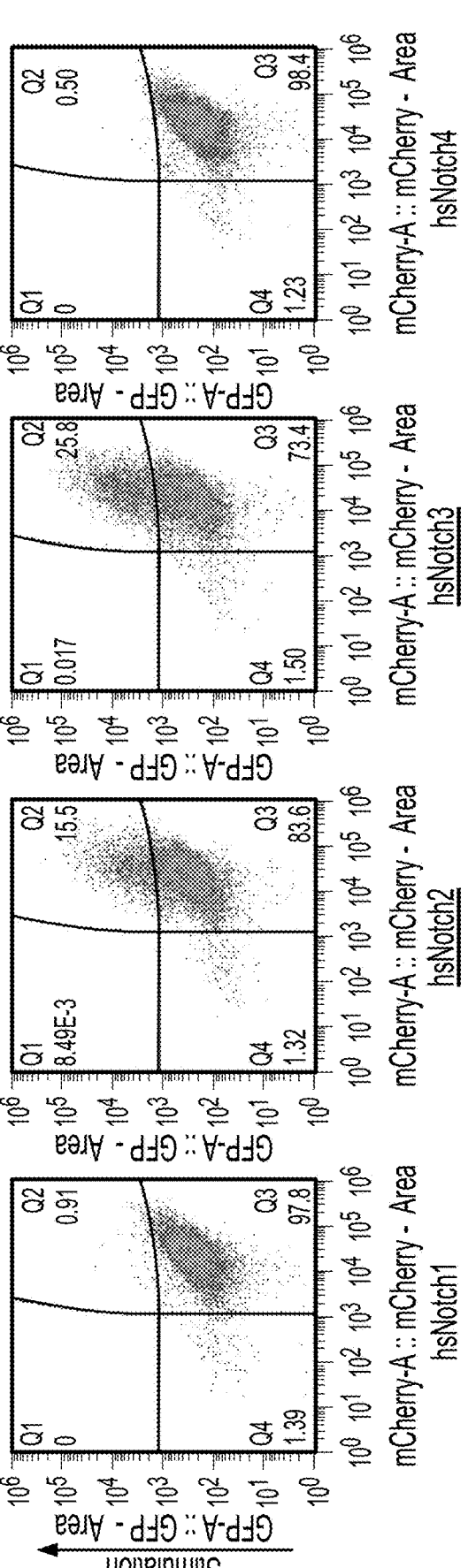
FIG. 2. Experimental data showing the relative performance of the four human Notch homologs in releasing GAL4-vp64 upon stimulation by an external myc-tag binding antigen to myc-bearing beads. hsNotch2 and hsNotch3 are the only homologs showing strong activity.
Figure 3A:
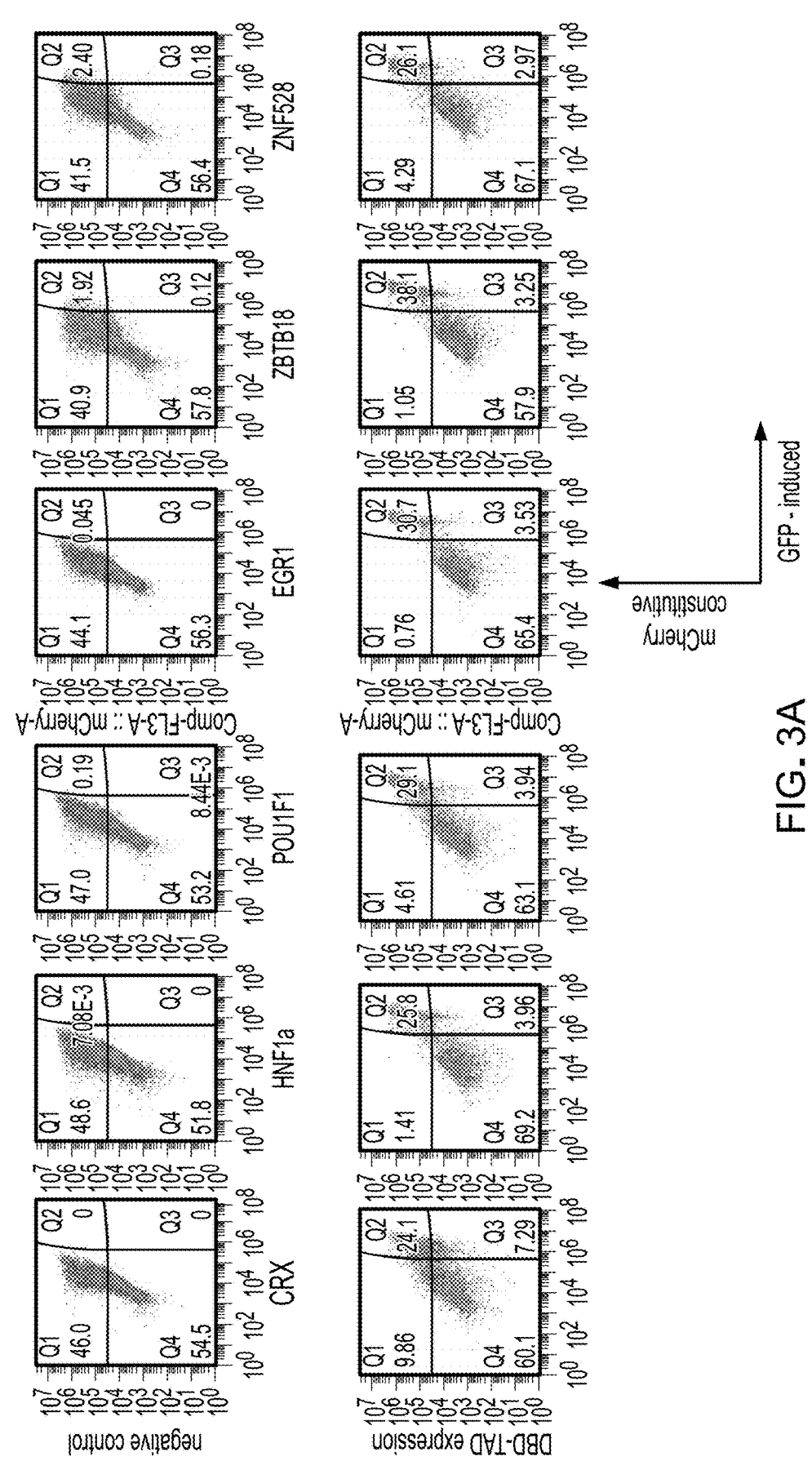
FIG. 3A. Experimental data showing the functional behavior of human DNA-binding domains fused to p65 transactivation domain upregulating GFP expression.
Figure 3B:
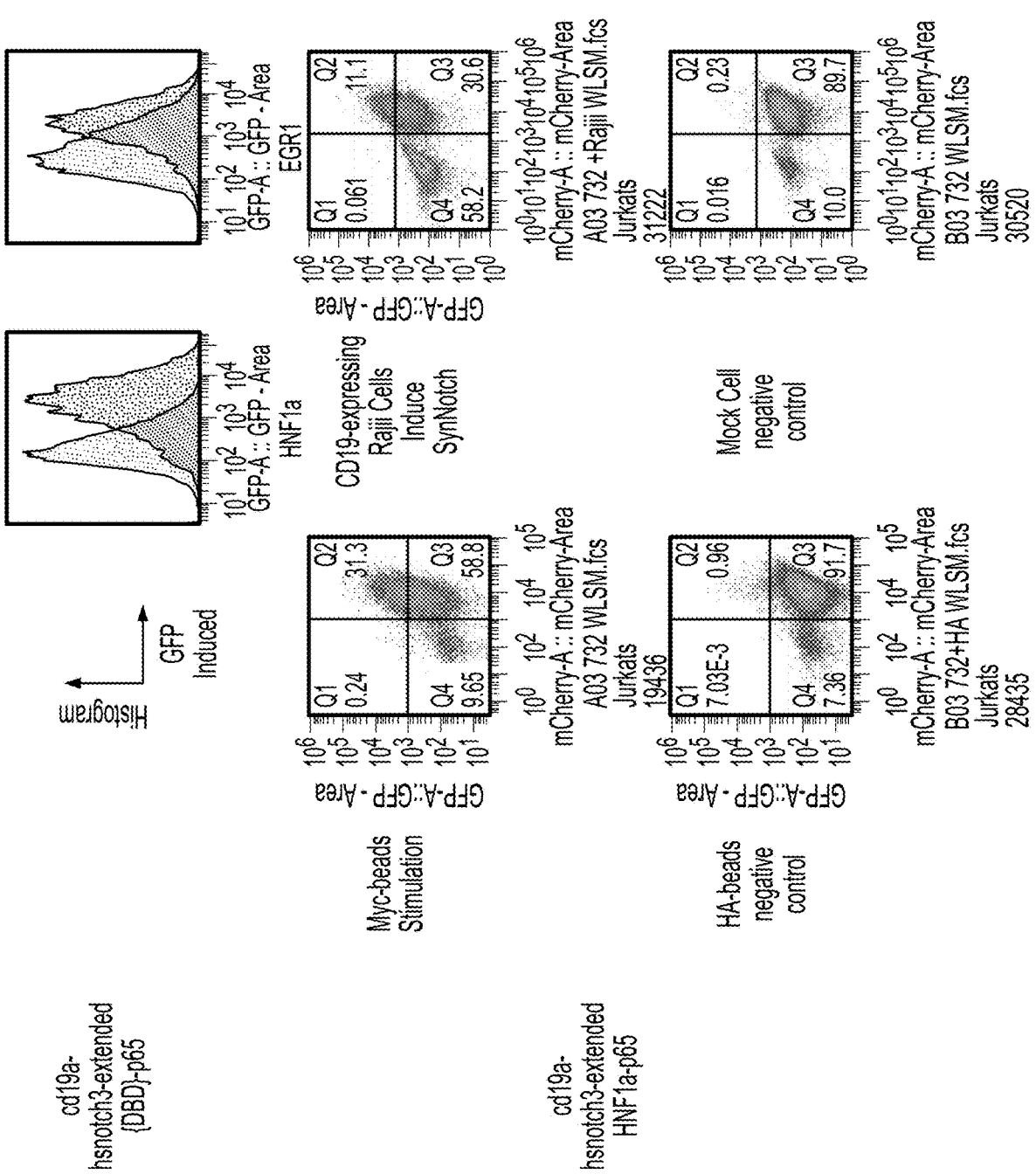
FIG. 3B. Experimental data showing the functional behavior of two working synthetic Notch human DNA-binding domains with p65 transactivation domains upregulating GFP expression.
Figure 4:
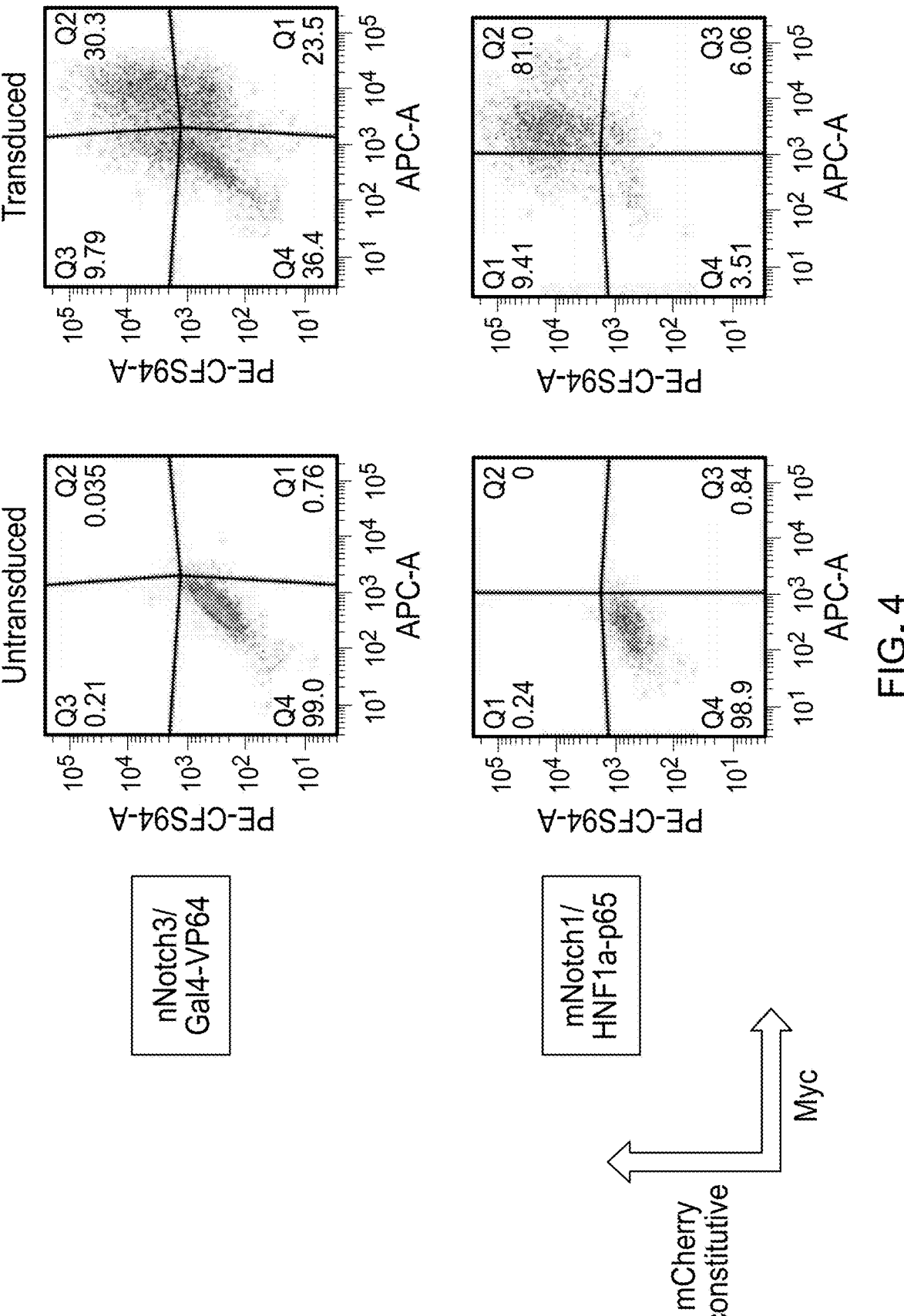
FIG. 4. Experimental data showing the expression of chimeric notch receptors in human monocyte-derived macrophage cells. Experimental data showing the percent transduction of mouse Notch 1 protein/Gal4 and VP64 transcription factors (top) and human Notch 3 protein/HNF1a and p65 transcription factors (bottom) relative to untransduced monocyte-derived macrophages (right).
Figure 5A:
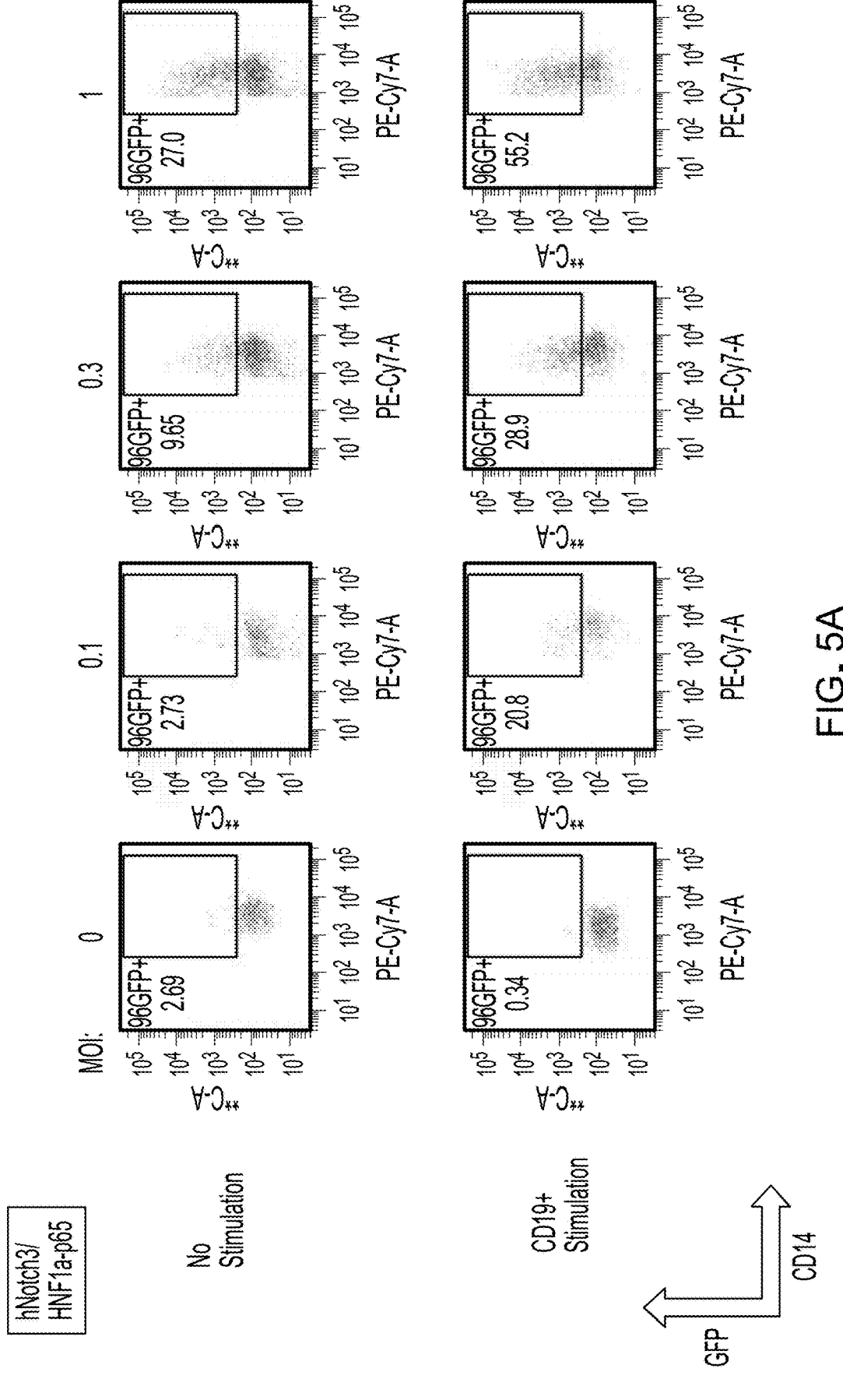
FIG. 5A. Experimental data showing the functional behavior of human Notch 3 and human DNA-binding domains fused to p65 transactivation domain upregulating GFP expression in human monocyte-derived macrophages.
Figure 5B:
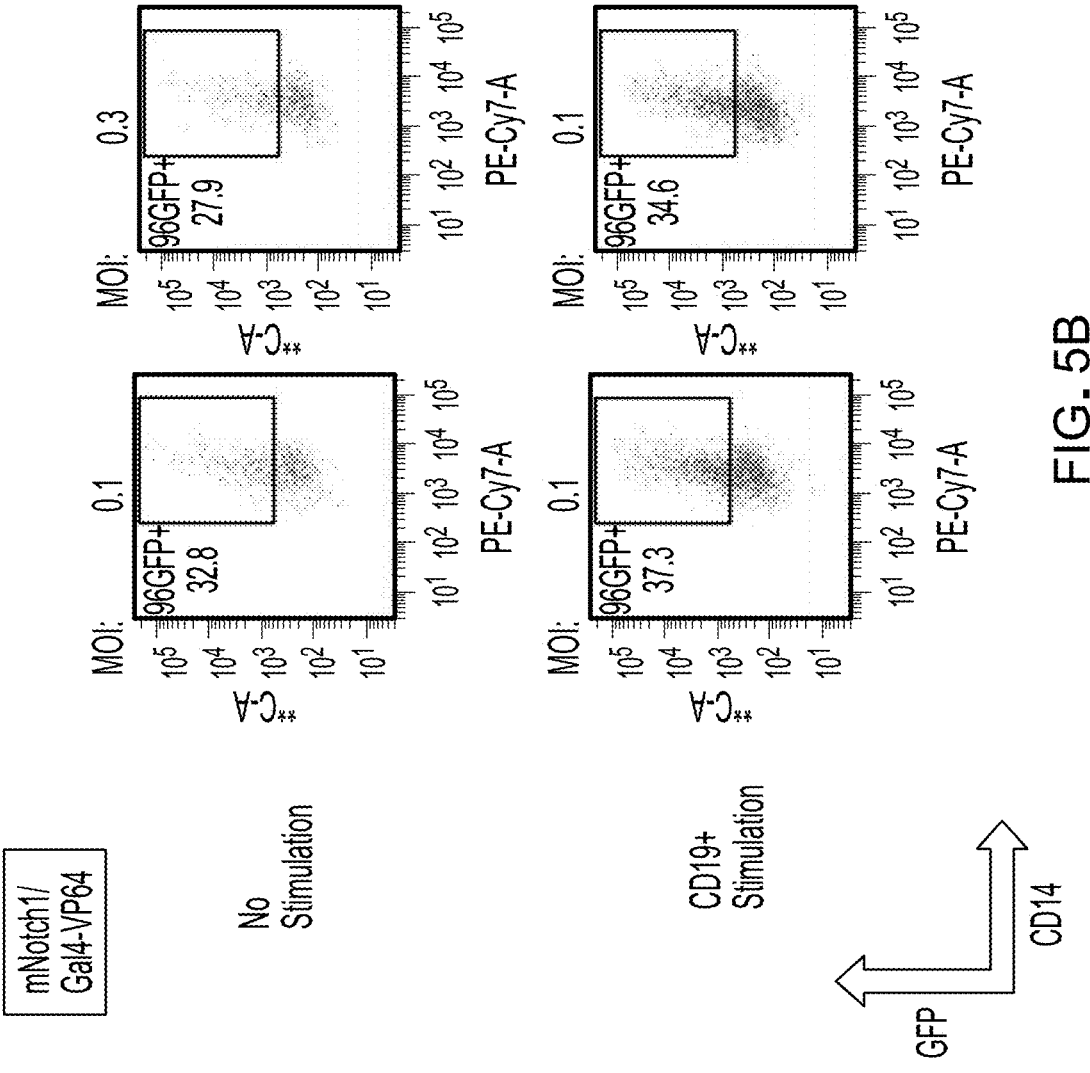
FIG. 5B. Experimental data showing the functional behavior of mouse Notch 1 and non-human Gal4 binding domains fused to VP64 transactivation upregulating GFP expression in human myeloid cells.

Overall, in monocyte-derived macrophages, the chimeric humanized Notch receptor, human Notch3-HNF1a-p65, induced unregulated expression of the reporter construct. The Notch, DNA-binding domain, and transactivation domain components of the protein were functional in macrophages. The chimeric mouse Notch receptor, Notch1-Gal4-VP64, did not induce the selective expression of GFP in response to an N-terminal extracellular CD19 scFv fusion binding to its cognate antigen compared to a negative control without any CD19 expression. See, FIGS. 2, 3A, 3B, 4, 5A, and 5B.

---

What is claimed is:

1. A method of treating a CD19-expressing cancer in a human subject in need thereof, the method comprising administering to the human subject a therapeutically effective amount of a T cell expressing a chimeric Notch polypeptide comprising from N-terminal to C-terminal and in covalent linkage:
   a) an extracellular domain comprising a binding agent that specifically binds to human CD19;
   b) a human Notch 2 or human Notch 3 core domain comprising one or more proteolytic cleavage sites; and
   c) an intracellular domain comprising a transcriptional regulator comprising a DNA binding domain of human origin and a transactivation domain of human origin; and
wherein said T cell also comprises a nucleic acid construct comprising a cognate DNA binding sequence for the DNA binding domain of human origin, a promoter sequence, and a nucleic acid sequence encoding either a cytokine that locally induces and recruits immune cells to the CD19-expressing cancer or a chimeric antigen receptor (CAR) that targets an antigen other than CD19 on cancer cells in the human subject.

2. The method of claim 1, wherein the DNA binding domain is from human Hepatocyte Nuclear Factor 1 α (HNF1α) or human Early Growth Response 1 α (EGR1 α).

3. The method of claim 2, wherein the DNA binding domain is from human HNF1α.

4. The method of claim 3, wherein the human HNF1α DNA-binding domain of the chimeric Notch polypeptide comprises the DNA-binding domain of any one of the amino acid sequences of SEQ ID NO: 5, SEQ ID NO: 6 and SEQ ID NO: 7.

5. The method of claim 3, wherein the human HNF1α DNA-binding domain of the chimeric Notch polypeptide consists of the amino acid sequence of amino acids 1-283 of SEQ ID NO: 5.

6. The method of claim 1, wherein the polypeptide comprises a human Notch 3 core domain.

7. The method of claim 6, wherein the human Notch 3 core domain of the chimeric Notch polypeptide comprises the amino acid sequence of amino acids 1374-1734 of SEQ ID NO: 27.

8. The method of claim 1, wherein the transactivation domain is from human RelA (p65), human WWTR1 (TAZ), or human CREB3 (LZIP).

9. The method of claim 1, wherein the transactivation domain is from human RelA (p65).

10. The method of claim 9, wherein the transactivation domain of the chimeric Notch polypeptides comprises the transactivation domain from any one of SEQ ID NOs: 12-17.

11. The method of claim 1, wherein the binding agent is an scFv, a VHH, a bispecific antibody, or a BiTE.

12. The method of claim 1, wherein the intracellular domain further comprises a Nuclear Localization Sequence (NLS) upstream of the transcriptional regulator.

13. The method of claim 12, wherein the NLS is a native human Notch 3 NLS.

14. The method of claim 1, wherein the chimeric Notch polypeptide further comprises one or more linkers.

15. The method of claim 14, wherein the one or more linkers comprise the amino acid sequence of one or more of SEQ ID NO: 3 and SEQ ID NO: 4.

16. The method of claim 1, wherein the human Notch 2 or human Notch 3 core domain comprises three Lin-12 repeat regions (LNRs) and a transmembrane domain.

17. The method of claim 1, wherein the chimeric Notch polypeptide comprises from N-terminal to C-terminal and in covalent linkage:
   a) an extracellular domain comprising a scFv that specifically binds to human CD19;
   b) a human Notch 3 core domain comprising one or more proteolytic cleavage sites;
   c) a first glycine serine linker; and
   d) an intracellular domain comprising a transcriptional regulator comprising a DNA binding domain of human HNF1α, a second glycine serine linker, and a human RelA (p65) transactivation domain.

18. The method of claim 17, wherein:
   the human Notch 3 core domain of the chimeric Notch polypeptide comprises the amino acid sequence of amino acids 1374-1734 or 1374-1738 of SEQ ID NO: 27;
   the first glycine serine linker comprises the sequence set forth in SEQ ID NO:3;
   the DNA binding domain of human HNF1α comprises the DNA-binding domain of any one of the amino acid sequences of SEQ ID NO: 5, SEQ ID NO: 6 and SEQ ID NO: 7;
   the second glycine serine linker comprises the sequence set forth in SEQ ID NO:4; and
   wherein the human RelA transactivation domain is a transactivation domain from any one of the sequences of SEQ ID NOs: 12-17.

19. The method of claim 17, wherein the chimeric Notch polypeptide comprises a human CD8 alpha signal peptide immediately upstream of the scFv that specifically binds to human CD19.

20. A method of treating a CD19-expressing cancer in a human subject in need thereof, the method comprising administering to the human subject a therapeutically effective amount of a T cell expressing a chimeric Notch polypeptide comprising from N-terminal to C-terminal and in covalent linkage:
   a) an extracellular domain comprising an scFv that specifically binds to human CD19;

b) a human Notch 3 core domain comprising one or more proteolytic cleavage sites; and c) an intracellular domain comprising a transcriptional regulator comprising a human HNF1α DNA binding domain and a human RelA (p65) transactivation domain; and wherein said T cell also comprises a nucleic acid construct comprising a cognate DNA binding sequence for the HNF1a DNA binding domain, a promoter sequence, and a nucleic acid sequence encoding either a cytokine that locally induces and recruits immune cells to the CD19-expressing cancer or a chimeric antigen receptor (CAR) that targets an antigen other than CD19 on cancer cells in the human subject.

21. A method of treating a CD19-expressing cancer in a human subject in need thereof, the method comprising administering to the human subject a therapeutically effective amount of a macrophage expressing a chimeric Notch polypeptide comprising from N-terminal to C-terminal and in covalent linkage:

a) an extracellular domain comprising a binding agent that specifically binds to human CD19;

b) a human Notch 2 or human Notch 3 core domain comprising one or more proteolytic cleavage sites;

c) an intracellular domain comprising a transcriptional regulator comprising a DNA binding domain of human origin and a transactivation domain of human origin; and wherein said macrophage also comprises a nucleic acid construct comprising a cognate DNA binding sequence for the DNA binding domain of human origin, a promoter sequence, and a nucleic acid sequence encoding either a cytokine that locally induces and recruits immune cells to the CD19-expressing cancer or a chimeric antigen receptor (CAR) that targets an antigen other than CD19 on cancer cells in the human subject.

22. The method of claim 21, wherein the chimeric Notch polypeptide comprises from N-terminal to C-terminal and in covalent linkage:

a) an extracellular domain comprising an scFv that specifically binds to human CD19;

b) a human Notch 3 core domain comprising one or more proteolytic cleavage sites; and c) an intracellular domain comprising a transcriptional regulator comprising a human HNF1α DNA binding domain and a human RelA (p65) transactivation domain.

\* \* \* \* \*

SEQUENCE LISTING

<160> NUMBER OF SEQ ID NOS: 35

<210> SEQ ID NO 1
<211> LENGTH: 22
<212> TYPE: PRT
<213> ORGANISM: Homo sapiens

<400> SEQUENCE: 1

Met Ala Leu Pro Val Thr Ala Leu Leu Leu Pro Leu Ala Leu Leu Leu
1               5                   10                  15

His Ala Ala Arg Pro Ser
            20

<210> SEQ ID NO 2
<211> LENGTH: 10
<212> TYPE: PRT
<213> ORGANISM: Artificial Sequence
<220> FEATURE:
<223> OTHER INFORMATION: Myc tag

<400> SEQUENCE: 2

Glu Gln Lys Leu Ile Ser Glu Glu Asp Leu
1               5                   10

<210> SEQ ID NO 3
<211> LENGTH: 14

```
<212> TYPE: PRT
<213> ORGANISM: Artificial Sequence
<220> FEATURE:
<223> OTHER INFORMATION: GS linker

<400> SEQUENCE: 3

Gly Ser Ala Ala Ala Gly Gly Ser Gly Gly Ser Gly Gly Ser
1               5                   10

<210> SEQ ID NO 4
<211> LENGTH: 8
<212> TYPE: PRT
<213> ORGANISM: Artificial Sequence
<220> FEATURE:
<223> OTHER INFORMATION: GS linker

<400> SEQUENCE: 4

Gly Gly Gly Ser Gly Gly Gly Ser
1               5

<210> SEQ ID NO 5
<211> LENGTH: 638
<212> TYPE: PRT
<213> ORGANISM: Homo sapiens

<400> SEQUENCE: 5

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
                20                  25                  30

Pro Gly Pro Tyr Leu Leu Ala Gly Glu Gly Pro Leu Asp Lys Gly Glu
            35                  40                  45

Ser Cys Gly Gly Gly Arg Gly Glu Leu Ala Glu Leu Pro Asn Gly Leu
        50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
        130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
            195                 200                 205

Ala Ser Gln Gln Ile Leu Phe Gln Ala Tyr Glu Arg Gln Lys Asn Pro
        210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255
```

```
Asn Leu Val Thr Glu Val Arg Val Tyr Asn Trp Phe Ala Asn Arg Arg
            260             265             270

Lys Glu Glu Ala Phe Arg His Lys Leu Ala Met Asp Thr Tyr Ser Gly
            275             280             285

Pro Pro Pro Gly Pro Gly Pro Gly Pro Ala Leu Pro Ala His Ser Ser
            290             295             300

Pro Gly Leu Pro Pro Pro Ala Leu Ser Pro Ser Lys Val His Gly Val
305             310             315             320

Arg Tyr Gly Gln Pro Ala Thr Ser Glu Thr Ala Glu Val Pro Ser Ser
                325             330             335

Ser Gly Gly Pro Leu Val Thr Val Ser Thr Pro Leu His Gln Val Ser
            340             345             350

Pro Thr Gly Leu Glu Pro Ser His Ser Leu Leu Ser Thr Glu Ala Lys
            355             360             365

Leu Val Ser Ala Ala Gly Gly Pro Leu Pro Pro Val Ser Thr Leu Thr
            370             375             380

Ala Leu His Ser Leu Glu Gln Thr Ser Pro Gly Leu Asn Gln Gln Pro
385             390             395             400

Gln Asn Leu Ile Met Ala Ser Leu Pro Gly Val Met Thr Ile Gly Pro
                405             410             415

Gly Glu Pro Ala Ser Leu Gly Pro Thr Phe Thr Asn Thr Gly Ala Ser
            420             425             430

Thr Leu Val Ile Gly Leu Ala Ser Thr Gln Ala Gln Ser Val Pro Val
            435             440             445

Ile Asn Ser Met Gly Ser Ser Leu Thr Thr Leu Gln Pro Val Gln Phe
            450             455             460

Ser Gln Pro Leu His Pro Ser Tyr Gln Gln Pro Leu Met Pro Pro Val
465             470             475             480

Gln Ser His Val Thr Gln Ser Pro Phe Met Ala Thr Met Ala Gln Leu
                485             490             495

Gln Ser Pro His Ala Leu Tyr Ser His Lys Pro Glu Val Ala Gln Tyr
            500             505             510

Thr His Thr Gly Leu Leu Pro Gln Thr Met Leu Ile Thr Asp Thr Thr
            515             520             525

Asn Leu Ser Ala Leu Ala Ser Leu Thr Pro Thr Lys Gln Glu Ala Ala
            530             535             540

Leu Leu Pro Gln Val Phe Thr Ser Asp Thr Glu Ala Ser Ser Glu Ser
545             550             555             560

Gly Leu His Thr Pro Ala Ser Gln Ala Thr Thr Leu His Val Pro Ser
                565             570             575

Gln Asp Pro Ala Gly Ile Gln His Leu Gln Pro Ala His Arg Leu Ser
            580             585             590

Ala Ser Pro Thr Val Ser Ser Ser Ser Leu Val Leu Tyr Gln Ser Ser
            595             600             605

Asp Ser Ser Asn Gly Gln Ser His Leu Leu Pro Ser Asn His Ser Val
            610             615             620

Ile Glu Thr Phe Ile Ser Thr Gln Met Ala Ser Ser Ser Gln
625             630             635
```

<210> SEQ ID NO 6
<211> LENGTH: 631
<212> TYPE: PRT
<213> ORGANISM: Homo sapiens

<400> SEQUENCE: 6

```
Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
        50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
            115                 120                 125

Pro Gln Arg Glu Val Val Asp Thr Thr Gly Leu Asn Gln Ser His Leu
        130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
            245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
        275                 280                 285

Pro Pro Pro Gly Pro Gly Pro Gly Pro Ala Leu Pro Ala His Ser Ser
    290                 295                 300

Pro Gly Leu Pro Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
            325                 330                 335

Ser Gly Gly Pro Leu Val Thr Val Ser Thr Pro Leu His Gln Val Ser
            340                 345                 350

Pro Thr Gly Leu Glu Pro Ser His Ser Leu Leu Ser Thr Glu Ala Lys
        355                 360                 365

Leu Val Ser Ala Ala Gly Gly Pro Leu Pro Pro Val Ser Thr Leu Thr
        370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
                405                 410                 415
```

```
Gly Glu Pro Ala Ser Leu Gly Pro Thr Phe Thr Asn Thr Gly Ala Ser
            420             425             430

Thr Leu Val Ile Gly Leu Ala Ser Thr Gln Ala Gln Ser Val Pro Val
            435             440             445

Ile Asn Ser Met Gly Ser Ser Leu Thr Thr Leu Gln Pro Val Gln Phe
        450             455             460

Ser Gln Pro Leu His Pro Ser Tyr Gln Gln Pro Leu Met Pro Pro Val
465             470             475             480

Gln Ser His Val Thr Gln Ser Pro Phe Met Ala Thr Met Ala Gln Leu
                485             490             495

Gln Ser Pro His Ala Leu Tyr Ser His Lys Pro Glu Val Ala Gln Tyr
            500             505             510

Thr His Thr Gly Leu Leu Pro Gln Thr Met Leu Ile Thr Asp Thr Thr
            515             520             525

Asn Leu Ser Ala Leu Ala Ser Leu Thr Pro Thr Lys Gln Val Phe Thr
        530             535             540

Ser Asp Thr Glu Ala Ser Ser Glu Ser Gly Leu His Thr Pro Ala Ser
545             550             555             560

Gln Ala Thr Thr Leu His Val Pro Ser Gln Asp Pro Ala Gly Ile Gln
            565             570             575

His Leu Gln Pro Ala His Arg Leu Ser Ala Ser Pro Thr Val Ser Ser
            580             585             590

Ser Ser Leu Val Leu Tyr Gln Ser Ser Asp Ser Ser Asn Gly Gln Ser
            595             600             605

His Leu Leu Pro Ser Asn His Ser Val Ile Glu Thr Phe Ile Ser Thr
        610             615             620

Gln Met Ala Ser Ser Ser Gln
625             630
```

```
<210> SEQ ID NO 7
<211> LENGTH: 662
<212> TYPE: PRT
<213> ORGANISM: Homo sapiens

<400> SEQUENCE: 7

Met Val Ser Lys Leu Ser Gln Leu Gln Thr Glu Leu Leu Ala Ala Leu
1               5               10              15

Leu Glu Ser Gly Leu Ser Lys Glu Ala Leu Ile Gln Ala Leu Gly Glu
            20              25              30

Pro Gly Pro Tyr Leu Leu Ala Gly Glu Gly Pro Leu Asp Lys Gly Glu
            35              40              45

Ser Cys Gly Gly Gly Arg Gly Glu Leu Ala Glu Leu Pro Asn Gly Leu
        50              55              60

Gly Glu Thr Arg Gly Ser Glu Asp Glu Thr Asp Asp Gly Glu Asp
65              70              75              80

Phe Thr Pro Pro Ile Leu Lys Glu Leu Glu Asn Leu Ser Pro Glu Glu
            85              90              95

Ala Ala His Gln Lys Ala Val Val Glu Thr Leu Leu Gln Glu Asp Pro
            100             105             110

Trp Arg Val Ala Lys Met Val Lys Ser Tyr Leu Gln Gln His Asn Ile
            115             120             125

Pro Gln Arg Glu Val Val Asp Thr Thr Gly Leu Asn Gln Ser His Leu
            130             135             140

Ser Gln His Leu Asn Lys Gly Thr Pro Met Lys Thr Gln Lys Arg Ala
145             150             155             160
```

```
Ala Leu Tyr Thr Trp Tyr Val Arg Lys Gln Arg Glu Val Ala Gln Gln
            165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
            195                 200                 205

Ala Ser Gln Gln Ile Leu Phe Gln Ala Tyr Glu Arg Gln Lys Asn Pro
            210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
                260                 265                 270

Lys Glu Glu Ala Phe Arg His Lys Leu Ala Met Asp Thr Tyr Ser Gly
            275                 280                 285

Pro Pro Pro Gly Pro Gly Pro Gly Pro Ala Leu Pro Ala His Ser Ser
            290                 295                 300

Pro Gly Leu Pro Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
            340                 345                 350

Pro Thr Gly Leu Glu Pro Ser His Ser Leu Leu Ser Thr Glu Ala Lys
            355                 360                 365

Leu Val Ser Ala Ala Gly Gly Pro Leu Pro Pro Val Ser Thr Leu Thr
            370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
                405                 410                 415

Gly Glu Pro Ala Ser Leu Gly Pro Thr Phe Thr Asn Thr Gly Ala Ser
                420                 425                 430

Thr Leu Val Ile Gly Leu Ala Ser Thr Gln Ala Gln Ser Val Pro Val
                435                 440                 445

Ile Asn Ser Met Gly Ser Ser Leu Thr Thr Leu Gln Pro Val Gln Phe
            450                 455                 460

Ser Gln Pro Leu His Pro Ser Tyr Gln Gln Pro Leu Met Pro Pro Val
465                 470                 475                 480

Gln Ser His Val Thr Gln Ser Pro Phe Met Ala Thr Met Ala Gln Leu
                485                 490                 495

Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
            515                 520                 525

Asn Leu Ser Ala Leu Ala Ser Leu Thr Pro Thr Lys Gln Val Arg Ser
            530                 535                 540

Arg Pro Ala Gly Pro Pro Leu Ala Cys Asp Arg Ala Pro His Pro His
545                 550                 555                 560

Ile Pro Arg Ala Gln Glu Ala Ala Leu Leu Pro Gln Val Phe Thr Ser
                565                 570                 575
```

```
Asp Thr Glu Ala Ser Ser Glu Ser Gly Leu His Thr Pro Ala Ser Gln
            580                 585                 590

Ala Thr Thr Leu His Val Pro Ser Gln Asp Pro Ala Ser Ile Gln His
            595                 600                 605

Leu Gln Pro Ala His Arg Leu Ser Ala Ser Pro Thr Val Ser Ser Ser
        610                 615                 620

Ser Leu Val Leu Tyr Gln Ser Ser Asp Ser Ser Asn Gly Gln Ser His
625                 630                 635                 640

Leu Leu Pro Ser Asn His Ser Val Ile Glu Thr Phe Ile Ser Thr Gln
                645                 650                 655

Met Ala Ser Ser Ser Gln
            660
```

```
<210> SEQ ID NO 8
<211> LENGTH: 3438
<212> TYPE: DNA
<213> ORGANISM: Homo sapiens

<400> SEQUENCE: 8
```

```
ggggccctga ttcacgggcc gctggggcca gggttggggg ttgggggtgc ccacagggct      60
tggctagtgg ggtttttgggg gggcagtggg tgcaaggagt ttggtttgtg tctgccggcc     120
ggcaggcaaa cgcaacccac gcggtggggg aggcggctag cgtggtggac ccgggccgcg     180
tggccctgtg gcagccgagc catggtttct aaactgagcc agctgcagac ggagctcctg     240
gcggccctgc tcgagtcagg gctgagcaaa gaggcactga tccaggcact gggtgagccg     300
gggccctacc tcctggctgg agaaggcccc ctggacaagg gggagtcctg cggcggcggt     360
cgaggggagc tggctgagct gcccaatggg ctgggggaga ctcggggctc cgaggacgag     420
acggacgacg atggggaaga cttcacgcca cccatcctca aagagctgga gaacctcagc     480
cctgaggagg cggcccacca gaaagccgtg gtggagaccc ttctgcagga ggacccgtgg     540
cgtgtggcga gatggtcaa gtcctacctg cagcagcaca acatcccaca gcgggaggtg     600
gtcgatacca ctggcctcaa ccagtcccac ctgtcccaac acctcaacaa gggcactccc     660
atgaagacgc agaagcgggc cgccctgtac acctggtacg tccgcaagca gcgagaggtg     720
gcgcagcagt tcacccatgc agggcaggga gggctgattg aagagcccac aggtgatgag     780
ctaccaacca agaaggggcg gaggaaccgt ttcaagtggg gcccagcatc ccagcagatc     840
ctgttccagg cctatgagag gcagaagaac cctagcaagg aggagcgaga gacgctagtg     900
gaggagtgca ataggcgga atgcatccag agagggtgt ccccatcaca ggcacagggg     960
ctgggctcca acctcgtcac ggaggtgcgt gtctacaact ggtttgccaa ccggcgcaaa    1020
gaagaagcct tccggcacaa gctggccatg gacacgtaca gcgggccccc cccagggcca    1080
ggcccgggac ctgcgctgcc cgctcacagc tccctggcc tgcctccacc tgccctctcc    1140
cccagtaagg tccacggtgt gcgctatgga cagcctgcga ccagtgagac tgcagaagta    1200
ccctcaagca gcggcggtcc cttagtgaca gtgtctacac ccctccacca agtgtcccc     1260 acgggcctgg agcccagcca cagcctgctg agtacagaag ccaagctggt ctcagcagct    1320
gggggccccc tcccccctgt cagcaccctg acagcactgc acagcttgga gcagacatcc    1380
ccaggcctca accagcagcc ccagaacctc atcatggcct cacttcctgg ggtcatgacc    1440
atcgggcctg gtgagcctgc ctccctgggt cctacgttca ccaacacagg tgcctccacc    1500
ctggtcatcg gcctggcctc cacgcaggca cagagtgtgc cggtcatcaa cagcatgggc    1560
agcagcctga ccaccctgca gcccgtccag ttctcccagc cgctgcaccc ctcctaccag    1620
```

-continued

```
cagccgctca tgccacctgt gcagagccat gtgacccaga gcccttcat ggccaccatg    1680 gctcagctgc agagccccca cgccctctac agccacaagc ccgaggtggc ccagtacacc    1740
cacacgggcc tgctcccgca gactatgctc atcaccgaca ccaccaacct gagcgccctg    1800
gccagcctca cgcccaccaa gcaggaggct gctctgctcc cccaggtctt cacctcagac    1860
actgaggcct ccagtgagtc cgggcttcac acgccggcat ctcaggccac caccctccac    1920
gtccccagcc aggaccctgc cggcatccag cacctgcagc cggcccaccg gctcagcgcc    1980
agccccacag tgtcctccag cagcctggtg ctgtaccaga gctcagactc cagcaatggc    2040
cagagccacc tgctgccatc caaccacagc gtcatcgaga ccttcatctc cacccagatg    2100
gcctcttcct cccagtaacc acggcacctg ggccctgggg cctgtactgc ctgcttgggg    2160
ggtgatgagg gcagcagcca gccctgcctg gaggacctga gcctgccgag caaccgtggc    2220
ccttcctgga cagctgtgcc tcgctcccca ctctgctctg atgcatcaga aagggagggc    2280
tctgaggcgc cccaacccgt ggaggctgct cggggtgcac aggaggggt cgtggagagc     2340 taggagcaaa gcctgttcat ggcagatgta ggagggactg tcgctgcttc gtgggataca    2400
gtcttcttac ttggaactga aggggcggc ctatgacttg ggcacccca gcctgggcct      2460 atggagagcc ctgggaccgc tacaccactc tggcagccac acttctcagg acacaggcct    2520
gtgtagctgt gacctgctga gctctgagag gccctggatc agcgtggcct tgttctgtca    2580
ccaatgtacc caccgggcca ctccttcctg ccccaactcc ttccagctag tgacccacat    2640
gccatttgta ctgaccccat cacctactca cacaggcatt tcctgggtgg ctactctgtg    2700
ccagagcctg gggctctaac gcctgagccc agggaggccg aagctaacag ggaaggcagg    2760
cagggctctc ctggcttccc atccccagcg attccctctc ccaggcccca tgacctccag    2820
ctttcctgta tttgttccca agagcatcat gcctctgagg ccagcctggc ctcctgcctc    2880
tactgggaag gctacttcgg ggctgggaag tcgtccttac tcctgtggga gcctcgcaac    2940
ccgtgccaag tccaggtcct ggtggggcag ctcctctgtc tcgagcgccc tgcagaccct    3000
gcccttgttt ggggcaggag tagctgagct cacaaggcag caaggcccga gcagctgagc    3060
agggccgggg aactggccaa gctgaggtgc ccaggagaag aaagaggtga ccccagggca    3120
caggagctac ctgtgtggac aggactaaca ctcagaagcc tgggggcctg gctggctgag    3180
ggcagttcgc agccaccctg aggagtctga ggtcctgagc actgccagga gggacaaagg    3240
agcctgtgaa cccaggacaa gcatggtccc acatccctgg gcctgctgct gagaacctgg    3300
ccttcagtgt accgcgtcta ccctgggatt caggaaaagg cctggggtga cccggcaccc    3360
cctgcagctt gtagccagcc ggggcgagtg gcacgtttat ttaactttta gtaaagtcaa    3420
ggagaaatgc ggtggaaa                                                   3438
```

```
<210> SEQ ID NO 9
<211> LENGTH: 3417
<212> TYPE: DNA
<213> ORGANISM: Homo sapiens

<400> SEQUENCE: 9
ggggccctga ttcacgggcc gctggggcca gggttggggg ttgggggtgc ccacagggct      60
tggctagtgg ggtttttgggg gggcagtggg tgcaaggagt ttggtttgtg tctgccggcc    120
ggcaggcaaa cgcaacccac gcggtggggg aggcggctag cgtggtggac ccgggccgcg      180
tggccctgtg gcagccgagc catggtttct aaactgagcc agctgcagac ggagctcctg     240
```

```
gcggccctgc tcgagtcagg gctgagcaaa gaggcactga tccaggcact gggtgagccg      300
gggccctacc tcctggctgg agaaggcccc ctggacaagg gggagtcctg cggcggcggt      360
cgaggggagc tggctgagct gcccaatggg ctgggggaga ctcggggctc cgaggacgag      420
acggacgacg atgggggaaga cttcacgcca cccatcctca aagagctgga gaacctcagc      480
cctgaggagg cggcccacca gaaagccgtg gtggagaccc ttctgcagga ggacccgtgg      540
cgtgtggcga agatggtcaa gtcctacctg cagcagcaca acatcccaca gcgggaggtg      600
gtcgatacca ctggcctcaa ccagtcccac ctgtcccaac acctcaacaa gggcactccc      660
atgaagacgc agaagcgggc cgccctgtac acctggtacg tccgcaagca gcgagaggtg      720
gcgcagcagt tcacccatgc agggcaggga gggctgattg aagagcccac aggtgatgag      780
ctaccaacca agaaggggcg gaggaaccgt ttcaagtggg gcccagcatc ccagcagatc      840
ctgttccagg cctatgagag gcagaagaac cctagcaagg aggagcgaga gacgctagtg      900
gaggagtgca ataggcggga atgcatccag agaggggtgt ccccatcaca ggcacagggg      960
ctgggctcca acctcgtcac ggaggtgcgt gtctacaact ggtttgccaa ccggcgcaaa     1020
gaagaagcct tccggcacaa gctggccatg gacacgtaca gcgggccccc cccagggcca     1080
ggcccgggac ctgcgctgcc cgctcacagc tcccctggcc tgcctccacc tgccctctcc     1140
cccagtaagg tccacggtgt gcgctatgga cagcctgcga ccagtgagac tgcagaagta     1200
ccctcaagca gcggcggtcc cttagtgaca gtgtctacac ccctccacca agtgtccccc     1260
acgggcctgg agcccagcca cagcctgctg agtacagaag ccaagctggt ctcagcagct     1320
gggggccccc tccccctgt cagcaccctg acagcactgc acagcttgga gcagacatcc     1380
ccaggcctca accagcagcc ccagaacctc atcatggcct cacttcctgg ggtcatgacc     1440
atcgggcctg gtgagcctgc ctccctgggt cctacgttca ccaacacagg tgcctccacc     1500
ctggtcatcg gcctggcctc cacgcaggca cagagtgtgc cggtcatcaa cagcatgggc     1560
agcagcctga ccaccctgca gcccgtccag ttctcccagc cgctgcaccc ctcctaccag     1620
cagccgctca tgccacctgt gcagagccat gtgacccaga gccccttcat ggccaccatg     1680
gctcagctgc agagccccca cgccctctac agccacaagc ccgaggtggc ccagtacacc     1740
cacacgggcc tgctcccgca gactatgctc atcaccgaca ccaccaacct gagcgccctg     1800
gccagcctca cgcccaccaa gcaggtcttc acctcagaca ctgaggcctc cagtgagtcc     1860
gggcttcaca cgccggcatc tcaggccacc accctccacg tccccagcca ggaccctgcc     1920
ggcatccagc acctgcagcc ggccaccgg ctcagcgcca gccccacagt gtcctccagc     1980
agcctggtgc tgtaccagag ctcagactcc agcaatggcc agagccacct gctgccatcc     2040
aaccacagcg tcatcgagac cttcatctcc acccagatgg cctcttcctc ccagtaacca     2100
cggcacctgg gccctggggc ctgtactgcc tgcttggggg gtgatgaggg cagcagccag     2160
ccctgcctgg aggacctgag cctgccgagc aaccgtggcc cttcctggac agctgtgcct     2220
cgctccccac tctgctctga tgcatcagaa agggagggct ctgaggcgcc ccaacccgtg     2280
gaggctgctc ggggtgcaca ggaggggggtc gtggagagct aggagcaaag cctgttcatg     2340
gcagatgtag gagggactgt cgctgcttcg tgggatacag tcttcttact tggaactgaa     2400
gggggcggcc tatgacttgg gcaccccag cctgggccta tggagagccc tgggaccgct     2460
acaccactct ggcagccaca cttctcagga cacaggcctg tgtagctgtg acctgctgag     2520
ctctgagagg ccctggatca gcgtggcctt gttctgtcac caatgtaccc accgggccac     2580
tccttcctgc cccaactcct tccagctagt gacccacatg ccatttgtac tgaccccatc     2640
```

-continued

```
acctactcac acaggcattt cctgggtggc tactctgtgc cagagcctgg ggctctaacg      2700
cctgagccca gggaggccga agctaacagg gaaggcaggc agggctctcc tggcttccca      2760
tccccagcga ttccctctcc caggccccat gacctccagc tttcctgtat ttgttcccaa      2820
gagcatcatg cctctgaggc cagcctggcc tcctgcctct actgggaagg ctacttcggg      2880
gctgggaagt cgtccttact cctgtgggag cctcgcaacc cgtgccaagt ccaggtcctg      2940
gtggggcagc tcctctgtct cgagcgccct gcagaccctg cccttgtttg gggcaggagt      3000
agctgagctc acaaggcagc aaggcccgag cagctgagca gggccgggga actggccaag      3060
ctgaggtgcc caggagaaga aagaggtgac cccagggcac aggagctacc tgtgtggaca      3120
ggactaacac tcagaagcct gggggcctgg ctggctgagg gcagttcgca gccaccctga      3180
ggagtctgag gtcctgagca ctgccaggag ggacaaagga gcctgtgaac ccaggacaag      3240
catggtccca catccctggg cctgctgctg agaacctggc cttcagtgta ccgcgtctac      3300
cctgggattc aggaaaaggc ctggggtgac ccggcacccc ctgcagcttg tagccagccg      3360
gggcgagtgg cacgtttatt taactttttag taaagtcaag gagaaatgcg gtggaaa      3417
```

<210> SEQ ID NO 10
<211> LENGTH: 3563
<212> TYPE: DNA
<213> ORGANISM: Homo sapiens

<400> SEQUENCE: 10

```
ataaatatga accttggaga atttccccag ctccaatgta aacagaacag gcaggggccc        60
tgattcacgg gccgctgggg ccagggttgg gggttggggg tgcccacagg gcttggctag       120
tggggttttg gggggggcagt gggtgcaagg agtttggttt gtgtctgccg gccggcaggc       180
aaacgcaacc cacgcggtgg gggaggcggc tagcgtggtg gacccgggcc gcgtggccct       240
gtggcagccg agccatggtt tctaaactga gccagctgca gacggagctc ctggcggccc       300
tgctcgagtc agggctgagc aaagaggcac tgatccaggc actgggtgag ccggggccct       360
acctcctggc tggagaaggc cccctggaca agggggagtc ctgcggcggc ggtcgagggg       420
agctggctga gctgcccaat gggctggggg agactcgggg ctccgaggac gagacggacg       480
acgatgggga agacttcacg ccacccatcc tcaaagagct ggagaacctc agccctgagg       540
aggcggccca ccagaaagcc gtggtggaga cccttctgca ggaggacccg tggcgtgtgg       600
cgaagatggt caagtcctac ctgcagcagc acaacatccc acagcgggag gtggtcgata       660
ccactggcct caaccagtcc cacctgtccc aacacctcaa caagggcact cccatgaaga       720
cgcagaagcg ggccgccctg tacacctggt acgtccgcaa gcagcgagag gtggcgcagc       780
agttcaccca tgcagggcag ggagggctga ttgaagagcc cacaggtgat gagctaccaa       840
ccaagaaggg gcggaggaac cgtttcaagt ggggcccagc atcccagcag atcctgttcc       900
aggcctatga gaggcagaag aaccctagca aggaggagcg agagacgcta gtggaggagt       960
gcaatagggc ggaatgcatc cagagagggg tgtccccatc acaggcacag gggctgggct      1020
ccaacctcgt cacggaggtg cgtgtctaca ctggtttgc caaccggcgc aaagaagaag      1080
ccttccggca caagctggcc atggacacgt acagcgggcc cccccaggg ccaggcccgg      1140 gacctgcgct gccgctcac agctccctg gcctgcctcc acctgccctc tccccagta      1200 aggtccacgt gtgtgcgctat ggacagcctg cgaccagtga gactgcagaa gtaccctcaa      1260
gcagcggcgg tcccttagtg acagtgtcta caccctccca ccaagtgtcc cccacgggcc      1320
```

```
tggagcccag ccacagcctg ctgagtacag aagccaagct ggtctcagca gctgggggcc     1380
ccctcccccc tgtcagcacc ctgacagcac tgcacagctt ggagcagaca tccccaggcc     1440
tcaaccagca gccccagaac ctcatcatgg cctcacttcc tggggtcatg accatcgggc     1500
ctggtgagcc tgcctccctg ggtcctacgt tcaccaacac aggtgcctcc accctggtca     1560
tcggcctggc ctccacgcag gcacagagtg tgccggtcat caacagcatg ggcagcagcc     1620
tgaccaccct gcagcccgtc cagttctccc agccgctgca cccctcctac cagcagccgc     1680
tcatgccacc tgtgcagagc catgtgaccc agagcccctt catggccacc atggctcagc     1740
tgcagagccc ccacgccctc tacagccaca gcccgaggt ggcccagtac acccacacgg      1800
gcctgctccc gcagactatg ctcatcaccg acaccaccaa cctgagcgcc ctggccagcc     1860
tcacgcccac caagcaggta aggtccaggc ctgctggccc tcccttggcc tgtgacagag     1920
cccctcaccc ccacatcccc cgggctcagg aggctgctct gctcccccag gtcttcacct     1980
cagacactga ggcctccagt gagtccgggc ttcacacgcc ggcatctcag gccaccaccc     2040
tccacgtccc cagccaggac cctgccagca tccagcacct gcagccggcc caccggctca     2100
gcgccagccc cacagtgtcc tccagcagcc tggtgctgta ccagagctca gactccagca     2160
atggccagag ccacctgctg ccatccaacc acagcgtcat cgagaccttc atctccaccc     2220
agatggcctc ttcctcccag taaccacggc acctgggccc tggggcctgt actgcctgct     2280
tggggggtga tgagggcagc agccagccct gcctggagga cctgagcctg ccgagcaacc     2340
gtggcccttc ctggacagct gtgcctcgct ccccactctg ctctgatgca tcagaaaggg     2400
agggctctga ggcgccccaa cccgtggagg ctgctcgggg tgcacaggag ggggtcgtgg     2460
agagctagga gcaaagcctg ttcatggcag atgtaggagg gactgtcgct gcttcgtggg     2520
atacagtctt cttacttgga actgaagggg gcggcctatg acttgggcac ccccagcctg     2580
ggcctatgga gagccctggg accgctacac cactctggca gccacacttc tcaggacaca     2640
ggcctgtgta gctgtgacct gctgagctct gagaggccct ggatcagcgt ggccttgttc     2700
tgtcaccaat gtacccaccg ggccactcct tcctgcccca actccttcca gctagtgacc     2760
cacatgccat ttgtactgac cccatcacct actcacacag gcatttcctg ggtggctact     2820
ctgtgccaga gcctggggct ctaacgcctg agcccaggga ggccgaagct aacagggaag     2880
gcaggcaggg ctctcctggc ttcccatccc cagcgattcc ctctcccagg ccccatgacc     2940
tccagctttc ctgtatttgt tcccaagagc atcatgcctc tgaggccagc ctggcctcct     3000
gcctctactg ggaaggctac ttcggggctg ggaagtcgtc cttactcctg tgggagcctc     3060
gcaacccgtg ccaagtccag gtcctggtgg ggcagctcct ctgtctcgag cgccctgcag     3120
accctgccct tgtttggggc aggagtagct gagctcacaa ggcagcaagg cccgagcagc     3180
tgagcagggc cggggaactg gccaagctga ggtgcccagg agaagaaaga ggtgacccca     3240
gggcacagga gctacctgtg tggacaggac taacactcag aagcctgggg gcctggctgg     3300
ctgagggcag ttcgcagcca ccctgaggag tctgaggtcc tgagcactgc caggagggac     3360
aaaggagcct gtgaacccag acaagcatg gtcccacatc cctgggcctg ctgctgagaa      3420 cctgccttc agtgtaccgc gtctaccctg ggattcagga aaaggcctgg ggtgacccgg      3480 cacccctgc agcttgtagc cagccggggc gagtggcacg tttatttaac ttttagtaaa      3540
gtcaaggaga aatgcggtgg aaa                                            3563
```

<210> SEQ ID NO 11
<211> LENGTH: 13

```
<212> TYPE: DNA
<213> ORGANISM: Artificial Sequence
<220> FEATURE:
<223> OTHER INFORMATION: Synthetic Sequence (HNF1-alpha binding
      sequence)
<220> FEATURE:
<221> NAME/KEY: misc_feature
<222> LOCATION: (7)..(7)
<223> OTHER INFORMATION: nucleotide at position 7 can be any nucleotide

<400> SEQUENCE: 11
gttaatnatt aac                                                                     13

<210> SEQ ID NO 12
<211> LENGTH: 551
<212> TYPE: PRT
<213> ORGANISM: Homo sapiens

<400> SEQUENCE: 12

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
                20                  25                  30

Arg Phe Arg Tyr Lys Cys Glu Gly Arg Ser Ala Gly Ser Ile Pro Gly
            35                  40                  45

Glu Arg Ser Thr Asp Thr Thr Lys Thr His Pro Thr Ile Lys Ile Asn
        50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Ser His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Glu Asp Ile
    210                 215                 220

Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
            260                 265                 270

Arg Arg Pro Ser Asp Arg Glu Leu Ser Glu Pro Met Glu Phe Gln Tyr
        275                 280                 285

Leu Pro Asp Thr Asp Asp Arg His Arg Ile Glu Glu Lys Arg Lys Arg
    290                 295                 300
```

```
Thr Tyr Glu Thr Phe Lys Ser Ile Met Lys Lys Ser Pro Phe Ser Gly
305             310             315             320

Pro Thr Asp Pro Arg Pro Pro Arg Arg Ile Ala Val Pro Ser Arg
            325             330             335

Ser Ser Ala Ser Val Pro Lys Pro Ala Pro Gln Pro Tyr Pro Phe Thr
            340             345             350

Ser Ser Leu Ser Thr Ile Asn Tyr Asp Glu Phe Pro Thr Met Val Phe
            355             360             365

Pro Ser Gly Gln Ile Ser Gln Ala Ser Ala Leu Ala Pro Ala Pro Pro
            370             375             380

Gln Val Leu Pro Gln Ala Pro Ala Pro Ala Pro Ala Pro Ala Met Val
385             390             395             400

Ser Ala Leu Ala Gln Ala Pro Ala Pro Val Pro Val Leu Ala Pro Gly
            405             410             415

Pro Pro Gln Ala Val Ala Pro Pro Ala Pro Lys Pro Thr Gln Ala Gly
            420             425             430

Glu Gly Thr Leu Ser Glu Ala Leu Leu Gln Leu Gln Phe Asp Asp Glu
            435             440             445

Asp Leu Gly Ala Leu Leu Gly Asn Ser Thr Asp Pro Ala Val Phe Thr
            450             455             460

Asp Leu Ala Ser Val Asp Asn Ser Glu Phe Gln Gln Leu Leu Asn Gln
465             470             475             480

Gly Ile Pro Val Ala Pro His Thr Thr Glu Pro Met Leu Met Glu Tyr
            485             490             495

Pro Glu Ala Ile Thr Arg Leu Val Thr Gly Ala Gln Arg Pro Pro Asp
            500             505             510

Pro Ala Pro Ala Pro Leu Gly Ala Pro Gly Leu Pro Asn Gly Leu Leu
            515             520             525

Ser Gly Asp Glu Asp Phe Ser Ser Ile Ala Asp Met Asp Phe Ser Ala
            530             535             540

Leu Leu Ser Gln Ile Ser Ser
545             550
```

```
<210> SEQ ID NO 13
<211> LENGTH: 548
<212> TYPE: PRT
<213> ORGANISM: Homo sapiens

<400> SEQUENCE: 13
```

```
Met Asp Glu Leu Phe Pro Leu Ile Phe Pro Ala Glu Pro Ala Gln Ala
1               5               10              15

Ser Gly Pro Tyr Val Glu Ile Ile Glu Gln Pro Lys Gln Arg Gly Met
            20              25              30

Arg Phe Arg Tyr Lys Cys Glu Gly Arg Ser Ala Gly Ser Ile Pro Gly
            35              40              45

Glu Arg Ser Thr Asp Thr Thr Lys Thr His Pro Thr Ile Lys Ile Asn
            50              55              60

Gly Tyr Thr Gly Pro Gly Thr Val Arg Ile Ser Leu Val Thr Lys Asp
65              70              75              80

Pro Pro His Arg Pro His Pro His Glu Leu Val Gly Lys Asp Cys Arg
            85              90              95

Asp Gly Phe Tyr Glu Ala Glu Leu Cys Pro Asp Arg Cys Ile His Ser
            100             105             110

Phe Gln Asn Leu Gly Ile Gln Cys Val Lys Lys Arg Asp Leu Glu Gln
            115             120             125
```

```
Ala Ile Ser Gln Arg Ile Gln Thr Asn Asn Asn Pro Phe Gln Glu Glu
    130                 135                 140

Gln Arg Gly Asp Tyr Asp Leu Asn Ala Val Arg Leu Cys Phe Gln Val
145                 150                 155                 160

Thr Val Arg Asp Pro Ser Gly Arg Pro Leu Arg Leu Pro Pro Val Leu
                165                 170                 175

Ser His Pro Ile Phe Asp Asn Arg Ala Pro Asn Thr Ala Glu Leu Lys
            180                 185                 190

Ile Cys Arg Val Asn Arg Asn Ser Gly Ser Cys Leu Gly Gly Asp Glu
            195                 200                 205

Ile Phe Leu Leu Cys Asp Lys Val Gln Lys Glu Asp Ile Glu Val Tyr
    210                 215                 220

Phe Thr Gly Pro Gly Trp Glu Ala Arg Gly Ser Phe Ser Gln Ala Asp
225                 230                 235                 240

Val His Arg Gln Val Ala Ile Val Phe Arg Thr Pro Pro Tyr Ala Asp
                245                 250                 255

Pro Ser Leu Gln Ala Pro Val Arg Val Ser Met Gln Leu Arg Arg Pro
                260                 265                 270

Ser Asp Arg Glu Leu Ser Glu Pro Met Glu Phe Gln Tyr Leu Pro Asp
            275                 280                 285

Thr Asp Asp Arg His Arg Ile Glu Glu Lys Arg Lys Arg Thr Tyr Glu
    290                 295                 300

Thr Phe Lys Ser Ile Met Lys Lys Ser Pro Phe Ser Gly Pro Thr Asp
305                 310                 315                 320

Pro Arg Pro Pro Pro Arg Arg Ile Ala Val Pro Ser Arg Ser Ser Ala
                325                 330                 335

Ser Val Pro Lys Pro Ala Pro Gln Pro Tyr Pro Phe Thr Ser Ser Leu
            340                 345                 350

Ser Thr Ile Asn Tyr Asp Glu Phe Pro Thr Met Val Phe Pro Ser Gly
            355                 360                 365

Gln Ile Ser Gln Ala Ser Ala Leu Ala Pro Ala Pro Pro Gln Val Leu
    370                 375                 380

Pro Gln Ala Pro Ala Pro Ala Pro Ala Pro Ala Met Val Ser Ala Leu
385                 390                 395                 400

Ala Gln Ala Pro Ala Pro Val Pro Val Leu Ala Pro Gly Pro Pro Gln
                405                 410                 415

Ala Val Ala Pro Pro Ala Pro Lys Pro Thr Gln Ala Gly Glu Gly Thr
            420                 425                 430

Leu Ser Glu Ala Leu Leu Gln Leu Gln Phe Asp Asp Glu Asp Leu Gly
            435                 440                 445

Ala Leu Leu Gly Asn Ser Thr Asp Pro Ala Val Phe Thr Asp Leu Ala
    450                 455                 460

Ser Val Asp Asn Ser Glu Phe Gln Gln Leu Leu Asn Gln Gly Ile Pro
465                 470                 475                 480

Val Ala Pro His Thr Thr Glu Pro Met Leu Met Glu Tyr Pro Glu Ala
                485                 490                 495

Ile Thr Arg Leu Val Thr Gly Ala Gln Arg Pro Pro Asp Pro Ala Pro
                500                 505                 510

Ala Pro Leu Gly Ala Pro Gly Leu Pro Asn Gly Leu Leu Ser Gly Asp
            515                 520                 525

Glu Asp Phe Ser Ser Ile Ala Asp Met Asp Phe Ser Ala Leu Leu Ser
    530                 535                 540
```

Gln Ile Ser Ser
545

<210> SEQ ID NO 14
<211> LENGTH: 482
<212> TYPE: PRT
<213> ORGANISM: Homo sapiens

<400> SEQUENCE: 14

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
                20                  25                  30

Arg Phe Arg Tyr Lys Cys Glu Gly Arg Ser Ala Gly Ser Ile Pro Gly
            35                  40                  45

Glu Arg Ser Thr Asp Thr Thr Lys Thr His Pro Thr Ile Lys Ile Asn
        50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Ser His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Glu Asp Ile
    210                 215                 220

Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
            260                 265                 270

Arg Arg Pro Ser Asp Arg Glu Leu Ser Glu Pro Met Glu Phe Gln Tyr
        275                 280                 285

Leu Pro Asp Thr Asp Asp Arg His Arg Ile Glu Glu Lys Arg Lys Arg
    290                 295                 300

Thr Tyr Glu Thr Phe Lys Ser Ile Met Lys Lys Ser Pro Phe Ser Gly
305                 310                 315                 320

Pro Thr Asp Pro Arg Pro Pro Pro Arg Arg Ile Ala Val Pro Ser Arg
                325                 330                 335

Ser Ser Ala Ser Val Pro Lys Pro Ala Pro Gly Pro Pro Gln Ala Val
            340                 345                 350

Ala Pro Pro Ala Pro Lys Pro Thr Gln Ala Gly Glu Gly Thr Leu Ser
        355                 360                 365

-continued

```
Glu Ala Leu Leu Gln Leu Gln Phe Asp Asp Glu Asp Leu Gly Ala Leu
    370             375             380

Leu Gly Asn Ser Thr Asp Pro Ala Val Phe Thr Asp Leu Ala Ser Val
385             390             395             400

Asp Asn Ser Glu Phe Gln Gln Leu Leu Asn Gln Gly Ile Pro Val Ala
                405             410             415

Pro His Thr Thr Glu Pro Met Leu Met Glu Tyr Pro Glu Ala Ile Thr
            420             425             430

Arg Leu Val Thr Gly Ala Gln Arg Pro Pro Asp Pro Ala Pro Ala Pro
        435             440             445

Leu Gly Ala Pro Gly Leu Pro Asn Gly Leu Leu Ser Gly Asp Glu Asp
    450             455             460

Phe Ser Ser Ile Ala Asp Met Asp Phe Ser Ala Leu Leu Ser Gln Ile
465             470             475             480

Ser Ser
```

```
<210> SEQ ID NO 15
<211> LENGTH: 448
<212> TYPE: PRT
<213> ORGANISM: Homo sapiens

<400> SEQUENCE: 15
```

```
Met Asp Glu Leu Phe Pro Leu Ile Phe Pro Ala Glu Pro Ala Gln Ala
1               5               10              15

Ser Gly Pro Tyr Val Glu Ile Ile Glu Gln Pro Lys Gln Arg Gly Met
            20              25              30

Arg Phe Arg Tyr Lys Cys Glu Gly Arg Ser Ala Gly Ser Ile Pro Gly
        35              40              45

Glu Arg Ser Thr Asp Thr Thr Lys Thr His Pro Thr Ile Lys Ile Asn
    50              55              60

Gly Tyr Thr Gly Pro Gly Thr Val Arg Ile Ser Leu Val Thr Lys Asp
65              70              75              80

Pro Pro His Arg Pro His Pro His Glu Leu Val Gly Lys Asp Cys Arg
                85              90              95

Asp Gly Phe Tyr Glu Ala Glu Leu Cys Pro Asp Arg Cys Ile His Ser
            100             105             110

Phe Gln Asn Leu Gly Ile Gln Cys Val Lys Lys Arg Asp Leu Glu Gln
        115             120             125

Ala Ile Ser Gln Arg Ile Gln Thr Asn Asn Asn Pro Phe Gln Val Pro
    130             135             140

Ile Glu Glu Gln Arg Gly Asp Tyr Asp Leu Asn Ala Val Arg Leu Cys
145             150             155             160

Phe Gln Val Thr Val Arg Asp Pro Ser Gly Arg Pro Leu Arg Leu Pro
            165             170             175

Pro Val Leu Ser His Pro Ile Phe Asp Asn Arg Ala Pro Asn Thr Ala
            180             185             190

Glu Leu Lys Ile Cys Arg Val Asn Arg Asn Ser Gly Ser Cys Leu Gly
        195             200             205

Gly Asp Glu Ile Phe Leu Leu Cys Asp Lys Val Gln Lys Glu Asp Ile
        210             215             220

Glu Val Tyr Phe Thr Gly Pro Gly Trp Glu Ala Arg Gly Ser Phe Ser
225             230             235             240

Gln Ala Asp Val His Arg Gln Val Ala Ile Val Phe Arg Thr Pro Pro
            245             250             255
```

-continued

```
Tyr Ala Asp Pro Ser Leu Gln Ala Pro Val Arg Val Ser Met Gln Leu
        260                 265                 270

Arg Arg Pro Ser Asp Arg Glu Leu Ser Glu Pro Met Glu Phe Gln Tyr
        275                 280                 285

Leu Pro Asp Thr Asp Asp Arg His Arg Ile Glu Glu Lys Arg Lys Arg
        290                 295                 300

Thr Tyr Glu Thr Phe Lys Ser Ile Met Lys Lys Ser Pro Phe Ser Gly
305                 310                 315                 320

Pro Thr Asp Pro Arg Pro Pro Arg Arg Ile Ala Val Pro Ser Arg
                325                 330                 335

Ser Ser Ala Ser Val Pro Lys Pro Ala Pro Gln Pro Tyr Pro Phe Thr
        340                 345                 350

Ser Ser Leu Ser Thr Ile Asn Tyr Asp Glu Phe Pro Thr Met Val Phe
        355                 360                 365

Pro Ser Gly Gln Ile Ser Gln Ala Ser Ala Leu Ala Pro Ala Pro Pro
        370                 375                 380

Gln Val Leu Pro Gln Ala Pro Ala Pro Ala Pro Ala Pro Ala Met Val
385                 390                 395                 400

Ser Ala Leu Ala Gln Arg Pro Pro Asp Pro Ala Pro Ala Pro Leu Gly
                405                 410                 415

Ala Pro Gly Leu Pro Asn Gly Leu Leu Ser Gly Asp Glu Asp Phe Ser
                420                 425                 430

Ser Ile Ala Asp Met Asp Phe Ser Ala Leu Leu Ser Gln Ile Ser Ser
        435                 440                 445
```

```
<210> SEQ ID NO 16
<211> LENGTH: 480
<212> TYPE: PRT
<213> ORGANISM: Homo sapiens

<400> SEQUENCE: 16
```

```
Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Ser His Pro Ile Phe Asp Asn Arg Ala Pro Asn Thr Ala
```

```
            180             185             190
Glu Leu Lys Ile Cys Arg Val Asn Arg Asn Ser Gly Ser Cys Leu Gly
        195             200             205

Gly Asp Glu Ile Phe Leu Leu Cys Asp Lys Val Gln Lys Asp Asp Arg
        210             215             220

His Arg Ile Glu Glu Lys Arg Lys Arg Thr Tyr Glu Thr Phe Lys Ser
225             230             235             240

Ile Met Lys Lys Ser Pro Phe Ser Gly Pro Thr Asp Pro Arg Pro Pro
            245             250             255

Pro Arg Arg Ile Ala Val Pro Ser Arg Ser Ser Ala Ser Val Pro Lys
            260             265             270

Pro Ala Pro Gln Pro Tyr Pro Phe Thr Ser Ser Leu Ser Thr Ile Asn
        275             280             285

Tyr Asp Glu Phe Pro Thr Met Val Phe Pro Ser Gly Gln Ile Ser Gln
        290             295             300

Ala Ser Ala Leu Ala Pro Ala Pro Pro Gln Val Leu Pro Gln Ala Pro
305             310             315             320

Ala Pro Ala Pro Ala Pro Ala Met Val Ser Ala Leu Ala Gln Ala Pro
            325             330             335

Ala Pro Val Pro Val Leu Ala Pro Gly Pro Pro Gln Ala Val Ala Pro
            340             345             350

Pro Ala Pro Lys Pro Thr Gln Ala Gly Glu Gly Thr Leu Ser Glu Ala
        355             360             365

Leu Leu Gln Leu Gln Phe Asp Asp Glu Asp Leu Gly Ala Leu Leu Gly
        370             375             380

Asn Ser Thr Asp Pro Ala Val Phe Thr Asp Leu Ala Ser Val Asp Asn
385             390             395             400

Ser Glu Phe Gln Gln Leu Leu Asn Gln Gly Ile Pro Val Ala Pro His
            405             410             415

Thr Thr Glu Pro Met Leu Met Glu Tyr Pro Glu Ala Ile Thr Arg Leu
            420             425             430

Val Thr Gly Ala Gln Arg Pro Pro Asp Pro Ala Pro Ala Pro Leu Gly
        435             440             445

Ala Pro Gly Leu Pro Asn Gly Leu Leu Ser Gly Asp Glu Asp Phe Ser
        450             455             460

Ser Ile Ala Asp Met Asp Phe Ser Ala Leu Leu Ser Gln Ile Ser Ser
465             470             475             480
```

```
<210> SEQ ID NO 17
<211> LENGTH: 445
<212> TYPE: PRT
<213> ORGANISM: Homo sapiens

<400> SEQUENCE: 17
```

```
Met Asp Glu Leu Phe Pro Leu Ile Phe Pro Ala Glu Pro Ala Gln Ala
1               5               10              15

Ser Gly Pro Tyr Val Glu Ile Ile Glu Gln Pro Lys Gln Arg Gly Met
            20              25              30

Arg Phe Arg Tyr Lys Cys Glu Gly Arg Ser Ala Gly Ser Ile Pro Gly
        35              40              45

Glu Arg Ser Thr Asp Thr Thr Lys Thr His Pro Thr Ile Lys Ile Asn
        50              55              60

Gly Tyr Thr Gly Pro Gly Thr Val Arg Ile Ser Leu Val Thr Lys Asp
65              70              75              80
```

```
Pro Pro His Arg Pro His Pro His Glu Leu Val Gly Lys Asp Cys Arg
            85              90                  95

Asp Gly Phe Tyr Glu Ala Glu Leu Cys Pro Asp Arg Cys Ile His Ser
            100             105             110

Phe Gln Asn Leu Gly Ile Gln Cys Val Lys Lys Arg Asp Leu Glu Gln
            115             120             125

Ala Ile Ser Gln Arg Ile Gln Thr Asn Asn Asn Pro Phe Gln Val Pro
    130             135             140

Ile Glu Glu Gln Arg Gly Asp Tyr Asp Leu Asn Ala Val Arg Leu Cys
145             150             155             160

Phe Gln Val Thr Val Arg Asp Pro Ser Gly Arg Pro Leu Arg Leu Pro
            165             170             175

Pro Val Leu Ser His Pro Ile Phe Asp Asn His Asp Arg His Arg Ile
            180             185             190

Glu Glu Lys Arg Lys Arg Thr Tyr Glu Thr Phe Lys Ser Ile Met Lys
            195             200             205

Lys Ser Pro Phe Ser Gly Pro Thr Asp Pro Arg Pro Pro Pro Arg Arg
    210             215             220

Ile Ala Val Pro Ser Arg Ser Ser Ala Ser Val Pro Lys Pro Ala Pro
225             230             235             240

Gln Pro Tyr Pro Phe Thr Ser Ser Leu Ser Thr Ile Asn Tyr Asp Glu
            245             250             255

Phe Pro Thr Met Val Phe Pro Ser Gly Gln Ile Ser Gln Ala Ser Ala
            260             265             270

Leu Ala Pro Ala Pro Pro Gln Val Leu Pro Gln Ala Pro Ala Pro Ala
            275             280             285

Pro Ala Pro Ala Met Val Ser Ala Leu Ala Gln Ala Pro Ala Pro Val
    290             295             300

Pro Val Leu Ala Pro Gly Pro Pro Gln Ala Val Ala Pro Pro Ala Pro
305             310             315             320

Lys Pro Thr Gln Ala Gly Glu Gly Thr Leu Ser Glu Ala Leu Leu Gln
            325             330             335

Leu Gln Phe Asp Asp Glu Asp Leu Gly Ala Leu Leu Gly Asn Ser Thr
            340             345             350

Asp Pro Ala Val Phe Thr Asp Leu Ala Ser Val Asp Asn Ser Glu Phe
            355             360             365

Gln Gln Leu Leu Asn Gln Gly Ile Pro Val Ala Pro His Thr Thr Glu
    370             375             380

Pro Met Leu Met Glu Tyr Pro Glu Ala Ile Thr Arg Leu Val Thr Gly
385             390             395             400

Ala Gln Arg Pro Pro Asp Pro Ala Pro Ala Pro Leu Gly Ala Pro Gly
            405             410             415

Leu Pro Asn Gly Leu Leu Ser Gly Asp Glu Asp Phe Ser Ser Ile Ala
            420             425             430

Asp Met Asp Phe Ser Ala Leu Leu Ser Gln Ile Ser Ser
            435             440             445
```

```
<210> SEQ ID NO 18
<211> LENGTH: 2595
<212> TYPE: DNA
<213> ORGANISM: Homo sapiens

<400> SEQUENCE: 18
agcgcgcagg cgcggccgga ttccgggcag tgacgcgacg gcgggccgcg cggcgcattt      60
```

-continued

```
ccgcctctgg cgaatggctc gtctgtagtg cacgccgcgg gcccagctgc gaccccggcc      120
ccgcccccgg gaccccggcc atggacgaac tgttcccccct catcttcccg gcagagccag     180
cccaggcctc tggcccctat gtggagatca ttgagcagcc caagcagcgg ggcatgcgct      240
tccgctacaa gtgcgagggg cgctccgcgg gcagcatccc aggcgagagg agcacagata     300
ccaccaagac ccacccecacc atcaagatca atggctacac aggaccaggg acagtgcgca     360
tctccctggt caccaaggac cctcctcacc ggcctcaccc ccacgagctt gtaggaaagg     420
actgccggga tggcttctat gaggctgagc tctgcccgga ccgctgcatc cacagtttcc     480
agaacctggg aatccagtgt gtgaagaagc gggacctgga gcaggctatc agtcagcgca     540
tccagaccaa caacaacccc ttccaagttc ctatagaaga gcagcgtggg gactacgacc     600
tgaatgctgt gcggctctgc ttccaggtga cagtgcggga cccatcaggc aggcccctcc     660
gcctgccgcc tgtcctttct catcccatct ttgacaatcg tgcccccaac actgccgagc     720
tcaagatctg ccgagtgaac cgaaactctg gcagctgcct cggtgggggat gagatcttcc     780 tactgtgtga caaggtgcag aaagaggaca ttgaggtgta tttcacggga ccaggctggg     840
aggcccgagg ctccttttcg caagctgatg tgcaccgaca agtggccatt gtgttccgga     900 cccctccccta cgcagacccc agcctgcagg ctcctgtgcg tgtctccatg cagctgcggc     960
ggccttccga ccgggagctc agtgagccca tggaattcca gtacctgcca gatacagacg    1020
atcgtcaccg gattgaggag aaacgtaaaa ggacatatga gaccttcaag agcatcatga    1080
agaagagtcc tttcagcgga cccaccgacc cccggcctcc acctcgacgc attgctgtgc    1140
cttcccgcag ctcagcttct gtccccaagc cagcacccca gccctatccc tttacgtcat    1200
ccctgagcac catcaactat gatgagtttc ccaccatggt gtttccttct gggcagatca    1260
gccaggcctc ggccttggcc ccggcccctc cccaagtcct gccccaggct ccagcccctg    1320
cccctgctcc agccatggta tcagctctgg cccaggcccc agccctgtc ccagtcctag     1380 ccccaggccc tcctcaggct gtggccccac ctgccccccaa gccccacccag gctgggggaag    1440 gaacgctgtc agaggccctg ctgcagctgc agtttgatga tgaagacctg ggggccttgc    1500
ttggcaacag cacagaccca gctgtgttca cagacctggc atccgtcgac aactccgagt    1560
ttcagcagct gctgaaccag ggcataccttg tggccccccca cacaactgag cccatgctga    1620
tggagtaccc tgaggctata actcgcctag tgacagggggc ccagaggccc cccgacccag    1680
ctcctgctcc actggggggcc ccggggctcc ccaatggcct cctttcagga gatgaagact    1740
tctcctccat tgcggacatg gacttctcag ccctgctgag tcagatcagc tcctaagggg    1800
gtgacgcctg ccctcccccag agcactgggt tgcaggggat tgaagccctc caaaagcact    1860
tacggattct ggtgggggtgt gttccaactg cccccaactt tgtggatgtc ttccttggag    1920
gggggagcca tattttattc ttttattgtc agtatctgta tctctctctc tttttggagg    1980
tgcttaagca gaagcattaa cttctctgga aaggggggag ctgggaaac tcaaactttt     2040 cccctgtcct gatggtcagc tcccttctct gtagggaact ctggggtccc ccatccccat    2100
cctccagctt ctggtactct cctagagaca gaagcaggct ggaggtaagg cctttgagcc    2160
cacaaagcct tatcaagtgt cttccatcat ggattcatta cagcttaatc aaaataacgc    2220
cccagatacc agccctgta tggcactggc attgtccctg tgcctaacac cagcgtttga     2280
ggggctggcc ttcctgccct acagaggtct ctgccggctc tttccttgct caaccatggc    2340
tgaaggaaac cagtgcaaca gcactggctc tctccaggat ccagaagggg tttggtctgg    2400
gacttccttg ctctcccctct tctcaagtgc cttaatagta gggtaagttg ttaagagtgg    2460
```

-continued

```
gggagagcag gctggcagct ctccagtcag gaggcatagt ttttactgaa caatcaaagc    2520
acttggactc ttgctctttc tactctgaac taataaatct gttgccaagc tggctagaaa    2580
aaaaaaaaaa aaaaa                                                     2595

<210> SEQ ID NO 19
<211> LENGTH: 2586
<212> TYPE: DNA
<213> ORGANISM: Homo sapiens

<400> SEQUENCE: 19
agcgcgcagg cgcggccgga ttccgggcag tgacgcgacg gcgggccgcg cggcgcattt      60
ccgcctctgg cgaatggctc gtctgtagtg cacgccgcgg gcccagctgc gaccccggcc     120
ccgcccccgg gaccccggcc atggacgaac tgttcccccct catcttcccg gcagagccag     180
cccaggcctc tggcccctat gtggagatca ttgagcagcc caagcagcgg ggcatgcgct     240
tccgctacaa gtgcgagggg cgctccgcgg gcagcatccc aggcgagagg agcacagata     300
ccaccaagac ccaccccacc atcaagatca atggctacac aggaccaggg acagtgcgca     360
tctccctggt caccaaggac cctcctcacc ggcctcaccc ccacgagctt gtaggaaagg     420
actgccggga tggcttctat gaggctgagc tctgcccgga ccgctgcatc cacagtttcc     480
agaacctggg aatccagtgt gtgaagaagc gggacctgga gcaggctatc agtcagcgca     540
tccagaccaa caacaacccc ttccaagaag agcagcgtgg ggactacgac ctgaatgctg     600
tgcggctctg cttccaggtg acagtgcggg acccatcagg caggcccctc cgcctgccgc     660
ctgtcctttc tcatcccatc tttgacaatc gtgcccccaa cactgccgag ctcaagatct     720
gccgagtgaa ccgaaactct ggcagctgcc tcggtgggga tgagatcttc ctactgtgtg     780
acaaggtgca gaaagaggac attgaggtgt atttcacggg accaggctgg gaggcccgag     840
gctccttttc gcaagctgat gtgcaccgac aagtggccat tgtgttccgg acccctccct     900
acgcagaccc cagcctgcag gctcctgtgc gtgtctccat gcagctgcgg cggccttccg     960
accgggagct cagtgagccc atggaattcc agtacctgcc agatacagac gatcgtcacc    1020
ggattgagga gaaacgtaaa aggacatatg agaccttcaa gagcatcatg aagaagagtc    1080
ctttcagcgg acccaccgac ccccggcctc cacctcgacg cattgctgtg ccttcccgca    1140
gctcagcttc tgtccccaag ccagcacccc agccctatcc ctttacgtca tccctgagca    1200
ccatcaacta tgatgagttt cccaccatgg tgtttccttc tgggcagatc agccaggcct    1260
cggccttggc cccggcccct ccccaagtcc tgccccaggc tccagcccct gccccctgctc    1320 cagccatggt atcagctctg gcccaggccc cagcccctgt cccagtccta gccccaggcc    1380
ctcctcaggc tgtggcccca cctgccccca agcccaccca ggctggggaa ggaacgctgt    1440
cagaggccct gctgcagctg cagtttgatg atgaagacct gggggccttg cttggcaaca    1500
gcacagaccc agctgtgttc acagacctgg catccgtcga caactccgag tttcagcagc    1560
tgctgaacca gggcatacct gtggccccccc acacaactga gcccatgctg atggagtacc    1620
ctgaggctat aactcgccta gtgacagggg cccagaggcc ccccgaccca gctcctgctc    1680
cactgggggc cccgggggctc cccaatggcc tcctttcagg agatgaagac ttctcctcca    1740
ttgcggacat ggacttctca gccctgctga gtcagatcag ctcctaaggg ggtgacgcct    1800 gccctccccca gagcactggg ttgcagggga ttgaagccct ccaaaagcac ttacggattc    1860
tggtggggtg tgttccaact gcccccaact ttgtggatgt cttccttgga gggggggagcc    1920
```

-continued

```
atattttatt cttttattgt cagtatctgt atctctctct cttttttggag gtgcttaagc    1980 agaagcatta acttctctgg aaagggggga gctggggaaa ctcaaacttt tcccctgtcc    2040
tgatggtcag ctcccttctc tgtagggaac tctggggtcc cccatcccca tcctccagct    2100
tctggtactc tcctagagac agaagcaggc tggaggtaag gcctttgagc ccacaaagcc    2160
ttatcaagtg tcttccatca tggattcatt acagcttaat caaaataacg ccccagatac    2220
cagcccctgt atggcactgg cattgtccct gtgcctaaca ccagcgtttg aggggctggc    2280
cttcctgccc tacagaggtc tctgccggct cttttccttgc tcaaccatgg ctgaaggaaa    2340
ccagtgcaac agcactggct ctctccagga tccagaaggg gtttggtctg ggacttcctt    2400
gctctccctc ttctcaagtg ccttaatagt agggtaagtt gttaagagtg ggggagagca    2460
ggctggcagc tctccagtca ggaggcatag tttttactga acaatcaaag cacttggact    2520
cttgctcttt ctactctgaa ctaataaatc tgttgccaag ctggctagaa aaaaaaaaaa    2580
aaaaaa                                                              2586

<210> SEQ ID NO 20
<211> LENGTH: 2388
<212> TYPE: DNA
<213> ORGANISM: Homo sapiens

<400> SEQUENCE: 20
agcgcgcagg cgcggccgga ttccgggcag tgacgcgacg gcgggccgcg cggcgcattt      60
ccgcctctgg cgaatggctc gtctgtagtg cacgccgcgg gcccagctgc gaccccggcc     120
ccgcccccgg gaccccggcc atggacgaac tgttccccct catcttcccg gcagagccag     180
cccaggcctc tggcccctat gtggagatca ttgagcagcc caagcagcgg ggcatgcgct     240
tccgctacaa gtgcgagggg cgctccgcgg gcagcatccc aggcgagagg agcacagata     300
ccaccaagac ccaccccacc atcaagatca atggctacac aggaccaggg acagtgcgca     360
tctccctggt caccaaggac cctcctcacc ggcctcaccc ccacgagctt gtaggaaagg     420
actgccggga tggcttctat gaggctgagc tctgcccgga ccgctgcatc cacagtttcc     480
agaacctggg aatccagtgt gtgaagaagc gggacctgga gcaggctatc agtcagcgca     540
tccagaccaa caacaacccc ttccaagttc ctatagaaga gcagcgtggg gactacgacc     600
tgaatgctgt gcggctctgc ttccaggtga cagtgcggga cccatcaggc aggcccctcc     660
gcctgccgcc tgtcctttct catcccatct ttgacaatcg tgcccccaac actgccgagc     720
tcaagatctg ccgagtgaac cgaaactctg gcagctgcct cggtgggggat gagatcttcc     780 tactgtgtga caaggtgcag aaagaggaca ttgaggtgta tttcacggga ccaggctggg     840
aggcccgagg ctccttttcg caagctgatg tgcaccgaca agtggccatt gtgttccgga     900
cccctcccta cgcagacccc agcctgcagg ctcctgtgcg tgtctccatg cagctgcggc     960
ggccttccga ccgggagctc agtgagccca tggaattcca gtacctgcca gatacagacg    1020
atcgtcaccg gattgaggag aaacgtaaaa ggacatatga ccttcaag agcatcatga    1080 agaagagtcc tttcagcgga cccaccgacc cccggcctcc acctcgacgc attgctgtgc    1140
cttcccgcag ctcagcttct gtccccaagc cagccccagg ccctcctcag gctgtggccc    1200
cacctgcccc caagcccacc caggctgggg aaggaacgct gtcagaggcc ctgctgcagc    1260
tgcagtttga tgatgaagac ctggggggcct tgcttggcaa cagcacagac ccagctgtgt    1320
tcacagacct ggcatccgtc gacaactccg agtttcagca gctgctgaac cagggcatac    1380
ctgtggcccc ccacacaact gagcccatgc tgatggagta ccctgaggct ataactcgcc    1440
```

-continued

```
tagtgacagg ggcccagagg cccccccgacc cagctcctgc tccactgggg gccccggggc      1500
tccccaatgg cctcctttca ggagatgaag acttctcctc cattgcggac atggacttct      1560
cagccctgct gagtcagatc agctcctaag ggggtgacgc ctgccctccc cagagcactg      1620
ggttgcaggg gattgaagcc ctccaaaagc acttacggat tctggtgggg tgtgttccaa      1680
ctgcccccaa ctttgtggat gtcttccttg gaggggggag ccatattta  ttcttttatt      1740 gtcagtatct gtatctctct ctcttttggg aggtgcttaa gcagaagcat taacttctct      1800
ggaaaggggg gagctgggga aactcaaact tttcccctgt cctgatggtc agctcccttc      1860
tctgtaggga actctggggt cccccatccc catcctccag cttctggtac tctcctagag      1920
acagaagcag gctggaggta aggcctttga gcccacaaag ccttatcaag tgtcttccat      1980
catggattca ttacagctta atcaaaataa cgccccagat accagcccct gtatggcact      2040
ggcattgtcc ctgtgcctaa caccagcgtt tgaggggctg gccttcctgc cctacagagg      2100
tctctgccgg ctctttcctt gctcaaccat ggctgaagga aaccagtgca acagcactgg      2160
ctctctccag gatccagaag gggtttggtc tgggacttcc ttgctctccc tcttctcaag      2220
tgccttaata gtagggtaag ttgttaagag tgggggagag caggctggca gctctccagt      2280
caggaggcat agtttttact gaacaatcaa agcacttgga ctcttgctct ttctactctg      2340
aactaataaa tctgttgcca agctggctag aaaaaaaaaa aaaaaaaa              2388
```

```
<210> SEQ ID NO 21
<211> LENGTH: 2286
<212> TYPE: DNA
<213> ORGANISM: Homo sapiens

<400> SEQUENCE: 21
agcgcgcagg cgcggccgga ttccgggcag tgacgcgacg gcgggccgcg cggcgcattt        60
ccgcctctgg cgaatggctc gtctgtagtg cacgccgcgg gcccagctgc gaccccggcc       120
ccgcccccgg gaccccggcc atggacgaac tgttcccccct catcttcccg gcagagccag       180
cccaggcctc tggcccctat gtggagatca ttgagcagcc caagcagcgg ggcatgcgct       240
tccgctacaa gtgcgagggg cgctccgcgg gcagcatccc aggcgagagg agcacagata       300
ccaccaagac ccacccccacc atcaagatca atggctacac aggaccaggg acagtgcgca       360
tctccctggt caccaaggac cctcctcacc ggcctcaccc ccacgagctt gtaggaaagg       420
actgccggga tggcttctat gaggctgagc tctgcccgga ccgctgcatc cacagtttcc       480
agaacctggg aatccagtgt gtgaagaagc gggacctgga gcaggctatc agtcagcgca       540
tccagaccaa caacaacccc ttccaagttc ctatagaaga gcagcgtggg gactacgacc       600
tgaatgctgt gcggctctgc ttccaggtga cagtgcggga cccatcaggc aggcccctcc       660
gcctgccgcc tgtcctttct catcccatct ttgacaatcg tgcccccaac actgccgagc       720
tcaagatctg ccgagtgaac cgaaactctg gcagctgcct cggtgggat  gagatcttcc       780 tactgtgtga caaggtgcag aaagaggaca ttgaggtgta tttcacggga ccaggctggg       840
aggcccgagg ctcctttttcg caagctgatg tgcaccgaca agtggccatt gtgttccgga       900
cccctcccta cgcagacccc agcctgcagg ctcctgtgcg tgtctccatg cagctgcggc       960
ggccttccga ccgggagctc agtgagccca tggaattcca gtacctgcca gatacagacg      1020
atcgtcaccg gattgaggag aaacgtaaaa ggacatatga gaccttcaag agcatcatga      1080
agaagagtcc tttcagcgga cccaccgacc cccggcctcc acctcgacgc attgctgtgc      1140
```

-continued

```
cttcccgcag ctcagcttct gtccccaagc cagcacccca gccctatccc tttacgtcat    1200
ccctgagcac catcaactat gatgagtttc ccaccatggt gtttccttct gggcagatca    1260
gccaggcctc ggccttggcc ccggcccctc cccaagtcct gccccaggct ccagcccctg    1320
cccctgctcc agccatggta tcagctctgg cccagaggcc ccccgaccca gctcctgctc    1380
cactgggggc cccgggggctc cccaatggcc tcctttcagg agatgaagac ttctcctcca    1440
ttgcggacat ggacttctca gccctgctga gtcagatcag ctcctaaggg ggtgacgcct    1500
gccctcccca gagcactggg ttgcaggggga ttgaagccct ccaaaagcac ttacggattc    1560 tggtgggggtg tgttccaact gcccccaact ttgtggatgt cttccttgga ggggggagcc    1620
atattttatt cttttattgt cagtatctgt atctctctct cttttttggag gtgcttaagc    1680 agaagcatta acttctctgg aaaggggggga gctgggggaaa ctcaaacttt tcccctgtcc    1740
tgatggtcag ctcccttctc tgtagggaac tctggggtcc cccatcccca tcctccagct    1800
tctggtactc tcctagagac agaagcaggc tggaggtaag gcctttgagc ccacaaagcc    1860
ttatcaagtg tcttccatca tggattcatt acagcttaat caaaataacg ccccagatac    1920
cagcccctgt atggcactgg cattgtccct gtgcctaaca ccagcgtttg aggggctggc    1980
cttcctgccc tacagaggtc tctgccggct ctttccttgc tcaaccatgg ctgaaggaaa    2040
ccagtgcaac agcactggct ctctccagga tccagaaggg gtttggtctg ggacttcctt    2100
gctctccctc ttctcaagtg ccttaatagt agggtaagtt gttaagagtg ggggagagca    2160
ggctggcagc tctccagtca ggaggcatag ttttttactga acaatcaaag cacttggact    2220
cttgctcttt ctactctgaa ctaataaatc tgttgccaag ctggctagaa aaaaaaaaa    2280 aaaaaa                                                                          2286
```

<210> SEQ ID NO 22
<211> LENGTH: 2341
<212> TYPE: DNA
<213> ORGANISM: Homo sapiens

<400> SEQUENCE: 22

```
attccgggca gtgacgcgac ggcgggccgc gcggcgcatt tccgcctctg gcgaatggct      60
cgtctgtagt gcacgccgcg ggcccagctg cgaccccggc cccgccccg ggaccccggc     120 catggacgaa ctgttccccc tcatcttccc ggcagagcca gcccaggcct ctggcccta     180 tgtggagatc attgagcagc ccaagcagcg gggcatgcgc ttccgctaca agtgcgaggg     240
gcgctccgcg ggcagcatcc caggcgagag gagcacagat accaccaaga cccaccccac     300
catcaagatc aatggctaca caggaccagg gacagtgcgc atctccctgg tcaccaagga     360
ccctcctcac cggcctcacc cccacgagct tgtaggaaag gactgccggg atggcttcta     420
tgaggctgag ctctgcccgg accgctgcat ccacagtttc cagaacctgg gaatccagtg     480
tgtgaagaag cgggacctgg agcaggctat cagtcagcgc atccagacca acaacaaccc     540
cttccaagtt cctatagaag agcagcgtgg ggactacgac ctgaatgctg tgcggctctg     600
cttccaggtg acagtgcggg acccatcagg caggcccctc cgcctgccgc ctgtcctttc     660
tcatcccatc tttgacaatc gtgccccaa cactgccgag ctcaagatct gccgagtgaa     720
ccgaaactct ggcagctgcc tcggtgggga tgagatcttc ctactgtgtg acaaggtgca     780
gaaagacgat cgtcaccgga ttgaggaaa acgtaaaagg acatatgaga ccttcaagag     840
catcatgaag aagagtcctt tcagcggacc caccgacccc cggcctccac ctcgacgcat     900
tgctgtgcct tcccgcagct cagcttctgt ccccaagcca gcaccccagc cctatccctt     960
```

```
tacgtcatcc ctgagcacca tcaactatga tgagtttccc accatggtgt ttccttctgg     1020
gcagatcagc caggcctcgg ccttggcccc ggccctccc caagtcctgc cccaggctcc       1080
agcccctgcc cctgctccag ccatggtatc agctctggcc caggccccag ccctgtccc       1140 agtcctagcc ccaggccctc ctcaggctgt ggccccacct gcccccaagc ccacccaggc      1200
tggggaagga acgctgtcag aggccctgct gcagctgcag tttgatgatg aagacctggg      1260
ggccttgctt ggcaacagca cagacccagc tgtgttcaca gacctggcat ccgtcgacaa      1320
ctccgagttt cagcagctgc tgaaccaggg catacctgtg gccccccaca caactgagcc      1380
catgctgatg gagtaccctg aggctataac tcgcctagtg acaggggccc agaggccccc      1440
cgacccagct cctgctccac tgggggcccc ggggctcccc aatggcctcc tttcaggaga      1500
tgaagacttc tcctccattg cggacatgga cttctcagcc ctgctgagtc agatcagctc      1560
ctaagggggt gacgcctgcc ctccccagag cactgggttg caggggattg aagccctcca      1620
aaagcactta cggattctgg tggggtgtgt tccaactgcc cccaactttg tggatgtctt      1680
ccttggaggg gggagccata tttattcctt ttattgtcag tatctgtatc tctctctctt      1740
tttggaggtg cttaagcaga agcattaact tctctggaaa ggggggagct ggggaaactc      1800
aaacttttcc cctgtcctga tggtcagctc ccttctctgt agggaactct ggggtccccc      1860
atccccatcc tccagcttct ggtactctcc tagagacaga agcaggctgg aggtaaggcc      1920
tttgagccca caaagcctta tcaagtgtct tccatcatgg attcattaca gcttaatcaa      1980
aataacgccc cagataccag cccctgtatg gcactggcat tgtccctgtg cctaacacca      2040
gcgtttgagg ggctggcctt cctgccctac agaggtctct gccggctctt ccttgctca      2100 accatggctg aaggaaacca gtgcaacagc actggctctc tccaggatcc agaaggggtt      2160
tggtctggga cttccttgct ctccctcttc tcaagtgcct taatagtagg gtaagttgtt      2220
aagagtgggg gagagcaggc tggcagctct ccagtcagga ggcatagttt ttactgaaca      2280
atcaaagcac ttggactctt gctctttcta ctctgaacta ataaatctgt tgccaagctg      2340
g                                                                      2341
```

<210> SEQ ID NO 23
<211> LENGTH: 2236
<212> TYPE: DNA
<213> ORGANISM: Homo sapiens

<400> SEQUENCE: 23

```
attccgggca gtgacgcgac ggcgggccgc gcggcgcatt tccgcctctg gcgaatggct       60
cgtctgtagt gcacgccgcg ggcccagctg cgaccccggc cccgccccg ggaccccggc       120 catggacgaa ctgttccccc tcatcttccc ggcagagcca gcccaggcct ctggcccta       180 tgtggagatc attgagcagc ccaagcagcg gggcatgcgc ttccgctaca agtgcgaggg      240
gcgctccgcg ggcagcatcc caggcgagag gagcacagat accaccaaga cccacccac       300 catcaagatc aatggctaca caggaccagg gacagtgcgc atctccctgg tcaccaagga      360
ccctcctcac cggcctcacc cccacgagct gtgtaggaaag gactgccggg atggcttcta      420
tgaggctgag ctctgcccgg accgctgcat ccacagtttc cagaacctgg gaatccagtg      480
tgtgaagaag cgggacctgg agcaggctat cagtcagcgc atccagacca caacaacccc      540
cttccaagtt cctatagaag agcagcgtgg ggactacgac ctgaatgctg tgcggctctg      600
cttccaggtg acagtgcggg acccatcagg caggcccctc cgcctgccgc ctgtcctttc      660
```

-continued

```
tcatcccatc tttgacaatc acgatcgtca ccggattgag gagaaacgta aaaggacata   720
tgagaccttc aagagcatca tgaagaagag tcctttcagc ggacccaccg accccggcc    780 tccacctcga cgcattgctg tgccttcccg cagctcagct tctgtcccca agccagcacc   840
ccagccctat ccctttacgt catccctgag caccatcaac tatgatgagt ttcccaccat   900
ggtgtttcct tctgggcaga tcagccaggc ctcggccttg ccccggcccc ctccccaagt   960
cctgccccag gctccagccc ctgccctgc tccagccatg gtatcagctc tggcccaggc    1020
cccagcccct gtcccagtcc tagccccagg ccctcctcag gctgtggccc cacctgcccc    1080
caagcccacc caggctgggg aaggaacgct gtcagaggcc ctgctgcagc tgcagtttga    1140
tgatgaagac ctggggggcct tgcttggcaa cagcacagac ccagctgtgt tcacagacct   1200
ggcatccgtc gacaactccg agtttcagca gctgctgaac cagggcatac ctgtggcccc    1260
ccacacaact gagcccatgc tgatggagta ccctgaggct ataactcgcc tagtgacagg   1320
ggcccagagg cccccgacc cagctcctgc tccactgggg gccccggggc tccccaatgg     1380
cctcctttca ggagatgaag acttctcctc cattgcggac atggacttct cagccctgct    1440
gagtcagatc agctcctaag ggggtgacgc ctgccctccc cagagcactg ggttgcaggg   1500
gattgaagcc ctccaaaagc acttacggat tctggtgggg tgtgttccaa ctgcccccaa    1560
ctttgtggat gtcttccttg gaggggggag ccatattttta ttctttttatt gtcagtatct   1620 gtatctctct ctctttttgg aggtgcttaa gcagaagcat taacttctct ggaaaggggg    1680
gagctgggga aactcaaact tttcccctgt cctgatggtc agctcccttc tctgtaggga    1740
actctggggt ccccccatccc catcctccag cttctggtac tctcctagag acagaagcag   1800
gctggaggta aggcctttga gcccacaaag ccttatcaag tgtcttccat catggattca    1860
ttacagctta atcaaaataa cgccccagat accagcccct gtatggcact ggcattgtcc    1920
ctgtgcctaa caccagcgtt tgaggggctg gccttcctgc cctacagagg tctctgccgg    1980
ctctttcctt gctcaaccat ggctgaagga aaccagtgca acagcactgg ctctctccag    2040
gatccagaag gggtttggtc tgggacttcc ttgctctccc tcttctcaag tgccttaata   2100
gtagggtaag ttgttaagag tggggagag caggctggca gctctccagt caggaggcat     2160 agttttact gaacaatcaa agcacttgga ctcttgctct ttctactctg aactaataaa     2220
tctgttgcca agctgg                                                     2236
```

```
<210> SEQ ID NO 24
<211> LENGTH: 2555
<212> TYPE: PRT
<213> ORGANISM: Homo sapiens

<400> SEQUENCE: 24

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95
```

-continued

```
Leu Cys Leu Thr Pro Leu Asp Asn Ala Cys Leu Thr Asn Pro Cys Arg
            100             105             110

Asn Gly Gly Thr Cys Asp Leu Leu Thr Leu Thr Glu Tyr Lys Cys Arg
            115             120             125

Cys Pro Pro Gly Trp Ser Gly Lys Ser Cys Gln Gln Ala Asp Pro Cys
            130             135             140

Ala Ser Asn Pro Cys Ala Asn Gly Gly Gln Cys Leu Pro Phe Glu Ala
145             150             155             160

Ser Tyr Ile Cys His Cys Pro Pro Ser Phe His Gly Pro Thr Cys Arg
                165             170             175

Gln Asp Val Asn Glu Cys Gly Gln Lys Pro Gly Leu Cys Arg His Gly
            180             185             190

Gly Thr Cys His Asn Glu Val Gly Ser Tyr Arg Cys Val Cys Arg Ala
            195             200             205

Thr His Thr Gly Pro Asn Cys Glu Arg Pro Tyr Val Pro Cys Ser Pro
            210             215             220

Ser Pro Cys Gln Asn Gly Gly Thr Cys Arg Pro Thr Gly Asp Val Thr
225             230             235             240

His Glu Cys Ala Cys Leu Pro Gly Phe Thr Gly Gln Asn Cys Glu Glu
                245             250             255

Asn Ile Asp Asp Cys Pro Gly Asn Asn Cys Lys Asn Gly Gly Ala Cys
            260             265             270

Val Asp Gly Val Asn Thr Tyr Asn Cys Arg Cys Pro Pro Glu Trp Thr
            275             280             285

Gly Gln Tyr Cys Thr Glu Asp Val Asp Glu Cys Gln Leu Met Pro Asn
            290             295             300

Ala Cys Gln Asn Gly Gly Thr Cys His Asn Thr His Gly Gly Tyr Asn
305             310             315             320

Cys Val Cys Val Asn Gly Trp Thr Gly Glu Asp Cys Ser Glu Asn Ile
                325             330             335

Asp Asp Cys Ala Ser Ala Ala Cys Phe His Gly Ala Thr Cys His Asp
            340             345             350

Arg Val Ala Ser Phe Tyr Cys Glu Cys Pro His Gly Arg Thr Gly Leu
            355             360             365

Leu Cys His Leu Asn Asp Ala Cys Ile Ser Asn Pro Cys Asn Glu Gly
            370             375             380

Ser Asn Cys Asp Thr Asn Pro Val Asn Gly Lys Ala Ile Cys Thr Cys
385             390             395             400

Pro Ser Gly Tyr Thr Gly Pro Ala Cys Ser Gln Asp Val Asp Glu Cys
                405             410             415

Ser Leu Gly Ala Asn Pro Cys Glu His Ala Gly Lys Cys Ile Asn Thr
            420             425             430

Leu Gly Ser Phe Glu Cys Gln Cys Leu Gln Gly Tyr Thr Gly Pro Arg
            435             440             445

Cys Glu Ile Asp Val Asn Glu Cys Val Ser Asn Pro Cys Gln Asn Asp
            450             455             460

Ala Thr Cys Leu Asp Gln Ile Gly Glu Phe Gln Cys Ile Cys Met Pro
465             470             475             480

Gly Tyr Glu Gly Val His Cys Glu Val Asn Thr Asp Glu Cys Ala Ser
                485             490             495

Ser Pro Cys Leu His Asn Gly Arg Cys Leu Asp Lys Ile Asn Glu Phe
                500             505             510
```

-continued

```
Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
            595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
            675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
            755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
            835                 840                 845

Asp Tyr Glu Ser Phe Ser Cys Val Cys Pro Thr Gly Trp Gln Gly Gln
    850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
    915                 920                 925

Ala Phe Cys Asp Cys Leu Pro Gly Phe Arg Gly Thr Phe Cys Glu Glu
```

-continued

```
        930              935              940

Asp Ile Asn Glu Cys Ala Ser Asp Pro Cys Arg Asn Gly Ala Asn Cys
945              950              955              960

Thr Asp Cys Val Asp Ser Tyr Thr Cys Thr Cys Pro Ala Gly Phe Ser
                 965              970              975

Gly Ile His Cys Glu Asn Asn Thr Pro Asp Cys Thr Glu Ser Ser Cys
                 980              985              990

Phe Asn Gly Gly Thr Cys Val Asp  Gly Ile Asn Ser Phe  Thr Cys Leu
        995              1000              1005

Cys Pro  Pro Gly Phe Thr Gly  Ser Tyr Cys Gln His  Asp Val Asn
   1010              1015              1020

Glu Cys  Asp Ser Gln Pro Cys  Leu His Gly Gly Thr  Cys Gln Asp
   1025              1030              1035

Gly Cys  Gly Ser Tyr Arg Cys  Thr Cys Pro Gln Gly  Tyr Thr Gly
   1040              1045              1050

Pro Asn  Cys Gln Asn Leu Val  His Trp Cys Asp Ser  Ser Pro Cys
   1055              1060              1065

Lys Asn  Gly Gly Lys Cys Trp  Gln Thr His Thr Gln  Tyr Arg Cys
   1070              1075              1080

Glu Cys  Pro Ser Gly Trp Thr  Gly Leu Tyr Cys Asp  Val Pro Ser
   1085              1090              1095

Val Ser  Cys Glu Val Ala Ala  Gln Arg Gln Gly Val  Asp Val Ala
   1100              1105              1110

Arg Leu  Cys Gln His Gly Gly  Leu Cys Val Asp Ala  Gly Asn Thr
   1115              1120              1125

His His  Cys Arg Cys Gln Ala  Gly Tyr Thr Gly Ser  Tyr Cys Glu
   1130              1135              1140

Asp Leu  Val Asp Glu Cys Ser  Pro Ser Pro Cys Gln  Asn Gly Ala
   1145              1150              1155

Thr Cys  Thr Asp Tyr Leu Gly  Gly Tyr Ser Cys Lys  Cys Val Ala
   1160              1165              1170

Gly Tyr  His Gly Val Asn Cys  Ser Glu Glu Ile Asp  Glu Cys Leu
   1175              1180              1185

Ser His  Pro Cys Gln Asn Gly  Gly Thr Cys Leu Asp  Leu Pro Asn
   1190              1195              1200

Thr Tyr  Lys Cys Ser Cys Pro  Arg Gly Thr Gln Gly  Val His Cys
   1205              1210              1215

Glu Ile  Asn Val Asp Asp Cys  Asn Pro Pro Val Asp  Pro Val Ser
   1220              1225              1230

Arg Ser  Pro Lys Cys Phe Asn  Asn Gly Thr Cys Val  Asp Gln Val
   1235              1240              1245

Gly Gly  Tyr Ser Cys Thr Cys  Pro Pro Gly Phe Val  Gly Glu Arg
   1250              1255              1260

Cys Glu  Gly Asp Val Asn Glu  Cys Leu Ser Asn Pro  Cys Asp Ala
   1265              1270              1275

Arg Gly  Thr Gln Asn Cys Val  Gln Arg Val Asn Asp  Phe His Cys
   1280              1285              1290

Glu Cys  Arg Ala Gly His Thr  Gly Arg Arg Cys Glu  Ser Val Ile
   1295              1300              1305

Asn Gly  Cys Lys Gly Lys Pro  Cys Lys Asn Gly Gly  Thr Cys Ala
   1310              1315              1320

Val Ala  Ser Asn Thr Ala Arg  Gly Phe Ile Cys Lys  Cys Pro Ala
   1325              1330              1335
```

-continued

```
Gly Phe Glu Gly Ala Thr Cys Glu Asn Asp Ala Arg Thr Cys Gly
    1340            1345            1350

Ser Leu Arg Cys Leu Asn Gly Gly Thr Cys Ile Ser Gly Pro Arg
    1355            1360            1365

Ser Pro Thr Cys Leu Cys Leu Gly Pro Phe Thr Gly Pro Glu Cys
    1370            1375            1380

Gln Phe Pro Ala Ser Ser Pro Cys Leu Gly Gly Asn Pro Cys Tyr
    1385            1390            1395

Asn Gln Gly Thr Cys Glu Pro Thr Ser Glu Ser Pro Phe Tyr Arg
    1400            1405            1410

Cys Leu Cys Pro Ala Lys Phe Asn Gly Leu Leu Cys His Ile Leu
    1415            1420            1425

Asp Tyr Ser Phe Gly Gly Gly Ala Gly Arg Asp Ile Pro Pro Pro
    1430            1435            1440

Leu Ile Glu Glu Ala Cys Glu Leu Pro Glu Cys Gln Glu Asp Ala
    1445            1450            1455

Gly Asn Lys Val Cys Ser Leu Gln Cys Asn Asn His Ala Cys Gly
    1460            1465            1470

Trp Asp Gly Gly Asp Cys Ser Leu Asn Phe Asn Asp Pro Trp Lys
    1475            1480            1485

Asn Cys Thr Gln Ser Leu Gln Cys Trp Lys Tyr Phe Ser Asp Gly
    1490            1495            1500

His Cys Asp Ser Gln Cys Asn Ser Ala Gly Cys Leu Phe Asp Gly
    1505            1510            1515

Phe Asp Cys Gln Arg Ala Glu Gly Gln Cys Asn Pro Leu Tyr Asp
    1520            1525            1530

Gln Tyr Cys Lys Asp His Phe Ser Asp Gly His Cys Asp Gln Gly
    1535            1540            1545

Cys Asn Ser Ala Glu Cys Glu Trp Asp Gly Leu Asp Cys Ala Glu
    1550            1555            1560

His Val Pro Glu Arg Leu Ala Ala Gly Thr Leu Val Val Val Val
    1565            1570            1575

Leu Met Pro Pro Glu Gln Leu Arg Asn Ser Ser Phe His Phe Leu
    1580            1585            1590

Arg Glu Leu Ser Arg Val Leu His Thr Asn Val Val Phe Lys Arg
    1595            1600            1605

Asp Ala His Gly Gln Gln Met Ile Phe Pro Tyr Tyr Gly Arg Glu
    1610            1615            1620

Glu Glu Leu Arg Lys His Pro Ile Lys Arg Ala Ala Glu Gly Trp
    1625            1630            1635

Ala Ala Pro Asp Ala Leu Leu Gly Gln Val Lys Ala Ser Leu Leu
    1640            1645            1650

Pro Gly Gly Ser Glu Gly Gly Arg Arg Arg Glu Leu Asp Pro
    1655            1660            1665

Met Asp Val Arg Gly Ser Ile Val Tyr Leu Glu Ile Asp Asn Arg
    1670            1675            1680

Gln Cys Val Gln Ala Ser Ser Gln Cys Phe Gln Ser Ala Thr Asp
    1685            1690            1695

Val Ala Ala Phe Leu Gly Ala Leu Ala Ser Leu Gly Ser Leu Asn
    1700            1705            1710

Ile Pro Tyr Lys Ile Glu Ala Val Gln Ser Glu Thr Val Glu Pro
    1715            1720            1725
```

-continued

```
Pro Pro  Pro Ala Gln Leu His  Phe Met Tyr Val Ala  Ala Ala Ala
    1730              1735              1740

Phe Val  Leu Leu Phe Phe Val  Gly Cys Gly Val Leu  Leu Ser Arg
    1745              1750              1755

Lys Arg  Arg Arg Gln His Gly  Gln Leu Trp Phe Pro  Glu Gly Phe
    1760              1765              1770

Lys Val  Ser Glu Ala Ser Lys  Lys Lys Arg Arg Glu  Pro Leu Gly
    1775              1780              1785

Glu Asp  Ser Val Gly Leu Lys  Pro Leu Lys Asn Ala  Ser Asp Gly
    1790              1795              1800

Ala Leu  Met Asp Asp Asn Gln  Asn Glu Trp Gly Asp  Glu Asp Leu
    1805              1810              1815

Glu Thr  Lys Lys Phe Arg Phe  Glu Glu Pro Val Val  Leu Pro Asp
    1820              1825              1830

Leu Asp  Asp Gln Thr Asp His  Arg Gln Trp Thr Gln  Gln His Leu
    1835              1840              1845

Asp Ala  Ala Asp Leu Arg Met  Ser Ala Met Ala Pro  Thr Pro Pro
    1850              1855              1860

Gln Gly  Glu Val Asp Ala Asp  Cys Met Asp Val Asn  Val Arg Gly
    1865              1870              1875

Pro Asp  Gly Phe Thr Pro Leu  Met Ile Ala Ser Cys  Ser Gly Gly
    1880              1885              1890

Gly Leu  Glu Thr Gly Asn Ser  Glu Glu Glu Glu Asp  Ala Pro Ala
    1895              1900              1905

Val Ile  Ser Asp Phe Ile Tyr  Gln Gly Ala Ser Leu  His Asn Gln
    1910              1915              1920

Thr Asp  Arg Thr Gly Glu Thr  Ala Leu His Leu Ala  Ala Arg Tyr
    1925              1930              1935

Ser Arg  Ser Asp Ala Ala Lys  Arg Leu Leu Glu Ala  Ser Ala Asp
    1940              1945              1950

Ala Asn  Ile Gln Asp Asn Met  Gly Arg Thr Pro Leu  His Ala Ala
    1955              1960              1965

Val Ser  Ala Asp Ala Gln Gly  Val Phe Gln Ile Leu  Ile Arg Asn
    1970              1975              1980

Arg Ala  Thr Asp Leu Asp Ala  Arg Met His Asp Gly  Thr Thr Pro
    1985              1990              1995

Leu Ile  Leu Ala Ala Arg Leu  Ala Val Glu Gly Met  Leu Glu Asp
    2000              2005              2010

Leu Ile  Asn Ser His Ala Asp  Val Asn Ala Val Asp  Asp Leu Gly
    2015              2020              2025

Lys Ser  Ala Leu His Trp Ala  Ala Ala Val Asn Asn  Val Asp Ala
    2030              2035              2040

Ala Val  Val Leu Leu Lys Asn  Gly Ala Asn Lys Asp  Met Gln Asn
    2045              2050              2055

Asn Arg  Glu Glu Thr Pro Leu  Phe Leu Ala Ala Arg  Glu Gly Ser
    2060              2065              2070

Tyr Glu  Thr Ala Lys Val Leu  Leu Asp His Phe Ala  Asn Arg Asp
    2075              2080              2085

Ile Thr  Asp His Met Asp Arg  Leu Pro Arg Asp Ile  Ala Gln Glu
    2090              2095              2100

Arg Met  His His Asp Ile Val  Arg Leu Leu Asp Glu  Tyr Asn Leu
    2105              2110              2115

Val Arg  Ser Pro Gln Leu His  Gly Ala Pro Leu Gly  Gly Thr Pro
```

-continued

```
         2120                2125                2130

Thr Leu  Ser Pro Pro Leu Cys  Ser Pro Asn Gly Tyr  Leu Gly Ser
    2135                2140                2145

Leu Lys  Pro Gly Val Gln Gly  Lys Lys Val Arg Lys  Pro Ser Ser
    2150                2155                2160

Lys Gly  Leu Ala Cys Gly Ser  Lys Glu Ala Lys Asp  Leu Lys Ala
    2165                2170                2175

Arg Arg  Lys Lys Ser Gln Asp  Gly Lys Gly Cys Leu  Leu Asp Ser
    2180                2185                2190

Ser Gly  Met Leu Ser Pro Val  Asp Ser Leu Glu Ser  Pro His Gly
    2195                2200                2205

Tyr Leu  Ser Asp Val Ala Ser  Pro Pro Leu Leu Pro  Ser Pro Phe
    2210                2215                2220

Gln Gln  Ser Pro Ser Val Pro  Leu Asn His Leu Pro  Gly Met Pro
    2225                2230                2235

Asp Thr  His Leu Gly Ile Gly  His Leu Asn Val Ala  Ala Lys Pro
    2240                2245                2250

Glu Met  Ala Ala Leu Gly Gly  Gly Gly Arg Leu Ala  Phe Glu Thr
    2255                2260                2265

Gly Pro  Pro Arg Leu Ser His  Leu Pro Val Ala Ser  Gly Thr Ser
    2270                2275                2280

Thr Val  Leu Gly Ser Ser Ser  Gly Gly Ala Leu Asn  Phe Thr Val
    2285                2290                2295

Gly Gly  Ser Thr Ser Leu Asn  Gly Gln Cys Glu Trp  Leu Ser Arg
    2300                2305                2310

Leu Gln  Ser Gly Met Val Pro  Asn Gln Tyr Asn Pro  Leu Arg Gly
    2315                2320                2325

Ser Val  Ala Pro Gly Pro Leu  Ser Thr Gln Ala Pro  Ser Leu Gln
    2330                2335                2340

His Gly  Met Val Gly Pro Leu  His Ser Ser Leu Ala  Ala Ser Ala
    2345                2350                2355

Leu Ser  Gln Met Met Ser Tyr  Gln Gly Leu Pro Ser  Thr Arg Leu
    2360                2365                2370

Ala Thr  Gln Pro His Leu Val  Gln Thr Gln Gln Val  Gln Pro Gln
    2375                2380                2385

Asn Leu  Gln Met Gln Gln Gln  Asn Leu Gln Pro Ala  Asn Ile Gln
    2390                2395                2400

Gln Gln  Gln Ser Leu Gln Pro  Pro Pro Pro Pro Pro  Gln Pro His
    2405                2410                2415

Leu Gly  Val Ser Ser Ala Ala  Ser Gly His Leu Gly  Arg Ser Phe
    2420                2425                2430

Leu Ser  Gly Glu Pro Ser Gln  Ala Asp Val Gln Pro  Leu Gly Pro
    2435                2440                2445

Ser Ser  Leu Ala Val His Thr  Ile Leu Pro Gln Glu  Ser Pro Ala
    2450                2455                2460

Leu Pro  Thr Ser Leu Pro Ser  Ser Leu Val Pro Pro  Val Thr Ala
    2465                2470                2475

Ala Gln  Phe Leu Thr Pro Pro  Ser Gln His Ser Tyr  Ser Ser Pro
    2480                2485                2490

Val Asp  Asn Thr Pro Ser His  Gln Leu Gln Val Pro  Glu His Pro
    2495                2500                2505

Phe Leu  Thr Pro Ser Pro Glu  Ser Pro Asp Gln Trp  Ser Ser Ser
    2510                2515                2520
```

```
Ser Pro  His Ser Asn Val Ser  Asp Trp Ser Glu Gly  Val Ser Ser
    2525             2530             2535

Pro Pro  Thr Ser Met Gln Ser  Gln Ile Ala Arg Ile  Pro Glu Ala
    2540             2545             2550

Phe Lys
    2555

<210> SEQ ID NO 25
<211> LENGTH: 2471
<212> TYPE: PRT
<213> ORGANISM: Homo sapiens

<400> SEQUENCE: 25

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
            20                  25                  30

Glu Pro Cys Val Asn Glu Gly Met Cys Val Thr Tyr His Asn Gly Thr
        35                  40                  45

Gly Tyr Cys Lys Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
```

-continued

```
              325            330            335
Glu Asn Ile Asp Asp Cys Ala Phe Ala Ser Cys Thr Pro Gly Ser Thr
          340            345            350

Cys Ile Asp Arg Val Ala Ser Phe Ser Cys Met Cys Pro Glu Gly Lys
          355            360            365

Ala Gly Leu Leu Cys His Leu Asp Asp Ala Cys Ile Ser Asn Pro Cys
          370            375            380

His Lys Gly Ala Leu Cys Asp Thr Asn Pro Leu Asn Gly Gln Tyr Ile
385            390            395            400

Cys Thr Cys Pro Gln Gly Tyr Lys Gly Ala Asp Cys Thr Glu Asp Val
              405            410            415

Asp Glu Cys Ala Met Ala Asn Ser Asn Pro Cys Glu His Ala Gly Lys
          420            425            430

Cys Val Asn Thr Asp Gly Ala Phe His Cys Glu Cys Leu Lys Gly Tyr
          435            440            445

Ala Gly Pro Arg Cys Glu Met Asp Ile Asn Glu Cys His Ser Asp Pro
          450            455            460

Cys Gln Asn Asp Ala Thr Cys Leu Asp Lys Ile Gly Gly Phe Thr Cys
465            470            475            480

Leu Cys Met Pro Gly Phe Lys Gly Val His Cys Glu Leu Glu Ile Asn
              485            490            495

Glu Cys Gln Ser Asn Pro Cys Val Asn Asn Gly Gln Cys Val Asp Lys
          500            505            510

Val Asn Arg Phe Gln Cys Leu Cys Pro Pro Gly Phe Thr Gly Pro Val
          515            520            525

Cys Gln Ile Asp Ile Asp Asp Cys Ser Ser Thr Pro Cys Leu Asn Gly
          530            535            540

Ala Lys Cys Ile Asp His Pro Asn Gly Tyr Glu Cys Gln Cys Ala Thr
545            550            555            560

Gly Phe Thr Gly Val Leu Cys Glu Glu Asn Ile Asp Asn Cys Asp Pro
              565            570            575

Asp Pro Cys His His Gly Gln Cys Gln Asp Gly Ile Asp Ser Tyr Thr
          580            585            590

Cys Ile Cys Asn Pro Gly Tyr Met Gly Ala Ile Cys Ser Asp Gln Ile
          595            600            605

Asp Glu Cys Tyr Ser Ser Pro Cys Leu Asn Asp Gly Arg Cys Ile Asp
          610            615            620

Leu Val Asn Gly Tyr Gln Cys Asn Cys Gln Pro Gly Thr Ser Gly Val
625            630            635            640

Asn Cys Glu Ile Asn Phe Asp Asp Cys Ala Ser Asn Pro Cys Ile His
              645            650            655

Gly Ile Cys Met Asp Gly Ile Asn Arg Tyr Ser Cys Val Cys Ser Pro
          660            665            670

Gly Phe Thr Gly Gln Arg Cys Asn Ile Asp Ile Asp Glu Cys Ala Ser
          675            680            685

Asn Pro Cys Arg Lys Gly Ala Thr Cys Ile Asn Gly Val Asn Gly Phe
          690            695            700

Arg Cys Ile Cys Pro Glu Gly Pro His His Pro Ser Cys Tyr Ser Gln
705            710            715            720

Val Asn Glu Cys Leu Ser Asn Pro Cys Ile His Gly Asn Cys Thr Gly
              725            730            735

Gly Leu Ser Gly Tyr Lys Cys Leu Cys Asp Ala Gly Trp Val Gly Ile
          740            745            750
```

```
Asn Cys Glu Val Asp Lys Asn Glu Cys Leu Ser Asn Pro Cys Gln Asn
        755             760             765

Gly Gly Thr Cys Asp Asn Leu Val Asn Gly Tyr Arg Cys Thr Cys Lys
        770             775             780

Lys Gly Phe Lys Gly Tyr Asn Cys Gln Val Asn Ile Asp Glu Cys Ala
785             790             795             800

Ser Asn Pro Cys Leu Asn Gln Gly Thr Cys Phe Asp Asp Ile Ser Gly
            805             810             815

Tyr Thr Cys His Cys Val Leu Pro Tyr Thr Gly Lys Asn Cys Gln Thr
            820             825             830

Val Leu Ala Pro Cys Ser Pro Asn Pro Cys Glu Asn Ala Ala Val Cys
            835             840             845

Lys Glu Ser Pro Asn Phe Glu Ser Tyr Thr Cys Leu Cys Ala Pro Gly
    850             855             860

Trp Gln Gly Gln Arg Cys Thr Ile Asp Ile Asp Glu Cys Ile Ser Lys
865             870             875             880

Pro Cys Met Asn His Gly Leu Cys His Asn Thr Gln Gly Ser Tyr Met
            885             890             895

Cys Glu Cys Pro Pro Gly Phe Ser Gly Met Asp Cys Glu Glu Asp Ile
            900             905             910

Asp Asp Cys Leu Ala Asn Pro Cys Gln Asn Gly Gly Ser Cys Met Asp
            915             920             925

Gly Val Asn Thr Phe Ser Cys Leu Cys Leu Pro Gly Phe Thr Gly Asp
    930             935             940

Lys Cys Gln Thr Asp Met Asn Glu Cys Leu Ser Glu Pro Cys Lys Asn
945             950             955             960

Gly Gly Thr Cys Ser Asp Tyr Val Asn Ser Tyr Thr Cys Lys Cys Gln
            965             970             975

Ala Gly Phe Asp Gly Val His Cys Glu Asn Asn Ile Asn Glu Cys Thr
            980             985             990

Glu Ser Ser Cys Phe Asn Gly Gly  Thr Cys Val Asp Gly  Ile Asn Ser
        995             1000                1005

Phe Ser  Cys Leu Cys Pro Val  Gly Phe Thr Gly Ser  Phe Cys Leu
    1010            1015            1020

His Glu  Ile Asn Glu Cys Ser  Ser His Pro Cys Leu  Asn Glu Gly
    1025            1030            1035

Thr Cys  Val Asp Gly Leu Gly  Thr Tyr Arg Cys Ser  Cys Pro Leu
    1040            1045            1050

Gly Tyr  Thr Gly Lys Asn Cys  Gln Thr Leu Val Asn  Leu Cys Ser
    1055            1060            1065

Arg Ser  Pro Cys Lys Asn Lys  Gly Thr Cys Val Gln  Lys Lys Ala
    1070            1075            1080

Glu Ser  Gln Cys Leu Cys Pro  Ser Gly Trp Ala Gly  Ala Tyr Cys
    1085            1090            1095

Asp Val  Pro Asn Val Ser Cys  Asp Ile Ala Ala Ser  Arg Arg Gly
    1100            1105            1110

Val Leu  Val Glu His Leu Cys  Gln His Ser Gly Val  Cys Ile Asn
    1115            1120            1125

Ala Gly  Asn Thr His Tyr Cys  Gln Cys Pro Leu Gly  Tyr Thr Gly
    1130            1135            1140

Ser Tyr  Cys Glu Glu Gln Leu  Asp Glu Cys Ala Ser  Asn Pro Cys
    1145            1150            1155
```

-continued

```
Gln His  Gly Ala Thr Cys Ser  Asp Phe Ile Gly Gly  Tyr Arg Cys
    1160              1165              1170

Glu Cys  Val Pro Gly Tyr Gln  Gly Val Asn Cys Glu  Tyr Glu Val
    1175              1180              1185

Asp Glu  Cys Gln Asn Gln Pro  Cys Gln Asn Gly Gly  Thr Cys Ile
    1190              1195              1200

Asp Leu  Val Asn His Phe Lys  Cys Ser Cys Pro Pro  Gly Thr Arg
    1205              1210              1215

Gly Leu  Leu Cys Glu Glu Asn  Ile Asp Asp Cys Ala  Arg Gly Pro
    1220              1225              1230

His Cys  Leu Asn Gly Gly Gln  Cys Met Asp Arg Ile  Gly Gly Tyr
    1235              1240              1245

Ser Cys  Arg Cys Leu Pro Gly  Phe Ala Gly Glu Arg  Cys Glu Gly
    1250              1255              1260

Asp Ile  Asn Glu Cys Leu Ser  Asn Pro Cys Ser Ser  Glu Gly Ser
    1265              1270              1275

Leu Asp  Cys Ile Gln Leu Thr  Asn Asp Tyr Leu Cys  Val Cys Arg
    1280              1285              1290

Ser Ala  Phe Thr Gly Arg His  Cys Glu Thr Phe Val  Asp Val Cys
    1295              1300              1305

Pro Gln  Met Pro Cys Leu Asn  Gly Gly Thr Cys Ala  Val Ala Ser
    1310              1315              1320

Asn Met  Pro Asp Gly Phe Ile  Cys Arg Cys Pro Pro  Gly Phe Ser
    1325              1330              1335

Gly Ala  Arg Cys Gln Ser Ser  Cys Gly Gln Val Lys  Cys Arg Lys
    1340              1345              1350

Gly Glu  Gln Cys Val His Thr  Ala Ser Gly Pro Arg  Cys Phe Cys
    1355              1360              1365

Pro Ser  Pro Arg Asp Cys Glu  Ser Gly Cys Ala Ser  Ser Pro Cys
    1370              1375              1380

Gln His  Gly Gly Ser Cys His  Pro Gln Arg Gln Pro  Pro Tyr Tyr
    1385              1390              1395

Ser Cys  Gln Cys Ala Pro Pro  Phe Ser Gly Ser Arg  Cys Glu Leu
    1400              1405              1410

Tyr Thr  Ala Pro Pro Ser Thr  Pro Pro Ala Thr Cys  Leu Ser Gln
    1415              1420              1425

Tyr Cys  Ala Asp Lys Ala Arg  Asp Gly Val Cys Asp  Glu Ala Cys
    1430              1435              1440

Asn Ser  His Ala Cys Gln Trp  Asp Gly Gly Asp Cys  Ser Leu Thr
    1445              1450              1455

Met Glu  Asn Pro Trp Ala Asn  Cys Ser Ser Pro Leu  Pro Cys Trp
    1460              1465              1470

Asp Tyr  Ile Asn Asn Gln Cys  Asp Glu Leu Cys Asn  Thr Val Glu
    1475              1480              1485

Cys Leu  Phe Asp Asn Phe Glu  Cys Gln Gly Asn Ser  Lys Thr Cys
    1490              1495              1500

Lys Tyr  Asp Lys Tyr Cys Ala  Asp His Phe Lys Asp  Asn His Cys
    1505              1510              1515

Asp Gln  Gly Cys Asn Ser Glu  Glu Cys Gly Trp Asp  Gly Leu Asp
    1520              1525              1530

Cys Ala  Ala Asp Gln Pro Glu  Asn Leu Ala Glu Gly  Thr Leu Val
    1535              1540              1545

Ile Val  Val Leu Met Pro Pro  Glu Gln Leu Leu Gln  Asp Ala Arg
```

-continued

```
        1550              1555              1560

Ser Phe Leu Arg Ala Leu Gly Thr Leu Leu His Thr Asn Leu Arg
    1565              1570              1575

Ile Lys Arg Asp Ser Gln Gly Glu Leu Met Val Tyr Pro Tyr Tyr
    1580              1585              1590

Gly Glu Lys Ser Ala Ala Met Lys Lys Gln Arg Met Thr Arg Arg
    1595              1600              1605

Ser Leu Pro Gly Glu Gln Glu Gln Glu Val Ala Gly Ser Lys Val
    1610              1615              1620

Phe Leu Glu Ile Asp Asn Arg Gln Cys Val Gln Asp Ser Asp His
    1625              1630              1635

Cys Phe Lys Asn Thr Asp Ala Ala Ala Ala Leu Leu Ala Ser His
    1640              1645              1650

Ala Ile Gln Gly Thr Leu Ser Tyr Pro Leu Val Ser Val Val Ser
    1655              1660              1665

Glu Ser Leu Thr Pro Glu Arg Thr Gln Leu Leu Tyr Leu Leu Ala
    1670              1675              1680

Val Ala Val Val Ile Ile Leu Phe Ile Ile Leu Leu Gly Val Ile
    1685              1690              1695

Met Ala Lys Arg Lys Arg Lys His Gly Ser Leu Trp Leu Pro Glu
    1700              1705              1710

Gly Phe Thr Leu Arg Arg Asp Ala Ser Asn His Lys Arg Arg Glu
    1715              1720              1725

Pro Val Gly Gln Asp Ala Val Gly Leu Lys Asn Leu Ser Val Gln
    1730              1735              1740

Val Ser Glu Ala Asn Leu Ile Gly Thr Gly Thr Ser Glu His Trp
    1745              1750              1755

Val Asp Asp Glu Gly Pro Gln Pro Lys Lys Val Lys Ala Glu Asp
    1760              1765              1770

Glu Ala Leu Leu Ser Glu Glu Asp Asp Pro Ile Asp Arg Arg Pro
    1775              1780              1785

Trp Thr Gln Gln His Leu Glu Ala Ala Asp Ile Arg Arg Thr Pro
    1790              1795              1800

Ser Leu Ala Leu Thr Pro Pro Gln Ala Glu Gln Glu Val Asp Val
    1805              1810              1815

Leu Asp Val Asn Val Arg Gly Pro Asp Gly Cys Thr Pro Leu Met
    1820              1825              1830

Leu Ala Ser Leu Arg Gly Gly Ser Ser Asp Leu Ser Asp Glu Asp
    1835              1840              1845

Glu Asp Ala Glu Asp Ser Ser Ala Asn Ile Ile Thr Asp Leu Val
    1850              1855              1860

Tyr Gln Gly Ala Ser Leu Gln Ala Gln Thr Asp Arg Thr Gly Glu
    1865              1870              1875

Met Ala Leu His Leu Ala Ala Arg Tyr Ser Arg Ala Asp Ala Ala
    1880              1885              1890

Lys Arg Leu Leu Asp Ala Gly Ala Asp Ala Asn Ala Gln Asp Asn
    1895              1900              1905

Met Gly Arg Cys Pro Leu His Ala Ala Val Ala Ala Asp Ala Gln
    1910              1915              1920

Gly Val Phe Gln Ile Leu Ile Arg Asn Arg Val Thr Asp Leu Asp
    1925              1930              1935

Ala Arg Met Asn Asp Gly Thr Thr Pro Leu Ile Leu Ala Ala Arg
    1940              1945              1950
```

```
Leu Ala  Val Glu Gly Met Val  Ala Glu Leu Ile Asn  Cys Gln Ala
    1955             1960              1965

Asp Val  Asn Ala Val Asp Asp  His Gly Lys Ser Ala  Leu His Trp
    1970             1975              1980

Ala Ala  Ala Val Asn Asn Val  Glu Ala Thr Leu Leu  Leu Leu Lys
    1985             1990              1995

Asn Gly  Ala Asn Arg Asp Met  Gln Asp Asn Lys Glu  Glu Thr Pro
    2000             2005              2010

Leu Phe  Leu Ala Ala Arg Glu  Gly Ser Tyr Glu Ala  Ala Lys Ile
    2015             2020              2025

Leu Leu  Asp His Phe Ala Asn  Arg Asp Ile Thr Asp  His Met Asp
    2030             2035              2040

Arg Leu  Pro Arg Asp Val Ala  Arg Asp Arg Met His  His Asp Ile
    2045             2050              2055

Val Arg  Leu Leu Asp Glu Tyr  Asn Val Thr Pro Ser  Pro Pro Gly
    2060             2065              2070

Thr Val  Leu Thr Ser Ala Leu  Ser Pro Val Ile Cys  Gly Pro Asn
    2075             2080              2085

Arg Ser  Phe Leu Ser Leu Lys  His Thr Pro Met Gly  Lys Lys Ser
    2090             2095              2100

Arg Arg  Pro Ser Ala Lys Ser  Thr Met Pro Thr Ser  Leu Pro Asn
    2105             2110              2115

Leu Ala  Lys Glu Ala Lys Asp  Ala Lys Gly Ser Arg  Arg Lys Lys
    2120             2125              2130

Ser Leu  Ser Glu Lys Val Gln  Leu Ser Glu Ser Ser  Val Thr Leu
    2135             2140              2145

Ser Pro  Val Asp Ser Leu Glu  Ser Pro His Thr Tyr  Val Ser Asp
    2150             2155              2160

Thr Thr  Ser Ser Pro Met Ile  Thr Ser Pro Gly Ile  Leu Gln Ala
    2165             2170              2175

Ser Pro  Asn Pro Met Leu Ala  Thr Ala Ala Pro Pro  Ala Pro Val
    2180             2185              2190

His Ala  Gln His Ala Leu Ser  Phe Ser Asn Leu His  Glu Met Gln
    2195             2200              2205

Pro Leu  Ala His Gly Ala Ser  Thr Val Leu Pro Ser  Val Ser Gln
    2210             2215              2220

Leu Leu  Ser His His His Ile  Val Ser Pro Gly Ser  Gly Ser Ala
    2225             2230              2235

Gly Ser  Leu Ser Arg Leu His  Pro Val Pro Val Pro  Ala Asp Trp
    2240             2245              2250

Met Asn  Arg Met Glu Val Asn  Glu Thr Gln Tyr Asn  Glu Met Phe
    2255             2260              2265

Gly Met  Val Leu Ala Pro Ala  Glu Gly Thr His Pro  Gly Ile Ala
    2270             2275              2280

Pro Gln  Ser Arg Pro Pro Glu  Gly Lys His Ile Thr  Thr Pro Arg
    2285             2290              2295

Glu Pro  Leu Pro Pro Ile Val  Thr Phe Gln Leu Ile  Pro Lys Gly
    2300             2305              2310

Ser Ile  Ala Gln Pro Ala Gly  Ala Pro Gln Pro Gln  Ser Thr Cys
    2315             2320              2325

Pro Pro  Ala Val Ala Gly Pro  Leu Pro Thr Met Tyr  Gln Ile Pro
    2330             2335              2340
```

-continued

```
Glu Met  Ala Arg Leu Pro Ser  Val Ala Phe Pro Thr  Ala Met Met
    2345             2350             2355

Pro Gln  Gln Asp Gly Gln Val  Ala Gln Thr Ile Leu  Pro Ala Tyr
    2360             2365             2370

His Pro  Phe Pro Ala Ser Val  Gly Lys Tyr Pro Thr  Pro Pro Ser
    2375             2380             2385

Gln His  Ser Tyr Ala Ser Ser  Asn Ala Ala Glu Arg  Thr Pro Ser
    2390             2395             2400

His Ser  Gly His Leu Gln Gly  Glu His Pro Tyr Leu  Thr Pro Ser
    2405             2410             2415

Pro Glu  Ser Pro Asp Gln Trp  Ser Ser Ser Ser Pro  His Ser Ala
    2420             2425             2430

Ser Asp  Trp Ser Asp Val Thr  Thr Ser Pro Thr Pro  Gly Gly Ala
    2435             2440             2445

Gly Gly  Gly Gln Arg Gly Pro  Gly Thr His Met Ser  Glu Pro Pro
    2450             2455             2460

His Asn  Asn Met Gln Val Tyr  Ala
    2465             2470

<210> SEQ ID NO 26
<211> LENGTH: 1235
<212> TYPE: PRT
<213> ORGANISM: Homo sapiens

<400> SEQUENCE: 26

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
                20              25              30

Glu Pro Cys Val Asn Glu Gly Met Cys Val Thr Tyr His Asn Gly Thr
            35              40              45

Gly Tyr Cys Lys Cys Pro Glu Gly Phe Leu Gly Glu Tyr Cys Gln His
        50              55              60

Arg Asp Pro Cys Glu Lys Asn Arg Cys Gln Asn Gly Gly Thr Cys Val
65              70              75              80

Ala Gln Ala Met Leu Gly Lys Ala Thr Cys Arg Cys Ala Ser Gly Phe
                85              90              95

Thr Gly Glu Asp Cys Gln Tyr Ser Thr Ser His Pro Cys Phe Val Ser
            100             105             110

Arg Pro Cys Leu Asn Gly Gly Thr Cys His Met Leu Ser Arg Asp Thr
        115             120             125

Tyr Glu Cys Thr Cys Gln Val Gly Phe Thr Gly Lys Glu Cys Gln Trp
    130             135             140

Thr Asp Ala Cys Leu Ser His Pro Cys Ala Asn Gly Ser Thr Cys Thr
145             150             155             160

Thr Val Ala Asn Gln Phe Ser Cys Lys Cys Leu Thr Gly Phe Thr Gly
                165             170             175

Gln Lys Cys Glu Thr Asp Val Asn Glu Cys Asp Ile Pro Gly His Cys
            180             185             190

Gln His Gly Gly Thr Cys Leu Asn Leu Pro Gly Ser Tyr Gln Cys Gln
        195             200             205

Cys Pro Gln Gly Phe Thr Gly Gln Tyr Cys Asp Ser Leu Tyr Val Pro
    210             215             220

Cys Ala Pro Ser Pro Cys Val Asn Gly Gly Thr Cys Arg Gln Thr Gly
225             230             235             240
```

```
Asp Phe Thr Phe Glu Cys Asn Cys Leu Pro Gly Phe Glu Gly Ser Thr
            245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
            275                 280                 285

Gln Trp Thr Gly Gln Phe Cys Thr Glu Asp Val Asp Glu Cys Leu Leu
        290                 295                 300

Gln Pro Asn Ala Cys Gln Asn Gly Gly Thr Cys Ala Asn Arg Asn Gly
    305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
                340                 345                 350

Cys Ile Asp Arg Val Ala Ser Phe Ser Cys Met Cys Pro Glu Gly Lys
            355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
                420                 425                 430

Cys Val Asn Thr Asp Gly Ala Phe His Cys Glu Cys Leu Lys Gly Tyr
            435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
            515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
            595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655
```

-continued

```
Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Gly Ala Thr Cys Ile Asn Gly Val Asn Gly Phe
    690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asp Asn Leu Val Asn Gly Tyr Arg Cys Thr Cys Lys
    770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
            805                 810                 815

Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
            835                 840                 845

Lys Glu Ser Pro Asn Phe Glu Ser Tyr Thr Cys Leu Cys Ala Pro Gly
    850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
            885                 890                 895

Cys Glu Cys Pro Pro Gly Phe Ser Gly Met Asp Cys Glu Glu Asp Ile
            900                 905                 910

Asp Asp Cys Leu Ala Asn Pro Cys Gln Asn Gly Gly Ser Cys Met Asp
    915                 920                 925

Gly Val Asn Thr Phe Ser Cys Leu Cys Leu Pro Gly Phe Thr Gly Asp
    930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
            965                 970                 975

Ala Gly Phe Asp Gly Val His Cys Glu Asn Asn Ile Asn Glu Cys Thr
            980                 985                 990

Glu Ser Ser Cys Phe Asn Gly Gly  Thr Cys Val Asp Gly  Ile Asn Ser
        995                 1000                1005

Phe Ser  Cys Leu Cys Pro Val  Gly Phe Thr Gly Ser  Phe Cys Leu
    1010                1015                1020

His Glu  Ile Asn Glu Cys Ser  Ser His Pro Cys Leu  Asn Glu Gly
    1025                1030                1035

Thr Cys  Val Asp Gly Leu Gly  Thr Tyr Arg Cys Ser  Cys Pro Leu
    1040                1045                1050

Gly Tyr  Thr Gly Lys Asn Cys  Gln Thr Leu Val Asn  Leu Cys Ser
    1055                1060                1065

Arg Ser  Pro Cys Lys Asn Lys  Gly Thr Cys Val Gln  Lys Lys Ala
```

-continued

```
            1070                1075                1080

Glu  Ser  Gln  Cys  Leu  Cys  Pro  Ser  Gly  Trp  Ala  Gly  Ala  Tyr  Cys
     1085                1090                1095

Asp  Val  Pro  Asn  Val  Ser  Cys  Asp  Ile  Ala  Ala  Ser  Arg  Arg  Gly
     1100                1105                1110

Val  Leu  Val  Glu  His  Leu  Cys  Gln  His  Ser  Gly  Val  Cys  Ile  Asn
     1115                1120                1125

Ala  Gly  Asn  Thr  His  Tyr  Cys  Gln  Cys  Pro  Leu  Gly  Tyr  Thr  Gly
     1130                1135                1140

Ser  Tyr  Cys  Glu  Glu  Gln  Leu  Asp  Glu  Cys  Ala  Ser  Asn  Pro  Cys
     1145                1150                1155

Gln  His  Gly  Ala  Thr  Cys  Ser  Asp  Phe  Ile  Gly  Gly  Tyr  Arg  Cys
     1160                1165                1170

Glu  Cys  Val  Pro  Gly  Tyr  Gln  Gly  Val  Asn  Cys  Glu  Tyr  Glu  Val
     1175                1180                1185

Asp  Glu  Cys  Gln  Asn  Gln  Pro  Cys  Gln  Asn  Gly  Gly  Thr  Cys  Ile
     1190                1195                1200

Asp  Leu  Val  Asn  His  Phe  Lys  Cys  Ser  Cys  Pro  Pro  Gly  Thr  Arg
     1205                1210                1215

Gly  Met  Lys  Ser  Ser  Leu  Ser  Ile  Phe  His  Pro  Gly  His  Cys  Leu
     1220                1225                1230

Lys  Leu
     1235

<210> SEQ ID NO 27
<211> LENGTH: 2321
<212> TYPE: PRT
<213> ORGANISM: Homo sapiens

<400> SEQUENCE: 27

Met  Gly  Pro  Gly  Ala  Arg  Gly  Arg  Arg  Arg  Arg  Arg  Pro  Met  Ser
1                  5                  10                 15

Pro  Pro  Pro  Pro  Pro  Pro  Pro  Val  Arg  Ala  Leu  Pro  Leu  Leu  Leu
                   20                 25                 30

Leu  Ala  Gly  Pro  Gly  Ala  Ala  Ala  Pro  Pro  Cys  Leu  Asp  Gly  Ser  Pro
          35                 40                 45

Cys  Ala  Asn  Gly  Gly  Arg  Cys  Thr  Gln  Leu  Pro  Ser  Arg  Glu  Ala  Ala
     50                 55                 60

Cys  Leu  Cys  Pro  Pro  Gly  Trp  Val  Gly  Glu  Arg  Cys  Gln  Leu  Glu  Asp
65                 70                 75                 80

Pro  Cys  His  Ser  Gly  Pro  Cys  Ala  Gly  Arg  Gly  Val  Cys  Gln  Ser  Ser
               85                 90                 95

Val  Val  Ala  Gly  Thr  Ala  Arg  Phe  Ser  Cys  Arg  Cys  Pro  Arg  Gly  Phe
          100                105                110

Arg  Gly  Pro  Asp  Cys  Ser  Leu  Pro  Asp  Pro  Cys  Leu  Ser  Ser  Pro  Cys
     115                120                125

Ala  His  Gly  Ala  Arg  Cys  Ser  Val  Gly  Pro  Asp  Gly  Arg  Phe  Leu  Cys
     130                135                140

Ser  Cys  Pro  Pro  Gly  Tyr  Gln  Gly  Arg  Ser  Cys  Arg  Ser  Asp  Val  Asp
145                150                155                160

Glu  Cys  Arg  Val  Gly  Glu  Pro  Cys  Arg  His  Gly  Gly  Thr  Cys  Leu  Asn
               165                170                175

Thr  Pro  Gly  Ser  Phe  Arg  Cys  Gln  Cys  Pro  Ala  Gly  Tyr  Thr  Gly  Pro
          180                185                190
```

-continued

```
Leu Cys Glu Asn Pro Ala Val Pro Cys Ala Pro Ser Pro Cys Arg Asn
        195                 200             205

Gly Gly Thr Cys Arg Gln Ser Gly Asp Leu Thr Tyr Asp Cys Ala Cys
        210                 215             220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250             255

Thr Tyr Asn Cys Gln Cys Pro Pro Glu Trp Thr Gly Gln Phe Cys Thr
                260                 265             270

Glu Asp Val Asp Glu Cys Gln Leu Gln Pro Asn Ala Cys His Asn Gly
                275                 280             285

Gly Thr Cys Phe Asn Thr Leu Gly Gly His Ser Cys Val Cys Val Asn
        290                 295             300

Gly Trp Thr Gly Glu Ser Cys Ser Gln Asn Ile Asp Asp Cys Ala Thr
305                 310                 315             320

Ala Val Cys Phe His Gly Ala Thr Cys His Asp Arg Val Ala Ser Phe
                325                 330             335

Tyr Cys Ala Cys Pro Met Gly Lys Thr Gly Leu Leu Cys His Leu Asp
                340                 345             350

Asp Ala Cys Val Ser Asn Pro Cys His Glu Asp Ala Ile Cys Asp Thr
                355                 360             365

Asn Pro Val Asn Gly Arg Ala Ile Cys Thr Cys Pro Pro Gly Phe Thr
        370                 375             380

Gly Gly Ala Cys Asp Gln Asp Val Asp Glu Cys Ser Ile Gly Ala Asn
385                 390                 395             400

Pro Cys Glu His Leu Gly Arg Cys Val Asn Thr Gln Gly Ser Phe Leu
                405                 410             415

Cys Gln Cys Gly Arg Gly Tyr Thr Gly Pro Arg Cys Glu Thr Asp Val
                420                 425             430

Asn Glu Cys Leu Ser Gly Pro Cys Arg Asn Gln Ala Thr Cys Leu Asp
        435                 440             445

Arg Ile Gly Gln Phe Thr Cys Ile Cys Met Ala Gly Phe Thr Gly Thr
        450                 455             460

Tyr Cys Glu Val Asp Ile Asp Glu Cys Gln Ser Ser Pro Cys Val Asn
465                 470                 475             480

Gly Gly Val Cys Lys Asp Arg Val Asn Gly Phe Ser Cys Thr Cys Pro
                485                 490             495

Ser Gly Phe Ser Gly Ser Thr Cys Gln Leu Asp Val Asp Glu Cys Ala
                500                 505             510

Ser Thr Pro Cys Arg Asn Gly Ala Lys Cys Val Asp Gln Pro Asp Gly
        515                 520             525

Tyr Glu Cys Arg Cys Ala Glu Gly Phe Glu Gly Thr Leu Cys Asp Arg
        530                 535             540

Asn Val Asp Asp Cys Ser Pro Asp Pro Cys His His Gly Arg Cys Val
545                 550                 555             560

Asp Gly Ile Ala Ser Phe Ser Cys Ala Cys Ala Pro Gly Tyr Thr Gly
                565                 570             575

Thr Arg Cys Glu Ser Gln Val Asp Glu Cys Arg Ser Gln Pro Cys Arg
                580                 585             590

His Gly Gly Lys Cys Leu Asp Leu Val Asp Lys Tyr Leu Cys Arg Cys
        595                 600             605

Pro Ser Gly Thr Thr Gly Val Asn Cys Glu Val Asn Ile Asp Asp Cys
```

```
            610              615              620

Ala Ser Asn Pro Cys Thr Phe Gly Val Cys Arg Asp Gly Ile Asn Arg
625                  630              635                  640

Tyr Asp Cys Val Cys Gln Pro Gly Phe Thr Gly Pro Leu Cys Asn Val
                645              650                  655

Glu Ile Asn Glu Cys Ala Ser Ser Pro Cys Gly Glu Gly Gly Ser Cys
            660              665              670

Val Asp Gly Glu Asn Gly Phe Arg Cys Leu Cys Pro Pro Gly Ser Leu
        675              680              685

Pro Pro Leu Cys Leu Pro Pro Ser His Pro Cys Ala His Glu Pro Cys
        690              695              700

Ser His Gly Ile Cys Tyr Asp Ala Pro Gly Gly Phe Arg Cys Val Cys
705              710              715                  720

Glu Pro Gly Trp Ser Gly Pro Arg Cys Ser Gln Ser Leu Ala Arg Asp
                725              730                  735

Ala Cys Glu Ser Gln Pro Cys Arg Ala Gly Gly Thr Cys Ser Ser Asp
            740              745              750

Gly Met Gly Phe His Cys Thr Cys Pro Pro Gly Val Gln Gly Arg Gln
            755              760              765

Cys Glu Leu Leu Ser Pro Cys Thr Pro Asn Pro Cys Glu His Gly Gly
        770              775              780

Arg Cys Glu Ser Ala Pro Gly Gln Leu Pro Val Cys Ser Cys Pro Gln
785              790              795                  800

Gly Trp Gln Gly Pro Arg Cys Gln Gln Asp Val Asp Glu Cys Ala Gly
                805              810                  815

Pro Ala Pro Cys Gly Pro His Gly Ile Cys Thr Asn Leu Ala Gly Ser
            820              825              830

Phe Ser Cys Thr Cys His Gly Gly Tyr Thr Gly Pro Ser Cys Asp Gln
            835              840              845

Asp Ile Asn Asp Cys Asp Pro Asn Pro Cys Leu Asn Gly Gly Ser Cys
        850              855              860

Gln Asp Gly Val Gly Ser Phe Ser Cys Ser Cys Leu Pro Gly Phe Ala
865              870              875                  880

Gly Pro Arg Cys Ala Arg Asp Val Asp Glu Cys Leu Ser Asn Pro Cys
            885              890              895

Gly Pro Gly Thr Cys Thr Asp His Val Ala Ser Phe Thr Cys Thr Cys
            900              905              910

Pro Pro Gly Tyr Gly Gly Phe His Cys Glu Gln Asp Leu Pro Asp Cys
        915              920              925

Ser Pro Ser Ser Cys Phe Asn Gly Gly Thr Cys Val Asp Gly Val Asn
        930              935              940

Ser Phe Ser Cys Leu Cys Arg Pro Gly Tyr Thr Gly Ala His Cys Gln
945              950              955                  960

His Glu Ala Asp Pro Cys Leu Ser Arg Pro Cys Leu His Gly Gly Val
                965              970                  975

Cys Ser Ala Ala His Pro Gly Phe Arg Cys Thr Cys Leu Glu Ser Phe
            980              985              990

Thr Gly Pro Gln Cys Gln Thr Leu  Val Asp Trp Cys Ser  Arg Gln Pro
            995              1000             1005

Cys Gln  Asn Gly Gly Arg Cys  Val Gln Thr Gly Ala  Tyr Cys Leu
    1010              1015             1020

Cys Pro  Pro Gly Trp Ser Gly  Arg Leu Cys Asp Ile  Arg Ser Leu
    1025              1030             1035
```

-continued

```
Pro Cys Arg Glu Ala Ala Ala  Gln Ile Gly Val Arg  Leu Glu Gln
    1040              1045              1050

Leu Cys Gln Ala Gly Gly Gln  Cys Val Asp Glu Asp  Ser Ser His
    1055              1060              1065

Tyr Cys Val Cys Pro Glu Gly  Arg Thr Gly Ser His  Cys Glu Gln
    1070              1075              1080

Glu Val Asp Pro Cys Leu Ala  Gln Pro Cys Gln His  Gly Gly Thr
    1085              1090              1095

Cys Arg Gly Tyr Met Gly Gly  Tyr Met Cys Glu Cys  Leu Pro Gly
    1100              1105              1110

Tyr Asn Gly Asp Asn Cys Glu  Asp Asp Val Asp Glu  Cys Ala Ser
    1115              1120              1125

Gln Pro Cys Gln His Gly Gly  Ser Cys Ile Asp Leu  Val Ala Arg
    1130              1135              1140

Tyr Leu Cys Ser Cys Pro Pro  Gly Thr Leu Gly Val  Leu Cys Glu
    1145              1150              1155

Ile Asn Glu Asp Asp Cys Gly  Pro Gly Pro Pro Leu  Asp Ser Gly
    1160              1165              1170

Pro Arg Cys Leu His Asn Gly  Thr Cys Val Asp Leu  Val Gly Gly
    1175              1180              1185

Phe Arg Cys Thr Cys Pro Pro  Gly Tyr Thr Gly Leu  Arg Cys Glu
    1190              1195              1200

Ala Asp Ile Asn Glu Cys Arg  Ser Gly Ala Cys His  Ala Ala His
    1205              1210              1215

Thr Arg Asp Cys Leu Gln Asp  Pro Gly Gly Gly Phe  Arg Cys Leu
    1220              1225              1230

Cys His Ala Gly Phe Ser Gly  Pro Arg Cys Gln Thr  Val Leu Ser
    1235              1240              1245

Pro Cys Glu Ser Gln Pro Cys  Gln His Gly Gly Gln  Cys Arg Pro
    1250              1255              1260

Ser Pro Gly Pro Gly Gly Gly  Leu Thr Phe Thr Cys  His Cys Ala
    1265              1270              1275

Gln Pro Phe Trp Gly Pro Arg  Cys Glu Arg Val Ala  Arg Ser Cys
    1280              1285              1290

Arg Glu Leu Gln Cys Pro Val  Gly Val Pro Cys Gln  Gln Thr Pro
    1295              1300              1305

Arg Gly Pro Arg Cys Ala Cys  Pro Pro Gly Leu Ser  Gly Pro Ser
    1310              1315              1320

Cys Arg Ser Phe Pro Gly Ser  Pro Pro Gly Ala Ser  Asn Ala Ser
    1325              1330              1335

Cys Ala Ala Ala Pro Cys Leu  His Gly Gly Ser Cys  Arg Pro Ala
    1340              1345              1350

Pro Leu Ala Pro Phe Phe Arg  Cys Ala Cys Ala Gln  Gly Trp Thr
    1355              1360              1365

Gly Pro Arg Cys Glu Ala Pro  Ala Ala Ala Pro Glu  Val Ser Glu
    1370              1375              1380

Glu Pro Arg Cys Pro Arg Ala  Ala Cys Gln Ala Lys  Arg Gly Asp
    1385              1390              1395

Gln Arg Cys Asp Arg Glu Cys  Asn Ser Pro Gly Cys  Gly Trp Asp
    1400              1405              1410

Gly Gly Asp Cys Ser Leu Ser  Val Gly Asp Pro Trp  Arg Gln Cys
    1415              1420              1425
```

-continued

```
Glu Ala Leu Gln Cys Trp Arg Leu Phe Asn Asn Ser Arg Cys Asp
    1430              1435              1440

Pro Ala Cys Ser Ser Pro Ala Cys Leu Tyr Asp Asn Phe Asp Cys
    1445              1450              1455

His Ala Gly Gly Arg Glu Arg Thr Cys Asn Pro Val Tyr Glu Lys
    1460              1465              1470

Tyr Cys Ala Asp His Phe Ala Asp Gly Arg Cys Asp Gln Gly Cys
    1475              1480              1485

Asn Thr Glu Glu Cys Gly Trp Asp Gly Leu Asp Cys Ala Ser Glu
    1490              1495              1500

Val Pro Ala Leu Leu Ala Arg Gly Val Leu Val Leu Thr Val Leu
    1505              1510              1515

Leu Pro Pro Glu Glu Leu Leu Arg Ser Ser Ala Asp Phe Leu Gln
    1520              1525              1530

Arg Leu Ser Ala Ile Leu Arg Thr Ser Leu Arg Phe Arg Leu Asp
    1535              1540              1545

Ala His Gly Gln Ala Met Val Phe Pro Tyr His Arg Pro Ser Pro
    1550              1555              1560

Gly Ser Glu Pro Arg Ala Arg Arg Glu Leu Ala Pro Glu Val Ile
    1565              1570              1575

Gly Ser Val Val Met Leu Glu Ile Asp Asn Arg Leu Cys Leu Gln
    1580              1585              1590

Ser Pro Glu Asn Asp His Cys Phe Pro Asp Ala Gln Ser Ala Ala
    1595              1600              1605

Asp Tyr Leu Gly Ala Leu Ser Ala Val Glu Arg Leu Asp Phe Pro
    1610              1615              1620

Tyr Pro Leu Arg Asp Val Arg Gly Glu Pro Leu Glu Pro Pro Glu
    1625              1630              1635

Pro Ser Val Pro Leu Leu Pro Leu Leu Val Ala Gly Ala Val Leu
    1640              1645              1650

Leu Leu Val Ile Leu Val Leu Gly Val Met Val Ala Arg Arg Lys
    1655              1660              1665

Arg Glu His Ser Thr Leu Trp Phe Pro Glu Gly Phe Ser Leu His
    1670              1675              1680

Lys Asp Val Ala Ser Gly His Lys Gly Arg Arg Glu Pro Val Gly
    1685              1690              1695

Gln Asp Ala Leu Gly Met Lys Asn Met Ala Lys Gly Glu Ser Leu
    1700              1705              1710

Met Gly Glu Val Ala Thr Asp Trp Met Asp Thr Glu Cys Pro Glu
    1715              1720              1725

Ala Lys Arg Leu Lys Val Glu Glu Pro Gly Met Gly Ala Glu Glu
    1730              1735              1740

Ala Val Asp Cys Arg Gln Trp Thr Gln His His Leu Val Ala Ala
    1745              1750              1755

Asp Ile Arg Val Ala Pro Ala Met Ala Leu Thr Pro Pro Gln Gly
    1760              1765              1770

Asp Ala Asp Ala Asp Gly Met Asp Val Asn Val Arg Gly Pro Asp
    1775              1780              1785

Gly Phe Thr Pro Leu Met Leu Ala Ser Phe Cys Gly Gly Ala Leu
    1790              1795              1800

Glu Pro Met Pro Thr Glu Glu Asp Glu Ala Asp Asp Thr Ser Ala
    1805              1810              1815

Ser Ile Ile Ser Asp Leu Ile Cys Gln Gly Ala Gln Leu Gly Ala
```

```
      1820                 1825                 1830

Arg Thr  Asp Arg Thr Gly Glu  Thr Ala Leu His Leu  Ala Ala Arg
    1835                 1840                 1845

Tyr Ala  Arg Ala Asp Ala Ala  Lys Arg Leu Leu Asp  Ala Gly Ala
    1850                 1855                 1860

Asp Thr  Asn Ala Gln Asp His  Ser Gly Arg Thr Pro  Leu His Thr
    1865                 1870                 1875

Ala Val  Thr Ala Asp Ala Gln  Gly Val Phe Gln Ile  Leu Ile Arg
    1880                 1885                 1890

Asn Arg  Ser Thr Asp Leu Asp  Ala Arg Met Ala Asp  Gly Ser Thr
    1895                 1900                 1905

Ala Leu  Ile Leu Ala Ala Arg  Leu Ala Val Glu Gly  Met Val Glu
    1910                 1915                 1920

Glu Leu  Ile Ala Ser His Ala  Asp Val Asn Ala Val  Asp Glu Leu
    1925                 1930                 1935

Gly Lys  Ser Ala Leu His Trp  Ala Ala Ala Val Asn  Asn Val Glu
    1940                 1945                 1950

Ala Thr  Leu Ala Leu Leu Lys  Asn Gly Ala Asn Lys  Asp Met Gln
    1955                 1960                 1965

Asp Ser  Lys Glu Glu Thr Pro  Leu Phe Leu Ala Ala  Arg Glu Gly
    1970                 1975                 1980

Ser Tyr  Glu Ala Ala Lys Leu  Leu Leu Asp His Phe  Ala Asn Arg
    1985                 1990                 1995

Glu Ile  Thr Asp His Leu Asp  Arg Leu Pro Arg Asp  Val Ala Gln
    2000                 2005                 2010

Glu Arg  Leu His Gln Asp Ile  Val Arg Leu Leu Asp  Gln Pro Ser
    2015                 2020                 2025

Gly Pro  Arg Ser Pro Pro Gly  Pro His Gly Leu Gly  Pro Leu Leu
    2030                 2035                 2040

Cys Pro  Pro Gly Ala Phe Leu  Pro Gly Leu Lys Ala  Ala Gln Ser
    2045                 2050                 2055

Gly Ser  Lys Lys Ser Arg Arg  Pro Pro Gly Lys Ala  Gly Leu Gly
    2060                 2065                 2070

Pro Gln  Gly Pro Arg Gly Arg  Gly Lys Lys Leu Thr  Leu Ala Cys
    2075                 2080                 2085

Pro Gly  Pro Leu Ala Asp Ser  Ser Val Thr Leu Ser  Pro Val Asp
    2090                 2095                 2100

Ser Leu  Asp Ser Pro Arg Pro  Phe Gly Gly Pro Pro  Ala Ser Pro
    2105                 2110                 2115

Gly Gly  Phe Pro Leu Glu Gly  Pro Tyr Ala Ala Ala  Thr Ala Thr
    2120                 2125                 2130

Ala Val  Ser Leu Ala Gln Leu  Gly Gly Pro Gly Arg  Ala Gly Leu
    2135                 2140                 2145

Gly Arg  Gln Pro Pro Gly Gly  Cys Val Leu Ser Leu  Gly Leu Leu
    2150                 2155                 2160

Asn Pro  Val Ala Val Pro Leu  Asp Trp Ala Arg Leu  Pro Pro Pro
    2165                 2170                 2175

Ala Pro  Pro Gly Pro Ser Phe  Leu Leu Pro Leu Ala  Pro Gly Pro
    2180                 2185                 2190

Gln Leu  Leu Asn Pro Gly Thr  Pro Val Ser Pro Gln  Glu Arg Pro
    2195                 2200                 2205

Pro Pro  Tyr Leu Ala Val Pro  Gly His Gly Glu Glu  Tyr Pro Ala
    2210                 2215                 2220
```

```
Ala Gly Ala His Ser Ser Pro  Pro Lys Ala Arg Phe  Leu Arg Val
    2225                2230                2235

Pro Ser Glu His Pro Tyr Leu  Thr Pro Ser Pro Glu  Ser Pro Glu
    2240                2245                2250

His Trp Ala Ser Pro Ser Pro  Pro Ser Leu Ser Asp  Trp Ser Glu
    2255                2260                2265

Ser Thr Pro Ser Pro Ala Thr  Ala Thr Gly Ala Met  Ala Thr Thr
    2270                2275                2280

Thr Gly Ala Leu Pro Ala Gln  Pro Leu Pro Leu Ser  Val Pro Ser
    2285                2290                2295

Ser Leu Ala Gln Ala Gln Thr  Gln Leu Gly Pro Gln  Pro Glu Val
    2300                2305                2310

Thr Pro Lys Arg Gln Val Leu  Ala
    2315                2320

<210> SEQ ID NO 28
<211> LENGTH: 2003
<212> TYPE: PRT
<213> ORGANISM: Homo sapiens

<400> SEQUENCE: 28

Met Gln Pro Pro Ser Leu Leu Leu Leu Leu Leu Leu Leu Leu Leu
1               5               10              15

Cys Val Ser Val Val Arg Pro Arg Gly Leu Leu Cys Gly Ser Phe Pro
            20              25              30

Glu Pro Cys Ala Asn Gly Gly Thr Cys Leu Ser Leu Ser Leu Gly Gln
        35              40              45

Gly Thr Cys Gln Cys Ala Pro Gly Phe Leu Gly Glu Thr Cys Gln Phe
    50              55              60

Pro Asp Pro Cys Gln Asn Ala Gln Leu Cys Gln Asn Gly Gly Ser Cys
65              70              75              80

Gln Ala Leu Leu Pro Ala Pro Leu Gly Leu Pro Ser Ser Pro Ser Pro
            85              90              95

Leu Thr Pro Ser Phe Leu Cys Thr Cys Leu Pro Gly Phe Thr Gly Glu
            100             105             110

Arg Cys Gln Ala Lys Leu Glu Asp Pro Cys Pro Pro Ser Phe Cys Ser
        115             120             125

Lys Arg Gly Arg Cys His Ile Gln Ala Ser Gly Arg Pro Gln Cys Ser
    130             135             140

Cys Met Pro Gly Trp Thr Gly Glu Gln Cys Gln Leu Arg Asp Phe Cys
145             150             155             160

Ser Ala Asn Pro Cys Val Asn Gly Gly Val Cys Leu Ala Thr Tyr Pro
            165             170             175

Gln Ile Gln Cys His Cys Pro Pro Gly Phe Glu Gly His Ala Cys Glu
            180             185             190

Arg Asp Val Asn Glu Cys Phe Gln Asp Pro Gly Pro Cys Pro Lys Gly
        195             200             205

Thr Ser Cys His Asn Thr Leu Gly Ser Phe Gln Cys Leu Cys Pro Val
    210             215             220

Gly Gln Glu Gly Pro Arg Cys Glu Leu Arg Ala Gly Pro Cys Pro Pro
225             230             235             240

Arg Gly Cys Ser Asn Gly Gly Thr Cys Gln Leu Met Pro Glu Lys Asp
            245             250             255

Ser Thr Phe His Leu Cys Leu Cys Pro Pro Gly Phe Ile Gly Pro Asp
```

```
                260             265                 270

Cys Glu Val Asn Pro Asp Asn Cys Val Ser His Gln Cys Gln Asn Gly
        275             280                 285

Gly Thr Cys Gln Asp Gly Leu Asp Thr Tyr Thr Cys Leu Cys Pro Glu
        290             295             300

Thr Trp Thr Gly Trp Asp Cys Ser Glu Asp Val Asp Glu Cys Glu Thr
305                 310             315                 320

Gln Gly Pro Pro His Cys Arg Asn Gly Gly Thr Cys Gln Asn Ser Ala
            325             330             335

Gly Ser Phe His Cys Val Cys Val Ser Gly Trp Gly Gly Thr Ser Cys
            340             345             350

Glu Glu Asn Leu Asp Asp Cys Ile Ala Ala Thr Cys Ala Pro Gly Ser
        355             360             365

Thr Cys Ile Asp Arg Val Gly Ser Phe Ser Cys Leu Cys Pro Pro Gly
    370             375             380

Arg Thr Gly Leu Leu Cys His Leu Glu Asp Met Cys Leu Ser Gln Pro
385             390             395             400

Cys His Gly Asp Ala Gln Cys Ser Thr Asn Pro Leu Thr Gly Ser Thr
            405             410             415

Leu Cys Leu Cys Gln Pro Gly Tyr Ser Gly Pro Thr Cys His Gln Asp
            420             425             430

Leu Asp Glu Cys Leu Met Ala Gln Gln Gly Pro Ser Pro Cys Glu His
            435             440             445

Gly Gly Ser Cys Leu Asn Thr Pro Gly Ser Phe Asn Cys Leu Cys Pro
        450             455             460

Pro Gly Tyr Thr Gly Ser Arg Cys Glu Ala Asp His Asn Glu Cys Leu
465             470             475             480

Ser Gln Pro Cys His Pro Gly Ser Thr Cys Leu Asp Leu Leu Ala Thr
            485             490             495

Phe His Cys Leu Cys Pro Pro Gly Leu Glu Gly Gln Leu Cys Glu Val
            500             505             510

Glu Thr Asn Glu Cys Ala Ser Ala Pro Cys Leu Asn His Ala Asp Cys
        515             520             525

His Asp Leu Leu Asn Gly Phe Gln Cys Ile Cys Leu Pro Gly Phe Ser
        530             535             540

Gly Thr Arg Cys Glu Glu Asp Ile Asp Glu Cys Arg Ser Ser Pro Cys
545             550             555             560

Ala Asn Gly Gly Gln Cys Gln Asp Gln Pro Gly Ala Phe His Cys Lys
            565             570             575

Cys Leu Pro Gly Phe Glu Gly Pro Arg Cys Gln Thr Glu Val Asp Glu
            580             585             590

Cys Leu Ser Asp Pro Cys Pro Val Gly Ala Ser Cys Leu Asp Leu Pro
            595             600             605

Gly Ala Phe Phe Cys Leu Cys Pro Ser Gly Phe Thr Gly Gln Leu Cys
        610             615             620

Glu Val Pro Leu Cys Ala Pro Asn Leu Cys Gln Pro Lys Gln Ile Cys
625             630             635             640

Lys Asp Gln Lys Asp Lys Ala Asn Cys Leu Cys Pro Asp Gly Ser Pro
            645             650             655

Gly Cys Ala Pro Pro Glu Asp Asn Cys Thr Cys His His Gly His Cys
            660             665             670

Gln Arg Ser Ser Cys Val Cys Asp Val Gly Trp Thr Gly Pro Glu Cys
        675             680             685
```

```
Glu Ala Glu Leu Gly Gly Cys Ile Ser Ala Pro Cys Ala His Gly Gly
    690             695             700

Thr Cys Tyr Pro Gln Pro Ser Gly Tyr Asn Cys Thr Cys Pro Thr Gly
705             710             715             720

Tyr Thr Gly Pro Thr Cys Ser Glu Glu Met Thr Ala Cys His Ser Gly
            725             730             735

Pro Cys Leu Asn Gly Gly Ser Cys Asn Pro Ser Pro Gly Gly Tyr Tyr
            740             745             750

Cys Thr Cys Pro Pro Ser His Thr Gly Pro Gln Cys Gln Thr Ser Thr
            755             760             765

Asp Tyr Cys Val Ser Ala Pro Cys Phe Asn Gly Gly Thr Cys Val Asn
    770             775             780

Arg Pro Gly Thr Phe Ser Cys Leu Cys Ala Met Gly Phe Gln Gly Pro
785             790             795             800

Arg Cys Glu Gly Lys Leu Arg Pro Ser Cys Ala Asp Ser Pro Cys Arg
            805             810             815

Asn Arg Ala Thr Cys Gln Asp Ser Pro Gln Gly Pro Arg Cys Leu Cys
            820             825             830

Pro Thr Gly Tyr Thr Gly Gly Ser Cys Gln Thr Leu Met Asp Leu Cys
            835             840             845

Ala Gln Lys Pro Cys Pro Arg Asn Ser His Cys Leu Gln Thr Gly Pro
    850             855             860

Ser Phe His Cys Leu Cys Leu Gln Gly Trp Thr Gly Pro Leu Cys Asn
865             870             875             880

Leu Pro Leu Ser Ser Cys Gln Lys Ala Ala Leu Ser Gln Gly Ile Asp
            885             890             895

Val Ser Ser Leu Cys His Asn Gly Gly Leu Cys Val Asp Ser Gly Pro
            900             905             910

Ser Tyr Phe Cys His Cys Pro Pro Gly Phe Gln Gly Ser Leu Cys Gln
            915             920             925

Asp His Val Asn Pro Cys Glu Ser Arg Pro Cys Gln Asn Gly Ala Thr
    930             935             940

Cys Met Ala Gln Pro Ser Gly Tyr Leu Cys Gln Cys Ala Pro Gly Tyr
945             950             955             960

Asp Gly Gln Asn Cys Ser Lys Glu Leu Asp Ala Cys Gln Ser Gln Pro
            965             970             975

Cys His Asn His Gly Thr Cys Thr Pro Lys Pro Gly Gly Phe His Cys
            980             985             990

Ala Cys Pro Pro Gly Phe Val Gly  Leu Arg Cys Glu Gly  Asp Val Asp
            995             1000            1005

Glu Cys  Leu Asp Gln Pro Cys  His Pro Thr Gly Thr  Ala Ala Cys
    1010            1015            1020

His Ser  Leu Ala Asn Ala Phe  Tyr Cys Gln Cys Leu  Pro Gly His
    1025            1030            1035

Thr Gly  Gln Trp Cys Glu Val  Glu Ile Asp Pro Cys  His Ser Gln
    1040            1045            1050

Pro Cys  Phe His Gly Gly Thr  Cys Glu Ala Thr Ala  Gly Ser Pro
    1055            1060            1065

Leu Gly  Phe Ile Cys His Cys  Pro Lys Gly Phe Glu  Gly Pro Thr
    1070            1075            1080

Cys Ser  His Arg Ala Pro Ser  Cys Gly Phe His His  Cys His His
    1085            1090            1095
```

Gly Gly Leu Cys Leu Pro Ser Pro Lys Pro Gly Phe Pro Pro Arg
    1100              1105              1110

Cys Ala Cys Leu Ser Gly Tyr Gly Gly Pro Asp Cys Leu Thr Pro
    1115              1120              1125

Pro Ala Pro Lys Gly Cys Gly Pro Pro Ser Pro Cys Leu Tyr Asn
    1130              1135              1140

Gly Ser Cys Ser Glu Thr Thr Gly Leu Gly Gly Pro Gly Phe Arg
    1145              1150              1155

Cys Ser Cys Pro His Ser Ser Pro Gly Pro Arg Cys Gln Lys Pro
    1160              1165              1170

Gly Ala Lys Gly Cys Glu Gly Arg Ser Gly Asp Gly Ala Cys Asp
    1175              1180              1185

Ala Gly Cys Ser Gly Pro Gly Gly Asn Trp Asp Gly Gly Asp Cys
    1190              1195              1200

Ser Leu Gly Val Pro Asp Pro Trp Lys Gly Cys Pro Ser His Ser
    1205              1210              1215

Arg Cys Trp Leu Leu Phe Arg Asp Gly Gln Cys His Pro Gln Cys
    1220              1225              1230

Asp Ser Glu Glu Cys Leu Phe Asp Gly Tyr Asp Cys Glu Thr Pro
    1235              1240              1245

Pro Ala Cys Thr Pro Ala Tyr Asp Gln Tyr Cys His Asp His Phe
    1250              1255              1260

His Asn Gly His Cys Glu Lys Gly Cys Asn Thr Ala Glu Cys Gly
    1265              1270              1275

Trp Asp Gly Gly Asp Cys Arg Pro Glu Asp Gly Asp Pro Glu Trp
    1280              1285              1290

Gly Pro Ser Leu Ala Leu Leu Val Val Leu Ser Pro Pro Ala Leu
    1295              1300              1305

Asp Gln Gln Leu Phe Ala Leu Ala Arg Val Leu Ser Leu Thr Leu
    1310              1315              1320

Arg Val Gly Leu Trp Val Arg Lys Asp Arg Asp Gly Arg Asp Met
    1325              1330              1335

Val Tyr Pro Tyr Pro Gly Ala Arg Ala Glu Glu Lys Leu Gly Gly
    1340              1345              1350

Thr Arg Asp Pro Thr Tyr Gln Glu Arg Ala Ala Pro Gln Thr Gln
    1355              1360              1365

Pro Leu Gly Lys Glu Thr Asp Ser Leu Ser Ala Gly Phe Val Val
    1370              1375              1380

Val Met Gly Val Asp Leu Ser Arg Cys Gly Pro Asp His Pro Ala
    1385              1390              1395

Ser Arg Cys Pro Trp Asp Pro Gly Leu Leu Leu Arg Phe Leu Ala
    1400              1405              1410

Ala Met Ala Ala Val Gly Ala Leu Glu Pro Leu Leu Pro Gly Pro
    1415              1420              1425

Leu Leu Ala Val His Pro His Ala Gly Thr Ala Pro Pro Ala Asn
    1430              1435              1440

Gln Leu Pro Trp Pro Val Leu Cys Ser Pro Val Ala Gly Val Ile
    1445              1450              1455

Leu Leu Ala Leu Gly Ala Leu Leu Val Leu Gln Leu Ile Arg Arg
    1460              1465              1470

Arg Arg Arg Glu His Gly Ala Leu Trp Leu Pro Pro Gly Phe Thr
    1475              1480              1485

Arg Arg Pro Arg Thr Gln Ser Ala Pro His Arg Arg Arg Pro Pro

-continued

```
        1490                    1495                    1500

Leu Gly Glu Asp Ser Ile Gly Leu Lys Ala Leu Lys Pro Lys Ala
    1505                    1510                    1515

Glu Val Asp Glu Asp Gly Val Val Met Cys Ser Gly Pro Glu Glu
    1520                    1525                    1530

Gly Glu Glu Val Gly Gln Ala Glu Glu Thr Gly Pro Pro Ser Thr
    1535                    1540                    1545

Cys Gln Leu Trp Ser Leu Ser Gly Gly Cys Gly Ala Leu Pro Gln
    1550                    1555                    1560

Ala Ala Met Leu Thr Pro Pro Gln Glu Ser Glu Met Glu Ala Pro
    1565                    1570                    1575

Asp Leu Asp Thr Arg Gly Pro Asp Gly Val Thr Pro Leu Met Ser
    1580                    1585                    1590

Ala Val Cys Cys Gly Glu Val Gln Ser Gly Thr Phe Gln Gly Ala
    1595                    1600                    1605

Trp Leu Gly Cys Pro Glu Pro Trp Glu Pro Leu Leu Asp Gly Gly
    1610                    1615                    1620

Ala Cys Pro Gln Ala His Thr Val Gly Thr Gly Glu Thr Pro Leu
    1625                    1630                    1635

His Leu Ala Ala Arg Phe Ser Arg Pro Thr Ala Ala Arg Arg Leu
    1640                    1645                    1650

Leu Glu Ala Gly Ala Asn Pro Asn Gln Pro Asp Arg Ala Gly Arg
    1655                    1660                    1665

Thr Pro Leu His Ala Ala Val Ala Ala Asp Ala Arg Glu Val Cys
    1670                    1675                    1680

Gln Leu Leu Leu Arg Ser Arg Gln Thr Ala Val Asp Ala Arg Thr
    1685                    1690                    1695

Glu Asp Gly Thr Thr Pro Leu Met Leu Ala Ala Arg Leu Ala Val
    1700                    1705                    1710

Glu Asp Leu Val Glu Glu Leu Ile Ala Ala Gln Ala Asp Val Gly
    1715                    1720                    1725

Ala Arg Asp Lys Trp Gly Lys Thr Ala Leu His Trp Ala Ala Ala
    1730                    1735                    1740

Val Asn Asn Ala Arg Ala Ala Arg Ser Leu Leu Gln Ala Gly Ala
    1745                    1750                    1755

Asp Lys Asp Ala Gln Asp Asn Arg Glu Gln Thr Pro Leu Phe Leu
    1760                    1765                    1770

Ala Ala Arg Glu Gly Ala Val Glu Val Ala Gln Leu Leu Leu Gly
    1775                    1780                    1785

Leu Gly Ala Ala Arg Glu Leu Arg Asp Gln Ala Gly Leu Ala Pro
    1790                    1795                    1800

Ala Asp Val Ala His Gln Arg Asn His Trp Asp Leu Leu Thr Leu
    1805                    1810                    1815

Leu Glu Gly Ala Gly Pro Pro Glu Ala Arg His Lys Ala Thr Pro
    1820                    1825                    1830

Gly Arg Glu Ala Gly Pro Phe Pro Arg Ala Arg Thr Val Ser Val
    1835                    1840                    1845

Ser Val Pro Pro His Gly Gly Gly Ala Leu Pro Arg Cys Arg Thr
    1850                    1855                    1860

Leu Ser Ala Gly Ala Gly Pro Arg Gly Gly Gly Ala Cys Leu Gln
    1865                    1870                    1875

Ala Arg Thr Trp Ser Val Asp Leu Ala Ala Arg Gly Gly Gly Ala
    1880                    1885                    1890
```

```
Tyr Ser  His Cys Arg Ser Leu  Ser Gly Val Gly Ala  Gly Gly Gly
    1895              1900              1905

Pro Thr  Pro Arg Gly Arg Arg  Phe Ser Ala Gly Met  Arg Gly Pro
    1910              1915              1920

Arg Pro  Asn Pro Ala Ile Met  Arg Gly Arg Tyr Gly  Val Ala Ala
    1925              1930              1935

Gly Arg  Gly Gly Arg Val Ser  Thr Asp Asp Trp Pro  Cys Asp Trp
    1940              1945              1950

Val Ala  Leu Gly Ala Cys Gly  Ser Ala Ser Asn Ile  Pro Ile Pro
    1955              1960              1965

Pro Pro  Cys Leu Thr Pro Ser  Pro Glu Arg Gly Ser  Pro Gln Leu
    1970              1975              1980

Asp Cys  Gly Pro Pro Ala Leu  Gln Glu Met Pro Ile  Asn Gln Gly
    1985              1990              1995

Gly Glu  Gly Lys Lys
    2000

<210> SEQ ID NO 29
<211> LENGTH: 9322
<212> TYPE: DNA
<213> ORGANISM: Homo sapiens

<400> SEQUENCE: 29
atgccgccgc tcctggcgcc cctgctctgc ctggcgctgc tgcccgcgct cgccgcacga      60
ggcccgcgat gctcccagcc cggtgagacc tgcctgaatg gcgggaagtg tgaagcggcc     120
aatggcacgg aggcctgcgt ctgtggcggg gccttcgtgg gcccgcgatg ccaggacccc     180
aacccgtgcc tcagcacccc ctgcaagaac gccgggacat gccacgtggt ggaccgcaga     240
ggcgtggcag actatgcctg cagctgtgcc ctgggcttct ctgggcccct ctgcctgaca     300
cccctggaca atgcctgcct caccaacccc tgccgcaacg ggggcacctg cgacctgctc     360
acgctgacgg agtacaagtg ccgctgcccg cccggctggt cagggaaatc gtgccagcag     420
gctgacccgt gcgcctccaa cccctgcgcc aacggtggcc agtgcctgcc cttcgaggcc     480
tcctacatct gccactgccc acccagcttc atggccccca cctgccggca ggatgtcaac     540
gagtgtggcc agaagcccgg gctttgccgc acggaggca cctgccacaa cgaggtcggc     600
tcctaccgct gcgtctgccg cgccacccac actggcccca actgcgagcg ccctacgtg     660 ccctgcagcc cctcgccctg ccagaacggg ggcacctgcc gccccacggg cgacgtcacc     720
cacgagtgtg cctgcctgcc aggcttcacc ggcagaact gtgaggaaaa tatcgacgat     780
tgtccaggaa acaactgcaa gaacgggggt gcctgtgtgg acggcgtgaa cacctacaac     840
tgccgctgcc cgccagagtg gacaggtcag tactgtaccg aggatgtgga cgagtgccag     900
ctgatgccaa atgcctgcca gaacggcggg acctgccaca cacccacgg tggctacaac     960 tgcgtgtgtg tcaacggctg gactggtgag gactgcagcg agaacattga tgactgtgcc    1020
agcgccgcct gcttccacgg cgccacctgc catgaccgtg tggcctcctt ctactgcgag    1080
tgtccccatg ccgcacagg tctgctgtgc cacctcaacg acgcatgcat cagcaacccc    1140
tgtaacgagg ctccaactg cgacaccaac cctgtcaatg caaggccat ctgcacctgc    1200 ccctcggggt acacgggccc ggcctgcagc caggacgtgg atgagtgctc gctgggtgcc    1260 aaccctgcg agcatgcggg caagtgcatc aacacgctgg ctccttcga gtgccagtgt    1320 ctgcagggct acacgggccc ccgatgcgag atcgacgtca cgagtgcgt ctcgaacccg    1380
```

-continued

```
tgccagaacg acgccacctg cctggaccag attggggagt tccagtgcat ctgcatgccc    1440
ggctacgagg gtgtgcactg cgaggtcaac acagacgagt gtgccagcag cccctgcctg    1500
cacaatggcc gctgcctgga caagatcaat gagttccagt gcgagtgccc cacgggcttc    1560
actgggcatc tgtgccagta cgatgtggac gagtgtgcca gcaccccctg caagaatggt    1620
gccaagtgcc tggacggacc caacacttac acctgtgtgt gcacggaagg gtacacgggg    1680
acgcactgcg aggtggacat cgatgagtgc gaccccgacc cctgccacta cggctcctgc    1740
aaggacggcg tcgccacctt cacctgcctc tgccgcccag gctacacggg ccaccactgc    1800
gagaccaaca tcaacgagtg ctccagccag ccctgccgcc acgggggcac ctgccaggac    1860
cgcgacaacg cctacctctg cttctgcctg aaggggacca caggacccaa ctgcgagatc    1920
aacctggatg actgtgccag cagcccctgc gactcgggca cctgtctgga caagatcgat    1980
ggctacgagt gtgcctgtga gccgggctac acagggagca tgtgtaacat caacatcgat    2040
gagtgtgcgg gcaacccctg ccacaacggg ggcacctgcg aggacggcat caatggcttc    2100
acctgccgct gccccgaggg ctaccacgac cccacctgcc tgtctgaggt caatgagtgc    2160
aacagcaacc cctgcgtcca cggggcctgc cgggacagcc tcaacgggta caagtgcgac    2220
tgtgaccctg ggtggagtgg gaccaactgt gacatcaaca caatgagtg tgaatccaac    2280 ccttgtgtca acggcggcac ctgcaaagac atgaccagtg gctacgtgtg cacctgccgg    2340
gagggcttca gcggtcccaa ctgccagacc aacatcaacg agtgtgcgtc caacccatgt    2400
ctgaaccagg gcacgtgtat tgacgacgtt gccgggtaca agtgcaactg cctgctgccc    2460
tacacaggtg ccacgtgtga ggtggtgctg gccccgtgtg cccccagccc ctgcagaaac    2520 ggcgggagt gcaggcaatc cgaggactat gagagcttct cctgtgtctg ccccacgggc    2580
tggcaagggc agacctgtga ggtcgacatc aacgagtgcg ttctgagccc gtgccggcac    2640
ggcgcatcct gccagaacac ccacggcggc taccgctgcc actgccaggc cggctacagt    2700
gggcgcaact gcgagaccga catcgacgac tgccggccca acccgtgtca caacggggc    2760 tcctgcacag acggcatcaa cacggccttc tgcgactgcc tgcccggctt ccggggcact    2820
ttctgtgagg aggacatcaa cgagtgtgcc agtgaccct gccgcaacgg gccaactgc    2880 acggactgcg tggacagcta cacgtgcacc tgccccgcag gcttcagcgg gatccactgt    2940
gagaacaaca cgcctgactg cacagagagc tcctgcttca acggtggcac ctgcgtggac    3000
ggcatcaact cgttcacctg cctgtgtcca cccggcttca cgggcagcta ctgccagcac    3060
gatgtcaatg agtgcgactc acagccctgc ctgcatggcg gcacctgtca ggacggctgc    3120
ggctcctaca ggtgcacctg cccccagggc tacactggcc ccaactgcca gaaccttgtg    3180
cactggtgtg actcctcgcc ctgcaagaac ggcggcaaat gctggcagac ccacacccag    3240
taccgctgcg agtgccccag cggctggacc ggcctttact gcgacgtgcc cagcgtgtcc    3300
tgtgaggtgg ctgcgcagcg acaaggtgtt gacgttgccc gcctgtgcca gcatggaggg    3360
ctctgtgtgg acgcgggcaa cacgcaccac tgccgctgcc aggcgggcta cacaggcagc    3420
tactgtgagg acctggtgga cgagtgctca cccagcccct gccagaacgg ggccacctgc    3480
acggactacc tgggcggcta ctcctgcaag tgcgtggccg gctaccacgg ggtgaactgc    3540
tctgaggaga tcgacgagtg cctctcccac ccctgccaga acgggggcac ctgcctcgac    3600
ctccccaaca cctacaagtg ctcctgccca cggggcactc agggtgtgca ctgtgagatc    3660
aacgtggacg actgcaatcc ccccgttgac cccgtgtccc ggagcccaa gtgctttaac    3720 aacggcacct gcgtggacca ggtgggcggc tacagctgca cctgcccgcc gggcttcgtg    3780
```

```
ggtgagcgct gtgaggggga tgtcaacgag tgcctgtcca atccctgcga cgcccgtggc   3840
acccagaact gcgtgcagcg cgtcaatgac ttccactgcg agtgccgtgc tggtcacacc   3900
gggcgccgct gcgagtccgt catcaatggc tgcaaaggca agccctgcaa gaatgggggc   3960
acctgcgccg tggcctccaa caccgcccgc gggttcatct gcaagtgccc tgcgggcttc   4020
gagggcgcca cgtgtgagaa tgacgctcgt acctgcggca gcctgcgctg cctcaacggc   4080
ggcacatgca tctccggccc gcgcagcccc acctgcctgt gcctgggccc cttcacgggc   4140
cccgaatgcc agttcccggc cagcagcccc tgcctgggcg gcaaccccctg ctacaaccag   4200 gggacctgtg agcccacatc cgagagcccc ttctaccgtt gcctgtgccc cgccaaattc   4260
aacgggctct tgtgccacat cctggactac agcttcgggg gtggggccgg gcgcgacatc   4320 ccccccgccgc tgatcgagga ggcgtgcgag ctgcccgagt gccaggagga cgcgggcaac   4380
aaggtctgca gcctgcagtg caacaaccac gcgtgcggct gggacggcgg tgactgctcc   4440
ctcaacttca tgacccctg gaagaactgc acgcagtctc tgcagtgctg gaagtacttc   4500
agtgacggcc actgtgacag ccagtgcaac tcagccggct gcctcttcga cggctttgac   4560
tgccagcgtg cggaaggcca gtgcaacccc ctgtacgacc agtactgcaa ggaccacttc   4620
agcgacgggc actgcgacca gggctgcaac agcgcgcgagt gcgagtggga cgggctggac   4680
tgtgcggagc atgtacccga gaggctggcg gccggcacgc tggtggtggt ggtgctgatg   4740
ccgccggagc agctgcgcaa cagctccttc cacttcctgc gggagctcag ccgcgtgctg   4800
cacaccaacg tggtcttcaa gcgtgacgca cacggccagc agatgatctt ccctactac   4860 ggccgcgagg aggagctgcg caagcacccc atcaagcgtg ccgccgaggg ctgggccgca   4920
cctgacgccc tgctgggcca ggtgaaggcc tcgctgctcc ctggtggcag cgagggtggg   4980
cggcggcgga gggagctgga ccccatggac gtccgcggct ccatcgtcta cctggagatt   5040
gacaaccggc agtgtgtgca ggcctcctcg cagtgcttcc agagtgccac cgacgtggcc   5100
gcattcctgg gagcgctcgc ctcgctgggc agcctcaaca tcccctacaa gatcgaggcc   5160
gtgcagagtg agaccgtgga gccgcccccg ccggcgcagc tgcacttcat gtacgtggcg   5220
gcggccgcct ttgtgcttct gttcttcgtg ggctgcgggg tgctgctgtc ccgcaagcgc   5280
cggcggcagc atggccagct ctggttccct gagggcttca aagtgtctga ggccagcaag   5340
aagaagcggc gggagcccct cggcgaggac tccgtgggcc tcaagcccct gaagaacgct   5400
tcagacggtg ccctcatgga cgacaaccag aatgagtggg gggacgagga cctggagacc   5460
aagaagttcc ggttcgagga gcccgtggtt ctgcctgacc tggacgacca gacagaccac   5520
cggcagtgga ctcagcagca cctggatgcc gctgacctgc gcatgtctgc catggccccc   5580
acaccgcccc agggtgaggt tgacgccgac tgcatggacg tcaatgtccg cgggcctgat   5640
ggcttcaccc cgctcatgat cgcctcctgc agcgggggcg gcctggagac gggcaacagc   5700
gaggaagagg aggacgcgcc ggccgtcatc tccgacttca tctaccaggg cgccagcctg   5760
cacaaccaga cagaccgcac gggcgagacc gccttgcacc tggccgcccg ctactcacgc   5820
tctgatgccg ccaagcgcct gctggaggcc agcgcagatg ccaacatcca ggacaacatg   5880
ggccgcaccc cgctgcatgc ggctgtgtct gccgacgcac aaggtgtctt ccagatcctg   5940
atccggaacc gagccacaga cctggatgcc cgcatgcatg atggcacgac gccactgatc   6000
ctggctgccc gcctggccgt ggagggcatg ctggaggacc tcatcaactc acacgccgac   6060
gtcaacgccg tagatgacct gggcaagtcc gccctgcact gggccgccgc cgtgaacaat   6120
```

-continued

```
gtggatgccg cagttgtgct cctgaagaac ggggctaaca aagatatgca gaacaacagg    6180
gaggagacac ccctgtttct ggccgcccgg gagggcagct acgagaccgc caaggtgctg    6240
ctggaccact ttgccaaccg ggacatcacg gatcatatgg accgcctgcc gcgcgacatc    6300
gcacaggagc gcatgcatca cgacatcgtg aggctgctgg acgagtacaa cctggtgcgc    6360
agcccgcagc tgcacggagc cccgctgggg ggcacgccca ccctgtcgcc cccgctctgc    6420
tcgcccaacg gctacctggg cagcctcaag cccggcgtgc agggcaagaa ggtccgcaag    6480
cccagcagca aaggcctggc ctgtggaagc aaggaggcca aggacctcaa ggcacggagg    6540
aagaagtccc aggacggcaa gggctgcctg ctggacagct ccggcatgct ctcgcccgtg    6600
gactccctgg agtcacccca tggctacctg tcagacgtgg cctcgccgcc actgctgccc    6660
tccccgttcc agcagtctcc gtccgtgccc ctcaaccacc tgcctgggat gcccgacacc    6720
cacctgggca tcgggcacct gaacgtggcg gccaagcccg agatggcggc gctgggtggg    6780
ggcggccggc tggcctttga gactggccca cctcgtctct cccacctgcc tgtggcctct    6840
ggcaccagca ccgtcctggg ctccagcagc ggaggggccc tgaatttcac tgtgggcggg    6900
tccaccagtt tgaatggtca atgcgagtgg ctgtcccggc tgcagagcgg catggtgccg    6960
aaccaataca accctctgcg ggggagtgtg caccaggcc ccctgagcac acaggccccc    7020
tccctgcagc atggcatggt aggcccgctg cacagtagcc ttgctgccag cgccctgtcc    7080
cagatgatga gctaccaggg cctgcccagc acccggctgg ccacccagcc tcacctggtg    7140
cagacccagc aggtgcagcc acaaaactta cagatgcagc agcagaacct gcagccagca    7200
aacatccagc agcagcaaag cctgcagccg ccaccaccac caccacagcc gcaccttggc    7260
gtgagctcag cagccagcgg ccacctgggc cggagcttcc tgagtggaga gccgagccag    7320
gcagacgtgc agccactggg ccccagcagc ctggcggtgc acactattct gccccaggag    7380
agccccgccc tgcccacgtc gctgccatcc tcgctggtcc cacccgtgac cgcagcccag    7440
ttcctgacgc ccccctcgca gcacagctac tcctcgcctg tggacaacac ccccagccac    7500
cagctacagg tgcctgagca ccccttcctc accccgtccc ctgagtcccc tgaccagtgg    7560
tccagctcgt ccccgcattc caacgtctcc gactggtccg agggcgtctc cagccctccc    7620
accagcatgc agtcccagat cgcccgcatt ccggaggcct tcaagtaaac ggcgcgcccc    7680
acgagacccc ggcttccttt cccaagcctt cgggcgtctg tgtgcgctct gtggatgcca    7740
gggccgacca gaggagcctt tttaaaacac atgttttat acaaaataag aacgaggatt    7800 ttaattttt ttagtattta tttatgtact tttattttac acagaaacac tgcctttta    7860 tttatatgta ctgttttatc tggccccagg tagaaacttt tatctattct gagaaaacaa    7920
gcaagttctg agagccaggg ttttcctacg taggatgaaa agattcttct gtgtttataa    7980
aatataaaca aagattcatg atttataaat gccatttatt tattgattcc tttttttcaaa    8040 atccaaaaag aaatgatgtt ggagaaggga agttgaacga gcatagtcca aaaagctcct    8100
ggggcgtcca ggccgcgccc tttccccgac gcccacccaa ccccaagcca gcccggccgc    8160
tccaccagca tcacctgcct gttaggagaa gctgcatcca gaggcaaacg gaggcaaagc    8220
tggctcacct tccgcacgcg gattaatttg catctgaaat aggaaacaag tgaaagcata    8280
tgggttagat gttgccatgt gttttagatg gtttcttgca agcatgcttg tgaaaatgtg    8340
ttctcggagt gtgtatgcca agagtgcacc catggtacca atcatgaatc tttgtttcag    8400
gttcagtatt atgtagttgt tcgttggtta tacaagttct tggtccctcc agaaccaccc    8460
cggccccctg cccgttcttg aaatgtaggc atcatgcatg tcaaacatga gatgtgtgga    8520
```

-continued

```
ctgtggcact tgcctgggtc acacacggag gcatcctacc cttttctggg gaaagacact    8580
gcctgggctg accccggtgg cggccccagc acctcagcct gcacagtgtc ccccaggttc    8640
cgaagaagat gctccagcaa cacagcctgg gccccagctc gcgggacccg accccccgtg    8700
ggctcccgtg ttttgtagga gacttgccag agccgggcac attgagctgt gcaacgccgt    8760
gggctgcgtc ctttggtcct gtccccgcag ccctggcagg gggcatgcgg tcgggcaggg    8820
gctggaggga ggcgggggct gcccttgggc cacccctcct agtttgggag gagcagattt    8880
ttgcaatacc aagtatagcc tatggcagaa aaaatgtctg taaatatgtt tttaaaggtg    8940
gattttgttt aaaaaatctt aatgaatgag tctgttgtgt gtcatgccag tgagggacgt    9000
cagacttggc tcagctcggg gagccttagc cgcccatgca ctggggacgc tccgctgccg    9060
tgccgcctgc actcctcagg gcagcctccc ccggctctac ggggggccgcg tggtgccatc    9120 cccaggggggc atgaccagat gcgtcccaag atgttgattt ttactgtgtt ttataaaata    9180
gagtgtagtt tacagaaaaa gactttaaaa gtgatctaca tgaggaactg tagatgatgt    9240
atttttttca tctttttttgt taactgattt gcaataaaaa tgatactgat ggtgatctgg    9300
cttccaaaaa aaaaaaaaaa aa                                              9322
```

```
<210> SEQ ID NO 30
<211> LENGTH: 11474
<212> TYPE: DNA
<213> ORGANISM: Homo sapiens

<400> SEQUENCE: 30
gcttgcggtg ggaggaggcg gctgaggcgg aaggacacac gaggctgctt cgttgcacac      60
ccgagaaagt ttcagccaaa cttcgggcgg cggctgaggc ggcggccgag gagcggcgga     120
ctcggggcgc ggggagtcga ggcatttgcg cctgggcttc ggagcgtagc gccagggcct     180
gagcctttga agcaggagga ggggaggaga gagtgggggct cctctatcgg gacccctcc     240 ccatgtggat ctgcccaggc ggcggcggcg gcggcggagg aggaggcgac cgagaagatg     300
cccgccctgc gccccgctct gctgtggggcg ctgctggcgc tctggctgtg ctgcgcggcc     360
cccgcgcatg cattgcagtg tcgagatggc tatgaaccct gtgtaaatga aggaatgtgt     420
gttacctacc acaatggcac aggatactgc aaatgtccag aaggcttctt gggggaatat     480
tgtcaacatc gagacccctg tgagaagaac cgctgccaga atggtgggac ttgtgtggcc     540
caggccatgc tggggaaagc cacgtgccga tgtgcctcag ggtttacagg agaggactgc     600
cagtactcaa catctcatcc atgctttgtg tctcgaccct gcctgaatgg cggcacatgc     660
catatgctca gccgggatac ctatgagtgc acctgtcaag tcgggtttac aggtaaggag     720
tgccaatgga cggatgcctg cctgtctcat ccctgtgcaa atggaagtac ctgtaccact     780
gtggccaacc agttctcctg caaatgcctc acaggcttca cagggcagaa atgtgagact     840
gatgtcaatg agtgtgacat tccaggacac tgccagcatg gtggcacctg cctcaacctg     900
cctggttcct accagtgcca gtgccctcag ggcttcacag gccagtactg tgacagcctg     960
tatgtgccct gtgcaccctc accttgtgtc aatggaggca cctgtcggca gactggtgac    1020
ttcacttttg agtgcaactg ccttccaggt tttgaaggga gcacctgtga gaggaatatt    1080
gatgactgcc ctaaccacag gtgtcagaat ggaggggttt gtgtggatgg ggtcaacact    1140
tacaactgcc gctgtccccc acaatggaca ggacagttct gcacagagga gtgtggatgaa    1200 tgcctgctgc agcccaatgc ctgtcaaaat ggggggcacct gtgccaaccg caatggaggc    1260
```

-continued

```
tatggctgtg tatgtgtcaa cggctggagt ggagatgact gcagtgagaa cattgatgat   1320
tgtgccttcg cctcctgtac tccaggctcc acctgcatcg accgtgtggc ctccttctct   1380
tgcatgtgcc cagaggggaa ggcaggtctc ctgtgtcatc tggatgatgc atgcatcagc   1440
aatccttgcc acaagggggc actgtgtgac accaaccccc taaatgggca atatatttgc   1500
acctgcccac aaggctacaa aggggctgac tgcacagaag atgtggatga atgtgccatg   1560
gccaatagca atccttgtga gcatgcagga aaatgtgtga acacggatgg cgccttccac   1620
tgtgagtgtc tgaagggtta tgcaggacct cgttgtgaga tggacatcaa tgagtgccat   1680
tcagacccct gccagaatga tgctacctgt ctggataaga ttggaggctt cacatgtctg   1740
tgcatgccag gtttcaaagg tgtgcattgt gaattagaaa taaatgaatg tcagagcaac   1800
ccttgtgtga acaatgggca gtgtgtggat aaagtcaatc gtttccagtg cctgtgtcct   1860
cctggtttca ctgggccagt ttgccagatt gatattgatg actgttccag tactccgtgt   1920
ctgaatgggg caaagtgtat cgatcacccg aatggctatg aatgccagtg tgccacaggt   1980
ttcactggtg tgttgtgtga ggagaacatt gacaactgtg accccgatcc ttgccaccat   2040
ggtcagtgtc aggatggtat tgattcctac acctgcatct gcaatcccgg gtacatgggc   2100
gccatctgca gtgaccagat tgatgaatgt tacagcagcc cttgcctgaa cgatggtcgc   2160
tgcattgacc tggtcaatgg ctaccagtgc aactgccagc caggcacgtc aggggttaat   2220
tgtgaaatta attttgatga ctgtgcaagt aaccccttgta tccatggaat ctgtatggat   2280
ggcattaatc gctacagttg tgtctgctca ccaggattca cagggcagag atgtaacatt   2340
gacattgatg agtgtgcctc caatccctgt cgcaagggtg caacatgtat caacggtgtg   2400
aatggtttcc gctgtatatg ccccgaggga ccccatcacc ccagctgcta ctcacaggtg   2460
aacgaatgcc tgagcaatcc ctgcatccat ggaaactgta ctggaggtct cagtggatat   2520
aagtgtctct gtgatgcagg ctgggttggc atcaactgtg aagtggacaa aaatgaatgc   2580
ctttcgaatc catgccagaa tggaggaact tgtgacaatc tggtgaatgg atacaggtgt   2640
acttgcaaga agggcttaa aggctataac tgccaggtga atattgatga atgtgcctca   2700
aatccatgcc tgaaccaagg aacctgcttt gatgacataa gtggctacac ttgccactgt   2760
gtgctgccat acacaggcaa gaattgtcag acagtattgg ctccctgttc cccaaaccct   2820
tgtgagaatg ctgctgtttg caaagagtca ccaaattttg agagttatac ttgcttgtgt   2880
gctcctggct ggcaaggtca gcggtgtacc attgacattg acgagtgtat ctccaagccc   2940
tgcatgaacc atggtctctg ccataacacc caggcagct acatgtgtga atgtccacca   3000
ggcttcagtg gtatggactg tgaggaggac attgatgact gccttgccaa tccttgccag   3060
aatgagggtt cctgtatgga tggagtgaat actttctcct gcctctgcct tccgggtttc   3120
actggggata agtgccagac agacatgaat gagtgtctga gtgaaccctg taagaatgga   3180
gggacctgct ctgactacgt caacagttac acttgcaagt gccaggcagg atttgatgga   3240
gtccattgtg agaacaacat caatgagtgc actgagagct cctgtttcaa tggtggcaca   3300
tgtgttgatg ggattaactc cttctcttgc ttgtgccctg tgggtttcac tggatccttc   3360
tgcctccatg agatcaatga atgcagctct catccatgcc tgaatgaggg aacgtgtgtt   3420
gatggcctgg gtacctaccg ctgcagctgc cccctgggct acactgggaa aaactgtcag   3480
accctggtga atctctgcag tcggtctcca tgtaaaaaca aaggtacttg cgttcagaaa   3540
aaagcagagt cccagtgcct atgtccatct ggatgggctg gtgcctattg tgacgtgccc   3600
aatgtctctt gtgacatagc agcctccagg agaggtgtgc ttgttgaaca cttgtgccag   3660
```

```
cactcaggtg tctgcatcaa tgctggcaac acgcattact gtcagtgccc cctgggctat    3720
actgggagct actgtgagga gcaactcgat gagtgtgcgt ccaacccctg ccagcacggg    3780
gcaacatgca gtgacttcat tggtggatac agatgcgagt gtgtcccagg ctatcagggt    3840
gtcaactgtg agtatgaagt ggatgagtgc cagaatcagc cctgccagaa tggaggcacc    3900
tgtattgacc ttgtgaacca tttcaagtgc tcttgcccac caggcactcg gggcctactc    3960
tgtgaagaga acattgatga ctgtgcccgg ggtccccatt gccttaatgg tggtcagtgc    4020
atggatagga ttggaggcta cagttgtcgc tgcttgcctg gctttgctgg ggagcgttgt    4080
gagggagaca tcaacgagtg cctctccaac ccctgcagct ctgagggcag cctggactgt    4140
atacagctca ccaatgacta cctgtgtgtt tgccgtagtg cctttactgg ccggcactgt    4200
gaaaccttcg tcgatgtgtg tccccagatg ccctgcctga atggagggac ttgtgctgtg    4260
gccagtaaca tgcctgatgg tttcatttgc cgttgtcccc cgggattttc cggggcaagg    4320
tgccagagca gctgtggaca agtgaaatgt aggaaggggg agcagtgtgt gcacaccgcc    4380
tctggacccc gctgcttctg ccccagtccc cgggactgcg agtcaggctg tgccagtagc    4440
ccctgccagc acggggggcag ctgccaccct cagcgccagc ctccttatta ctcctgccag    4500
tgtgccccac cattctcggg tagccgctgt gaactctaca cggcacccccc cagcaccccct    4560 cctgccacct gtctgagcca gtattgtgcc gacaaagctc gggatggcgt ctgtgatgag    4620
gcctgcaaca gccatgcctg ccagtgggat gggggtgact gttctctcac catggagaac    4680
ccctgggcca actgctcctc cccacttccc tgctgggatt atatcaacaa ccagtgtgat    4740
gagctgtgca acacggtcga gtgcctgttt gacaactttg aatgccaggg gaacagcaag    4800
acatgcaagt atgacaaata ctgtgcagac cacttcaaag acaaccactg tgaccagggg    4860
tgcaacagtg aggagtgtgg ttgggatggg ctggactgtg ctgctgacca acctgagaac    4920
ctggcagaag gtaccctggt tattgtggta ttgatgccac ctgaacaact gctccaggat    4980
gctcgcagct tcttgcgggc actgggtacc ctgctccaca ccaacctgcg cattaagcgg    5040
gactcccagg gggaactcat ggtgtacccc tattatggtg agaagtcagc tgctatgaag    5100
aaacagagga tgacacgcag atcccttcct ggtgaacaag aacaggaggt ggctggctct    5160
aaagtctttc tggaaattga caaccgccag tgtgttcaag actcagacca ctgcttcaag    5220
aacacggatg cagcagcagc tctcctggcc tctcacgcca tacaggggac cctgtcatac    5280
cctcttgtgt ctgtcgtcag tgaatccctg actccagaac gcactcagct cctctatctc    5340
cttgctgttg ctgttgtcat cattctgttt attattctgc tgggggtaat catggcaaaa    5400
cgaaagcgta agcatggctc tctctggctg cctgaaggtt tcactcttcg ccgagatgca    5460
agcaatcaca gcgtcgtga gccagtggga caggatgctg tggggctgaa aaatctctca    5520
gtgcaagtct cagaagctaa cctaattggt actggaacaa gtgaacactg ggtcgatgat    5580
gaagggcccc agccaaagaa agtaaaggct gaagatgagg ccttactctc agaagaagat    5640
gaccccattg atcgacggcc atggacacag cagcaccttg aagctgcaga catccgtagg    5700
acaccatcgc tggctctcac ccctcctcag gcagagcagg aggtggatgt gttagatgtg    5760
aatgtccgtg gcccagatgg ctgcacccca ttgatgttgg cttctctccg aggaggcagc    5820
tcagatttga gtgatgaaga tgaagatgca gaggactctt ctgctaacat catcacagac    5880
ttggtctacc agggtgccag cctccaggcc cagacagacc ggactggtga gatggccctg    5940
caccttgcag cccgctactc acgggctgat gctgccaagc gtctcctgga tgcaggtgca    6000
```

-continued

```
gatgccaatg cccaggacaa catgggccgc tgtccactcc atgctgcagt ggcagctgat    6060
gcccaaggtg tcttccagat tctgattcgc aaccgagtaa ctgatctaga tgccaggatg    6120
aatgatggta ctacacccct gatcctggct gcccgcctgg ctgtggaggg aatggtggca    6180
gaactgatca actgccaagc ggatgtgaat gcagtggatg accatggaaa atctgctctt    6240
cactgggcag ctgctgtcaa taatgtggag gcaactcttt tgttgttgaa aaatggggcc    6300
aaccgagaca tgcaggacaa caaggaagag acacctctgt ttcttgctgc ccgggagggg    6360
agctatgaag cagccaagat cctgttagac cattttgcca atcgagacat cacagaccat    6420
atggatcgtc ttccccggga tgtggctcgg gatcgcatgc accatgacat tgtgcgcctt    6480
ctggatgaat acaatgtgac cccaagccct ccaggcaccg tgttgacttc tgctctctca    6540
cctgtcatct gtgggcccaa cagatctttc ctcagcctga agcacacccc aatgggcaag    6600
aagtctagac ggcccagtgc caagagtacc atgcctacta gcctccctaa ccttgccaag    6660
gaggcaaagg atgccaaggg tagtaggagg aagaagtctc tgagtgagaa ggtccaactg    6720
tctgagagtt cagtaacttt atccctgtt gattccctag aatctcctca cacgtatgtt    6780
tccgacacca catcctctcc aatgattaca tccctgggaa tcttacaggc ctcacccaac    6840
cctatgttgg ccactgccgc ccctcctgcc ccagtccatg cccagcatgc actatctttt    6900
tctaaccttc atgaaatgca gcctttggca catgggccca gcactgtgct tccctcagtg    6960
agccagttgc tatcccacca ccacattgtg tctccaggca gtggcagtgc tggaagcttg    7020
agtaggctcc atccagtccc agtcccagca gattggatga accgcatgga ggtgaatgag    7080
acccagtaca atgagatgtt tggtatggtc ctggctccag ctgagggcac ccatcctggc    7140
atagctcccc agagcaggcc acctgaaggg aagcacataa ccacccctcg ggagcccttg    7200
ccccccattg tgactttcca gctcatccct aaaggcagta ttgcccaacc agcgggggct    7260
ccccagcctc agtccacctg ccctccagct gttgcgggcc ccctgcccac catgtaccag    7320
attccagaaa tggcccgttt gcccagtgtg gctttcccca ctgccatgat gccccagcag    7380
gacgggcagg tagctcagac cattctccca gcctatcatc cttttccagc ctctgtgggc    7440
aagtacccca caccccttc acagcacagt tatgcttcct caaatgctgc tgagcgaaca    7500
cccagtcaca gtggtcacct ccagggtgag catccctacc tgacaccatc cccagagtct    7560
cctgaccagt ggtcaagttc atcaccccac tctgcttctg actggtcaga tgtgaccacc    7620
agccctaccc ctgggggtgc tggaggaggt cagcggggac ctgggacaca catgtctgag    7680
ccaccacaca acaacatgca ggtttatgcg tgagagagtc cacctccagt gtagagacat    7740
aactgacttt tgtaaatgct gctgaggaac aaatgaaggt catccgggag agaaatgaag    7800
aaatctctgg agccagcttc tagaggtagg aaagagaaga tgttcttatt cagataatgc    7860
aagagaagca attcgtcagt ttcactgggt atctgcaagg cttattgatt attctaatct    7920
aataagacaa gtttgtggaa atgcaagatg aatacaagcc ttgggtccat gtttactctc    7980
ttctatttgg agaataagat ggatgcttat tgaagcccag acattcttgc agcttggact    8040
gcattttaag ccctgcaggc ttctgccata tccatgagaa gattctacac tagcgtcctg    8100
ttgggaatta tgccctggaa ttctgcctga attgacctac gcatctcctc ctccttggac    8160
attcttttgt cttcatttgg tgcttttggt tttgcacctc tccgtgattg tagccctacc    8220
agcatgttat agggcaagac ctttgtgctt ttgatcattc tggcccatga aagcaacttt    8280
ggtctccttt cccctcctgt cttccggta tcccttggag tctcacaagg tttactttgg    8340
tatggttctc agcacaaacc tttcaagtat gttgtttctt tggaaaatgg acatactgta    8400
```

-continued

```
ttgtgttctc ctgcatatat cattcctgga gagagaaggg gagaagaata cttttcttca    8460
acaaattttg ggggcaggag atcccttcaa gaggctgcac cttaattttt cttgtctgtg    8520
tgcaggtctt catataaact ttaccaggaa gaagggtgtg agtttgttgt ttttctgtgt    8580
atgggcctgg tcagtgtaaa gttttatcct tgatagtcta gttactatga ccctccccac    8640
ttttttaaaa ccagaaaaag gtttggaatg ttggaatgac caagagacaa gttaactcgt    8700
gcaagagcca gttacccacc cacaggtccc cctacttcct gccaagcatt ccattgactg    8760
cctgtatgga acacatttgt cccagatctg agcattctag gcctgtttca ctcactcacc    8820
cagcatatga aactagtctt aactgttgag cctttccttt catatccaca gaagacactg    8880
tctcaaatgt tgtacccttg ccatttagga ctgaactttc cttagcccaa gggacccagt    8940
gacagttgtc ttccgtttgt cagatgatca gtctctactg attatcttgc tgcttaaagg    9000
cctgctcacc aatctttctt tcacaccgtg tggtccgtgt tactggtata cccagtatgt    9060
tctcactgaa gacatggact ttatatgttc aagtgcagga attggaaagt tggacttgtt    9120
ttctatgatc caaaacagcc ctataagaag gttggaaaag gaggaactat atagcagcct    9180
ttgctatttt ctgctaccat ttcttttcct ctgaagcggc catgacattc cctttggcaa    9240
ctaacgtaga aactcaacag aacattttcc tttcctagag tcacctttta gatgataatg    9300
gacaactata gacttgctca ttgttcagac tgattgcccc tcacctgaat ccactctctg    9360
tattcatgct cttggcaatt tctttgactt tcttttaagg gcagaagcat tttagttaat    9420
tgtagataaa gaatagtttt cttcctcttc tccttgggcc agttaataat tggtccatgg    9480
ctacactgca acttccgtcc agtgctgtga tgcccatgac acctgcaaaa taagttctgc    9540
ctgggcattt tgtagatatt aacaggtgaa ttcccgactc ttttggtttg aatgacagtt    9600
ctcattcctt ctatggctgc aagtatgcat cagtgcttcc cacttacctg atttgtctgt    9660
cggtggcccc atatggaaac cctgcgtgtc tgttggcata atagtttaca aatggttttt    9720
tcagtcctat ccaaatttat tgaaccaaca aaaataatta cttctgccct gagataagca    9780
gattaagttt gttcattctc tgctttattc tctccatgtg gcaacattct gtcagcctct    9840
ttcatagtgt gcaaacattt tatcattcta aatggtgact ctctgccctt ggacccattt    9900
attattcaca gatgggggaga acctatctgc atggacctct gtggaccaca gcgtacctgc    9960
ccctttctgc cctcctgctc cagccccact tctgaaagta tcagctactg atccagccac   10020
tggatatttt atatcctccc ttttcctaa gcacaatgtc agaccaaatt gcttgtttct   10080
ttttcttgga ctactttaat ttggatcctt tgggtttgga gaaagggaat gtgaaagctg   10140
tcattacaga caacaggttt cagtgatgag gaggacaaca ctgcctttca aactttttac   10200
tgatctctta gattttaaga actcttgaat tgtgtggtat ctaataaaag ggaaggtaag   10260
atggataatc actttctcat ttgggttctg aattggagac tcagttttta tgagacacat   10320
cttttatgcc atgtatagat cctcccctgc tattttتggt ttattttat tgttataaat   10380 gctttctttc tttgactcct cttctgcctg cctttgggga taggtttttt tgtttgttta   10440
tttgcttcct ctgtttttgtt ttaagcatca ttttcttatg tgaggtgggg aagggaaagg   10500
tatgagggaa agagagtctg agaattaaaa tattttagta taagcaattg gctgtgatgc   10560
tcaaatccat tgcatcctct tattgaattt gccaatttgt aatttttgca taataaagaa   10620
ccaaaggtgt aatgttttgt tgagaggtgg tttagggatt ttggccctaa ccaatacatt   10680
gaatgtatga tgactatttg ggaggacaca tttatgtacc cagaggcccc cactaataag   10740
```

-continued

```
tggtactatg gttacttcct tgtgtacatt tctcttaaaa gtgatattat atctgtttgt    10800
atgagaaacc cagtaaccaa taaaatgacc gcatattcct gactaaacgt agtaaggaaa    10860
atgcacactt tgtttttact tttccgtttc attctaaagg tagttaagat gaaatttata    10920
tgaaagcatt tttatcacaa aataaaaaag gtttgccaag ctcagtggtg ttgtattttt    10980
tattttccaa tactgcatcc atggcctggc agtgttacct catgatgtca taatttgctg    11040
agagagcaaa ttttcttttc tttctgaatc ccacaaagcc tagcaccaaa cttctttttt    11100
tcttccttta attagatcat aaataaatga tcctggggaa aaagcatctg tcaaatagga    11160
aacatcacaa aactgagcac tcttctgtgc actagccata gctggtgaca aacagatggt    11220
tgctcaggga caaggtgcct tccaatggaa atgcgaagta gttgctatag caagaattgg    11280
gaactgggat ataagtcata atattaatta tgctgttatg taaatgattg gtttgtaaca    11340
ttccttaagt gaaatttgtg tagaacttaa tatacaggat tataaaataa tattttgtgt    11400
ataaatttgt tataagttca cattcataca tttatttata aagtcagtga gatatttgaa    11460
catgaaaaaa aaaa                                                      11474

<210> SEQ ID NO 31
<211> LENGTH: 4326
<212> TYPE: DNA
<213> ORGANISM: Homo sapiens

<400> SEQUENCE: 31
gcttgcggtg ggaggaggcg gctgaggcgg aaggacacac gaggctgctt cgttgcacac      60
ccgagaaagt ttcagccaaa cttcgggcgg cggctgaggc ggcggccgag gagcggcgga     120
ctcggggcgc ggggagtcga ggcatttgcg cctgggcttc ggagcgtagc gccagggcct     180
gagcctttga agcaggagga ggggaggaga gagtgggggct cctctatcgg gacccccctcc    240 ccatgtggat ctgcccaggc ggcggcggcg gcggcggagg aggaggcgac cgagaagatg     300 cccgcccctgc gccccgctct gctgtgggcg ctgctggcgc tctggctgtg ctgcgcggcc    360
cccgcgcatg cattgcagtg tcgagatggc tatgaaccct gtgtaaatga aggaatgtgt     420
gttacctacc acaatggcac aggatactgc aaatgtccag aaggcttctt gggggaatat     480
tgtcaacatc gagacccctg tgagaagaac cgctgccaga atggtgggac ttgtgtggcc     540
caggccatgc tggggaaagc cacgtgccga tgtgcctcag ggtttacagg agaggactgc     600
cagtactcaa catctcatcc atgctttgtg tctcgaccct gcctgaatgg cggcacatgc     660
catatgctca gccgggatac ctatgagtgc acctgtcaag tcgggtttac aggtaaggag     720
tgccaatgga cggatgcctg cctgtctcat ccctgtgcaa atggaagtac ctgtaccact     780
gtggccaacc agttctcctg caaatgcctc acaggcttca cagggcagaa atgtgagact     840
gatgtcaatg agtgtgacat ccaggacac tgccagcatg gtggcacctg cctcaacctg     900
cctggttcct accagtgcca gtgccctcag ggcttcacag gccagtactg tgacagcctg     960
tatgtgccct gtgcaccctc accttgtgtc aatggaggca cctgtcggca gactggtgac    1020
ttcacttttg agtgcaactg ccttccaggt tttgaaggga gcacctgtga gaggaatatt    1080
gatgactgcc ctaaccacag gtgtcagaat ggaggggttt gtgtggatgg ggtcaacact    1140
tacaactgcc gctgtcccc acaatggaca ggacagttct gcacagagga tgtggatgaa    1200
tgcctgctgc agcccaatgc ctgtcaaaat ggggcacct gtgccaaccg caatggaggc    1260
tatgctgtgt atgtgtcaa cggctggagt ggagatgact gcagtgagaa cattgatgat    1320
tgtgccttcg cctcctgtac tccaggctcc acctgcatcg accgtgtggc ctccttctct    1380
```

```
tgcatgtgcc cagaggggaa ggcaggtctc ctgtgtcatc tggatgatgc atgcatcagc   1440
aatccttgcc acaagggggc actgtgtgac accaacccccc taaatgggca atatatttgc   1500
acctgcccac aaggctacaa aggggctgac tgcacagaag atgtggatga atgtgccatg   1560
gccaatagca atccttgtga gcatgcagga aaatgtgtga acacggatgg cgccttccac   1620
tgtgagtgtc tgaagggtta tgcaggacct cgttgtgaga tggacatcaa tgagtgccat   1680
tcagacccct gccagaatga tgctacctgt ctggataaga ttggaggctt cacatgtctg   1740
tgcatgccag gtttcaaagg tgtgcattgt gaattagaaa taaatgaatg tcagagcaac   1800
ccttgtgtga acaatgggca gtgtgtggat aaagtcaatc gtttccagtg cctgtgtcct   1860
cctggtttca ctgggccagt ttgccagatt gatattgatg actgttccag tactccgtgt   1920
ctgaatgggg caaagtgtat cgatcacccg aatggctatg aatgccagtg tgccacaggt   1980
ttcactggtg tgttgtgtga ggagaacatt gacaactgtg accccgatcc ttgccaccat   2040
ggtcagtgtc aggatggtat tgattcctac acctgcatct gcaatcccgg gtacatgggc   2100
gccatctgca gtgaccagat tgatgaatgt tacagcagcc cttgcctgaa cgatggtcgc   2160
tgcattgacc tggtcaatgg ctaccagtgc aactgccagc caggcacgtc aggggttaat   2220
tgtgaaatta attttgatga ctgtgcaagt aacccttgta tccatggaat ctgtatggat   2280
ggcattaatc gctacagttg tgtctgctca ccaggattca cagggcagag atgtaacatt   2340
gacattgatg agtgtgcctc caatccctgt cgcaagggtg caacatgtat caacggtgtg   2400
aatggtttcc gctgtatatg ccccgaggga ccccatcacc ccagctgcta ctcacaggtg   2460
aacgaatgcc tgagcaatcc ctgcatccat ggaaactgta ctggaggtct cagtggatat   2520
aagtgtctct gtgatgcagg ctgggttggc atcaactgtg aagtggacaa aaatgaatgc   2580
ctttcgaatc catgccagaa tggaggaact tgtgacaatc tggtgaatgg atacaggtgt   2640
acttgcaaga agggctttaa aggctataac tgccaggtga atattgatga atgtgcctca   2700
aatccatgcc tgaaccaagg aacctgcttt gatgacataa gtggctacac ttgccactgt   2760
gtgctgccat acacaggcaa gaattgtcag acagtattgg ctccctgttc cccaaaccct   2820
tgtgagaatg ctgctgtttg caaagagtca ccaaattttg agagttatac ttgcttgtgt   2880
gctcctggct ggcaaggtca gcggtgtacc attgacattg acgagtgtat ctccaagccc   2940
tgcatgaacc atggtctctg ccataacacc cagggcagct acatgtgtga atgtccacca   3000
ggcttcagtg gtatggactg tgaggaggac attgatgact gccttgccaa tccttgccag   3060
aatggaggtt cctgtatgga tggagtgaat actttctcct gcctctgcct tccgggtttc   3120 actgggggata agtgccagac agacatgaat gagtgtctga gtgaaccctg taagaatgga   3180
gggacctgct ctgactacgt caacagttac acttgcaagt gccaggcagg atttgatgga   3240
gtccattgtg agaacaacat caatgagtgc actgagagct cctgtttcaa tggtggcaca   3300
tgtgttgatg gattaactc cttctcttgc ttgtgccctg tgggtttcac tggatccttc   3360
tgcctccatg agatcaatga atgcagctct catccatgcc tgaatgaggg aacgtgtgtt   3420
gatggcctgg gtacctaccg ctgcagctgc cccctgggct acactgggaa aaactgtcag   3480
accctggtga atctctgcag tcggtctcca tgtaaaaaca aaggtacttg cgttcagaaa   3540
aaagcagagt cccagtgcct atgtccatct ggatgggctg gtgcctattg tgacgtgccc   3600
aatgtctctt gtgacatagc agcctccagg agaggtgtgc ttgttgaaca cttgtgccag   3660
cactcaggtg tctgcatcaa tgctggcaac acgcattact gtcagtgccc cctgggctat   3720
```

```
actgggagct actgtgagga gcaactcgat gagtgtgcgt ccaacccctg ccagcacggg   3780
gcaacatgca gtgacttcat tggtggatac agatgcgagt gtgtcccagg ctatcagggt   3840
gtcaactgtg agtatgaagt ggatgagtgc cagaatcagc cctgccagaa tggaggcacc   3900
tgtattgacc ttgtgaacca tttcaagtgc tcttgcccac caggcactcg gggtatgaaa   3960
tcatccttat ccattttcca tccagggcat tgtcttaagt tataaatcca ttcttagtgt   4020
tcaggggatt ttataaaatt aaagatagga agactagctt cattccaagc atttagttct   4080
acatcctagt aattcaagcc attttattct cccatctctt gctagctctg atgttgtggt   4140
ttatgttgtc agttttatct ggttgtttgg catcttgata ttccatgaaa cacagaatat   4200
ggaagggata caacattagc ataacattaa aaaattagcc tggtcagtaa gatttcttgt   4260
tgcttcacag aaaagcaact aatggcctct aaaataaaca atttacattt aaaaaaaaaa   4320
aaaaaa                                                             4326

<210> SEQ ID NO 32
<211> LENGTH: 8089
<212> TYPE: DNA
<213> ORGANISM: Homo sapiens

<400> SEQUENCE: 32
gcggcgcgga ggctggcccg ggacgcgccc ggagcccagg gaaggaggga ggaggggagg     60
gtcgcggccg gccgccatgg ggccgggggc ccgtggccgc cgccgccgcc gtcgcccgat    120
gtcgccgcca ccgccaccgc cacccgtgcg ggcgctgccc ctgctgctgc tgctagcggg    180
gccgggggct gcagcccccc cttgcctgga cggaagcccg tgtgcaaatg gaggtcgttg    240
cacccagctg ccctcccggg aggctgcctg cctgtgcccg cctggctggg tgggtgagcg    300
gtgtcagctg gaggacccct gtcactcagg ccctgtgct ggccgtggtg tctgccagag    360
ttcagtggtg gctggcaccg cccgattctc atgccggtgc ccccgtggct tccgaggccc    420
tgactgctcc ctgccagatc cctgcctcag cagcccttgt gcccacggtg cccgctgctc    480
agtggggccc gatggacgct tcctctgctc ctgcccacct ggctaccagg ccgcagctg     540 ccgaagcgac gtggatgagt gccgggtggg tgagccctgc cgccatggtg gcacctgcct    600
caacacacct ggctccttcc gctgccagtg tccagctggc tacacagggc cactatgtga    660
gaaccccgcg gtgccctgtg caccctcacc atgccgtaac gggggcacct gcaggcagag    720
tggcgacctc acttacgact gtgcctgtct tcctgggttt gagggtcaga attgtgaagt    780
gaacgtggac gactgtccag dacaccgatg tctcaatggg gggacatgcg tggatggcgt    840
caacacctat aactgccagt gccctcctga gtggacaggc cagttctgca cggaggacgt    900
ggatgagtgt cagctgcagc ccaacgcctg ccacaatggg ggtacctgct tcaacacgct    960
gggtggccac agctgcgtgt gtgtcaatgg ctggacaggc gagagctgca gtcagaatat   1020
cgatgactgt ccacagccg tgtgcttcca tgggggccacc tgccatgacc gcgtggcttc   1080
tttctactgt gcctgcccca tgggcaagac tggcctcctg tgtcacctgg atgacgcctg   1140
tgtcagcaac ccctgccacg aggatgctat ctgtgacaca aatccggtga acggccgggc   1200
catttgcacc tgtcctcccg gcttcacggg tgggcatgt gaccaggatg tggacgagtg   1260
ctctatcggc gccaacccct gcgagcactt gggcaggtgc gtgaacacgc agggctcctt   1320
cctgtgccag tgcggtcgtg gctacactgg acctcgctgt gagaccgatg tcaacgagtg   1380
tctgtcgggg ccctgccgaa accaggccac gtgcctcgac cgcataggcc agttcacctg   1440
tatctgtatg gcaggcttca caggaaccta ttgcgaggtg gacattgacg agtgtcagag   1500
```

-continued

```
tagcccctgt gtcaacggtg gggtctgcaa ggaccgagtc aatggcttca gctgcacctg     1560
cccctcgggc ttcagcggct ccacgtgtca gctggacgtg gacgaatgcg ccagcacgcc     1620
ctgcaggaat ggcgccaaat gcgtggacca gcccgatggc tacgagtgcc gctgtgccga     1680
gggctttgag ggcacgctgt gtgatcgcaa cgtggacgac tgctcccctg acccatgcca     1740
ccatggtcgc tgcgtggatg gcatcgccag cttctcatgt gcctgtgctc ctggctacac     1800
gggcacacgt gcgagagcc aggtggacga atgccgcagc cagccctgcc gccatggcgg     1860
caaatgccta gacctggtgg acaagtacct ctgccgctgc ccttctggga ccacaggtgt     1920
gaactgcgaa gtgaacattg acgactgtgc cagcaacccc tgcacctttg gagtctgccg     1980
tgatggcatc aaccgctacg actgtgtctg ccaacctggc ttcacagggc cctttgtaa     2040 cgtggagatc aatgagtgtg cttccagccc atgcggcgag ggaggttcct gtgtggatgg     2100
ggaaaatggc ttccgctgcc tctgcccgcc tggctccttg cccccactct gcctcccccc     2160
gagccatccc tgtgcccatg agccctgcag tcacggcatc tgctatgatg cacctggcgg     2220
gttccgctgt gtgtgtgagc ctggctggag tggccccgc tgcagccaga gcctggcccg     2280
agacgcctgt gagtcccagc cgtgcagggc cggtgggaca tgcagcagcg atggaatggg     2340
tttccactgc acctgcccgc ctggtgtcca gggacgtcag tgtgaactcc tctccccctg     2400 cacccgaac ccctgtgagc atggggggccg ctgcgagtct gccctggcc agctgcctgt     2460 ctgctcctgc ccccagggct ggcaaggccc acgatgccag caggatgtgg acgagtgtgc     2520
tggccccgca ccctgtggcc ctcatggtat ctgcaccaac ctggcaggga gtttcagctg     2580
cacctgccat ggagggtaca ctggcccttc ctgcgatcag gacatcaatg actgtgaccc     2640
caacccatgc ctgaacgtg gctcgtgcca agacggcgtg ggctcctttt cctgctcctg     2700 cctcctggt ttcgccggcc cacgatgcgc ccgcgatgtg gatgagtgcc tgagcaaccc     2760
ctgcggcccg ggcacctgta ccgaccacgt ggcctccttc acctgcacct gcccgccagg     2820
ctacggaggc ttccactgcg aacaggacct gcccgactgc agccccagct cctgcttcaa     2880
tggcgggacc tgtgtggacg gcgtgaactc gttcagctgc ctgtgccgtc ccggctacac     2940
aggagcccac tgccaacatg aggcagaccc ctgcctctcg cggccctgcc tacacggggg     3000
cgtctgcagc gccgcccacc ctggcttccg ctgcacctgc ctcgagagct tcacgggccc     3060
gcagtgccag acgctggtgg attggtgcag ccgccagcct tgtcaaaacg ggggtcgctg     3120
cgtccagact ggggcctatt gcctttgtcc ccctggatgg agcggacgcc tctgtgacat     3180
ccgaagcttg ccctgcaggg aggccgcagc ccagatcggg gtgcggctgg agcagctgtg     3240
tcaggcgggt gggcagtgtg tggatgaaga cagctcccac tactgcgtgt gcccagaggg     3300
ccgtactggt agccactgtg agcaggaggt ggaccctgc ttggcccagc cctgccagca     3360
tggggggacc tgccgtggct atatggggggg ctacatgtgt gagtgtcttc ctggctacaa     3420
tggtgataac tgtgaggacg acgtggacga gtgtgcctcc cagccctgcc agcacggggg     3480
ttcatgcatt gacctcgtgg cccgctatct ctgctcctgt ccccaggaa cgctgggggt     3540 gctctgcgag attaatgagg atgactgcgg cccaggccca ccgctggact cagggccccg     3600
gtgcctacac aatggcacct gcgtggacct ggtgggtggt ttccgctgca cctgtccccc     3660
aggatacact ggtttgcgct gcgaggcaga catcaatgag tgtcgctcag gtgcctgcca     3720
cgcggcacac acccgggact gcctgcagga cccaggcgga ggtttccgtt gcctttgtca     3780
tgctggcttc tcaggtcctc gctgtcagac tgtcctgtct ccctgcgagt cccagccatg     3840
```

-continued

```
ccagcatgga ggccagtgcc gtcctagccc gggtcctggg ggtgggctga ccttcacctg      3900
tcactgtgcc cagccgttct ggggtccgcg ttgcgagcgg gtggcgcgct cctgccggga      3960
gctgcagtgc ccggtgggcg tcccatgcca gcagacgccc cgcgggccgc gctgcgcctg      4020
cccccagggg ttgtcgggac cctcctgccg cagcttcccg gggtcgccgc cggggggccag     4080 caacgccagc tgcgcggccg cccccctgtct ccacgggggc tcctgccgcc ccgcgccgct    4140
cgcgcccttc ttccgctgcg cttgcgcgca gggctggacc gggccgcgct gcgaggcgcc      4200
cgccgcggca cccgaggtct cggaggagcc gcggtgcccg cgcgccgcct gccaggccaa      4260
gcgcggggac cagcgctgcg accgcgagtg caacagccca ggctgcggct gggacggcgg      4320
cgactgctcg ctgagcgtgg gcgacccctg gcggcaatgc gaggcgctgc agtgctggcg      4380
cctcttcaac aacagccgct gcgacccccgc ctgcagctcg cccgcctgcc tctacgacaa    4440
cttcgactgc cacgccggtg gccgcgagcg cacttgcaac ccggtgtacg agaagtactg      4500
cgccgaccac tttgccgacg gccgctgcga ccagggctgc aacacggagg agtgcggctg      4560
ggatgggctg gattgtgcca gcgaggtgcc ggccctgctg gcccgcggcg tgctggtgct      4620
cacagtgctg ctgccgccag aggagctact gcgttccagc gccgactttc tgcagcggct      4680
cagcgccatc ctgcgcacct cgctgcgctt ccgcctggac gcgcacggcc aggccatggt      4740
cttcccttac caccggccta gtcctggctc cgaaccccgg gcccgtcggg agctggcccc      4800
cgaggtgatc ggctcggtag taatgctgga gattgacaac cggctctgcc tgcagtcgcc      4860
tgagaatgat cactgcttcc ccgatgccca gagcgccgct gactacctgg gagcgttgtc      4920
agcggtggag cgcctggact tcccgtaccc actgcgggac gtgcgggggg agccgctgga      4980
gcctccagaa cccagcgtcc cgctgctgcc actgctagtg gcgggcgctg tcttgctgct      5040
ggtcattctc gtcctgggtg tcatggtggc ccggcgcaag cgcgagcaca gcaccctctg      5100
gttccctgag ggcttctcac tgcacaagga cgtggcctct ggtcacaagg ccggcggga       5160 acccgtgggc caggacgcgc tgggcatgaa gaacatggcc aagggtgaga gcctgatggg      5220
ggaggtggcc acagactgga tggacacaga gtgcccagag gccaagcggc taaaggtaga      5280
ggagccaggc atgggggctg aggaggctgt ggattgccgt cagtggactc aacaccatct      5340
ggttgctgct gacatccgcg tggcaccagc catggcactg acaccaccac agggcgacgc      5400
agatgctgat ggcatggatg tcaatgtgcg tggcccagat ggcttcaccc cgctaatgct      5460
ggcttccttc tgtggggggg ctctggagcc aatgccaact gaagaggatg aggcagatga      5520
cacatcagct agcatcatct ccgacctgat ctgccagggg gctcagcttg gggcacggac      5580
tgaccgtact ggcgagactg ctttgcacct ggctgcccgt tatgcccgtg ctgatgcagc      5640
caagcggctg ctggatgctg gggcagacac caatgcccag gaccactcag gccgcactcc      5700
cctgcacaca gctgtcacag ccgatgccca gggtgtcttc cagattctca tccgaaaccg      5760
ctctacagac ttggatgccc gcatggcaga tggctcaacg gcactgatcc tggcggcccg      5820
cctggcagta gagggcatgg tggaagagct catcgccagc catgctgatg tcaatgctgt      5880
ggatgagctt gggaaatcag ccttacactg gctgcggct gtgaacaacg tggaagccac      5940
tttggccctg ctcaaaaatg gagccaataa ggacatgcag gatagcaagg aggagacccc      6000
cctattcctg gccgcccgcg agggcagcta tgaggctgcc aagctgctgt tggaccactt      6060
tgccaaccgt gagatcaccg accacctgga caggctgccg cgggacgtag cccaggagag      6120
actgcaccag gacatcgtgc gcttgctgga tcaacccagt gggcccccgca gcccccccgg      6180 tcccccacggc ctggggcctc tgctctgtcc tccaggggcc ttcctccctg gcctcaaagc      6240
```

-continued

```
ggcacagtcg gggtccaaga agagcaggag gccccccggg aaggcggggc tggggccgca      6300 gggtcccccgg gggcggggca agaagctgac gctggcctgc ccgggccccc tggctgacag      6360
ctcggtcacg ctgtcgcccg tggactcgct ggactccccg cggcctttcg gtgggccccc      6420 tgcttccect ggtggcttcc cccttgaggg gccctatgca gctgccactg ccactgcagt      6480
gtctctggca cagcttggtg gcccaggccg ggcgggtcta gggcgccagc cccctggagg      6540
atgtgtactc agcctgggcc tgctgaaccc tgtggctgtg cccctcgatt gggcccggct      6600
gcccccacct gccctccag gccctcgtt cctgctgcca ctggcgccgg gaccccagct      6660
gctcaaccca gggaccccg tctccccgca ggagcggccc ccgccttacc tggcagtccc      6720
aggacatggc gaggagtacc cggcggctgg ggcacacagc agccccccaa aggcccgctt      6780
cctgcgggtt cccagtgagc acccttacct gaccccatcc cccgaatccc ctgagcactg      6840
ggccagcccc tcacctccct ccctctcaga ctggtccgaa tccacgccta gcccagccac      6900
tgccactggg gccatggcca ccaccactgg ggcactgcct gcccagccac ttcccttgtc      6960
tgttcccagc tcccttgctc aggcccagac ccagctgggg ccccagccgg aagttacccc      7020
caagaggcaa gtgttggcct gagacgctcg tcagttctta gatcttgggg gcctaaagag      7080 accccgtcc tgcctccttt cttctctgt ctcttcctc cttttagtct ttttcatcct      7140 cttctcttc caccaaccct cctgcatcct tgccttgcag cgtgaccgag ataggtcatc      7200 agcccaggc ttcagtcttc ctttatttat aatgggtggg ggctaccacc caccctctca      7260
gtcttgtgaa gagtctggga cctccttctt ccccacttct ctcttccctc attcctttct      7320
ctctccttct ggcctctcat ttccttacac tctgacatga atgaattatt attattttta      7380
ttttcttttt tttttttaca ttttgtatag aaacaaattc atttaaacaa acttattatt      7440 attattttt acaaaatata tatatggaga tgctccctcc ccctgtgaac cccccagtgc      7500
ccccgtgggg ctgagtctgt gggcccattc ggccaagctg gattctgtgt acctagtaca      7560
caggcatgac tgggatcccg tgtaccgagt acacgaccca ggtatgtacc aagtaggcac      7620
ccttgggcgc acccactggg gccaggggtc ggggagtgt tgggagcctc ctccccaccc      7680
cacctccctc acttcactgc attccagatg ggacatgttc catagccttg ctggggaagg      7740
gcccactgcc aactccctct gccccagccc caccccttggc catctcccct tgggaactag      7800
ggggctgctg gtgggaaatg ggagccaggg cagatgtatg cattcctttg tgtccctgta      7860
aatgtgggac tacaagaaga ggagctgcct gagtggtact ttctcttcct ggtaatcctc      7920
tggcccagcc tcatggcaga atagaggtat ttttaggcta tttttgtaat atggcttctg      7980
gtcaaaatcc ctgtgtagct gaattcccaa gccctgcatt gtacagcccc ccactcccct      8040
caccacctaa taaaggaata gttaacactc aaaaaaaaaa aaaaaaaaa      8089
```

```
<210> SEQ ID NO 33
<211> LENGTH: 6762
<212> TYPE: DNA
<213> ORGANISM: Homo sapiens

<400> SEQUENCE: 33
agacgtgagg cttgcagcag gccgaggagg aagaagaggg gcagtgggag cagaggaggt        60
ggctcctgcc ccagtgagag ctctgagggt ccctgcctga agagggacag ggaccggggc       120
ttggagaagg ggctgtggaa tgcagccccc ttcactgctg ctgctgctgc tgctgctgct       180
gctgctatgt gtctcagtgg tcagacccag agggctgctg tgtgggagtt cccagaacc       240
```

-continued

```
ctgtgccaat ggaggcacct gcctgagcct gtctctggga caagggacct gccagtgtgc      300
ccctggcttc ctgggtgaga cgtgccagtt tcctgacccc tgccagaacg cccagctctg      360
ccaaaatgga ggcagctgcc aagccctgct tcccgctccc ctagggctcc ccagctctcc      420
ctctccattg acacccagct tcttgtgcac ttgcctccct ggcttcactg gtgagagatg      480
ccaggccaag cttgaagacc cttgtcctcc ctccttctgt tccaaaaggg gccgctgcca      540
catccaggcc tcgggccgcc cacagtgctc ctgcatgcct ggatggacag gtgagcagtg      600
ccagcttcgg gacttctgtt cagccaaccc atgtgttaat ggaggggtgt gtctggccac      660
atacccccag atccagtgcc actgcccacc gggcttcgag ggccatgcct gtgaacgtga      720
tgtcaacgag tgcttccagg acccaggacc ctgccccaaa ggcacctcct gccataacac      780
cctgggctcc ttccagtgcc tctgccctgt ggggcaggag ggtccacgtt gtgagctgcg      840
ggcaggaccc tgccctccta ggggctgttc gaatgggggc acctgccagc tgatgccaga      900
gaaagactcc acctttcacc tctgcctctg tccccaggt ttcataggcc cagactgtga      960
ggtgaatcca gacaactgtg tcagccacca gtgtcagaat gggggcactt gccaggatgg     1020
gctggacacc tacacctgcc tctgcccaga aacctggaca ggctgggact gctccgaaga     1080
tgtggatgag tgtgagaccc agggtccccc tcactgcaga aacggggca cctgccagaa      1140 ctctgctggt agctttcact gcgtgtgtgt gagtggctgg ggcggcacaa gctgtgagga     1200
gaacctggat gactgtattg ctgccacctg tgccccggga tccacctgca ttgaccgggt     1260
gggctctttc tcctgcctct gcccacctgg acgcacagga ctcctgtgcc acttggaaga     1320
catgtgtctg agccagccgt gccatgggga tgcccaatgc agcaccaacc ccctcacagg     1380
ctccacactc tgcctgtgtc agcctggcta ttcggggccc acctgccacc aggacctgga     1440
cgagtgtctg atggcccagc aaggcccaag tccctgtgaa catggcggtt cctgcctcaa     1500
cactcctggc tccttcaact gcctctgtcc acctggctac acaggctccc gttgtgaggc     1560
tgatcacaat gagtgcctct cccagccctg ccacccagga agcacctgtc tggacctact     1620
tgccaccttc cactgcctct gcccgccagg cttagaaggg cagctctgtg aggtggagac     1680
caacgagtgt gcctcagctc cctgcctgaa ccacgcggat tgccatgacc tgctcaacgg     1740
cttccagtgc atctgcctgc ctggattctc cggcacccga tgtgaggagg atatcgatga     1800
gtgcagaagc tctccctgtg ccaatggtgg gcagtgccag gaccagcctg gagccttcca     1860
ctgcaagtgt ctcccaggct ttgaagggcc acgctgtcaa acagaggtgg atgagtgcct     1920
gagtgaccca tgtcccgttg gagccagctg ccttgatctt ccaggagcct tcttttgcct     1980
ctgcccctct ggtttcacag gccagctctg tgaggttccc ctgtgtgctc ccaacctgtg     2040
ccagcccaag cagatatgta aggaccagaa agacaaggcc aactgcctct gtcctgatgg     2100
aagccctggc tgtgccccac ctgaggacaa ctgcacctgc caccacgggc actgccagag     2160
atcctcatgt gtgtgtgacg tgggttggac ggggccagag tgtgaggcag agctagggggg     2220 ctgcatctct gcaccctgtg cccatggggg gacctgctac ccccagccct ctggctacaa     2280
ctgcacctgc cctacaggct acacaggacc cacctgtagt gaggagatga cagcttgtca     2340
ctcagggcca tgtctcaatg gcggctcctg caacccctagc cctggaggct actactgcac     2400
ctgccctcca agccacacag ggccccagtg ccaaaccagc actgactact gtgtgtctgc     2460
cccgtgcttc aatggggta cctgtgtgaa caggcctggc accttctcct gcctctgtgc     2520
catgggcttc cagggcccgc gctgtgaggg aaagctccgc cccagctgtg cagacagccc     2580
ctgtaggaat agggcaacct gccaggacag ccctcagggt ccccgctgcc tctgccccac     2640
```

```
tggctacacc ggaggcagct gccagactct gatggactta tgtgcccaga agccctgccc    2700
acgcaattcc cactgcctcc agactgggcc ctccttccac tgcttgtgcc tccagggatg    2760
gaccgggcct ctctgcaacc ttccactgtc ctcctgccag aaggctgcac tgagccaagg    2820
catagacgtc tcttcccttt gccacaatgg aggcctctgt gtcgacagcg gcccctccta    2880
tttctgccac tgcccccctg gattccaagg cagcctgtgc caggatcacg tgaacccatg    2940
tgagtccagg ccttgccaga acggggccac ctgcatggcc cagcccagtg ggtatctctg    3000
ccagtgtgcc ccaggctacg atggacagaa ctgctcaaag gaactcgatg cttgtcagtc    3060
ccaaccctgt cacaaccatg gaacctgtac tcccaaacct ggaggattcc actgtgcctg    3120
ccctccaggc tttgtggggc tacgctgtga gggagacgtg gacgagtgtc tggaccagcc    3180
ctgccacccc acaggcactg cagcctgcca ctctctggcc aatgccttct actgccagtg    3240
tctgcctgga cacacaggcc agtggtgtga ggtggagata gacccctgcc acagccaacc    3300
ctgctttcat ggagggacct gtgaggccac agcaggatca ccctgggtt tcatctgcca     3360 ctgccccaag ggttttgaag gccccacctg cagccacagg gccccttcct gcggcttcca    3420
tcactgccac cacggaggcc tgtgtctgcc ctccctaag ccaggcttcc caccacgctg      3480
tgcctgcctc agtggctatg ggggtcctga ctgcctgacc ccaccagctc ctaaaggctg    3540
tggccctccc tccccatgcc tatacaatgg cagctgctca gagaccacgg gcttggggggg   3600 cccaggcttt cgatgctcct gccctcacag ctctccaggg ccccggtgtc agaaacccgg    3660
agccaagggg tgtgagggca gaagtggaga tggggcctgc gatgctggct gcagtggccc    3720
gggaggaaac tgggatggag gggactgctc tctgggagtc ccagacccct ggaagggctg    3780
cccctcccac tctcggtgct ggcttctctt ccgggacggg cagtgccacc cacagtgtga    3840
ctctgaagag tgtctgtttg atggctacga ctgtgagacc cctccagcct gcactccagc    3900
ctatgaccag tactgccatg atcacttcca caacgggcac tgtgagaaag gctgcaacac    3960
tgcagagtgt ggctgggatg gaggtgactg caggcctgaa gatggggacc cagagtgggg    4020
gccctccctg gccctgctgg tggtactgag ccccccagcc ctagaccagc agctgttttgc    4080 cctggcccgg gtgctgtccc tgactctgag ggtaggactc tgggtaagga aggatcgtga    4140
tggcagggac atggtgtacc cctatcctgg ggcccgggct gaagaaaagc taggaggaac    4200
tcgggacccc acctatcagg agagagcagc ccctcaaacg cagcccctgg gcaaggagac    4260
cgactccctc agtgctgggt ttgtggtggt catgggtgtg gatttgtccc gctgtggccc    4320
tgaccacccg gcatcccgct gtccctggga ccctgggctt ctactccgct tccttgctgc    4380
gatggctgca gtgggagccc tggagcccct gctgcctgga ccactgctgg ctgtccaccc    4440
tcatgcaggg accgcacccc ctgccaacca gcttccctgg cctgtgctgt gctccccagt    4500
ggccggggtg attctcctgg ccctaggggc tcttctcgtc ctccagctca tccggcgtcg    4560
acgccgagag catggagctc tctggctgcc ccctggtttc actcgacggc ctcggactca    4620
gtcagctccc caccgacgcc ggcccccact aggcgaggac agcattggtc tcaaggcact    4680
gaagccaaag gcagaagttg atgaggatgg agttgtgatg tgctcaggcc ctgaggaggg    4740
agaggaggtg ggccaggctg aagaaacagg cccacccctcc acgtgccagc tctggtctct   4800
gagtggtggc tgtggggcgc tccctcaggc agccatgcta actcctcccc aggaatctga    4860
gatggaagcc cctgacctgg acacccgtgg aacctgatgg gtgacacccc tgatgtcagc    4920
agtttgctgt ggggaagtac agtccgggac cttccaaggg gcatggttgg gatgtcctga    4980
```

```
gccctgggaa cctctgctgg atggaggggc ctgtccccag gctcacaccg tgggcactgg    5040
ggagaccccc ctgcacctgg ctgcccgatt ctcccggcca accgctgccc gccgcctcct    5100
tgaggctgga gccaaccccca accagccaga ccgggcaggg cgcacacccc ttcatgctgc    5160
tgtggctgct gatgctcggg aggtctgcca gcttctgctc cgtagcagac aaactgcagt    5220
ggacgctcgc acagaggacg ggaccacacc cttgatgctg gctgccaggc tggcggtgga    5280
agacctggtt gaagaactga ttgcagccca agcagacgtg ggggcagag ataaatgggg    5340 gaaaactgcg ctgcactggg ctgctgccgt gaacaacgcc cgagccgccc gctcgcttct    5400
ccaggccgga gccgataaag atgcccagga caacagggag cagacgccgc tattcctggc    5460
ggcgcgggaa ggagcggtgg aagtagccca gctactgctg gggctggggg cagcccgaga    5520
gctgcgggac caggctgggc tagcgccggc ggacgtcgct caccaacgta accactggga    5580
tctgctgacg ctgctggaag gggctgggcc accagaggcc cgtcacaaag ccacgccggg    5640
ccgcgaggct gggcccttcc cgcgcgcacg gacggtgtca gtaagcgtgc ccccgcatgg    5700 gggcgggggct ctgccgcgct gccggacgct gtcagccgga gcaggccctc gtgggggcgg    5760
agcttgtctg caggctcgga cttggtccgt agacttggct gcgcgggggg gcggggccta    5820
ttctcattgc cggagcctct cgggagtagg agcaggagga ggcccgaccc ctcgcggccg    5880
taggttttct gcaggcatgc gcgggcctcg gcccaaccct gcgataatgc gaggaagata    5940
cggagtggct gccgggcgcg gaggcagggt ctcaacggat gactggccct gtgattgggt    6000
ggccctggga gcttgcggtt ctgcctccaa cattccgatc ccgcctcctt gccttactcc    6060
gtccccggag cggggatcac ctcaacttga ctgtggtccc ccagccctcc aagaaatgcc    6120
cataaaccaa ggaggagagg gtaaaaaata gaagaataca tggtagggag gaattccaaa    6180
aatgattacc cattaaaagg caggctggaa ggccttcctg gtttttaagat ggatccccca    6240 aaatgaaggg ttgtgagttt agtttctctc ctaaaatgaa tgtatgccca ccagagcaga    6300
catcttccac gtggagaagc tgcagctctg gaaagagggt ttaagatgct aggatgaggc    6360
aggcccagtc ctcctccaga aaataagaca ggccacagga gggcagagtg gagtggaaat    6420 accccctaagt tggaaccaag aattgcaggc atatgggatg taagatgttc tttcctatat    6480
atggtttcca aagggtgccc ctatgatcca ttgtccccac tgcccacaaa tggctgacaa    6540
atatttattg ggcacctact atgtgccagg cactgtgtag gtgctgaaaa gtggccaagg    6600 gccaccccg ctgatgactc cttgcattcc ctcccctcac aacaaagaac tccactgtgg    6660
ggatgaagcg cttcttctag ccactgctat cgctatttaa gaaccctaaa tctgtcaccc    6720
ataataaagc tgatttgaag tgttaaaaaa aaaaaaaaaa aa                        6762

<210> SEQ ID NO 34
<211> LENGTH: 200
<212> TYPE: DNA
<213> ORGANISM: Artificial Sequence
<220> FEATURE:
<223> OTHER INFORMATION: CMV promoter

<400> SEQUENCE: 34
atcgatgtta ataattaaca tatatgttaa tcattaacta tatagttaat tattaaccgc      60
tatgttaatg attaacacta gttaggcgtg tacggtggga ggcctatata agcagagctc     120
gtttagtgaa ccgtcagatc gcctggagac gccatccacg ctgttttgac ctccatagaa     180
gacaccggga ccgatccagc                                                  200
```

-continued

```
<210> SEQ ID NO 35
<211> LENGTH: 9
<212> TYPE: DNA
<213> ORGANISM: Artificial Sequence
<220> FEATURE:
<223> OTHER INFORMATION: Kozak sequence

<400> SEQUENCE: 35 gccgccacc                                                                               9
```